US012673994B2

(12) United States Patent
Rademaker et al.

(10) Patent No.: US 12,673,994 B2
(45) Date of Patent: **\*Jul. 7, 2026**

(54) HUMANIZED OR CHIMERIC CD3 ANTIBODIES

(71) Applicant: GENMAB A/S, Valby (DK)

(72) Inventors: Rik Rademaker, Utrecht (NL); Isil Altintas, Utrecht (NL); Patrick Engelberts, Utrecht (NL); Janine Schuurman, Utrecht (NL); Paul Parren, Utrecht (NL)

(73) Assignee: GENMAB A/S, Valby (DK)

( * ) Notice: Subject to any disclaimer, the term of this patent is extended or adjusted under 35 U.S.C. 154(b) by 836 days.

This patent is subject to a terminal disclaimer.

(21) Appl. No.: 17/739,923

(22) Filed: May 9, 2022

(65) Prior Publication Data

US 2022/0380464 A1     Dec. 1, 2022

Related U.S. Application Data

(62) Division of application No. 15/744,317, filed as application No. PCT/EP2016/066845 on Jul. 14, 2016, now Pat. No. 11,359,015.

(30) Foreign Application Priority Data

| Jul. 15, 2015 | (DK) | ............................ | PA 2015 00414 |
| Jul. 15, 2015 | (DK) | ............................ | PA201500413 |
| Jul. 16, 2015 | (DK) | ............................ | PA201500416 |
| Jan. 8, 2016 | (WO) | ................. | PCT/EP2016/050296 |

(51) Int. Cl.
| *C07K 16/00* | (2006.01) |
| *C07K 16/28* | (2006.01) |
| *C07K 16/32* | (2006.01) |
| *A61K 39/00* | (2006.01) |

(52) U.S. Cl.
CPC .......... *C07K 16/2809* (2013.01); *C07K 16/32* (2013.01); *A61K 2039/505* (2013.01); *C07K 2317/24* (2013.01); *C07K 2317/31* (2013.01); *C07K 2317/526* (2013.01); *C07K 2317/55* (2013.01); *C07K 2317/565* (2013.01); *C07K 2317/73* (2013.01); *C07K 2317/92* (2013.01)

(58) Field of Classification Search
CPC .............. C07K 16/2809; C07K 16/32; C07K 2317/24; C07K 2317/31; C07K 2317/526; C07K 2317/565; A61K 2039/505
See application file for complete search history.

(56) References Cited

U.S. PATENT DOCUMENTS

| 4,699,880 A | 10/1987 | Goldstein |
| 5,057,313 A | 10/1991 | Shih et al. |
| 5,589,466 A | 12/1996 | Felgner et al. |
| 5,973,972 A | 10/1999 | Kwon et al. |
| 6,077,835 A | 6/2000 | Hanson et al. |
| 6,331,175 B1 | 12/2001 | Goldenberg |
| 7,262,028 B2 | 8/2007 | Van Berkel et al. |
| 7,612,181 B2 | 11/2009 | Wu et al. |
| 7,951,918 B2 | 5/2011 | Glaser et al. |
| 8,236,308 B2 | 8/2012 | Kischel et al. |
| 9,150,663 B2 | 10/2015 | Abrijn et al. |
| 9,212,230 B2 | 12/2015 | Schuurman et al. |
| 10,344,050 B2 | 7/2019 | Gramer et al. |
| 10,407,501 B2 | 9/2019 | Van Den Brink et al. |
| 10,465,006 B2 | 11/2019 | Van Den Brink et al. |
| 10,544,220 B2 | 1/2020 | Engelberts et al. |
| 10,590,206 B2 | 3/2020 | Labrijn et al. |
| 10,597,464 B2 | 3/2020 | Abrijn et al. |
| 10,906,991 B2 | 2/2021 | Schuurman et al. |
| 11,008,399 B2 | 5/2021 | Satijn et al. |
| 11,130,819 B2 | 9/2021 | Satijn et al. |
| 11,180,572 B2 | 11/2021 | De Jong et al. |
| 11,261,254 B1 | 3/2022 | Koopman et al. |
| 11,359,015 B2 | 6/2022 | Rademaker et al. |
| 11,485,796 B2 | 11/2022 | Labrijn et al. |
| 11,492,371 B2 | 11/2022 | Gramer et al. |
| 11,613,575 B2 | 3/2023 | Van Den Brink et al. |
| 11,866,514 B2 | 1/2024 | Labrijn et al. |
| 11,970,544 B2 | 4/2024 | Satijn et al. |
| 2010/0105874 A1 | 4/2010 | Schuurman et al. |
| 2010/0155133 A1 | 6/2010 | Makwinski et al. |
| 2013/0039913 A1 | 2/2013 | Labrijn et al. |
| 2014/0303356 A1 | 10/2014 | Gramer et al. |
| 2015/0175707 A1 | 6/2015 | De Jong et al. |

(Continued)

FOREIGN PATENT DOCUMENTS

| CN | 102250246 A | 11/2011 |
| EP | 0629240 A1 | 12/1994 |

(Continued)

OTHER PUBLICATIONS

Paul, Fundamental Immunology, 3rd Edition, 1993, pp. 292-295, under the heading Fv Structure and Diversity in Three Dimensions (Year: 1993).*
Rudikoff et al (Proc. Natl. Acad. Sci. USA 1982 vol. 79: p. 1979 (Year: 1979).*
Casset et al (BBRC 307, 198-205 2003 (Year: 2003).*
Pascalis et al (The Journal of Immunology vol. 169, 3076-3084, 2002 (Year: 2002).*
U.S. Appl. No. 17/939,736, filed Sep. 7, 2022, Michael Gramer.
Almagro J. C. et al, "Humanization of Antibodies," Frontiers in BioScience, vol. 13:1619-1633 (2008).

(Continued)

*Primary Examiner* — Lei Yao

(74) *Attorney, Agent, or Firm* — Nelson Mullins Riley & Scarborough LLP; Jane E. Remillard, Esq.; Christopher L. Frank

(57) ABSTRACT

The present invention relates to humanized or chimeric antibodies binding CD3. It furthermore relates to bispecific antibodies, compositions, pharmaceutical compositions, use of said antibodies in the treatment of a disease, and method of treatment.

20 Claims, 13 Drawing Sheets

Specification includes a Sequence Listing.

(56)                    References Cited

U.S. PATENT DOCUMENTS

| | | |
|---|---|---|
| 2015/0337049 A1 | 11/2015 | Abrijn et al. |
| 2016/0159930 A1 | 6/2016 | Schuurman et al. |
| 2016/0168247 A1 | 6/2016 | Van Den Brink et al. |
| 2016/0333095 A1 | 11/2016 | Van Den Brink et al. |
| 2017/0233497 A1 | 8/2017 | Labrijn et al. |
| 2017/0355767 A1 | 12/2017 | Engelberts et al. |
| 2019/0284278 A1 | 9/2019 | Rademaker et al. |
| 2020/0048304 A1 | 2/2020 | Gramer et al. |
| 2020/0123255 A1 | 4/2020 | Van Den Brink et al. |
| 2020/0199229 A1 | 6/2020 | Van Den Brink et al. |
| 2020/0199231 A1 | 6/2020 | Engelberts et al. |
| 2020/0262932 A1 | 8/2020 | Abrijn et al. |
| 2020/0332022 A1 | 10/2020 | Labrijn et al. |
| 2021/0070877 A1 | 3/2021 | Satijn et al. |
| 2021/0230296 A1 | 7/2021 | Satijn et al. |
| 2021/0230301 A1 | 7/2021 | De Jong et al. |
| 2021/0292418 A1 | 9/2021 | Koopman et al. |
| 2022/0048999 A1 | 2/2022 | Koopman et al. |
| 2022/0049013 A1 | 2/2022 | Satijn et al. |
| 2022/0324980 A1 | 10/2022 | Koopman et al. |
| 2022/0389101 A1 | 12/2022 | Rademaker et al. |
| 2023/0027394 A1 | 1/2023 | Rademaker et al. |
| 2023/0227495 A1 | 7/2023 | Gramer et al. |
| 2023/0310599 A1 | 10/2023 | Benonisson et al. |
| 2023/0322947 A1 | 10/2023 | Labrijn et al. |
| 2023/0365714 A1 | 11/2023 | Koopman et al. |
| 2023/0374131 A1 | 11/2023 | Van Den Brink et al. |
| 2024/0209117 A1 | 6/2024 | Labrijn et al. |
| 2024/0301078 A1 | 9/2024 | Elliott et al. |
| 2024/0368297 A1 | 11/2024 | Li et al. |
| 2024/0392032 A1 | 11/2024 | Satijn et al. |
| 2025/0340647 A1 | 11/2025 | Koopman et al. |

FOREIGN PATENT DOCUMENTS

| | | |
|---|---|---|
| EP | 1870459 A1 | 12/2007 |
| WO | 92/22653 A1 | 12/1992 |
| WO | 9850431 A2 | 11/1998 |
| WO | 200046147 A2 | 8/2000 |
| WO | 00/70087 A1 | 11/2000 |
| WO | 2002/020039 A2 | 3/2002 |
| WO | 2007059782 A1 | 5/2007 |
| WO | 2007/110205 A2 | 10/2007 |
| WO | 2008/003116 A2 | 1/2008 |
| WO | 2008119567 A2 | 10/2008 |
| WO | 2008157379 A2 | 12/2008 |
| WO | 2009058383 A2 | 5/2009 |
| WO | 2009/080254 A1 | 7/2009 |
| WO | 2009/089004 A1 | 7/2009 |
| WO | 2010/015792 A1 | 2/2010 |
| WO | 2010026923 A1 | 3/2010 |
| WO | 2010059315 A1 | 5/2010 |
| WO | 2010/080538 A1 | 7/2010 |
| WO | 2010111625 A1 | 9/2010 |
| WO | 2010/129304 A2 | 11/2010 |
| WO | 2010134666 A1 | 11/2010 |
| WO | 2011/028952 A1 | 3/2011 |
| WO | 2011066501 | 6/2011 |
| WO | 2011/117329 A1 | 9/2011 |
| WO | 2011110642 A2 | 9/2011 |
| WO | 2011/131746 A2 | 10/2011 |
| WO | 2011143545 A1 | 11/2011 |
| WO | 2012023053 A2 | 2/2012 |
| WO | 2012025525 A1 | 3/2012 |
| WO | 2012025530 A1 | 3/2012 |
| WO | 2012/058768 A1 | 5/2012 |
| WO | 2012/143524 A2 | 10/2012 |
| WO | 2012162067 A2 | 11/2012 |
| WO | 2013060867 A2 | 5/2013 |
| WO | 2013157953 A1 | 10/2013 |
| WO | 2013/186613 A1 | 12/2013 |
| WO | 2013/188693 A1 | 12/2013 |
| WO | 2014081202 A1 | 5/2014 |
| WO | 2014108483 A1 | 7/2014 |
| WO | WO2014108483 | * 7/2014 |
| WO | 2015001085 A1 | 1/2015 |
| WO | 2017123650 A2 | 7/2017 |

OTHER PUBLICATIONS

Bokemeyer et al., 2009, J Clin Oncol (Meeting Abstracts), 3036.
Bortoletto, N et al. "Optimizing anti-CD3 affinity for effective T cell targeting against tumor cells," European Journal of Immunology, vol. 32 (11): 3102-3107 (2002).
Bostrom, J. et al., "Variants of the Antibody Herceptin That Interact with HER2 and VEGF at the Antigen Binding Site," Science, vol. 323: 1610-1614 (2009).
Casset et al., BBRC, vol. 307:198-205 (2003).
Doppalapudi, V.R., et al., "Chemically programmed antibodies: Endothelin receptor targeting CovX-Bodies," Bioorg. Med. Chem. Lett., vol. 17: 501-506 (2007).
Heiss, M. et al., "The trifunctional antibody catumaxomab for the treatment of malignant ascites due to epithelial cancer: results of a prospective randomized phase II/III trial ," Int J Cancer, vol. 127: 2209-2221 (2010).
Herold, K. et al., "A Single Course of Anti-CD3 Monoclonal Antibody hOKT3 1(Ala-Ala) Results in Improvement in Peptide Responses and Clinical Parameters for at Least 2 Years after Onset of Type 1 Diabetes," Diabetes, vol. 54 (6):1763-1769 (2005).
Himila, I. et al., "A bispecific nanobody to provide full protection against lethal scorpion envenoming ," FASEB J., vol. 24: 3479-3489 (2010).
Hinojosa, L. et al., "Construction of a Recombinant Non-Mitogenic Anti-Human CD3 Antibody," Hybridoma, vol. 29 (2):115-124 (2010).
Jones, K. et al., "Evolving novel anti-HER2 strategies," Lancet Oncol., vol. 10:1179-1187 (2009).
Kiewe, P. et al., "Phase 1 Trial of the Trifunctional Anti-HER2 X Anti-CD3 Antibody Ertumaxomab in Metastatic Breast Cancer" Clinical Cancer Research, vol. 12 (10): 3085-3091 (2006).
LaFleur, D. et al., "Monoclonal antibody therapeutics with up to five specificities: functional enhancement through fusion of target-specific peptides," MAbs, vol. 5(2):208-218 (2013).
Lawrence, L. et al., "Orientation of antigen binding sites in dimeric and trimeric single chain Fv antibody fragments," FEBS Lett., vol. 425(3):479-484 (1998).
Lewis' S. et al., "Generation of bispecific igG antibodies by structure-based design of an orthogonal Fab interface," Nat Biotechnol, vol. 32(2):191-198 (2014).
Li, J. J et al. "Phase I trial of a humanized, Fc receptor nonbinding anti-CD3 antibody, hu12F6mu in patients receiving renal allografts," MABS, vol. 2(4): 3085-3091 (2010).
Linke, R. et al., "Catumaxomab: clinical development and future directions," MAbs, vol. 2: 129-136 (2010).
Lum, L. et al., "Targeting T cells with bispecific antibodies for cancer therapy," BioDrugs, vol. 25: 365-379 (2011).
Molhoj, M. et al., "CD19-/CD3-bispecific antibody of the BITE class is far superior to tandem diabody with respect to redirected tumor cell lysis," Molecular Immunology, vol. 44(8)3038 (2007).
Muller, D. et al., "Bispecific antibodies for cancer immunotherapy: Current perspectives," BioDrugs, vol. 24: 89-98 (2010).
Pascalis et al., The Journal of Immunology, vol. 169, 3076-3084 (2002).
Paul, Fundamental Immunology, 3rd Edition, pp. 292-295, under the heading Fv Structure and Diversity in Three Dimensions (1993).
Pearce, L et al., "Linear gene fusions of antibody fragments with streptavidin can be linked to biotin labelled secondary molecules to form bispecific reagents," Biochem Mol Biol Int., vol. 42(6):1179-1188 (1997).
Reusch, U. et al., "A travalent bispecific TandAb (CD19/CD3), AFM11, efficiently recruits T cells for the potent lysis of CD19(+) tumor cells," Mabs, vol. 7(3):584-604 (2015).
Reusch, U. et al., "Anti-CD3 x anti-epidermal growth factor receptor (EGFR) bispecific antibody redirects T-cell cytolytic activity to EGFR-positive cancers in vitro and in an animal model," Clin Cancer Res., vol. 12(1):183-190 (2006).

(56)                    References Cited

OTHER PUBLICATIONS

Rudikoff et al. (Proc. Natl. Acad. Sci. USA, 79: 1979-1983, Mar. 1982) (Year: 1982.

Ruf, P. et al., "Pharmacokinetics, immunogenicity and bioactivity of the therapeutic antibody catumaxomab intraperitoneally administered to cancer patients," Br J Clin Pharmacol_ vol. 69: 617-625 (2010).

Staerz, U. et al., "Hybrid antibodies can target sites for attack by T cells," Nature, vol. 314:628-631 (1985).

Vidarsson, G et al, "igG Subclasses and Allotypes: from structure to Effector Functions", Frontiers in Immunology, vol. 5, 2014, 1-17.

Viola, k et al., "T cell activation determined by T cell receptor number and tunable thresholds," Science, vol. 273 (5271) 104-106 (1996).

Webster, D. et al., "Engineering antibody affinity and specificity," Int J Cancer Suppl., vol. 3:13-16 (1998).

Wu et al., 2010, Generation and Characterization of a Dual Variable Domain Immunoglobulin (DVD-IgIN) Molecule, In Antibody Engineering, Springer Berlin Heidelberg, 8 pages.

Xu, D. et al., "In vitro characterization of five humanized OKT3 effector function variant antibodies," Cell Immunol., vol. 200(1):16-26 (2000).

Zhu X. et al., "COMBODY: one-domain antibody multimer with improved avidity," Immunol Cell Biol., vol. 88 (6):667-75 (2010).

Ausubel, F. et al., ed. Current Protocols in Molecular Biology, Greene Publishing and Wiley InterScience New York , 43 pages (1987).

Barbas, C. et al., "Molecular Profile of an Antibody Response to HIV-1 as Probed by Combinatorial Libraries," Academic Press., vol. 230(3): 812-823 (1993).

Benvenisty, N. et al., "Direct introduction of genes into rats and expression of the genes," PNAS, vol. 83:9551-9555 (1986).

Bird, R.E. et al., "Single-chain antigen-binding proteins," Science, vol. 242(4877):423-426 (1988).

Bitter, G.A., et al., "Expression and secretion vectors for yeast," Methods in Enzymol., vol. 153: 516-544 (1987).

Blankenship JW, et al., "Abstract #5465: CD79BxDR SCORPIONTM molecule: a single chain, bispecific immunotherapeutic with potent in vitro activity against B cell lymphoma ," AACR 100th Annual Meeting, Cancer Res/, vol. 69 (9_Supplement):4 pages (2009).

Bostrom, J. et al., "Variants of the antibody herceptin that interact with HER2 and VEGF at the antigen binding site," Science, vol. 323 (5921): 1610-1614 (2009).

Brochet X., "IMGT/V-Quest: the highly customized and integrated system for IG and TR standardized V-J and V-D-J sequence analysis," Nucl Acids Res., vol. 36:W503-508 (2008).

Brown, JM, Clinical use of monoclonal antibodies, pp. 227-249—Book, 1993, Chapman and Hall.

Bruhns, P. et al., "Specificity and affinity of human Fcgamma receptors and their polymorphic variants for human IgG subclasses," Blood, vol. 113(16): 3716-3725 (2009).

Bryson, C. et al., "Prediction of immunogenicity of therapeutic proteins: validity of computational tools," vol. 24 (1): 1-8, (2010).

Canfield, S.M. et al., "The Binding Affinity of Human IgG for its High Affinity Fc Receptor Is Determined by Multiple Amino Acids in the CH2 Domain and Is Modulated by the Hinge Region," J. Exp. Med., vol. 173:1483-1491 (1991).

Corsaro and Pearson, "Enhancing the efficiency of DNA-mediated gene transfer in mammalian cells," Somatic Cell Genetics, vol. 7(5):603-615 (1981).

Dall'Acqua, W.F. et al., "Modulation of the Effector Functions of a Human IgG1 through Engineering of Its Hinge Region," The Journal of Immunology, vol. 177(2):1129-1138 (2006).

De Pascalis, R. et al., "Grafting of "abbreviated" complementarity-determining regions containing specificity-determining residues essential for ligand contact to engineer a less immunogenic humanized monoclonal antibody," J. Immunol., vol. 169(6): 3076-3084 (2002).

Dimasi N, et al., "The design and characterization of oligospecific antibodies for simultaneous targeting of multiple disease mediators," J Mol Biol., vol. 393(3):672-92 (2009).

Duncan, A.R. et al., "The Binding Site for C1q on IgG," Nature, vol. 332: 738-740 (1988).

Guidicelli, V. et al., "IMGT/V-Quest: IMGT Standardized Analysis of the Immunoglobulin (IG) and T Cell Receptor (TR) Nucleotide Sequences," Cold Spring Harbor Protocols, vol. 2011(6):695-716 (2011).

Huston, J. et al., "Protein engineering of antibody binding sites: recovery of specific activity in an anti-digoxin single-chain Fv analogue produced in Escherichia coli," PNAS, vol. 85(16): 5879-5883 (1988).

Idusogie EE, et al., "Mapping of the C1q binding site on rituxan, a chimeric antibody with a human IgG1 Fc," J Immunol., vol. 164: 4178-4184 (2000).

Kabat et al., Sequences of Proteins of Immunological Interest, Fifth Edition. 1991 NIH Publication No. 91-3242, 11 pages.

Leabman M.L. et al., "Effects of altered FcγR binding on antibody pharmacokinetics in cynomolgus monkeys," Mabs, vol. 5(6):896-903 (2013).

Lefranc MP, et al., "IMGT, the international ImMunoGeneTics database.," Nucleic Acids Res., vol. 27(1):209-212 (1999).

Lightle S, et al., "Mutations within a human IgG2 antibody form distinct and homogeneous disulfide isomers but do not affect Fc gamma receptor or C1q binding" Protein Sci., vol. 19(4):753-62 (2010).

Myers EW et al., "Optimal alignments in linear space," Comput Appl Biosci., vol. 4(1):11-17 (1988).

Needleman and Wunsch, J., "A general method applicable to the search for similarities in the amino acid sequence of two proteins," Mol. Biol., vol. 48(3): 444-453 (1970).

Oganesyan, V. et al., "Structural characterization of a human Fc fragment engineered for lack of effector functions," Acta Crystallographica, D64:700-704 (2008).

Parren PW, et al., "On the interaction of IgG subclasses with the low affinity Fc gamma RIIa (CD32) on human monocytes, neutrophils, and platelets, Analysis of a functional polymorphism to human IgG2," J Clin Invest., vol. 90 (4):1537-46 (1992).

Paul, W, Fundamental Immunology, 2nd Edition, Raven Press, Chapter 12, 332-337 (1989).

Perry, L.C. et al., "New approaches to prediction of immune responses to therapeutic proteins during preclinical development," Drugs in R&D, vol. 9(6): 385-396 (2008).

Remington, Medical Applications of Radioisotopes, 18 Ed., pp. 624-652—Book, 1990, Mack Publishing Co., Gennaro.

Remington: The Science and Practice of Pharmacy, 19th Edition, Gennaro, Ed., Mack Publishing Co., Easton, PA,, 1993 pages (1995).

Ritter, G. et al., "Serological analysis of human anti-human antibody responses in colon cancer patients treated with repeated doses of humanized monoclonal antibody A33," Cancer Research, vol. 61(18): 6851-6859 (2001).

Robinson, J.R., "Sustained and controlled release drug delivery systems," Book, Marcel Dekker, 395 pages,(1978).

Sambrook et al., 1989, Molecular Cloning: A laboratory Manual, New York: Cold Spring Harbor Laboratory Press, Ch. 15, 43 pages.

Schakowski F, et al., "A novel minimal-size vector (MIDGE) improves transgene expression in colon carcinoma cells and avoids transfection of undesired DNA," Mol Ther., vol. 3(5 Pt 1):793-800 (2001).

Shields, R. L. et al., "High Resolution Mapping of the Binding Site on Human FcgR for FcgRI, FcgRII, FcgRIII, and FcRn and Design of IgG1 Variants with Improved Binding to the FcgR*," The Journal of Biological Chemistry, vol. 276 (9):6591-6604 (2001).

Sleebom et al., "MDA-MB-231 Breast Cancer Cells and Their CSC Population Migrate Towards Low Oxygen in a Microfluidic Gradient Device," International Journal of Molecular Sciences, vol. 19 (3047)1-15 (2018).

Sykes KF, et al., "Linear expression elements: a rapid, in vivo, method to screen for gene functions," Nat Biotechnol., vol. 17(4):355-9 (1999).

T cell Epitope Database, www.IEDB.org, 1page.

Thompson et al., "Clustal W: improving the sensitivity of progressive multiple sequence alignment through sequence weighting,

(56)         References Cited

OTHER PUBLICATIONS position-specific gap penalties and weight matrix choice", Nucleic Acids Rest., vol. 22(22): 4673-80 (1994).

Van Heeke G, et al. "Expression of human asparagine synthetase in *Escherichia coli*," J Biol Chem., vol. 264 (10):5503-9 (1989).

Welch et al., "Potential Labeling of Monoclonal Antibodies With Positron Emitters," Srivastava, Plenum Press , 2 pages (1988).

Wigler M., et al. "Biochemical transfer of single-copy eucaryotic genes using total cellular DNA as donor," Cell, vol. 14 (3):725-31 (1978).

Wranik BJ et al., "LUZ-Y, a novel platform for the mammalian cell production of full-length IgG-bispecific antibodies," J Biol Chem., vol. 287(52):43331-9 (2012).

Zheng, L., et al., "Expression Improvement and Mechanistic Study of the Retro-Diels-Alderase Catalytic Antibody 10F11 by Site-directed Mutagenesis," Journal of Molecular Biology, vol. 341(3), 807-14 (2004).

Bostrom et al., "High Affinity Antigen Recognition of the Dual Specific Variants of Herceptin Is Entropy-Driven in Spite of Structural Plasticity," PLOS One, ,vol. 6(4):1-12 (2011).

Haber et al., "Generation ofT-cell redirecting bispecifc antibodies with differentiated profiles of cytosine release and bio-distribution by CD3 affinity tuning," Scientific Reports, vol. 11: 1-17 (2021).

* cited by examiner

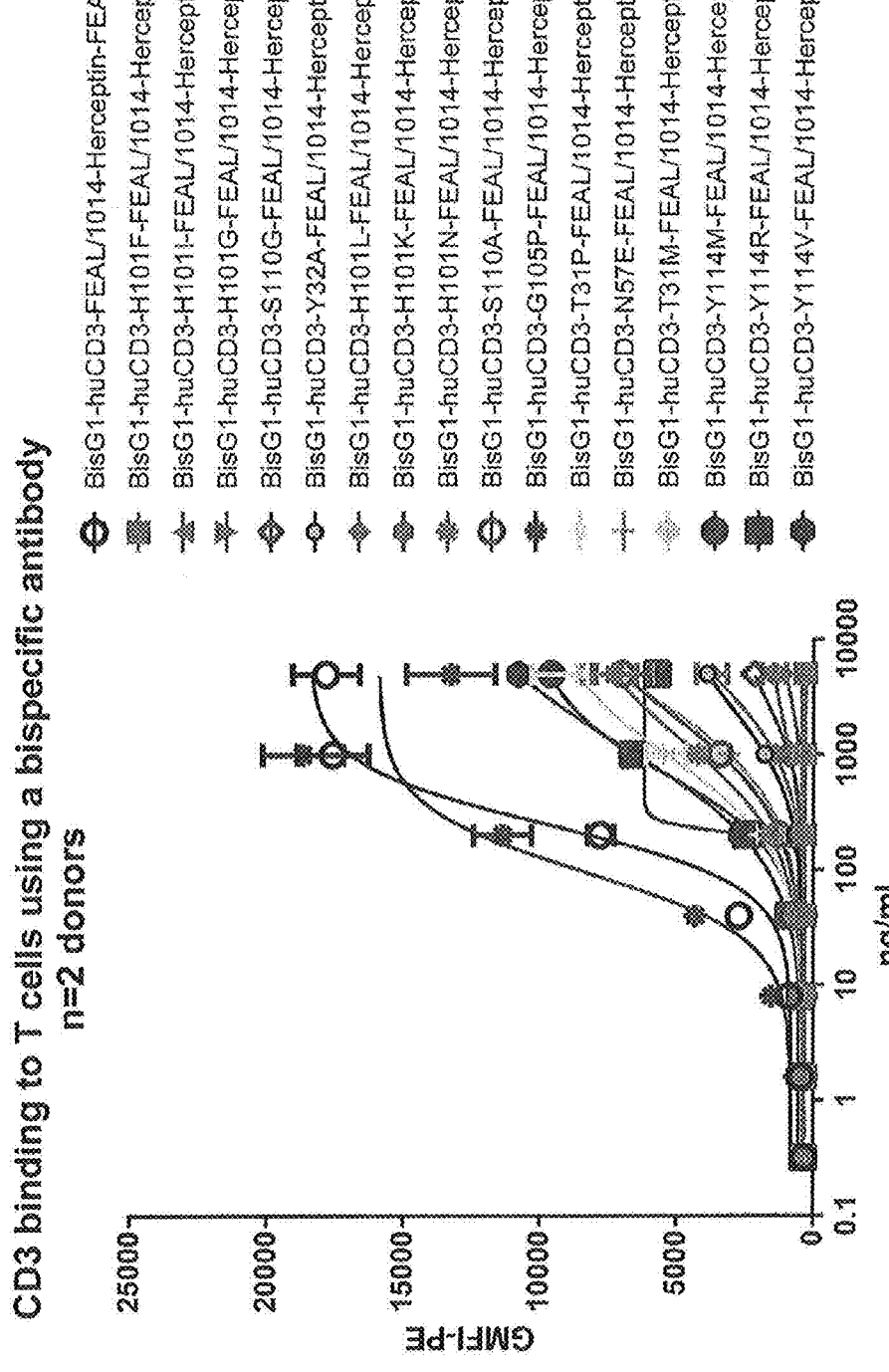

CD3 binding to T cells using a bispecific antibody
n=2 donors

BisG1-huCD3-FEAL/1014-Herceptin-FEAR
BisG1-huCD3-H101F-FEAL/1014-Herceptin-FEAR
BisG1-huCD3-H101I-FEAL/1014-Herceptin-FEAR
BisG1-huCD3-H101G-FEAL/1014-Herceptin-FEAR
BisG1-huCD3-S110G-FEAL/1014-Herceptin-FEAR
BisG1-huCD3-Y32A-FEAL/1014-Herceptin-FEAR
BisG1-huCD3-H101L-FEAL/1014-Herceptin-FEAR
BisG1-huCD3-H101K-FEAL/1014-Herceptin-FEAR
BisG1-huCD3-H101N-FEAL/1014-Herceptin-FEAR
BisG1-huCD3-S110A-FEAL/1014-Herceptin-FEAR
BisG1-huCD3-G105P-FEAL/1014-Herceptin-FEAR
BisG1-huCD3-T31P-FEAL/1014-Herceptin-FEAR
BisG1-huCD3-N57E-FEAL/1014-Herceptin-FEAR
BisG1-huCD3-T31M-FEAL/1014-Herceptin-FEAR
BisG1-huCD3-Y114M-FEAL/1014-Herceptin-FEAR
BisG1-huCD3-Y114R-FEAL/1014-Herceptin-FEAR
BisG1-huCD3-Y114V-FEAL/1014-Herceptin-FEAR

HUMANIZED OR CHIMERIC CD3 ANTIBODIES

CROSS-REFERENCE TO RELATED APPLICATIONS

This application is a division of application Ser. No. 15/744,317 filed Jan. 12, 2018, which is a 35 U.S.C. 371 national stage filing of International Application No. PCT/EP2016/066845, filed Jul. 14, 2016, which claims priority to International Application No. PCT/EP2016/050296, filed Jan. 8, 2016, which claims priority to Danish Patent Application Nos. PA 2015 00413 filed Jul. 15, 2015, PA 2015 00414 filed Jul. 15, 2015, and PA 2015 00416 filed Jul. 16, 2015. The entire contents of these applications are incorporated herein by reference in their entirety.

SEQUENCE LISTING

The Instant application contains a Sequence Listing which has been submitted electronically in ASCII format and is hereby incorporated by reference in its entirety. Said ASCII copy, created on May 9, 2022, is named GMI-147USFADV_SequenceListing_20220509.txt and is 298,446 bytes in size.

FIELD OF INVENTION

The present invention relates to a humanized or chimeric antibody binding to human CD3, compositions comprising said humanized or chimeric antibody, and use of said humanized or chimeric antibodies in treatment of a disease.

BACKGROUND

The Cluster of Differentiation 3 (CD3) has been known for many years and therefore has been subject of interest in many aspects. Specifically antibodies raised against CD3 or the T cell Receptor Complex, which CD3 is part of, are known. An in vitro characterization of recombinant chimeric CD3 isotype variants as well as a number of humanized OKT3 effector function variant antibodies has been described [1].

CD3 antibodies, e.g. muromonab-CD3, have been widely used in the treatment of acute allograft rejection. In addition, treatment with the anti-CD3 monoclonal antibody hOKT3gamma1(Ala-Ala) results in improved C-peptide responses and clinical parameters for at least 2 years after onset of type 1 diabetes in absence of continued immunosuppressive medications [2].

A promising approach to improve targeted antibody therapy is by delivering cytotoxic cells specifically to the antigen-expressing cancer cells. This concept of using T cells for efficient killing of tumor cells has been described [3]. However, initial clinical studies were rather disappointing mainly due to low efficacy, severe adverse effects (cytokine storm) and immunogenicity of the bispecific antibodies [4]. Advances in the design and application of bispecific antibodies have partially overcome the initial barrier of cytokine storm and improved clinical effectiveness without dose-limiting toxicities [5].

For example, certain bispecific antibodies targeting with one arm the antigen on the tumor cell and with the other arm for instance CD3 on T cells, and containing an active Fc fragment providing Fc receptor binding have been shown to induce tumor cell killing. Upon binding, a complex of T cells, tumor cells and effector cells that bind the antibody Fc region is potentially formed, leading to killing of the tumor cells [4]. Catumaxomab consists of a mouseIgG2a/ratIgG2b heavy chain heterodimer and has been found successful for the treatment of cancer-associated ascites after intraperitoneal application [6]. However, the mouse/rat hybrid is immunogenic [7] and cannot be applied for long-term treatment in humans. Frequent treatment-related adverse events attributed to catumaxomab included cytokine-release-related symptoms (i.e. pyrexia, nausea, vomiting, chills, tachycardia and hypotension) [8]-[9], which relate the potent polyclonal T cell activation by catumaxomab due to its active Fc fragment. Another antibody is ertumaxomab (HER2×CD3), which induces cytotoxicity in cell lines with HER2 expression. Ertumaxomab has been in Phase II clinical development for metastatic breast cancer [10]-[11].

Efficacy of CD3 bispecific antibodies and other CD3 bispecific antibody-based formats is dependent on several properties of bispecific antibodies, such as the affinity of the CD3 arm and/or the affinity to the target of the second arm and the target copy number on target cells. Some CD3 bispecific antibodies show high efficacy when the CD3 affinity is low (EpCamxCD3—Bortoletto 2002 PMID 12385030, MT103/Blinatumomab vs TandAb—Molhoj 2007 PMID 17083975), while other CD3 bispecifics demonstrate high efficacy using a high CD3 affinity (Reusch 2015, Mabs, PMID 25875246). In some cases high CD3 affinity is required, for example when arming ex vivo expanded activated T cells from patients with a bispecific antibody comprised of an anti-CD3 targeting arm and a second arm directed at a selected tumor-associated antigen. In the latter case, CD3 affinity should be high to retain the interaction with the expanded T cell when the product is infused back into the patient to mediate cytolysis of tumor cells (Reusch 2006 Clin Cancer Res PMID 16397041). However, high affinity antibodies to CD3, in contrast to low affinity ligands, are much less effective in TCR triggering at low copy number, since they display a stoichiometry of ~1:1 and a linear dose-response curve, Indicative of a single cycle rather than a serial triggering mode of T cell response (Viola 1996 Science, PMID 8658175). In other words, low affinity of CD3 arm can allow T cells to flexibly move from one target and/or target cell to the other (Hoffman 2005, PMID: 15688411).

Low CD3 affinity can potentially prevent the biased localization of the bispecific antibody to T cells (due to first encounter in circulation) and thus improve biodistribution and minimize interference with normal T cell immune responses. Depending on the target of the second arm and target copy number, the indication and/or administration route, desirable CD3 affinity can be customized to enhance a product's maximum efficacy. A panel of CD3 variants covering a range of CD3 affinity can be essential to suit these specific tailor-made needs per antibody product.

CD3 antibodies cross-reactive to cynomolgus and/or rhesus monkey CD3 have been described [12]-[13], however, further improvements for such cross-reactive antibodies are needed.

SUMMARY OF INVENTION

The object of the present invention is to provide humanized or chimeric CD3 antibodies with an optimized affinity to CD3. Thus it is an object of the present invention to provide humanized or chimeric CD3 antibodies which are optimized compared to a reference antibody such as an antibody specified by the VH sequence SEQ ID NO:4 and the VL sequence SEQ ID NO:8. Hence, such antibodies may have a reduced or increased affinity to CD3 compared to a reference antibody specified by the VH sequence SEQ ID NO:4 and the VL sequence SEQ ID NO:8. It is a further object of the present invention to provide antibodies with a lower binding affinity to CD3 than the antibody specified by the VH sequence SEQ ID NO:4 and the VL sequence SEQ ID NO:8. The inventors found that antibodies with a reduced binding affinity to the CD3 peptide as set forth in SEQ ID NO: 402 compared to a reference antibody having the VH region sequence set forth in SEQ ID NO: 4 maintain the same or similar cytotoxic activity in vitro and in vivo compared to the reference antibody. Another object of the present invention is to provide CD3 antibodies with reduced binding affinity to CD3 compared to a reference antibody specified by the VH sequence SEQ ID NO:4 and the VL sequence SEQ ID NO:8, but retaining the same cytolytic activity as the reference antibody. It is yet another object of the present invention to provide antibodies with a higher binding affinity to CD3 than the antibody specified by the VH sequence SEQ ID NO:4 and the VL sequence SEQ ID NO:8.

The present invention provides in one aspect a humanized or chimeric antibody binding to human CD3, wherein said antibody comprises a binding region comprising a heavy chain variable (VH) region, wherein said VH region comprises a mutation in one of the three CDR sequences of a reference antibody having the VH CDR sequences set forth in CDR1 SEQ ID NO: 1, CDR2 SEQ ID NO: 2 and CDR3 SEQ ID NO: 3, which mutation is in one of the positions selected from the group consisting of: T31M, T31P, N57, H101, G105, S110 and Y114, wherein the positions are numbered according to the reference sequence of the SEQ ID NO: 4. The amino acids in SEQ ID NO: 4 are numbered according to a direct numerical numbering scheme from the first amino acid to number 125 in the direction from N-terminus to the C-terminus. The numerical numbering of positions corresponding to SEQ ID NO:4 Is Illustrated in FIG. 2. Further, the VH CDR regions have been annotated according to the IMGT definitions.

In one embodiment of the invention, the antibody has a reduced or increased binding affinity to human CD3 compared to the reference antibody having the VH CDR sequences set forth in CDR1 SEQ ID NO: 1, CDR2 SEQ ID NO: 2 and CDR3 SEQ ID NO: 3.

In some embodiments of the invention, an antibody with reduced binding affinity to a human CD3 molecule, such as a CD3 peptide e.g. SEQ ID NO:402, compared to a reference antibody may maintain the same cytolytic activity against a target cell as the reference antibody.

In one embodiment of the invention the antibody comprises a mutation in the position corresponding to N57 of SEQ ID NO: 4. In one embodiment the mutation is N57E.

In one embodiment of the invention the antibody comprises a mutation in the position corresponding to H101G of SEQ ID NO: 4. In one embodiment the mutation is H101G or H101N.

In one embodiment of the invention the antibody comprises a mutation in the position corresponding to G105 of SEQ ID NO: 4. In one embodiment the mutation is G105P.

In one embodiment of the invention the antibody comprises a mutation in the position corresponding to Y114 of SEQ ID NO: 4. In one embodiment the mutation is Y114M, Y114R or Y114V.

In one embodiment, the present invention provides a humanized or chimeric antibody binding to human CD3, wherein said antibody comprises a binding region comprising heavy chain variable (VH) region, wherein said VH region comprises the CDR1, CDR2, and CDR3 regions having the CDR sequences selected from one of the groups consisting of;

a) CDR1, CDR2 and CDR3 sequences set forth in SEQ ID NO: 12, 2, 3;
b) CDR1, CDR2 and CDR3 sequences set forth in SEQ ID NO: 14, 2, 3;
c) CDR1, CDR2 and CDR3 sequences set forth in SEQ ID NO: 16, 2, 3;
d) CDR1, CDR2 and CDR3 sequences set forth in SEQ ID NO: 18, 2, 3;
e) CDR1, CDR2 and CDR3 sequences set forth in SEQ ID NO: 20, 2, 3;
f) CDR1, CDR2 and CDR3 sequences set forth in SEQ ID NO: 22, 2, 3;
g) CDR1, CDR2 and CDR3 sequences set forth in SEQ ID NO: 24, 2, 3;
h) CDR1, CDR2 and CDR3 sequences set forth in SEQ ID NO: 26, 2, 3;
i) CDR1, CDR2 and CDR3 sequences set forth in SEQ ID NO: 28, 2, 3;
j) CDR1, CDR2 and CDR3 sequences set forth in SEQ ID NO: 30, 2, 3;
k) CDR1, CDR2 and CDR3 sequences set forth in SEQ ID NO: 32, 2, 3;
l) CDR1, CDR2 and CDR3 sequences set forth in SEQ ID NO: 34, 2, 3;
m) CDR1, CDR2 and CDR3 sequences set forth in SEQ ID NO: 36, 2, 3;
n) CDR1, CDR2 and CDR3 sequences set forth in SEQ ID NO: 38, 2, 3;
o) CDR1, CDR2 and CDR3 sequences set forth in SEQ ID NO: 40, 2, 3;
p) CDR1, CDR2 and CDR3 sequences set forth in SEQ ID NO: 42, 2, 3;
q) CDR1, CDR2 and CDR3 sequences set forth in SEQ ID NO: 44, 2, 3;
r) CDR1, CDR2 and CDR3 sequences set forth in SEQ ID NO: 46, 2, 3;
s) CDR1, CDR2 and CDR3 sequences set forth in SEQ ID NO: 48, 2, 3;
t) CDR1, CDR2 and CDR3 sequences set forth in SEQ ID NO: 50, 2, 3;
u) CDR1, CDR2 and CDR3 sequences set forth in SEQ ID NO: 52, 2, 3;
v) CDR1, CDR2 and CDR3 sequences set forth in SEQ ID NO: 54, 2, 3;
w) CDR1, CDR2 and CDR3 sequences set forth in SEQ ID NO: 56, 2, 3;
x) CDR1, CDR2 and CDR3 sequences set forth in SEQ ID NO: 58, 2, 3;
y) CDR1, CDR2 and CDR3 sequences set forth in SEQ ID NO: 60, 2, 3;
z) CDR1, CDR2 and CDR3 sequences set forth in SEQ ID NO: 62, 2, 3;
aa) CDR1, CDR2 and CDR3 sequences set forth in SEQ ID NO: 64, 2, 3;
bb) CDR1, CDR2 and CDR3 sequences set forth in SEQ ID NO: 66, 2, 3;
cc) CDR1, CDR2 and CDR3 sequences set forth in SEQ ID NO: 68, 2, 3;
dd) CDR1, CDR2 and CDR3 sequences set forth in SEQ ID NO: 70, 2, 3;
ee) CDR1, CDR2 and CDR3 sequences set forth in SEQ ID NO: 72, 2, 3;
ff) CDR1, CDR2 and CDR3 sequences set forth in SEQ ID NO: 74, 2, 3;

gg) CDR1, CDR2 and CDR3 sequences set forth in SEQ ID NO: 76, 2, 3;

hh) CDR1, CDR2 and CDR3 sequences set forth in SEQ ID NO: 78, 2, 3;

II) CDR1, CDR2 and CDR3 sequences set forth in SEQ ID NO: 80, 2, 3;

ii) CDR1, CDR2 and CDR3 sequences set forth in SEQ ID NO: 82, 2, 3;

kk) CDR1, CDR2 and CDR3 sequences set forth in SEQ ID NO: 84, 2, 3;

ll) CDR1, CDR2 and CDR3 sequences set forth in SEQ ID NO: 86, 2, 3;

mm) CDR1, CDR2 and CDR3 sequences set forth in SEQ ID NO: 88, 2, 3;

nn) CDR1, CDR2 and CDR3 sequences set forth in SEQ ID NO: 90, 2, 3;

oo) CDR1, CDR2 and CDR3 sequences set forth in SEQ ID NO: 92, 2, 3;

pp) CDR1, CDR2 and CDR3 sequences set forth in SEQ ID NO: 94, 2, 3;

qq) CDR1, CDR2 and CDR3 sequences set forth in SEQ ID NO: 96, 2, 3;

rr) CDR1, CDR2 and CDR3 sequences set forth in SEQ ID NO: 98, 2, 3;

ss) CDR1, CDR2 and CDR3 sequences set forth in SEQ ID NO: 1, 100, 3;

tt) CDR1, CDR2 and CDR3 sequences set forth in SEQ ID NO: 1, 102, 3;

uu) CDR1, CDR2 and CDR3 sequences set forth in SEQ ID NO: 1, 104, 3;

vv) CDR1, CDR2 and CDR3 sequences set forth in SEQ ID NO: 1, 106, 3;

ww) CDR1, CDR2 and CDR3 sequences set forth in SEQ ID NO: 1, 108, 3;

xx) CDR1, CDR2 and CDR3 sequences set forth in SEQ ID NO: 1, 110, 3;

yy) CDR1, CDR2 and CDR3 sequences set forth in SEQ ID NO: 1, 112, 3;

zz) CDR1, CDR2 and CDR3 sequences set forth in SEQ ID NO: 1, 114, 3;

aaa) CDR1, CDR2 and CDR3 sequences set forth in SEQ ID NO: 1, 116, 3;

bbb) CDR1, CDR2 and CDR3 sequences set forth in SEQ ID NO: 1, 118, 3;

ccc) CDR1, CDR2 and CDR3 sequences set forth in SEQ ID NO: 1, 120, 3;

ddd) CDR1, CDR2 and CDR3 sequences set forth in SEQ ID NO: 1, 122, 3;

eee) CDR1, CDR2 and CDR3 sequences set forth in SEQ ID NO: 1, 124, 3;

fff) CDR1, CDR2 and CDR3 sequences set forth in SEQ ID NO: 1, 126, 3;

ggg) CDR1, CDR2 and CDR3 sequences set forth in SEQ ID NO: 1, 128, 3;

hhh) CDR1, CDR2 and CDR3 sequences set forth in SEQ ID NO: 1, 130, 3;

iii) CDR1, CDR2 and CDR3 sequences set forth in SEQ ID NO: 1, 132, 3;

jjj) CDR1, CDR2 and CDR3 sequences set forth in SEQ ID NO: 1, 134, 3;

kkk) CDR1, CDR2 and CDR3 sequences set forth in SEQ ID NO: 1, 136, 3;

lll) CDR1, CDR2 and CDR3 sequences set forth in SEQ ID NO: 1, 138, 3;

mmm) CDR1, CDR2 and CDR3 sequences set forth in SEQ ID NO: 1, 140, 3;

nnn) CDR1, CDR2 and CDR3 sequences set forth in SEQ ID NO: 1, 142, 3;

ooo) CDR1, CDR2 and CDR3 sequences set forth in SEQ ID NO: 1, 144, 3;

ppp) CDR1, CDR2 and CDR3 sequences set forth in SEQ ID NO: 1, 146, 3;

qqq) CDR1, CDR2 and CDR3 sequences set forth in SEQ ID NO: 1, 148, 3;

rrr) CDR1, CDR2 and CDR3 sequences set forth in SEQ ID NO: 1, 150, 3;

sss) CDR1, CDR2 and CDR3 sequences set forth in SEQ ID NO: 1, 152, 3;

ttt) CDR1, CDR2 and CDR3 sequences set forth in SEQ ID NO: 1, 154, 3;

uuu) CDR1, CDR2 and CDR3 sequences set forth in SEQ ID NO: 1, 156, 3;

vvv) CDR1, CDR2 and CDR3 sequences set forth in SEQ ID NO: 1, 158, 3;

www) CDR1, CDR2 and CDR3 sequences set forth in SEQ ID NO: 1, 160, 3;

xxx) CDR1, CDR2 and CDR3 sequences set forth in SEQ ID NO: 1, 162, 3;

yyy) CDR1, CDR2 and CDR3 sequences set forth in SEQ ID NO: 1, 164, 3;

zzz) CDR1, CDR2 and CDR3 sequences set forth in SEQ ID NO: 1, 166, 3;

aaaa) CDR1, CDR2 and CDR3 sequences set forth in SEQ ID NO: 1, 168, 3;

bbbb) CDR1, CDR2 and CDR3 sequences set forth in SEQ ID NO: 1, 2, 170;

cccc) CDR1, CDR2 and CDR3 sequences set forth in SEQ ID NO: 1, 2, 172;

dddd) CDR1, CDR2 and CDR3 sequences set forth in SEQ ID NO: 1, 2, 174;

eeee) CDR1, CDR2 and CDR3 sequences set forth in SEQ ID NO: 1, 2, 176;

ffff) CDR1, CDR2 and CDR3 sequences set forth in SEQ ID NO: 1, 2, 178;

gggg) CDR1, CDR2 and CDR3 sequences set forth in SEQ ID NO: 1, 2, 180;

hhhh) CDR1, CDR2 and CDR3 sequences set forth in SEQ ID NO: 1, 2, 182;

iiii) CDR1, CDR2 and CDR3 sequences set forth in SEQ ID NO: 1, 2, 184;

jjjj) CDR1, CDR2 and CDR3 sequences set forth in SEQ ID NO: 1, 2, 186;

kkkk) CDR1, CDR2 and CDR3 sequences set forth in SEQ ID NO: 1, 2, 188;

llll) CDR1, CDR2 and CDR3 sequences set forth in SEQ ID NO: 1, 2, 190;

mmmm) CDR1, CDR2 and CDR3 sequences set forth in SEQ ID NO: 1, 2, 192;

nnnn) CDR1, CDR2 and CDR3 sequences set forth in SEQ ID NO: 1, 2, 194;

oooo) CDR1, CDR2 and CDR3 sequences set forth in SEQ ID NO: 1, 2, 196;

pppp) CDR1, CDR2 and CDR3 sequences set forth in SEQ ID NO: 1, 2, 198;

qqqq) CDR1, CDR2 and CDR3 sequences set forth in SEQ ID NO: 1, 2, 200;

rrrr) CDR1, CDR2 and CDR3 sequences set forth in SEQ ID NO: 1, 2, 202;

ssss) CDR1, CDR2 and CDR3 sequences set forth in SEQ ID NO: 1, 2, 204;

tttt) CDR1, CDR2 and CDR3 sequences set forth in SEQ ID NO: 1, 2, 206;

uuuu) CDR1, CDR2 and CDR3 sequences set forth in SEQ ID NO: 1, 2, 208;

vvvv) CDR1, CDR2 and CDR3 sequences set forth in SEQ ID NO: 1, 2, 210;

wwww) CDR1, CDR2 and CDR3 sequences set forth in SEQ ID NO: 1, 2, 212;

xxxx) CDR1, CDR2 and CDR3 sequences set forth in SEQ ID NO: 1, 2, 214;

yyyy) CDR1, CDR2 and CDR3 sequences set forth in SEQ ID NO: 1, 2, 216;

zzzz) CDR1, CDR2 and CDR3 sequences set forth in SEQ ID NO: 1, 2, 218;

aaaaa) CDR1, CDR2 and CDR3 sequences set forth in SEQ ID NO: 1, 2, 220;

bbbbb) CDR1, CDR2 and CDR3 sequences set forth in SEQ ID NO: 1, 2, 222;

ccccc) CDR1, CDR2 and CDR3 sequences set forth in SEQ ID NO: 1, 2, 224;

ddddd) CDR1, CDR2 and CDR3 sequences set forth in SEQ ID NO: 1, 2, 226;

eeeee) CDR1, CDR2 and CDR3 sequences set forth in SEQ ID NO: 1, 2, 228;

fffff) CDR1, CDR2 and CDR3 sequences set forth in SEQ ID NO: 1, 2, 230;

ggggg) CDR1, CDR2 and CDR3 sequences set forth in SEQ ID NO: 1, 2, 232;

hhhhh) CDR1, CDR2 and CDR3 sequences set forth in SEQ ID NO: 1, 2, 234;

iiiii) CDR1, CDR2 and CDR3 sequences set forth in SEQ ID NO: 1, 2, 236;

jjjjj) CDR1, CDR2 and CDR3 sequences set forth in SEQ ID NO: 1, 2, 238;

kkkkk) CDR1, CDR2 and CDR3 sequences set forth in SEQ ID NO: 1, 2, 240;

lllll) CDR1, CDR2 and CDR3 sequences set forth in SEQ ID NO: 1, 2, 242;

mmmmm) CDR1, CDR2 and CDR3 sequences set forth in SEQ ID NO: 1, 2, 244;

nnnnn) CDR1, CDR2 and CDR3 sequences set forth in SEQ ID NO: 1, 2, 246;

ooooo) CDR1, CDR2 and CDR3 sequences set forth in SEQ ID NO: 1, 2, 248;

ppppp) CDR1, CDR2 and CDR3 sequences set forth in SEQ ID NO: 1, 2, 250;

qqqqq) CDR1, CDR2 and CDR3 sequences set forth in SEQ ID NO: 1, 2, 252;

rrrrr) CDR1, CDR2 and CDR3 sequences set forth in SEQ ID NO: 1, 2, 254;

sssss) CDR1, CDR2 and CDR3 sequences set forth in SEQ ID NO: 1, 2, 256;

ttttt) CDR1, CDR2 and CDR3 sequences set forth in SEQ ID NO: 1, 2, 258;

uuuuu) CDR1, CDR2 and CDR3 sequences set forth in SEQ ID NO: 1, 2, 260;

vvvvv) CDR1, CDR2 and CDR3 sequences set forth in SEQ ID NO: 1, 2, 262;

wwwww) CDR1, CDR2 and CDR3 sequences set forth in SEQ ID NO: 1, 2, 264;

xxxxx) CDR1, CDR2 and CDR3 sequences set forth in SEQ ID NO: 1, 2, 266;

yyyyy) CDR1, CDR2 and CDR3 sequences set forth in SEQ ID NO: 1, 2, 268;

zzzzz) CDR1, CDR2 and CDR3 sequences set forth in SEQ ID NO: 1, 2, 270;

aaaaaa) CDR1, CDR2 and CDR3 sequences set forth in SEQ ID NO: 1, 2, 272;

bbbbbb) CDR1, CDR2 and CDR3 sequences set forth in SEQ ID NO: 1, 2, 274;

cccccc) CDR1, CDR2 and CDR3 sequences set forth in SEQ ID NO: 1, 2, 276;

dddddd) CDR1, CDR2 and CDR3 sequences set forth in SEQ ID NO: 1, 2, 278;

eeeeee) CDR1, CDR2 and CDR3 sequences set forth in SEQ ID NO: 1, 2, 280;

ffffff) CDR1, CDR2 and CDR3 sequences set forth in SEQ ID NO: 1, 2, 282;

gggggg) CDR1, CDR2 and CDR3 sequences set forth in SEQ ID NO: 1, 2, 284;

hhhhhh) CDR1, CDR2 and CDR3 sequences set forth in SEQ ID NO: 1, 2, 286;

iiiiii) CDR1, CDR2 and CDR3 sequences set forth in SEQ ID NO: 1, 2, 288;

jjjjjj) CDR1, CDR2 and CDR3 sequences set forth in SEQ ID NO: 1, 2, 290;

kkkkkk) CDR1, CDR2 and CDR3 sequences set forth in SEQ ID NO: 1, 2, 292;

llllll) CDR1, CDR2 and CDR3 sequences set forth in SEQ ID NO: 1, 2, 294;

mmmmmm) CDR1, CDR2 and CDR3 sequences set forth in SEQ ID NO: 1, 2, 296;

nnnnnn) CDR1, CDR2 and CDR3 sequences set forth in SEQ ID NO: 1, 2, 298 and oooooo) CDR1, CDR2 and CDR3 sequences set forth in SEQ ID NO: 1, 2, 300.

That Is, the inventors of the present invention in a first aspect of the invention found that humanized or chimeric antibodies of said sequences had an optimized binding affinity to a CD3 peptide SEQ ID NO: 402 compared to a reference antibody such as an antibody specified by the VH sequence SEQ ID NO:4 and the VL sequence SEQ ID NO:8. The reference antibody specified by SEQ ID NO:4 and the VL sequence SEQ ID NO:8 has a binding affinity to the CD3 peptide of SEQ ID NO:402 of $1.5 \times 10^{-8}$ M as illustrated by example 7. In some embodiments of the present invention the antibodies have a lower binding affinity to the CD3 peptide of SEQ ID NO:402 than $1.5 \times 10^{-8}$ M such as a binding affinity from $1.6 \times 10^{-8}$ M to $9.9 \times 10^{-8}$ M or such as a binding affinity from $1.0 \times 10^{-7}$ to $9.9 \times 10^{-7}$ M when determined by Bio-Layer Interferometry as described in Table 6 in example 7. In some embodiments of the present invention the antibodies have a higher binding affinity to CD3 peptide of SEQ ID NO: 402 than $1.5 \times 10^{-8}$ M, such as from $1.4 \times 10^{-8}$ to $1.0 \times 10^{-8}$ M, such as $9.9 \times 10^{-8}$ to $1 \times 10^{-8}$ M or such as $9.9 \times 10^{-8}$ to $1 \times 10^{-9}$ M. The binding affinity corresponds to the $K_D$ value.

In one aspect of the present invention, the present invention relates to a humanized or chimeric antibody binding to human CD3, wherein said antibody comprises a binding region comprising a heavy chain variable (VH) region, wherein said VH region comprises the CDR1, CDR2, and CDR3 regions having the CDR sequences selected from one of the groups consisting of;

a) CDR1, CDR2 and CDR3 sequences set forth in SEQ ID NO: 54, 2, 3 [T31M];

b) CDR1, CDR2 and CDR3 sequence set forth in SEQ ID NO: 58, 2, 3 [T31P];

c) CDR1, CDR2 and CDR3 sequences set forth in SEQ ID NO: 1, 106, 3 [N57E];

d) CDR1, CDR2 and CDR3 sequences set forth in SEQ ID NO: 1, 2, 176 [H101G];

e) CDR1, CDR2 and CDR3 sequences set forth in SEQ ID NO: 1, 2, 184 [H101N];

f) CDR1, CDR2 and CDR3 sequences set forth in SEQ ID NO: 1, 2, 220 [G105P];

g) CDR1, CDR2 and CDR3 sequences set forth in SEQ ID NO: 1, 2, 236 [S110A];

h) CDR1, CDR2 and CDR3 sequences set forth in SEQ ID NO: 1, 2, 244 [S110G];

i) CDR1, CDR2 and CDR3 sequences set forth in SEQ ID NO: 1, 2, 284 [Y114M];

j) CDR1, CDR2 and CDR3 sequences set forth in SEQ ID NO: 1, 2, 292 [Y114R];

k) CDR1, CDR2 and CDR3 sequences set forth in SEQ ID NO: 1, 2, 298 [Y114V] and l) CDR1, CDR2 and CDR3 sequences having at least 90% or at least 95% amino acid sequence identity, in total across the three CDR sequences, to any one of the three CDR sequences as set forth in a) to k), provided that the CDR1, CDR2 and CDR3 sequences do not have the sequences as set forth in SEQ ID NO: 1, 2, 3.

In another aspect, the present invention relates to a humanized or chimeric antibody, wherein said binding region comprises a variable light chain (VL) region, wherein said VL region comprises CDR1, CDR2, and CDR3 regions having the CDR as set forth in SEQ ID NO: 6, GTN, 7.

In a further aspect, the present invention relates to a method of reducing the binding affinity of an antibody binding to human CD3 compared to a reference antibody comprising a heavy chain variable (VH) region, wherein said VH region comprises the CDR1, CDR2, and CDR3 sequences set forth in SEQ ID NO: 1, 2, 3, which method comprises introducing a mutation in one of the three CDR sequences of the said reference antibody selected from a mutation in one of the positions selected from the group of T31M, T31P, N57, H101, S110 and Y114, wherein the positions are numbered according to the reference sequence of the SEQ ID NO: 4.

In one embodiment of the present invention the method comprises introducing a mutation in the VH region CDR1 region sequence corresponding to T31M or T31P. In another embodiment of the present invention the method comprises introducing a mutation in the VH region CDR2 region corresponding to N57E. In a further embodiment of the present invention the method comprises introducing a mutation in the VH region CDR3 region selected from H101G, H101N, G105P, S110A, S110G, Y114M, Y114R or Y114V.

In one embodiment CD3 is human CD3 epsilon.

In another aspect, the present invention relates to a bispecific antibody comprising a first binding region of an antibody according to the invention, and a second binding region which binds a different target than said first antigen binding region.

In another aspect, the present invention relates to a nucleic acid construct encoding one or more amino acid sequences according to the invention.

In another aspect, the present invention relates to an expression vector comprising (i) a nucleic acid sequence encoding a heavy chain sequence of a humanized or chimeric antibody according to the invention, (ii) a nucleic acid sequence encoding a light chain sequence of a humanized or chimeric antibody according to the invention, or (iii) both (i) and (ii).

In another aspect, the present invention relates to a host cell comprising an expression vector according to the invention.

In another aspect, the present invention relates to a composition comprising the antibody or bispecific antibody according to the invention.

In another aspect, the present invention relates to a pharmaceutical composition comprising the antibody or bispecific antibody according to the invention and a pharmaceutical acceptable carrier.

In another aspect, the present invention relates to the antibody or bispecific antibody, the composition, or the pharmaceutical composition according to the invention for use as a medicament.

In another aspect, the present invention relates to the antibody or bispecific antibody, the composition, or the pharmaceutical composition according to the invention for use in the treatment of a disease.

In another aspect, the present invention relates to a method of treatment of a disease comprising administering the antibody or bispecific antibody, the composition, or the pharmaceutical composition according to the invention, to a subject in need thereof.

In another aspect, the present invention relates to a method of administering the antibody or bispecific antibody, wherein the antibody or bispecific antibody is administered by subcutaneous or local administration.

In one aspect, the present invention relates to a method of diagnosing a disease characterized by involvement or accumulation of CD3-expressing cells, comprising administering the humanized or chimeric antibody, the composition or the pharmaceutical composition according to the invention to a subject, optionally wherein said humanized or chimeric antibody is labeled with a detectable agent.

In another aspect, the present invention relates to a method for producing an antibody or a bispecific antibody according to the invention, comprising the steps of a) culturing a host cell according to the invention, and b) purifying the antibody from the culture media.

In another aspect, the present invention relates to a diagnostic composition comprising an antibody or bispecific antibody according to any one of the embodiments as disclosed herein.

In one embodiment, the diagnostic composition is a companion diagnostic which is used to screen and select those patients who will benefit from treatment with the bispecific antibody.

In another aspect, the present invention relates to a method for detecting the presence of CD3 antigen, or a cell expressing CD3, in a sample comprising the steps of a) contacting the sample with an antibody or bispecific antibody according to the invention, under conditions that allow for formation of a complex between the antibody or bispecific antibody and CD3, and b) analyzing whether a complex has been formed.

In another aspect, the present invention relates to a kit for detecting the presence of CD3 antigen, or a cell expressing CD3, in a sample comprising i) an antibody or bispecific antibody according to the invention, and ii) instructions for use of the kit.

In another aspect, the present invention relates to an anti-idiotypic antibody or a pair of anti-idiotypic antibodies which bind to an antibody according to the invention.

BRIEF DESCRIPTION OF FIGURES

FIG. 2: Alignment of selected CD3 affinity variants in the generated library with mutations in the VH. CDRs are underlined in the humanized wild type sequence (SEQ ID NO:4) HuCD3-H1. Highlighted amino acids are the substitutions.

FIG. 5: T cell binding curves of selected VH affinity variants of humanized CD3 (BisG1-huCD3-H1L1-X-FEAL/1014-Herceptin-FEAR) antibodies as determined by flow cytometry. Affinity variants depicted cover a broad range of T cell binding capacity between the wild type response and undetectable response.

(FIG. 6A) NCI-N87 cells, Effector cells (T cells): Tumor cell (NCI-N87 cell) ratio=3:1, 48 hours of incubation, n=2 donors (FIG. 6B) SKOV3 cells, T cells: SKOV3 cell ratio=4:1, 48 hours of incubation, n=2 donors (FIG. 6C) MDA-MB-231 cells, T cells: MDA-MB-231 cell ratio=8:1, 48 hours of incubation, n=2 donors. The tested affinity variants depicted cover a broad range of cytotoxicity between wild type response and no observed cytotoxicity for all tested tumor cell lines.

(FIG. 8A) Average tumor volume followed over time after treatment with 0.05 mg/kg of antibody (n=4 per group). (FIG. 8B) Average tumor volume followed over time after treatment with 0.5 mg/kg of antibody (n=4 per group). (FIG. 8C) Average tumor volume at day 44 after treatment with 0.05 mg/kg of antibody at day 0 (n=4 per group). (FIG. 8D) Average tumor volume at day 44 after treatment with 0.5 mg/kg of antibody at day 0 (n=4 per group). Statistics has been performed on data for C and D.

DETAILED DESCRIPTION

Figure 1:
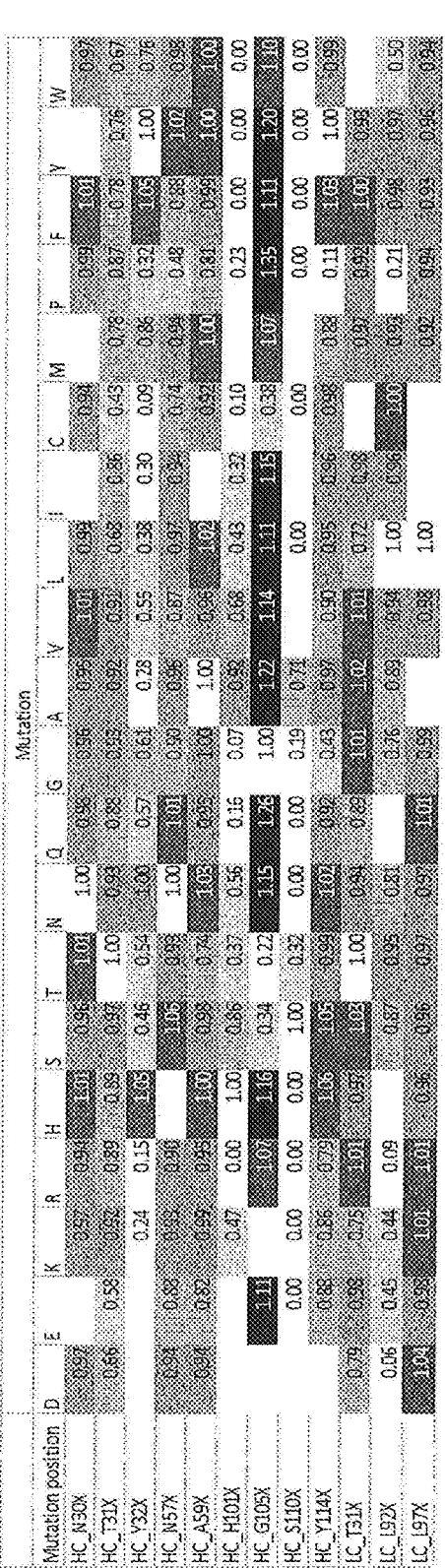
FIG. 1: Heat plot with binding ratios of mutant versus wt UniTE-huCD3-H1L1-T41K molecules. Ratios above 1 Indicate stronger binding than wt, while ratios below 1 Indicate weaker binding than wt. Binding was determined on Freestyle 293-F cells transfected with CD3/TCR-LC13.
Figure 3:
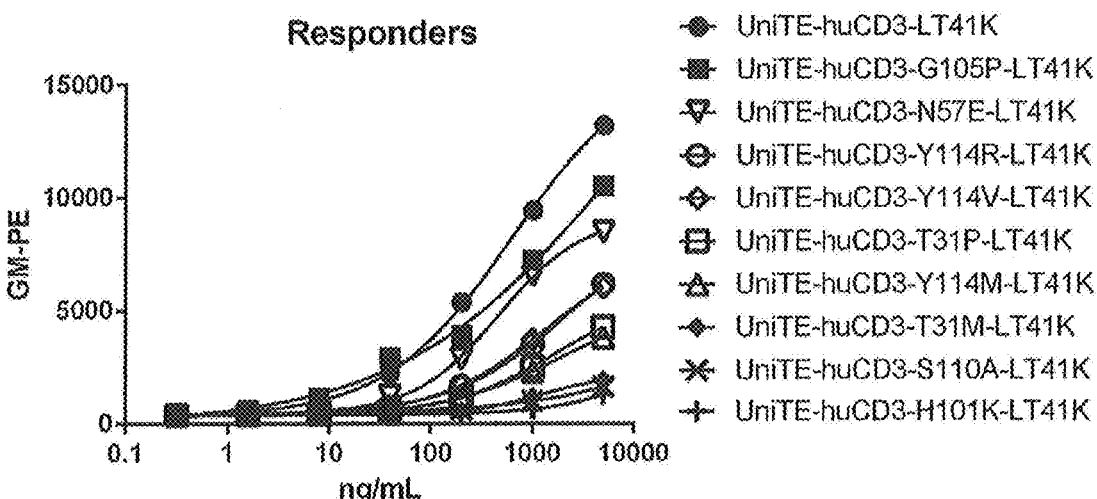
FIG. 3: T cell binding curves of selected VH affinity variants of humanized CD3 (UniTE-huCD3-H1L1-T41K) antibodies as determined by flow cytometry Affinity variants depicted cover a broad range of T cell binding capacity between the wild type response and undetectable response.

In one aspect, the present invention relates to a humanized or chimeric antibody binding to human CD3 with an optimized affinity to CD3. Thus it is an object of the present invention to provide humanized or chimeric CD3 antibodies which are optimized compared to a reference antibody such as the antibody specified by the VH sequence SEQ ID NO:4 and the VL sequence SEQ ID NO:8. It is a further object of the invention to provide antibodies with optimized in vivo efficacy compared to a reference antibody such as the antibody specified by the VH sequence SEQ ID NO:4 and the VL sequence SEQ ID NO:8. It is a further object of the present invention to provide antibodies with a lower binding affinity to CD3 than the antibody specified by the VH sequence SEQ ID NO:4 and the VL sequence SEQ ID NO:8. It is yet another object of the present invention to provide antibodies with a higher binding affinity to CD3 than the antibody specified by the VH sequence SEQ ID NO:4 and the VL sequence SEQ ID NO:8.

Figure 2:
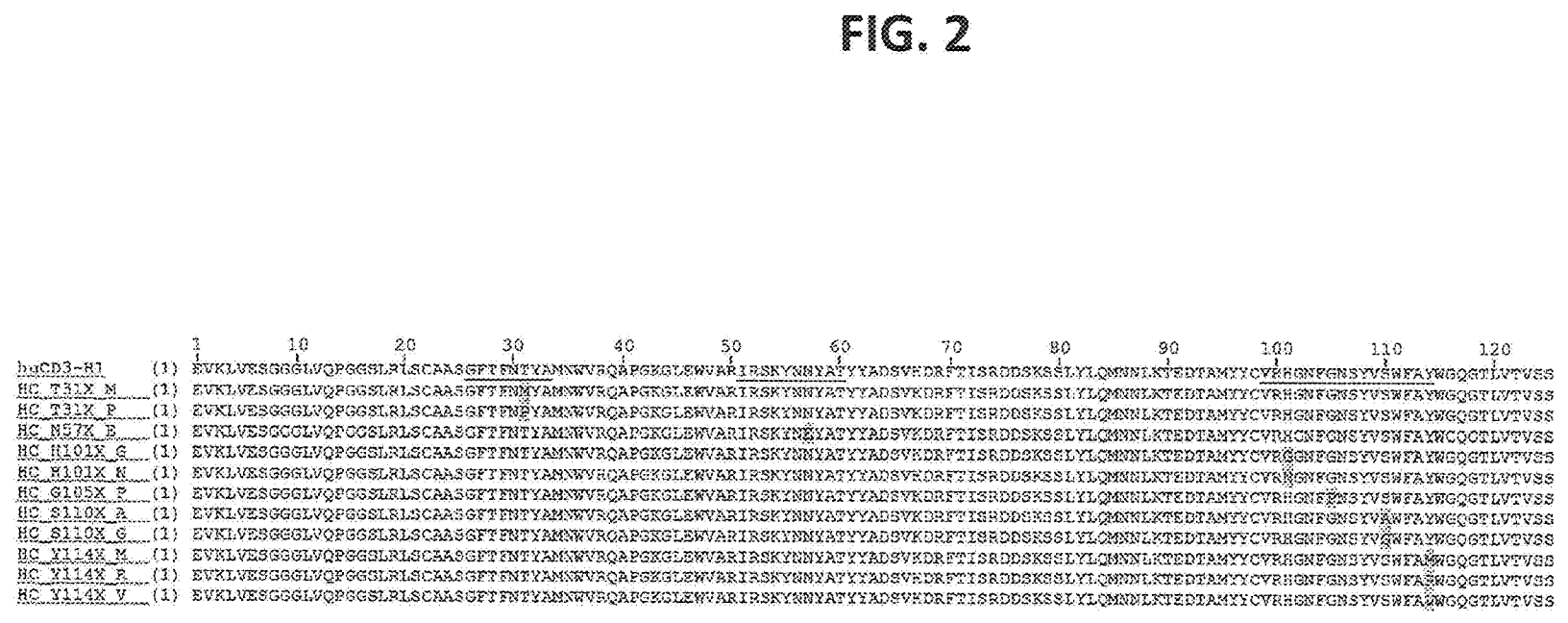

In one aspect the invention release to a humanized or chimeric antibody binding to human CD3, wherein said antibody comprises a binding region comprising a heavy chain variable (VH) region, wherein said VH region comprises a mutation in one of the three CDR sequences of a reference antibody having the CDR sequences set forth in CDR1 SEQ ID NO: 1, CDR2 SEQ ID NO: 2 and CDR3 SEQ ID NO: 3, which mutation is in one of the positions selected from the group consisting of: T31M, T31P, N57, H101, G105, S110 and Y114, wherein the positions are numbered according to the reference sequence of the SEQ ID NO: 4. The amino acids in SEQ ID NO: 4 are numbered according to a direct numerical numbering scheme from the first amino acid to number 125 in the direction from N-terminus to the C-terminus. The numerical numbering of positions corresponding to SEQ ID NO: 4 is illustrated in FIG. 2. Further, The CDR regions have been annotated according to the IMGT definitions.

In one embodiment of the invention, the antibody has a reduced or increased binding affinity to human CD3 compared to the reference antibody having the VH CDR sequences set forth in CDR1 SEQ ID NO: 1, CDR2 SEQ ID NO: 2 and CDR3 SEQ ID NO: 3.

In some embodiments of the invention, an antibody with reduced binding affinity to a CD3 molecule, such a CD3 peptide e.g. SEQ ID NO:402, compared to a reference antibody may maintain the same cytolytic activity against a target cell as the reference antibody.

In one embodiment of the invention the antibody comprises a T31M or T31P mutation. Position T31 is in accordance to SEQ ID NO:4.

In one embodiment of the invention the antibody comprises a mutation in the position N57. Position N57 is in accordance to SEQ ID NO:4. In one embodiment the mutation is N57E.

In one embodiment of the invention the antibody comprises a mutation in the position H101. Position H101 is in accordance to SEQ ID NO: 4. In one embodiment the mutation is H101G or H101N.

In one embodiment of the invention the antibody comprises a mutation in the position G105. Position G105 is in accordance to SEQ ID NO: 4. In one embodiment the mutation is G105P.

In one embodiment of the invention the antibody comprises a mutation in the position Y114. Position Y114 is in accordance to of SEQ ID NO: 4. In one embodiment the mutation is Y114M, Y114R or Y114V.

The reference antibody specified by SEQ ID NO:4 and the VL sequence SEQ ID NO:8 has a binding affinity to the CD3 peptide of SEQ ID NO:402 corresponding to a $K_D$ value of $1.5 \times 10^{-8}$ M as illustrated by example 7.

In some embodiments of the present invention the antibodies have a lower binding affinity to the CD3 peptide of SEQ ID NO:402 than $1.5 \times 10^{-8}$ M, such as a binding affinity from $1.6 \times 10^{-8}$ M to $9.9 \times 10^{-8}$ M or such as a binding affinity from $1.0 \times 10^{-7}$ to $9.9 \times 10^{-7}$ M when determined by Bio-Layer Interferometry as described in Example 7. In some embodiments of the present invention the antibodies have a higher binding affinity to the CD3 peptide of SEQ ID NO:402 than $1.5 \times 10^{-8}$ M such as from $1.4 \times 10^{-8}$ to $1.0 \times 10^{-8}$ M, such as, such as such as $9.9 \times 10^{-9}$ to $1.0 \times 10^{-9}$ M.

In one embodiment, the present invention relates to a humanized or chimeric antibody binding to human CD3, wherein said antibody comprises a binding region comprising heavy chain variable (VH) region, wherein said VH region comprises the CDR1, CDR2, and CDR3 having the CDR sequences selected from one of the groups consisting of;

a) CDR1, CDR2 and CDR3 sequences set forth in SEQ ID NO: 12, 2, 3;

b) CDR1, CDR2 and CDR3 sequences set forth in SEQ ID NO: 14, 2, 3;

c) CDR1, CDR2 and CDR3 sequences set forth in SEQ ID NO: 16, 2, 3;

d) CDR1, CDR2 and CDR3 sequences set forth in SEQ ID NO: 18, 2, 3;

e) CDR1, CDR2 and CDR3 sequences set forth in SEQ ID NO: 20, 2, 3;

f) CDR1, CDR2 and CDR3 sequences set forth in SEQ ID NO: 22, 2, 3;

g) CDR1, CDR2 and CDR3 sequences set forth in SEQ ID NO: 24, 2, 3;

h) CDR1, CDR2 and CDR3 sequences set forth in SEQ ID NO: 26, 2, 3;

i) CDR1, CDR2 and CDR3 sequences set forth in SEQ ID NO: 28, 2, 3;

j) CDR1, CDR2 and CDR3 sequences set forth in SEQ ID NO: 30, 2, 3;

k) CDR1, CDR2 and CDR3 sequences set forth in SEQ ID NO: 32, 2, 3;

l) CDR1, CDR2 and CDR3 sequences set forth in SEQ ID NO: 34, 2, 3;

m) CDR1, CDR2 and CDR3 sequences set forth in SEQ ID NO: 36, 2, 3;

n) CDR1, CDR2 and CDR3 sequences set forth in SEQ ID NO: 38, 2, 3;

o) CDR1, CDR2 and CDR3 sequences set forth in SEQ ID NO: 40, 2, 3;

p) CDR1, CDR2 and CDR3 sequences set forth in SEQ ID NO: 42, 2, 3;

q) CDR1, CDR2 and CDR3 sequences set forth in SEQ ID NO: 44, 2, 3;

r) CDR1, CDR2 and CDR3 sequences set forth in SEQ ID NO: 46, 2, 3;

s) CDR1, CDR2 and CDR3 sequences set forth in SEQ ID NO: 48, 2, 3;

t) CDR1, CDR2 and CDR3 sequences set forth in SEQ ID NO: 50, 2, 3;

u) CDR1, CDR2 and CDR3 sequences set forth in SEQ ID NO: 52, 2, 3;

v) CDR1, CDR2 and CDR3 sequences set forth in SEQ ID NO: 54, 2, 3;

w) CDR1, CDR2 and CDR3 sequences set forth in SEQ ID NO: 56, 2, 3;

x) CDR1, CDR2 and CDR3 sequences set forth in SEQ ID NO: 58, 2, 3;

y) CDR1, CDR2 and CDR3 sequences set forth in SEQ ID NO: 60, 2, 3;

z) CDR1, CDR2 and CDR3 sequences set forth in SEQ ID NO: 62, 2, 3;

aa) CDR1, CDR2 and CDR3 sequences set forth in SEQ ID NO: 64, 2, 3;

bb) CDR1, CDR2 and CDR3 sequences set forth in SEQ ID NO: 66, 2, 3;

cc) CDR1, CDR2 and CDR3 sequences set forth in SEQ ID NO: 68, 2, 3;

dd) CDR1, CDR2 and CDR3 sequences set forth in SEQ ID NO: 70, 2, 3;

ee) CDR1, CDR2 and CDR3 sequences set forth in SEQ ID NO: 72, 2, 3;

ff) CDR1, CDR2 and CDR3 sequences set forth in SEQ ID NO: 74, 2, 3;

gg) CDR1, CDR2 and CDR3 sequences set forth in SEQ ID NO: 76, 2, 3;

hh) CDR1, CDR2 and CDR3 sequences set forth in SEQ ID NO: 78, 2, 3;

ii) CDR1, CDR2 and CDR3 sequences set forth in SEQ ID NO: 80, 2, 3;

jj) CDR1, CDR2 and CDR3 sequences set forth in SEQ ID NO: 82, 2, 3;

kk) CDR1, CDR2 and CDR3 sequences set forth in SEQ ID NO: 84, 2, 3;

ll) CDR1, CDR2 and CDR3 sequences set forth in SEQ ID NO: 86, 2, 3;

mm) CDR1, CDR2 and CDR3 sequences set forth in SEQ ID NO: 88, 2, 3;

nn) CDR1, CDR2 and CDR3 sequences set forth in SEQ ID NO: 90, 2, 3;

oo) CDR1, CDR2 and CDR3 sequences set forth in SEQ ID NO: 92, 2, 3;

pp) CDR1, CDR2 and CDR3 sequences set forth in SEQ ID NO: 94, 2, 3;

qq) CDR1, CDR2 and CDR3 sequences set forth in SEQ ID NO: 96, 2, 3;

rr) CDR1, CDR2 and CDR3 sequences set forth in SEQ ID NO: 98, 2, 3;

ss) CDR1, CDR2 and CDR3 sequences set forth in SEQ ID NO: 1, 100, 3;

tt) CDR1, CDR2 and CDR3 sequences set forth in SEQ ID NO: 1, 102, 3;

uu) CDR1, CDR2 and CDR3 sequences set forth in SEQ ID NO: 1, 104, 3;

vv) CDR1, CDR2 and CDR3 sequences set forth in SEQ ID NO: 1, 106, 3;

ww) CDR1, CDR2 and CDR3 sequences set forth in SEQ ID NO: 1, 108, 3;

xx) CDR1, CDR2 and CDR3 sequences set forth in SEQ ID NO: 1, 110, 3;

yy) CDR1, CDR2 and CDR3 sequences set forth in SEQ ID NO: 1, 112, 3;

zz) CDR1, CDR2 and CDR3 sequences set forth in SEQ ID NO: 1, 114, 3;

aaa) CDR1, CDR2 and CDR3 sequences set forth in SEQ ID NO: 1, 116, 3;

bbb) CDR1, CDR2 and CDR3 sequences set forth in SEQ ID NO: 1, 118, 3;

ccc) CDR1, CDR2 and CDR3 sequences set forth in SEQ ID NO: 1, 120, 3;

ddd) CDR1, CDR2 and CDR3 sequences set forth in SEQ ID NO: 1, 122, 3;

eee) CDR1, CDR2 and CDR3 sequences set forth in SEQ ID NO: 1, 124, 3;

fff) CDR1, CDR2 and CDR3 sequences set forth in SEQ ID NO: 1, 126, 3;

ggg) CDR1, CDR2 and CDR3 sequences set forth in SEQ ID NO: 1, 128, 3;

hhh) CDR1, CDR2 and CDR3 sequences set forth in SEQ ID NO: 1, 130, 3;

iii) CDR1, CDR2 and CDR3 sequences set forth in SEQ ID NO: 1, 132, 3;

jjj) CDR1, CDR2 and CDR3 sequences set forth in SEQ ID NO: 1, 134, 3;

kkk) CDR1, CDR2 and CDR3 sequences set forth in SEQ ID NO: 1, 136, 3;

lll) CDR sequences set forth in SEQ ID NO: 1, 138, 3;

mmm) CDR1, CDR2 and CDR3 sequences set forth in SEQ ID NO: 1, 140, 3;

nnn) CDR1, CDR2 and CDR3 sequences set forth in SEQ ID NO: 1, 142, 3;

ooo) CDR1, CDR2 and CDR3 sequences set forth in SEQ ID NO: 1, 144, 3;

ppp) CDR1, CDR2 and CDR3 sequences set forth in SEQ ID NO: 1, 146, 3;

qqq) CDR1, CDR2 and CDR3 sequences set forth in SEQ ID NO: 1, 148, 3;

rrr) CDR1, CDR2 and CDR3 sequences set forth in SEQ ID NO: 1, 150, 3;

sss) CDR1, CDR2 and CDR3 sequences set forth in SEQ ID NO: 1, 152, 3;

ttt) CDR sequences set forth in SEQ ID NO: 1, 154, 3;

uuu) CDR1, CDR2 and CDR3 sequences set forth in SEQ ID NO: 1, 156, 3;

vvv) CDR1, CDR2 and CDR3 sequences set forth in SEQ ID NO: 1, 158, 3;

www) CDR1, CDR2 and CDR3 sequences set forth in SEQ ID NO: 1, 160, 3;

xxx) CDR1, CDR2 and CDR3 sequences set forth in SEQ ID NO: 1, 162, 3;

yyy) CDR1, CDR2 and CDR3 sequences set forth in SEQ ID NO: 1, 164, 3;

zzz) CDR1, CDR2 and CDR3 sequences set forth in SEQ ID NO: 1, 166, 3;

aaaa) CDR1, CDR2 and CDR3 sequences set forth in SEQ ID NO: 1, 168, 3;

bbbb) CDR1, CDR2 and CDR3 sequences set forth in SEQ ID NO: 1, 2, 170;

cccc) CDR1, CDR2 and CDR3 sequences set forth in SEQ ID NO: 1, 2, 172;

dddd) CDR1, CDR2 and CDR3 sequences set forth in SEQ ID NO: 1, 2, 174;

eeee) CDR1, CDR2 and CDR3 sequences set forth in SEQ ID NO: 1, 2, 176;

ffff) CDR1, CDR2 and CDR3 sequences set forth in SEQ ID NO: 1, 2, 178;

gggg) CDR1, CDR2 and CDR3 sequences set forth in SEQ ID NO: 1, 2, 180;

hhhh) CDR1, CDR2 and CDR3 sequences set forth in SEQ ID NO: 1, 2, 182;

iiii) CDR sequences set forth in SEQ ID NO: 1, 2, 184;

jjjj) CDR1, CDR2 and CDR3 sequences set forth in SEQ ID NO: 1, 2, 186;

kkkk) CDR1, CDR2 and CDR3 sequences set forth in SEQ ID NO: 1, 2, 188;

llll) CDR sequences set forth in SEQ ID NO: 1, 2, 190;

mmmm) CDR1, CDR2 and CDR3 sequences set forth in SEQ ID NO: 1, 2, 192;

nnnn) CDR1, CDR2 and CDR3 sequences set forth in SEQ ID NO: 1, 2, 194;

oooo) CDR1, CDR2 and CDR3 sequences set forth in SEQ ID NO: 1, 2, 196;

pppp) CDR1, CDR2 and CDR3 sequences set forth in SEQ ID NO: 1, 2, 198;

qqqq) CDR1, CDR2 and CDR3 sequences set forth in SEQ ID NO: 1, 2, 200;

rrrr) CDR1, CDR2 and CDR3 sequences set forth in SEQ ID NO: 1, 2, 202;

ssss) CDR1, CDR2 and CDR3 sequences set forth in SEQ ID NO: 1, 2, 204;

tttt) CDR1, CDR2 and CDR3 sequences set forth in SEQ ID NO: 1, 2, 206;

uuuu) CDR1, CDR2 and CDR3 sequences set forth in SEQ ID NO: 1, 2, 208;

vvvv) CDR1, CDR2 and CDR3 sequences set forth in SEQ ID NO: 1, 2, 210;

wwww) CDR1, CDR2 and CDR3 sequences set forth in SEQ ID NO: 1, 2, 212;

xxxx) CDR1, CDR2 and CDR3 sequences set forth in SEQ ID NO: 1, 2, 214;

yyyy) CDR1, CDR2 and CDR3 sequences set forth in SEQ ID NO: 1, 2, 216;

zzzz) CDR1, CDR2 and CDR3 sequences set forth in SEQ ID NO: 1, 2, 218;

aaaaa) CDR1, CDR2 and CDR3 sequences set forth in SEQ ID NO: 1, 2, 220;

bbbbb) CDR1, CDR2 and CDR3 sequences set forth in SEQ ID NO: 1, 2, 222;

ccccc) CDR1, CDR2 and CDR3 sequences set forth in SEQ ID NO: 1, 2, 224;

ddddd) CDR1, CDR2 and CDR3 sequences set forth in SEQ ID NO: 1, 2, 226;

eeeee) CDR1, CDR2 and CDR3 sequences set forth in SEQ ID NO: 1, 2, 228;

fffff) CDR1, CDR2 and CDR3 sequences set forth in SEQ ID NO: 1, 2, 230;

ggggg) CDR1, CDR2 and CDR3 sequences set forth in SEQ ID NO: 1, 2, 232;

hhhhh) CDR1, CDR2 and CDR3 sequences set forth in SEQ ID NO: 1, 2, 234;

lllll) CDR1, CDR2 and CDR3 sequences set forth in SEQ ID NO: 1, 2, 236;

jjjjj) CDR1, CDR2 and CDR3 sequences set forth in SEQ ID NO: 1, 2, 238;

kkkkk) CDR1, CDR2 and CDR3 sequences set forth in SEQ ID NO: 1, 2, 240;

lllll) CDR1, CDR2 and CDR3 sequences set forth in SEQ ID NO: 1, 2, 242;

mmmmm) CDR1, CDR2 and CDR3 sequences set forth in SEQ ID NO: 1, 2, 244;

nnnnn) CDR1, CDR2 and CDR3 sequences set forth in SEQ ID NO: 1, 2, 246;

ooooo) CDR1, CDR2 and CDR3 sequences set forth in SEQ ID NO: 1, 2, 248;

ppppp) CDR1, CDR2 and CDR3 sequences set forth in SEQ ID NO: 1, 2, 250;

qqqqq) CDR1, CDR2 and CDR3 sequences set forth in SEQ ID NO: 1, 2, 252;

rrrrr) CDR1, CDR2 and CDR3 sequences set forth in SEQ ID NO: 1, 2, 254;

sssss) CDR1, CDR2 and CDR3 sequences set forth in SEQ ID NO: 1, 2, 256;

ttttt) CDR1, CDR2 and CDR3 sequences set forth in SEQ ID NO: 1, 2, 258;

uuuuu) CDR1, CDR2 and CDR3 sequences set forth in SEQ ID NO: 1, 2, 260;

vvvvv) CDR1, CDR2 and CDR3 sequences set forth in SEQ ID NO: 1, 2, 262;

wwwww) CDR1, CDR2 and CDR3 sequences set forth in SEQ ID NO: 1, 2, 264;

xxxxx) CDR1, CDR2 and CDR3 sequences set forth in SEQ ID NO: 1, 2, 266;

yyyyy) CDR1, CDR2 and CDR3 sequences set forth in SEQ ID NO: 1, 2, 268;

zzzzz) CDR1, CDR2 and CDR3 sequences set forth in SEQ ID NO: 1, 2, 270;

aaaaaa) CDR1, CDR2 and CDR3 sequences set forth in SEQ ID NO: 1, 2, 272;

bbbbbb) CDR1, CDR2 and CDR3 sequences set forth in SEQ ID NO: 1, 2, 274;

cccccc) CDR1, CDR2 and CDR3 sequences set forth in SEQ ID NO: 1, 2, 276;

dddddd) CDR1, CDR2 and CDR3 sequences set forth in SEQ ID NO: 1, 2, 278;

eeeeee) CDR1, CDR2 and CDR3 sequences set forth in SEQ ID NO: 1, 2, 280;

ffffff) CDR1, CDR2 and CDR3 sequences set forth in SEQ ID NO: 1, 2, 282;

gggggg) CDR1, CDR2 and CDR3 sequences set forth in SEQ ID NO: 1, 2, 284;

hhhhhh) CDR1, CDR2 and CDR3 sequences set forth in SEQ ID NO: 1, 2, 286;

iiiiii) CDR1, CDR2 and CDR3 sequences set forth in SEQ ID NO: 1, 2, 288;

jjjjjj) CDR1, CDR2 and CDR3 sequences set forth in SEQ ID NO: 1, 2, 290;

kkkkkk) CDR1, CDR2 and CDR3 sequences set forth in SEQ ID NO: 1, 2, 292;

llllll) CDR1, CDR2 and CDR3 sequences set forth in SEQ ID NO: 1, 2, 294;

mmmmmm) CDR1, CDR2 and CDR3 sequences set forth in SEQ ID NO: 1, 2, 296;

nnnnnn) CDR1, CDR2 and CDR3 sequences set forth in SEQ ID NO: 1, 2, 298 and oooooo) CDR1, CDR2 and CDR3 sequences set forth in SEQ ID NO: 1, 2, 300.

In one embodiment, the present invention relates to a humanized or chimeric antibody binding to human CD3, wherein said antibody comprises a binding region comprising a heavy chain variable (VH) region, wherein said VH region comprises the CDR1, CDR2, and CDR3 regions having the CDR sequences selected from one of the groups consisting of;

a) CDR1, CDR2 and CDR3 sequences set forth in SEQ ID NO: 54, 2, 3 [T31M];

b) CDR1, CDR2 and CDR3 sequence set forth in SEQ ID NO: 58, 2, 3 [T31P];

c) CDR1, CDR2 and CDR3 sequences set forth in SEQ ID NO: 1, 106, 3 [N57E];

d) CDR1, CDR2 and CDR3 sequences set forth in SEQ ID NO: 1, 2, 176 [H101G];

e) CDR1, CDR2 and CDR3 sequences set forth in SEQ ID NO: 1, 2, 184 [H101N];

f) CDR1, CDR2 and CDR3 sequences set forth in SEQ ID NO: 1, 2, 220 [G105P];

g) CDR1, CDR2 and CDR3 sequences set forth in SEQ ID NO: 1, 2, 236 [S110A];

h) CDR1, CDR2 and CDR3 sequences set forth in SEQ ID NO: 1, 2, 244 [S110G];

i) CDR1, CDR2 and CDR3 sequences set forth in SEQ ID NO: 1, 2, 284 [Y114M];

j) CDR1, CDR2 and CDR3 sequences set forth in SEQ ID NO: 1, 2, 292 [Y114R];

k) CDR1, CDR2 and CDR3 sequences set forth in SEQ ID NO: 1, 2, 298 [Y114V] and l) CDR1, CDR2 and CDR3 sequences having at least 90% or at least 95% amino acid sequence identity, in total across the three CDR sequences, to any one of the three CDR sequences as set forth in a) to k), provided that the CDR1, CDR2 and CDR3 sequences do not have the sequences as set forth in SEQ ID NO: 1, 2, 3.

In one embodiment, the present invention relates to a humanized or chimeric antibody binding to human CD3, wherein said antibody comprises a binding region comprising a heavy chain variable (VH) region, wherein said VH region comprises the CDR1, CDR2, and CDR3 regions having the CDR sequences selected from one of the groups consisting of;

a) CDR1, CDR2 and CDR3 sequences set forth in SEQ ID NO: 54, 2, 3 [T31M];

b) CDR1, CDR2 and CDR3 sequence set forth in SEQ ID NO: 58, 2, 3 [T31P];

c) CDR1, CDR2 and CDR3 sequences set forth in SEQ ID NO: 1, 106, 3 [N57E];

d) CDR1, CDR2 and CDR3 sequences set forth in SEQ ID NO: 1, 2, 176 [H101G];

e) CDR1, CDR2 and CDR3 sequences set forth in SEQ ID NO: 1, 2, 184 [H101N];

f) CDR1, CDR2 and CDR3 sequences set forth in SEQ ID NO: 1, 2, 220 [G105P];

g) CDR1, CDR2 and CDR3 sequences set forth in SEQ ID NO: 1, 2, 236 [S110A];

h) CDR1, CDR2 and CDR3 sequences set forth in SEQ ID NO: 1, 2, 244 [S110G];

i) CDR1, CDR2 and CDR3 sequences set forth in SEQ ID NO: 1, 2, 284 [Y114M];

j) CDR1, CDR2 and CDR3 sequences set forth in SEQ ID NO: 1, 2, 292 [Y114R];

k) CDR1, CDR2 and CDR3 sequences set forth in SEQ ID NO: 1, 2, 298 [Y114V]; and a. and l) CDR1, CDR2 and CDR3 sequences as specified in a) to k) having at most 5 further mutations or substitutions, at most 4 further mutations or substitutions, at most 3 further mutations or substitutions, at most 2 further mutations or substitutions, or at most 1 further mutation or substitution, in total across the three CDR sequences, and which mutations or substitutions preferably do not modify the binding affinity to human CD3.

In one embodiment, the present invention relates to a humanized or chimeric antibody binding to human CD3, wherein said antibody comprises a binding region comprising a heavy chain variable (VH) region), wherein said VH region comprises one of the VH sequences from the group consisting of;

a) a VH sequence as set forth in SEQ ID NO: 13;

b) a VH sequence as set forth in SEQ ID NO: 15;

c) a VH sequence as set forth in SEQ ID NO: 17;

d) a VH sequence as set forth in SEQ ID NO: 19;

e) a VH sequence as set forth in SEQ ID NO: 21;

f) a VH sequence as set forth in SEQ ID NO: 23;

g) a VH sequence as set forth in SEQ ID NO: 25;

h) a VH sequence as set forth in SEQ ID NO: 27;

i) a VH sequence as set forth in SEQ ID NO: 29;

j) a VH sequence as set forth in SEQ ID NO: 31;

k) a VH sequence as set forth in SEQ ID NO: 33;

l) a VH sequence as set forth in SEQ ID NO: 35;

m) a VH sequence as set forth in SEQ ID NO: 37;

n) a VH sequence as set forth in SEQ ID NO: 39;

o) a VH sequence as set forth in SEQ ID NO: 41;

p) a VH sequence as set forth in SEQ ID NO: 43;

q) a VH sequence as set forth in SEQ ID NO: 45;

r) a VH sequence as set forth in SEQ ID NO: 47;

s) a VH sequence as set forth in SEQ ID NO: 49;

t) a VH sequence as set forth in SEQ ID NO: 51;

u) a VH sequence as set forth in SEQ ID NO: 53;

v) a VH sequence as set forth in SEQ ID NO: 55;

w) a VH sequence as set forth in SEQ ID NO: 57;

x) a VH sequence as set forth in SEQ ID NO: 59;

y) a VH sequence as set forth in SEQ ID NO: 61;

z) a VH sequence as set forth in SEQ ID NO: 63;

aa) a VH sequence as set forth in SEQ ID NO: 65;

bb) a VH sequence as set forth in SEQ ID NO: 67;
cc) a VH sequence as set forth in SEQ ID NO: 69;
dd) a VH sequence as set forth in SEQ ID NO: 71;
ee) a VH sequence as set forth in SEQ ID NO: 73;
ff) a VH sequence as set forth in SEQ ID NO: 75;
gg) a VH sequence as set forth in SEQ ID NO: 77;
hh) a VH sequence as set forth in SEQ ID NO: 79;
ii) a VH sequence as set forth in SEQ ID NO: 81;
jj) a VH sequence as set forth in SEQ ID NO: 83;
kk) a VH sequence as set forth in SEQ ID NO: 85;
ll) a VH sequence as set forth in SEQ ID NO: 87;
mm) a VH sequence as set forth in SEQ ID NO: 89;
nn) a VH sequence as set forth in SEQ ID NO: 91;
oo) a VH sequence as set forth in SEQ ID NO: 93;
pp) a VH sequence as set forth in SEQ ID NO: 95;
qq) a VH sequence as set forth in SEQ ID NO: 97;
rr) a VH sequence as set forth in SEQ ID NO: 99;
ss) a VH sequence as set forth in SEQ ID NO: 101;
tt) a VH sequence as set forth in SEQ ID NO: 103;
uu) a VH sequence as set forth in SEQ ID NO: 105;
vv) a VH sequence as set forth in SEQ ID NO: 107;
ww) a VH sequence as set forth in SEQ ID NO: 109;
xx) a VH sequence as set forth in SEQ ID NO: 111;
yy) a VH sequence as set forth in SEQ ID NO: 113;
zz) a VH sequence as set forth in SEQ ID NO: 115;
aaa) a VH sequence as set forth in SEQ ID NO: 117;
bbb) a VH sequence as set forth in SEQ ID NO: 119;
ccc) a VH sequence as set forth in SEQ ID NO: 121;
ddd) a VH sequence as set forth in SEQ ID NO: 123;
eee) a VH sequence as set forth in SEQ ID NO: 125;
fff) a VH sequence as set forth in SEQ ID NO: 127;
ggg) a VH sequence as set forth in SEQ ID NO: 129;
hhh) a VH sequence as set forth in SEQ ID NO: 131;
iii) a VH sequence as set forth in SEQ ID NO: 133;
jjj) a VH sequence as set forth in SEQ ID NO: 135;
kkk) a VH sequence as set forth in SEQ ID NO: 137;
lll) a VH sequence as set forth in SEQ ID NO: 139;
mmm) a VH sequence as set forth in SEQ ID NO: 141;
nnn) a VH sequence as set forth in SEQ ID NO: 143;
ooo) a VH sequence as set forth in SEQ ID NO: 145;
ppp) a VH sequence as set forth in SEQ ID NO: 147;
qqq) a VH sequence as set forth in SEQ ID NO: 149;
rrr) a VH sequence as set forth in SEQ ID NO: 151;
sss) a VH sequence as set forth in SEQ ID NO: 153;
ttt) a VH sequence as set forth in SEQ ID NO: 155;
uuu) a VH sequence as set forth in SEQ ID NO: 157;
vvv) a VH sequence as set forth in SEQ ID NO: 159;
www) a VH sequence as set forth in SEQ ID NO: 161;
xxx) a VH sequence as set forth in SEQ ID NO: 163;
yyy) a VH sequence as set forth in SEQ ID NO: 165;
zzz) a VH sequence as set forth in SEQ ID NO: 167;
aaaa) a VH sequence as set forth in SEQ ID NO: 169;
bbbb) a VH sequence as set forth in SEQ ID NO: 171;
cccc) a VH sequence as set forth in SEQ ID NO: 173;
dddd) a VH sequence as set forth in SEQ ID NO: 175;
eeee) a VH sequence as set forth in SEQ ID NO: 177;
ffff) a VH sequence as set forth in SEQ ID NO: 179;
gggg) a VH sequence as set forth in SEQ ID NO: 181;
hhhh) a VH sequence as set forth in SEQ ID NO: 183;
iiii) a VH sequence as set forth in SEQ ID NO: 185;
jjjj) a VH sequence as set forth in SEQ ID NO: 187;
kkkk) a VH sequence as set forth in SEQ ID NO: 189;
llll) a VH sequence as set forth in SEQ ID NO: 191;
mmmm) a VH sequence as set forth in SEQ ID NO: 193;
nnnn) a VH sequence as set forth in SEQ ID NO: 195;
oooo) a VH sequence as set forth in SEQ ID NO: 197;
pppp) a VH sequence as set forth in SEQ ID NO: 199;

qqqq) a VH sequence as set forth in SEQ ID NO: 201;
rrrr) a VH sequence as set forth in SEQ ID NO: 203;
ssss) a VH sequence as set forth in SEQ ID NO: 205;
tttt) a VH sequence as set forth in SEQ ID NO: 207;
uuuu) a VH sequence as set forth in SEQ ID NO: 209;
vvvv) a VH sequence as set forth in SEQ ID NO: 211;
wwww) a VH sequence as set forth in SEQ ID NO: 213;
xxxx) a VH sequence as set forth in SEQ ID NO: 215;
yyyy) a VH sequence as set forth in SEQ ID NO: 217;
zzzz) a VH sequence as set forth in SEQ ID NO: 219;
aaaaa) a VH sequence as set forth in SEQ ID NO: 221;
bbbbb) a VH sequence as set forth in SEQ ID NO: 223;
ccccc) a VH sequence as set forth in SEQ ID NO: 225;
ddddd) a VH sequence as set forth in SEQ ID NO: 227;
eeeee) a VH sequence as set forth in SEQ ID NO: 229;
fffff) a VH sequence as set forth in SEQ ID NO: 221;
ggggg) a VH sequence as set forth in SEQ ID NO: 223;
hhhhh) a VH sequence as set forth in SEQ ID NO: 225;
iiiii) a VH sequence as set forth in SEQ ID NO: 227;
jjjjj) a VH sequence as set forth in SEQ ID NO: 229;
kkkkk) a VH sequence as set forth in SEQ ID NO: 231;
lllll) a VH sequence as set forth in SEQ ID NO: 233;
mmmmm) a VH sequence as set forth in SEQ ID NO: 235;
nnnnn) a VH sequence as set forth in SEQ ID NO: 237;
ooooo) a VH sequence as set forth in SEQ ID NO: 239;
ppppp) a VH sequence as set forth in SEQ ID NO: 241;
qqqqq) a VH sequence as set forth in SEQ ID NO: 243;
rrrrr) a VH sequence as set forth in SEQ ID NO: 245;
sssss) a VH sequence as set forth in SEQ ID NO: 247;
ttttt) a VH sequence as set forth in SEQ ID NO: 249;
uuuuu) a VH sequence as set forth in SEQ ID NO: 251;
vvvvv) a VH sequence as set forth in SEQ ID NO: 253;
wwwww) a VH sequence as set forth in SEQ ID NO: 255;
xxxxx) a VH sequence as set forth in SEQ ID NO: 257;
yyyyy) a VH sequence as set forth in SEQ ID NO: 259;
zzzzz) a VH sequence as set forth in SEQ ID NO: 261;
aaaaaa) a VH sequence as set forth in SEQ ID NO: 263;
bbbbbb) a VH sequence as set forth in SEQ ID NO: 265;
cccccc) a VH sequence as set forth in SEQ ID NO: 267;
dddddd) a VH sequence as set forth in SEQ ID NO: 269;
eeeeee) a VH sequence as set forth in SEQ ID NO: 271;
ffffff) a VH sequence as set forth in SEQ ID NO: 273;
gggggg) a VH sequence as set forth in SEQ ID NO: 275;
hhhhhh) a VH sequence as set forth in SEQ ID NO: 277;
iiiiii) a VH sequence as set forth in SEQ ID NO: 279;
jjjjjj) a VH sequence as set forth in SEQ ID NO: 281;
kkkkkk) a VH sequence as set forth in SEQ ID NO: 283;
llllll) a VH sequence as set forth in SEQ ID NO: 285;
mmmmmm) a VH sequence as set forth in SEQ ID NO: 287;
nnnnnn) a VH sequence as set forth in SEQ ID NO: 289;
oooooo) a VH sequence as set forth in SEQ ID NO: 291;
pppppp) a VH sequence as set forth in SEQ ID NO: 293;
qqqqqq) a VH sequence as set forth in SEQ ID NO: 295;
rrrrrr) a VH sequence as set forth in SEQ ID NO: 297;
ssssss) a VH sequence as set forth in SEQ ID NO: 299 and
tttttt) a VH sequence as set forth in SEQ ID NO: 301.

In one embodiment, the present invention relates to a humanized or chimeric antibody binding to human CD3, wherein said antibody comprises a binding region comprising a heavy chain variable (VH) region, wherein said VH region comprises one of the VH sequences selected from the group consisting of;
a) a VH sequence as set forth in SEQ ID NO: 55[T31M],
b) a VH sequence as set forth in SEQ ID NO: 59 [T31P],
c) a VH sequence as set forth in SEQ ID NO: 107 [N57E]

d) a VH sequence as set forth in SEQ ID NO: 177 [H101G], e) a VH sequence as set forth in SEQ ID NO: 185 [H101N], f) a VH sequence as set forth in SEQ ID NO: 221 [G105P], g) a VH sequence as set forth in SEQ ID NO: 237 [S110A], h) a VH sequence as set forth in SEQ ID NO: 245 [S110G], i) a VH sequence as set forth in SEQ ID NO: 285 [Y114M], j) a VH sequence as set forth in SEQ ID NO: 293 [Y114R], and k) a VH sequence as set forth in SEQ ID NO: 299 [Y114V].

In one embodiment of the invention the humanized or chimeric antibody comprises a binding region, wherein said binding region comprises a variable light chain (VL) region, wherein said VL region comprises the CDR1, CDR2, and CDR3 having the CDR sequences selected from the group consisting of;

a) CDR1, CDR2 and CDR3 sequences as set forth in SEQ ID NO: 6, GTN, 7;

b) CDR1, CDR2 and CDR3 sequences as set forth in SEQ ID NO: 302, GTN, 7;

c) CDR1, CDR2 and CDR3 sequences as set forth in SEQ ID NO: 304, GTN, 7;

d) CDR1, CDR2 and CDR3 sequences as set forth in SEQ ID NO: 306, GTN, 7;

e) CDR1, CDR2 and CDR3 sequences as set forth in SEQ ID NO: 308, GTN, 7;

f) CDR1, CDR2 and CDR3 sequences as set forth in SEQ ID NO: 310, GTN, 7;

g) CDR1, CDR2 and CDR3 sequences as set forth in SEQ ID NO: 312, GTN, 7;

h) CDR1, CDR2 and CDR3 sequences as set forth in SEQ ID NO: 314, GTN, 7;

i) CDR1, CDR2 and CDR3 sequences as set forth in SEQ ID NO: 316, GTN, 7;

j) CDR1, CDR2 and CDR3 sequences as set forth in SEQ ID NO: 318, GTN, 7;

k) CDR1, CDR2 and CDR3 sequences as set forth in SEQ ID NO: 320, GTN, 7;

l) CDR1, CDR2 and CDR3 sequences as set forth in SEQ ID NO: 322, GTN, 7;

m) CDR1, CDR2 and CDR3 sequences as set forth in SEQ ID NO: 324, GTN, 7;

n) CDR1, CDR2 and CDR3 sequences as set forth in SEQ ID NO: 326, GTN, 7;

o) CDR1, CDR2 and CDR3 sequences as set forth in SEQ ID NO: 328, GTN, 7;

p) CDR1, CDR2 and CDR3 sequences as set forth in SEQ ID NO: 330, GTN, 7;

q) CDR1, CDR2 and CDR3 sequences as set forth in SEQ ID NO: 6, GTN, 332;

r) CDR1, CDR2 and CDR3 sequences as set forth in SEQ ID NO: 6, GTN, 334;

s) CDR1, CDR2 and CDR3 sequences as set forth in SEQ ID NO: 6, GTN, 336;

t) CDR1, CDR2 and CDR3 sequences as set forth in SEQ ID NO: 6, GTN, 338;

u) CDR1, CDR2 and CDR3 sequences as set forth in SEQ ID NO: 6, GTN, 340;

v) CDR1, CDR2 and CDR3 sequences as set forth in SEQ ID NO: 6, GTN, 342;

w) CDR1, CDR2 and CDR3 sequences as set forth in SEQ ID NO: 6, GTN, 344;

x) CDR1, CDR2 and CDR3 sequences as set forth in SEQ ID NO: 6, GTN, 346;

y) CDR1, CDR2 and CDR3 sequences as set forth in SEQ ID NO: 6, GTN, 348;

z) CDR1, CDR2 and CDR3 sequences as set forth in SEQ ID NO: 6, GTN, 350;

aa) CDR1, CDR2 and CDR3 sequences as set forth in SEQ ID NO: 6, GTN, 352;

bb) CDR1, CDR2 and CDR3 sequences as set forth in SEQ ID NO: 6, GTN, 354;

cc) CDR1, CDR2 and CDR3 sequences as set forth in SEQ ID NO: 6, GTN, 356;

dd) CDR1, CDR2 and CDR3 sequences as set forth in SEQ ID NO: 6, GTN, 358;

ee) CDR1, CDR2 and CDR3 sequences as set forth in SEQ ID NO: 6, GTN, 360;

ff) CDR1, CDR2 and CDR3 sequences as set forth in SEQ ID NO: 6, GTN, 362;

gg) CDR1, CDR2 and CDR3 sequences as set forth in SEQ ID NO: 6, GTN, 364;

hh) CDR1, CDR2 and CDR3 sequences as set forth in SEQ ID NO: 6, GTN, 366;

ii) CDR1, CDR2 and CDR3 sequences as set forth in SEQ ID NO: 6, GTN, 368;

jj) CDR1, CDR2 and CDR3 sequences as set forth in SEQ ID NO: 6, GTN, 370;

kk) CDR1, CDR2 and CDR3 sequences as set forth in SEQ ID NO: 6, GTN, 372;

ll) CDR1, CDR2 and CDR3 sequences as set forth in SEQ ID NO: 6, GTN, 374;

mm) CDR1, CDR2 and CDR3 sequences as set forth in SEQ ID NO: 6, GTN, 376;

nn) CDR1, CDR2 and CDR3 sequences as set forth in SEQ ID NO: 6, GTN, 378;

oo) CDR1, CDR2 and CDR3 sequences as set forth in SEQ ID NO: 6, GTN, 380;

pp) CDR1, CDR2 and CDR3 sequences as set forth in SEQ ID NO: 6, GTN, 382;

qq) CDR1, CDR2 and CDR3 sequences as set forth in SEQ ID NO: 6, GTN, 384;

rr) CDR1, CDR2 and CDR3 sequences as set forth in SEQ ID NO: 6, GTN, 386;

ss) CDR1, CDR2 and CDR3 sequences as set forth in SEQ ID NO: 6, GTN, 388;

tt) CDR1, CDR2 and CDR3 sequences as set forth in SEQ ID NO: 6, GTN, 390;

uu) CDR1, CDR2 and CDR3 sequences as set forth in SEQ ID NO: 6, GTN, 392 and vv) CDR1, CDR2 and CDR3 sequences as set forth in SEQ ID NO: 6, GTN, 394.

In another embodiment of the invention the humanized or chimeric antibody comprises a binding region comprising a variable light chain (VL) region, wherein said VL region comprises one of the VL sequences selected from the group consisting of;

a) a VL sequence as set forth in SEQ ID NO:8; and b) a VL sequence as set forth in SEQ ID NO:10;

The term "antibody" as used herein is intended to refer to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The binding region (or binding domain which may also be used herein, both terms having the same meaning) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells and T cells) and components of the complement system such as C1q, the first component in the classical pathway of complement activation. As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (1) a Fab' or Fab fragment, a monovalent fragment consisting of the $V_L$, $V_H$, $C_L$ and $C_H1$ domains, or a monovalent antibody as described in WO2007059782 (Genmab A/S); (ii) $F(ab')_2$ fragments, bivalent fragments comprising two Fab fragments linked by a disulfide bridge at the hinge region; (iii) a Fd fragment consisting essentially of the VH and $C_H1$ domains; and (iv) a Fv fragment consisting essentially of the $V_L$ and VH domains of a single arm of an antibody. Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "immunoglobulin heavy chain", "heavy chain of an immunoglobulin" or "heavy chain" as used herein is intended to refer to one of the chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The heavy chain constant region may further comprise a hinge region. The term "immunoglobulin" as used herein is intended to refer to a class of structurally related glycoproteins consisting of two pairs of polypeptide chains, one pair of light (L) chains and one pair of heavy (H) chains, all four potentially inter-connected by disulfide bonds. The structure of immunoglobulins has been well characterized (see for instance [14]). Within the structure of the immunoglobulin (e.g. IgG), the two heavy chains are inter-connected via disulfide bonds in the so-called "hinge region". Equally to the heavy chains each light chain is typically comprised of several regions; a light chain variable region (abbreviated herein as VL) and a light chain constant region (abbreviated herein as CL). The light chain constant region typically is comprised of one domain, CL. Furthermore, the VH and VL regions may be further subdivided into regions of hypervariability (or hypervariable regions which may be hypervariable in sequence and/or form structurally defined loops), also termed complementarity determining regions (CDRs), Interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see [15]). CDR sequences may be determined by use of the method provided by IMGT [16]-[17].

The term "isotype" as used herein, refers to the immunoglobulin (sub)class (for instance IgG1, IgG2, IgG3, IgG4, IgD, IgA, IgE, or IgM) or any allotype thereof, such as IgG1m(za) and IgG1m(f) [SEQ ID NO:407]) that is encoded by heavy chain constant region genes. Thus, in one embodiment, the antibody comprises a heavy chain of an immunoglobulin of the IgG1 class or any allotype thereof. Further, each heavy chain isotype can be combined with either a kappa (κ) or lambda (λ) light chain.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a generic term used for different kinds of modifications of antibodies, and which is a well-known process for the skilled person. In particular, a chimeric antibody may be generated by using standard DNA techniques as described in [18]. Thus, the chimeric antibody may be a genetically engineered recombinant antibody. Some chimeric antibodies may be both genetically or an enzymatically engineered. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see [19]-[20]). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The humanized or chimeric antibody according to any aspect or embodiment of the present invention may be termed "humanized or chimeric CD3 antibody", "humanized or chimeric antibody of the invention", "CD3 antibody", or "CD3 antibody of the invention", which all have the same meaning and purpose unless otherwise contradicted by context.

The amino acid sequence of an antibody of non-human origin is distinct from antibodies of human origin, and therefore a non-human antibody is potentially immunogenic when administered to human patients. However, despite the non-human origin of the antibody, its CDR segments are responsible for the ability of the antibody to bind to its target antigen and humanization aims to maintain the specificity and binding affinity of the antibody. Thus, humanization of non-human therapeutic antibodies is performed to minimize its immunogenicity in man while such humanized antibodies at the same time maintain the specificity and binding affinity of the antibody of non-human origin.

The term "binding region" as used herein, refers to a region of an antibody which is capable of binding to any molecule, such as a polypeptide, e.g. present on a cell, bacterium, or virion.

The term "binding" as used herein, refers to the binding of an antibody to a predetermined antigen or target to which binding typically is with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 Instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The degree with which the affinity is lower is dependent on the $K_D$ of the antibody, so that when the $K_D$ of the antibody is very low (that is, the antibody is highly specific), then the degree with which the affinity for the antigen is lower than the affinity for a non-specific antigen may be at least 10,000 fold. The term "$K_D$" (M), as used herein, refers to the dissociation equilibrium constant of a particular antibody-antigen interaction.

The term "human CD3" as used herein, refers to the human Cluster of Differentiation 3 protein which is part of the T cell co-receptor protein complex and is composed of four distinct chains. CD3 is also found in other species, and thus, the term "CD3" may be used herein and is not limited to human CD3 unless contradicted by context. In mammals, the complex contains a CD3γ (gamma) chain (human CD3γ chain Swissprot P09693, or cynomolgus monkey CD3γ Swissprot Q95LI7), a CD3δ (delta) chain (human CD3δ Swissprot P04234, or cynomolgus monkey CD3δ Swissprot Q95LI8), two CD3ε (epsilon) chains (human CD3ε Swissprot P07766; or cynomolgus CD3ε Swissprot Q95LI5), rhesus CD3ε (Swissprot G7NCB9), and a CD3ζ-chain (zeta) chain (human CD3ζ Swissprot P20963, cynomolgus monkey CD3ζ Swissprot Q09TK0). These chains associate with a molecule known as the T cell receptor (TCR) and generate an activation signal in T lymphocytes. The TCR and CD3 molecules together comprise the TCR complex.

It is within the knowledge of the skilled person that amino acid sequences referred to as Swissprot numbers include a signal peptide which is removed after translation of the protein. Thus, proteins, such as CD3, present on cell surfaces do not include the signal peptide. In particular, the amino acid sequences listed in Table 1 do not contain such signal peptide. Such proteins as listed in Table 1 may be termed "mature proteins". Thus, SEQ ID NO:398 shows the amino acid sequence of mature human CD3δ (delta), SEQ ID NO:399 shows the amino acid sequence of mature human CD3ε (epsilon), SEQ ID NO:403 shows the amino acid sequence of mature cynomolgus CD3ε, and SEQ ID NO:404 shows the amino acid sequence of mature rhesus CD3ε. Thus, the term "mature" as used herein, refers to a protein which does not comprise any signal or leader sequence.

It is well-known that signal peptide sequence homology, length, and the cleavage site position, varies significantly between different proteins. Signal peptides may be determined by different methods, e.g. SEQ ID NO:399 of the present invention has been determined according to the SignalP application (available on www.cbs.dtu.dk/services/SignalP/).

In a particular embodiment, the humanized or chimeric antibody of the present invention binds the epsilon chain of CD3, such as the epsilon chain of human CD3 (SEQ ID NO:399). In yet another particular embodiment, the humanized or chimeric antibody binds an epitope within amino acids 1-27 of the N-terminal part of human CD3ε (epsilon) (SEQ ID NO:402). In such a particular embodiment, the antibody may even further cross-react with other non-human primate species, such as cynomolgus monkeys (cynomolgus CD3 epsilon SEQ ID NO:403) and/or rhesus monkeys (rhesus CD3 epsilon SEQ ID NO:404).

An antibody according to the present invention comprising the CDR sequences as defined herein, further comprising framework regions may differ in sequence outside the CDR sequences but still retains the full binding ability as compared to the original antibody. Thus, the present invention also relates to antibodies comprising an amino acid sequence of the variable region having a certain sequence identity to any sequence herein described.

The term "sequence identity" as used in the context of the present invention, refers to the percent identity between two sequences as a function of the number of Identical positions shared by the sequences (i.e., % homology=# of Identical positions/total # of positions ×100), taking into account the number of gaps, and the length of each gap, which need to be Introduced for optimal alignment of the two sequences. The percent identity between two nucleotide or amino acid sequences may e.g. be determined using the algorithm of E. Meyers and W. Miller [21]. In addition, the percent identity between two amino acid sequences may be determined using the Needleman and Wunsch algorithm [22]. Multiple alignments are preferably performed using the Clustal W algorithm [23] (as used e.g., in Vector NTI Advance® software version 11.5; Invitrogen Inc.).

Thus, in one embodiment of the present invention, the antibody comprises a binding region comprising a heavy chain variable (VH) region, wherein said VH region comprises the CDR1, CDR2, and CDR3 regions having the three CDR sequences selected from one of the groups consisting of;

a) CDR1, CDR2 and CDR3 sequences set forth in SEQ ID NO: 54, 2, 3 [T31M];

b) CDR1, CDR2 and CDR3 sequences set forth in SEQ ID NO: 58, 2, 3 [T31P];

c) CDR1, CDR2 and CDR3 sequences set forth in SEQ ID NO: 1, 106, 3 [N57E];

d) CDR1, CDR2 and CDR3 sequences set forth in SEQ ID NO: 1, 2, 176 [H101G];

e) CDR1, CDR2 and CDR3 sequences set forth in SEQ ID NO: 1, 2, 184 [H101N];

f) CDR1, CDR2 and CDR3 sequences set forth in SEQ ID NO: 1, 2, 220 [G105P];

g) CDR1, CDR2 and CDR3 sequences set forth in SEQ ID NO: 1, 2, 236 [S110A];

h) CDR1, CDR2 and CDR3 sequences set forth in SEQ ID NO: 1, 2, 244 [S110G];

i) CDR1, CDR2 and CDR3 sequences set forth in SEQ ID NO: 1, 2, 284 [Y114M];

j) CDR1, CDR2 and CDR3 sequences set forth in SEQ ID NO: 1, 2, 292 [Y114R];

k) CDR1, CDR2 and CDR3 sequences set forth in SEQ ID NO: 1, 2, 298 [Y114V]; and l) CDR1, CDR2 and CDR3 sequences having at least 90% or at least 95% amino acid sequence identity, in total across the three CDR sequences, to any one of the three CDR sequences as set forth in a) to k), provided that the CDR1, CDR2 and CDR3 sequences do not have the sequences as set forth in SEQ ID NO: 1, 2, 3.

The VH region, as Illustrate in the sequence table 1 of the present document, consists of 125 amino acid sequence. Thus a second VH sequence consisting of 125 amino acids whereof 124 amino acid positions are Identical with the one of the first VH sequences listed above has 99.2% sequence identity with said first VH sequence. A second sequence consisting of 125 amino acids whereof 120 amino acid positions are Identical with one of the first VH sequences listed above have 96% sequence identity with said first VH sequence. A second sequence consisting of 125 amino acids whereof 115 amino acid positions are Identical with one of the first VH sequences listed above have 92% sequence identity with said first VH sequence.

In a particular embodiment thereof, the VH region has at least 96% amino acid sequence identity to at least one of the VH sequences as specified in said group.

In one embodiment of the invention the mutations are located in the frame work regions of the VH region. Hence, in some embodiments the three CDR sequences of the VH region are 100% Identical to the antibodies of the present invention, but amino acid variation may occur in the frame work region of the VH region. Such amino acid variation in the frame work region may preferably not change the binding affinity of the antibody to CD3 compare to the antibody when the CDRs are comprised in the reference frame of SEQ ID NO: 407.

The mutations in the VH sequence causing variations in the sequence identity may preferably be conservative, physical or functional amino acids. Substituting amino acids with similar amino acids may Increase the likelihood of keeping the functionality of the parent antibody.

In one embodiment of the invention the antibody is a humanized antibody.

In one embodiment of the invention the antibody is a full-length antibody.

The humanized antibody according to the present invention may be generated by comparison of the heavy and light chain variable region amino acid sequences against a database of human germline variable region sequences in order to Identify the heavy and light chain human sequence with the appropriate degree of homology for use as human variable framework regions. A series of humanized heavy and light chain variable regions may be designed by grafting, e.g. the murine, CDRs onto the framework regions (identified as described above) and, if necessary, by back-mutation (mutation of one or more of the human amino acid residues in the framework regions back to the non-human amino acid at the specific position(s)) to the specific murine sequence of residues Identified which may be critical to the restoration of the antibody binding efficiency. Variant sequences with the lowest Incidence of potential T cell epitopes may then be selected as determined by application of in silico technologies; ITope™ and TCED™ ([24], [25], and [26]).

Furthermore, the humanized antibodies according to the present invention may also be "deimmunized". Deimmunization may be desired, as within a protein sequence, such as a humanized antibody according to the present invention, the presence of human T cell epitopes may Increase the immunogenicity risk profile as they have the potential to activate helper T cells. Such activation of helper T cells may be avoided by deimmunization. Deimmunization may be performed by Introducing a mutation in the amino acid sequence of the humanized antibody in order to remove the T cell epitopes without significantly reducing the binding affinity of the antibody.

Thus, in one embodiment of the present invention, the humanized antibody may be produced by a method comprising the steps of (1) comparing the non-human full variable heavy chain sequence and/or the full variable light chain sequence to a database of human germline sequences, (ii) selecting the human germline sequence having the highest homology to the non-human sequence to obtain a humanized sequence, (iii) optimizing the humanized sequence by back-mutation(s) If required, and (iv) expressing the sequence in a suitable expression system.

Thus, a full-length antibody according to the present invention may be produced by a method comprising the steps of (1) comparing the non-human variable heavy chain sequence and the variable light chain sequences to a database of human germline sequences, (ii) selecting the human germline sequence having the highest homology to the non-human sequence, (iii) grafting of the non-human CDRs in to the selected human germ-line to obtain a humanized sequence, (iv) optimizing the humanized sequences by back-mutation(s) If required, (v) Identifying constant heavy and light chain sequences, and (vi) expressing the complete heavy chain sequences and complete light chain sequences in suitable expression systems. A full-length antibody according to the present invention may, thus, be produced as described in Example 1. It is within the knowledge of the skilled person to produce a full-length antibody when starting out from either CDR sequences or full variable region sequences. Thus, the skilled person would know how to generate a full-length antibody according to the present invention.

The term "complete heavy chain sequences" as used herein, refers to a sequence consisting of variable heavy chain and constant heavy chain sequences.

The term "complete light chain sequences" as used herein, refers to a sequence consisting of variable light chain and constant light chain sequences.

Back-mutation(s) may be Introduced by standard DNA mutagenesis. Such standard techniques for DNA mutagenesis are described in [18]. Alternatively, use of commercially available kits such as Quickchange™ Site-Directed Mutagenesis Kit (Stratagene), or the desired back-mutations may be Introduced by de novo DNA synthesis.

Thus, in one embodiment, the antibody is a humanized antibody.

Chimeric antibodies may be generated by substituting all constant region sequences of a non-human (such as murine) antibody with constant region sequences of human origin. Thus, fully non-human variable region sequences are maintained in the chimeric antibody. Thus, a chimeric antibody according to the present invention may be produced by a method comprising the step of expressing the non-human variable heavy chain (SEQ ID NO:405), non-human variable light chain sequences (SEQ ID NO:406), human constant heavy chain and human constant light chain sequences in suitable expression systems, and thereby generating a full-length chimeric antibody. Alternative methods may be used. Such methods of producing a chimeric antibody is within the knowledge of the skilled person, and thus, the skilled person would know how to produce a chimeric antibody according to the present invention. Thus to make a chimeric antibody according to the present invention one would Introduce the mutations according to the invention in the non-human (such as murine) VH or VL sequence.

Thus, in one embodiment, the antibody is a chimeric antibody.

In one embodiment, the antibody is a full-length antibody. The term "full-length antibody" as used herein, refers to an antibody (e.g., a parent or variant antibody) which contains all heavy and light chain constant and variable domains correspond to those that are normally found in a wild-type antibody of that isotype.

In one embodiment, the antibody comprises an Fc region comprising a first and a second immunoglobulin heavy chain.

The term "Fc region" as used herein, refers to a region comprising, in the direction from the N- to C-terminal, at least a hinge region, a $CH_2$ region and a CH3 region. An Fc region may further comprise a CH1 region at the N-terminal end of the hinge region.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat.

Unless otherwise stated or contradicted by context, the amino acids of the constant region sequences are herein numbered according to the Eu-index of numbering (described in [27]) and may be termed "according to the Eu numbering as set forth in Kabat", "Eu numbering according to Kabat", or "according to the Eu numbering system".

The term "CH1 region" or "CH1 domain" as used herein, refers to the CH1 region of an immunoglobulin heavy chain. Thus, for example the CH1 region of a human IgG1 antibody corresponds to amino acids 118-215 according to the Eu numbering system. However, the CH1 region may also be any of the other subtypes as described herein.

The term "CH2 region" or "CH2 domain" as used herein, refers to the CH2 region of an immunoglobulin heavy chain. Thus, for example the CH2 region of a human IgG1 antibody corresponds to amino acids 231-340 according to the Eu numbering system. However, the CH2 region may also be any of the other subtypes as described herein.

The term "CH3 region" or "CH3 domain" as used herein, refers to the CH3 region of an immunoglobulin heavy chain. Thus, for example the CH3 region of a human IgG1 antibody corresponds to amino acids 341-447 according to the Eu numbering system. However, the CH3 region may also be any of the other subtypes as described herein.

In one embodiment, the isotype of the immunoglobulin heavy chain is selected from the group consisting of IgG1, IgG2, IgG3, and IgG4. The immunoglobulin heavy chain may be any allotype within each of the immunoglobulin classes, such as IgG1m(f) (SEQ ID NO:407). Thus, in one particular embodiment, the isotype of the immunoglobulin heavy chains is an IgG1, or any allotype thereof, such as IgG1m(f) (SEQ ID NO:407).

When targeting the antigen CD3 which is part of the T cell Receptor (TCR), the T cell specific mechanisms of cell killing is desirable. Other effector functions, e.g. complement activation, may not be wanted, and therefore, reduction of effector functions is desirable. C1q binding is the first step in the complement cascade, and therefore serves as an Indicator for complement-dependent cytotoxicity (CDC) capacity of antibodies. If binding of C1q to the antibody can be avoided, activation of the complement cascade can be avoided as well.

Thus, in one embodiment, the antibody comprises an Fc region which has been modified so that binding of C1q to said antibody is reduced compared to a wild-type antibody by at least 70%, at least 80%, at least 90%, at least 95%, at least 97%, at least 99%, at least 99.9% or 100%, wherein C1q binding is determined by ELISA. In a preferred embodiment the antibody comprises an Fc region, which has been modified so that the binding of C1q to said antibody is reduced compared to a wild-type antibody by at least 99% to a 100%, wherein C1q binding is determined by ELISA.

The term "modified" as used herein, refers to the amino acid sequence of an Fc region which is not Identical to the amino acid sequence of a wild-type Fc region. I.e. amino acid residues in specific positions of the wild-type Fc region have been substituted, deleted or Inserted in order to alter, for example, the binding site for C1q, binding site for other effector molecules or binding to Fc Receptors (FcRs). Such modification(s) of the amino acid sequence may be prepared by substituting one or more amino acids with a conservative amino acid or may be prepared by substituting one or more amino acids with an alternative amino acid which is physically and/or functionally similar to the amino acid present in the wild-type. Substitutions may also be prepared by substituting with a non-conservative amino acid.

In the context of the present Invention, amino acids may be described as conservative or non-conservative amino acids, and may therefore be classified accordingly. Amino acid residues may also be divided into classes defined by alternative physical and functional properties. Thus, classes of amino acids may be reflected in one or both of the following tables:

Amino Add Residue of Conservative Class

| Acidic Residues | D and E |
|---|---|
| Basic Residues | K, R, and H |

-continued

| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

Alternative Physical and Functional Classifications of Amino Acid Residues

| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

In the context of the present Invention, a substitution in an antibody, such as a humanized or chimeric antibody, is Indicated as:

Original amino acid—position—substituted amino acid;

Referring to the well-recognized nomenclature for amino acids, the three letter code, or one letter code, is used, including the codes Xaa and X to Indicate any amino acid residue. Accordingly, the notation "L234F" or "Leu234Phe" means, that the antibody comprises a substitution of Leucine with Phenylalanine in amino acid position 234.

Substitution of an amino acid at a given position to any other amino acid is referred to as:

Original amino acid—position; or e.g. "L234".

For a modification where the original amino acid(s) and/or substituted amino acid(s) may comprise more than one, but not all amino acid(s), the more than one amino acid may be separated by "," or "/". E.g. the substitution of Leucine for Phenylalanine, Arginine, Lysine or Tryptophan in position 234 is:

"Leu234Phe,Arg,Lys,Trp" or "Leu234Phe/Arg/Lys/Trp" or "L234F,R,K,W" or "L234F/R/K/W" or "L234 to F, R, K or W" Such designation may be used Interchangeably in the context of the invention but have the same meaning and purpose.

Furthermore, the term "a substitution" embraces a substitution into any one of the other nineteen natural amino acids, or into other amino acids, such as non-natural amino acids. For example, a substitution of amino acid L in position 234 Includes each of the following substitutions: 234A, 234C, 234D, 234E, 234F, 234G, 234H, 234I, 234K, 234M, 234N, 234Q, 234R, 234S, 234T, 234V, 234W, 234P, and 234Y. This is, by the way, equivalent to the designation 234X, wherein the X designates any amino acid other than the original amino acid. These substitutions can also be designated L234A, L234C, etc., or L234A,C, etc., or L234A/C/etc. The same applies by analogy to each and every position mentioned herein, to specifically Include herein any one of such substitutions.

The antibody according to the invention may also comprise a deletion of an amino acid residue. Such deletion may be denoted "del", and Includes, e.g., writing as L234del. Thus, in such embodiments, the Leucine in position 234 has been deleted from the amino acid sequence.

The terms "amino acid" and "amino acid residue" may herein be used Interchangeably.

In one embodiment of the invention, the antibody comprises a binding region comprising a heavy chain variable (VH) region, wherein said VH region comprises the CDR1, CDR2, and CDR3 regions having the three CDR sequences selected from one of the groups consisting of;

a) CDR1, CDR2 and CDR3 sequences set forth in SEQ ID NO: 54, 2, 3 [T31M];

b) CDR1, CDR2 and CDR3 sequences set forth in SEQ ID NO: 58, 2, 3 [T31P];

c) CDR1, CDR2 and CDR3 sequences set forth in SEQ ID NO: 1, 106, 3 [N57E];

d) CDR1, CDR2 and CDR3 sequences set forth in SEQ ID NO: 1, 2, 176 [H101G];

e) CDR1, CDR2 and CDR3 sequences set forth in SEQ ID NO: 1, 2, 184 [H101N];

f) CDR1, CDR2 and CDR3 sequences set forth in SEQ ID NO: 1, 2, 220 [G105P];

g) CDR1, CDR2 and CDR3 sequences set forth in SEQ ID NO: 1, 2, 236 [S110A];

h) CDR1, CDR2 and CDR3 sequences set forth in SEQ ID NO: 1, 2, 244 [S110G];

i) CDR1, CDR2 and CDR3 sequences set forth in SEQ ID NO: 1, 2, 284 [Y114M];

j) CDR1, CDR2 and CDR3 sequences set forth in SEQ ID NO: 1, 2, 292 [Y114R];

k) CDR1, CDR2 and CDR3 sequences set forth in SEQ ID NO: 1, 2, 298 [Y114V], and l) CDR1, CDR2 and CDR3 sequences as specified in a) to k) having at most 5 further mutations or substitutions, at most 4 further mutations or substitutions, at most 3 further mutations or substitutions, at most 2 further mutations or substitutions, or at most 1 further mutation or substitution, in total across the three CDR sequences, and which mutations or substitutions preferably do not modify the binding affinity to human CD3.

In one embodiments of the invention the further mutations or substitutions are conservative, physical or functional amino acids.

In some embodiments binding to CD3 may be binding to full length CD3 such as CD3 present on a T cell. In other embodiments binding to CD3 may be binding to a CD3 peptide e.g. as set forth in SEQ ID NO: 402. Binding to the CD3 peptide and whether or not any further mutations may modify binding to CD3 can be determined by Bio-Layer Interferometry as disclosed in Example 7.

In one embodiment, the antibody comprises an Fc region comprising a first and a second immunoglobulin heavy chain.

The term "C1q binding" as used herein, refers to the binding of C1q to an antibody, when said antibody is bound to its antigen. The term "bound to its antigen" as used herein, refers to binding of an antibody to its antigen both in vivo and in vitro.

The term "reduced" as used herein when referring to C1q binding, refers to the ability of the antibody according to the invention to reduce, minimize or even completely Inhibit the binding of C1q to the antibody when compared to the C1q binding to a wild-type antibody.

The term "reduced" or "reducing" as used herein or any variation thereof when used in relation to binding affinity of an antibody binding to human CD3, refers to a binding affinity that is lower when compared to a reference binding affinity. In this context, the reference binding affinity may be the binding affinity of reference antibody specified by the VH sequence SEQ ID NO:4 and the VL sequence SEQ ID NO:8 when binding to the CD3 peptide as SEQ ID NO: 402 and determined by Bio-Layer Interferometry as described in example 7.

The term "binding affinity" as used herein refers to the binding of an antibody to a predetermined antigen or target to which binding typically is with an affinity corresponding to a $K_D$. The term "$K_D$" (M), as used herein, refers to the dissociation equilibrium constant of a particular antibody-antigen Interaction.

The term "wild-type antibody" as used herein, in relation to use in comparison assays of an antibody according to the present invention, refers to an antibody which is Identical to the antibody to be tested except for not being inert. In this context, the term "inert" refers to a modified Fc region having reduced or no binding of C1q, i.e. where C1q binding is determined by ELISA; reduced or no Fc-mediated T cell proliferation as determined in a PBMC based functional assay, i.e. T cell proliferation is measured in a peripheral blood mononuclear cell (PBMC)-based functional assay; and/or reduced or no Fc-mediated CD69 expression as determined in a PBMC-based functional assay. Thus, the wild-type antibody comprises the naturally occurring amino acids in the immunoglobulin heavy chains, i.e. an antibody which does not comprise any amino acid modifications which may alter or reduce the ability of the antibody to Interact with e.g. C1q, Fc Receptors or the like. Thus, such a wild-type antibody will remain an activating antibody which is able to bind e.g. C1q. A wild-type antibody and an antibody of the present invention may comprise other amino acid modifications than those affecting the antibody's ability of Inducing effector functions, in order to make the antibody a bispecific antibody or the like.

The term "ELISA" as used herein refers to enzyme-linked immunosorbent assay which is a test that uses antibodies and color change to Identify a substance. A first specific antibody is attached to the plate surface. Thereby the protein from a sample is added wherein binding to said first specific antibody is tested. A second antibody binding the antibody from the sample is added. The second antibody is linked to an enzyme, and, in the final step, a substance containing the enzyme's substrate is added. The subsequent reaction produces a detectable signal, most commonly a color change in the substrate. The concept of the ELISA method is well-known within the art and various ways of performing an ELISA are contemplated to be part of a method to evaluate the antibody according to the invention Specifically, the ability of an antibody according to the present invention to bind C1q may be determined by ELISA comprising the steps of (1) coating said antibody on a 96-well plate, (ii) adding 3% serum, (iii) adding an anti-human C1q antibody, (iv) developing the plate, and (v) measuring $OD_{405}$ nm. Thus, in one embodiment, the antibody comprises an Fc region which has been modified so that binding of C1q to said antibody is reduced compared to a wild-type antibody by at least 70%, at least 80%, at least 90%, at least 95%, at least 97%, or 100%, wherein C1q binding is determined by ELISA comprising the steps of (1) coating said antibodies on a 96-well plate, (ii) adding 3% serum, (iii) adding an anti-human C1q, (iv) developing the plate, and (v) measuring $OD_{405}$ nm.

The terms "Fc Receptor" or "FcR" as used herein, refers to a protein found on the surface of certain cells. FcRs bind to the Fc region of antibodies. There are several different types of FcRs which are classified based on the type of antibody they recognize. E.g. Fcγ (gamma) Receptors bind to antibodies of the IgG class.

The terms "Fcγ Receptor", "Fc gamma Receptor" or "FcγR" as used herein, refers to a group of Fc Receptors belonging to the immunoglobulin superfamily and is the most Important Fc receptors for Inducing phagocytosis of opsonized (coated) microbes. This family Includes several members, FcγRI (CD64), FcγRIIa (CD32a), FcγRIIb (CD32b), FcγRIIIa (CD16a), FcγRIIIb (CD16b), which differ in their antibody affinities due to their different molecular structure.

Fc-mediated effector functions form part of the biological activity of human immunoglobulin G (IgG) molecules. Examples of such effector functions Include e.g. antibody-dependent cell-mediated cytotoxicity (ADCC) and complement-dependent cytotoxicity (CDC) which are triggered by the binding of various effector molecules to the Fc region. In the context of the present invention, "Fc binding", "Fc Receptor binding", "FcR binding", and "binding of an antibody Fc region to FcR" refers to the binding of the Fc region to an Fc Receptor (FcR) or an effector molecule. The terms "FcγR binding" and "FcγRI binding" refer to binding to or with an Fc region to the Fc gamma Receptor and Fc gamma Receptor I, respectively. When a CD3 antibody binds T cells, the wild-type Fc region of the CD3 antibody binds to FcRs present on other cells, e.g. monocytes, which leads to non-specific, Fc-mediated activation of the T cell. Such non-specific, Fc-mediated activation of T cells may be undesired. T cells may also be activated by targeted, or target-specific, T cell activation. Such targeted T cell activation may be highly desirable for the treatment of a range of Indications, such as cancer. The term "targeted T cell activation" as used herein, refers to directing the T cells to specific cells, such as tumor cells by use of a bispecific antibody comprising a first binding region binding a specific target, such as a tumor target on a tumor cell, and a second binding region binding a T cell specific target, such as CD3. Thus, targeting of T cells to specific cells, e.g. tumor cells, may be facilitated by use of a bispecific antibody, wherein one of the binding regions binds CD3 present on the T cell and the other binding region binds a target specific antigen, e.g. on a tumor cell. Although, non-specific, Fc-mediated T cells activation may still be possible and therefore such undesired non-specific, Fc-mediated T cell activation via Fc-mediated cross-linking should be avoided and may be disabled by making the Fc region inert for such activity. Thereby, Interaction between said inert Fc region with Fc Receptors present is prevented.

An antibody according to the present invention may comprise modifications in the Fc region. When an antibody comprises such modifications it may become an inert, or non-activating, antibody. The term "inertness", "inert" or "non-activating" as used herein, refers to an Fc region which is at least not able to bind any Fcγ Receptors, Induce Fc-mediated cross-linking via FcRs, or induce FcR-mediated cross-linking of target antigens via the Fc region, or is not able to bind C1q. The Inertness of an Fc region of a humanized or chimeric CD3 antibody is advantageously tested using the antibody in a monospecific format although an inert Fc region so Identified can be used in bispecific or other humanized or chimeric multispecific CD3 antibodies.

Several variants can be constructed to make the Fc region of an antibody Inactive for Interactions with Fc gamma Receptors and C1q for therapeutic antibody development. Examples of such variants are described herein.

Thus, in one embodiment, the antibody comprises an Fc region which has been modified so that said antibody mediates reduced Fc-mediated T cell proliferation compared to a wild-type antibody by at least 50%, at least 60%, at least 70%, at least 80%, at least 90%, at least 99% or 100%, wherein said T cell proliferation is measured in a peripheral blood mononuclear cell (PBMC)-based functional assay.

The term "reduce" when referring to T cell proliferation, refers to the ability of the antibody according to the invention to reduce, minimize or even completely Inhibit the proliferation of T cells when compared to the proliferation of T cells bound by a wild-type antibody. The ability of an antibody to reduce T cell proliferation may be evaluated by a PBMC-based functional assay. In one embodiment the assay is performed with human PBMCs. In another embodiment the assay is performed with cynomolgus PBMCs. In yet another embodiment, the assay is performed with rhesus PBMCs. Since the antibodies according to the present invention are cross-reactive, a PBMC-based assay as herein described may be performed with any species PBMCs to show reduction of T cell proliferation as long as the species PBMC used are within the cross-reactivity spectra of the antibodies, e.g. human, cynomolgus or rhesus monkeys.

The term "peripheral blood mononuclear cell (PBMC)-based functional assay" as used herein refers to an assay used for evaluating a functional feature of the antibody of the present invention, such as the ability of said antibody to affect T cell proliferation or CD69 expression, wherein the only cells present are peripheral blood mononuclear cells. Thus, in one embodiment, T cell proliferation is measured by a method comprising the steps of Incubating PBMCs with antibody in the range of 1-1000 ng/mL at 37° C. in a 5% (vol/vol) $CO_2$ humidified Incubator for three days, adding a chemical compound, such as BrdU, which is Incorporated Into the DNA of proliferating cells, Incubating for five hrs., pelleting cells, drying cells, optionally storing the cells at 4° C., coating cells to ELISA plates, Incubating with anti-BrdU-peroxidase for 90 min at room temperature, developing for about 30 min with 1 mg/mL 2,2'-azino-bis (3-ethylbenzothiazoline-6-sulfonic acid), adding 100 μL 2% oxalic acid to stop the reaction, and measuring absorbance at 405 nm in a suitable microplate reader.

The term "proliferation" as used herein, refers to cell growth in the context of cell division.

The term "BrdU" as used herein, refers to 5-bromo-2'-deoxyuridine, which is a homologue to thymidine. When BrdU is added to cell culture for a limited period of time (e.g. 4 hours) It will be Incorporated Into the DNA of proliferating cells. After fixing the cells, detection of Incorporated BrdU may be performed in an ELISA using anti-BrdU-peroxidase. BrdU Incorporation is therefore a measure for proliferation.

In one embodiment, the antibody comprises an Fc region which has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

In particular, the term "reduce" when referring to expression level of the T cell activation marker CD69, refers to a reduction in expression level of CD69 when compared to expression level of CD69 when the T cell is bound by a wild-type antibody bound to CD3 and Interacting with an Fc receptor. An antibody's ability to reduce expression of CD69 may be evaluated by a PBMC-based functional. Thus, in one embodiment, expression of CD69 is measured by a method comprising the steps of incubating PBMCs with an antibody in the range of 1-1000 ng/mL at 37° C. in a 5% (vol/vol) $CO_2$ humidified Incubator for 16-24 hrs, washing the cells, staining the cells at 4° C. with a mouse anti-human CD28-PE and mouse-anti-human CD69-APC antibody, and determining CD69-expression on CD28 positive cells by flow cytometry.

The term "CD69" as used herein, refers to Cluster of Differentiation 69 which is a human transmembrane C-Type lectin protein encoded by the CD69 gene. Activation of T lymphocytes and natural killer (NK) cells, both in vivo and in vitro, Induces expression of CD69. CD69 function as a signal transmitting receptor Involved in cellular activation events Including proliferation, functions as a signal-transmitting receptor in lymphocytes, including natural killer cells and platelets, and the Induction of specific genes.

The term "peripheral blood mononuclear cell (PBMC)-based functional assay" as used herein refers to an assay used for evaluating a functional feature of the antibody of the present Invention, such as the ability of said antibody to affect T cell proliferation or CD69 expression, wherein the only cells present are peripheral blood mononuclear cells. A PBMC-based functional assay comprises the steps of (1) Incubating PBMCs with an antibody at 37° C. in a 5% (vol/vol) $CO_2$ humidified Incubator for about 16-24 hrs, (ii) washing the cells, (iii) staining the cells at 4° C. with a mouse anti-human CD28-PE and mouse-anti-human CD69-APC antibody, and (iv) determining the CD69 expression on CD28 positive cells by flow cytometry, when CD69 expression is evaluated.

Amino acids in the Fc region that play a dominant role in the Interactions with C1q and the Fc Gamma Receptors may be modified. Examples of amino acid positions that may be modified Include positions L234, L235 and P331. Combinations thereof, such as L234F/L235E/P331S, can cause a profound decrease in binding to human CD64, CD32A, CD16 and C1q.

Hence, in one embodiment, the amino acid in at least one position corresponding to L234, L235 and P331, may be A, A and S, respectively ([1], [28]). Also, L234F and L235E amino acid substitutions can result in Fc regions with abrogated Interactions with Fc Gamma Receptors and C1q ([29]-[30]). Hence, in one embodiment, the amino acids in the positions corresponding to L234 and L235, may be F and E, respectively. A D265A amino acid substitution can decrease binding to all Fc gamma Receptors and prevent ADCC ([31]). Hence, in one embodiment, the amino acid in the position corresponding to D265 may be A. Binding to C1q can be abrogated by mutating positions D270, K322, P329, and P331. Mutating these positions to either D270A or K322A or P329A or P331A can make the antibody deficient in CDC activity ([32]). Hence, in one embodiment, the amino acids in at least one position corresponding to D270, K322, P329 and P331, may be A, A, A, and A, respectively.

An alternative approach to minimize the Interaction of the Fc region with Fc gamma Receptors and C1q is by removal of the glycosylation site of an antibody. Mutating position N297 to e.g. Q, A, and E removes a glycosylation site which is critical for IgG-Fc gamma Receptor Interactions. Hence, in one embodiment, the amino acid in a position corresponding to N297, may be G, Q, A or E ([33]). Another alternative approach to minimize Interaction of the Fc region with Fc gamma Receptors may be obtained by the following mutations; P238A, A327Q, P329A or E233P/L234V/L235A/G236del ([31]).

Alternatively, human IgG2 and IgG4 subclasses are considered naturally compromised in their Interactions with C1q and Fc gamma Receptors although, Interactions with Fcγ Receptors (Fc gamma Receptors) were reported ([34]-[35]). Mutations abrogating these residual Interactions can be made in both isotypes, resulting in reduction of unwanted side-effects associated with FcR binding. For IgG2, these include L234A and G237A, and for IgG4, L235E. Hence, in one embodiment, the amino acid in a position corresponding to L234 and G237 in a human IgG2 heavy chain, may be A and A, respectively. In one embodiment, the amino acid in a position corresponding to L235 in a human IgG4 heavy chain, may be E.

Other approaches to further minimize the Interaction with Fc gamma Receptors and C1q in IgG2 antibodies include those described in [36] and [37].

The hinge region of the antibody can also be of Importance with respect to Interactions with Fc gamma Receptors and complement ([38]-[39]). Accordingly, mutations in or deletion of the hinge region can Influence effector functions of an antibody.

The term "cross-linking" as used herein, refers to the Indirect bridging of antibody Fab arm(s) (monovalently or bivalently) bound to the target antigen by FcR-bearing cell through binding to the antibody Fc region. Thus, an antibody which binds its target antigen on target antigen-bearing cells may cross-link with another cell expressing FcRs.

The term "unspecific killing" as used herein, refers to the killing of cells by the cytotoxic function of T cells or other effector cells, through tumor target antigen-Independent activation of said cells. Thus, by unspecific killing is meant that the tumor-target bearing cells may be killed by e.g. cytotoxic T cells and not by the antibody binding the tumor target by e.g. Induction of CDC.

A non-activating Fc region may be obtained by modifying one or more of at least five specific amino acid positions in the Fc region.

In one embodiment, the antibody comprises an Fc region comprising a first and a second immunoglobulin heavy chain.

Thus, in one embodiment, the antibody comprises a first and a second immunoglobulin heavy chain, wherein in at least one of said first and second immunoglobulin heavy chains one or more amino acids in the positions corresponding to positions L234, L235, D265, N297, and P331 in a human IgG1 heavy chain, are not L, L, D, N, and P, respectively.

In one embodiment, in both the first and second heavy chains one or more amino acids in the position corresponding to positions L234, L235, D265, N297, and P331 In a human IgG1 heavy chain, are not L, L, D, N, and P, respectively.

In another embodiment, in at least one of the first and second heavy chains one or more amino acids in the positions corresponding to positions L234, L235 and D265 In a human IgG1 heavy chain, are not L, L and D, respectively, and the amino acids in the positions corresponding to N297 and P331 in a human IgG1 heavy chain, are N and P, respectively.

The term "amino acid corresponding to positions" as used herein refers to an amino acid position number in a human IgG1 heavy chain. Unless otherwise stated or contradicted by context, the amino acids of the constant region sequences are herein numbered according to the Eu-index of numbering (described in [27]). Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% Identity to a human IgG1 heavy chain. It is considered well-known in the art how to align a sequence or segment in a sequence and thereby determine the corresponding position in a sequence to an amino acid position according to the present invention.

In the context of the present invention, the amino acid may be defined as described above.

The term "the amino acid is not" or similar wording when referring to amino acids in a heavy chain is to be understood to mean that the amino acid is any other amino acid than the specific amino acid mentioned. For example, the amino acid in the position corresponding to L234 in a human IgG1 heavy chain is not L, means that the amino acid may be any of the other naturally or non-naturally occurring amino acids than L.

In one embodiment, in at least one of said first and second heavy chains the amino acid in the position corresponding to position D265 in a human IgG1 heavy chain, is not D.

In one embodiment, in at least one of the first and second heavy chains the amino acid in the position corresponding to D265 in a human IgG1 heavy chain, is not D, and the amino acids in the positions corresponding to positions N297 and P331 in a human IgG1 heavy chain, are N and P, respectively.

In one embodiment, in at least one of said first and second heavy chains the amino acids in the positions corresponding to position D265 in a human IgG1 heavy chain is hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second heavy chains the amino acid in the position corresponding to position D265 in a human IgG1 heavy chain is selected from the group of amino acids consisting of; A, C, F, G, H, I, L, M, R, T, V, W and Y.

The term "polar" as used herein in relation to amino acid residues, refers to any amino acid residue selected from the group consisting of; C, D, E, H, K, N, Q, R, S, and T. Thus, in one embodiment, in at least one of said first and second heavy chains the amino acid in the position corresponding to position D265 in a human heavy chain is selected from the group consisting of; C, E, H, K, N, Q, R, S, and T.

In another embodiment, in at least one of said first and second heavy chains the amino acid in the position corresponding to position D265 in a human IgG1 heavy chain is an aliphatic uncharged, aromatic or acidic amino acid.

The term "aliphatic uncharged" as used herein in relation to amino acid residues, refers to any amino acid residue selected from the group consisting of: A, G, I, L, and V. Thus, in one embodiment, in at least one of said first and second heavy chains the amino acid in the position corresponding to position D265 in a human IgG1 heavy chain is selected from the group consisting of; A, G, I, L, and V.

The term "aromatic" as used herein in relation to amino acid residues, refers to any amino acid residue selected from the group consisting of: F, T, and W. Thus, in one embodiment, in at least one of said first and second heavy chains the amino acid in the position corresponding to position D265 in a human IgG1 heavy chain is selected from the group consisting of; F, T, and W.

The term "acidic" as used herein in relation to amino acid residues, refers to any amino acid residue chosen from the group consisting of: D and E. Thus, in one embodiment, in at least one of said first and second heavy chains the amino acid in the position corresponding to position D265 in a human IgG1 heavy chain is selected from the group consisting of; D and E.

In a particular embodiment, in at least one of said first and second heavy chains the amino acid in the position corresponding to position D265 in a human IgG1 heavy chain is selected from the group consisting of; A, E, F, G, I, L, T, V, and W.

In one embodiment, in both said first and second heavy chains the amino acid in the position corresponding to position D265 in a human IgG1 heavy chain, is not D.

In one embodiment, in both the first and second heavy chains the amino acid in the position corresponding to D265 in a human IgG1 heavy chain, is not D, and the amino acids in the positions corresponding to positions N297 and P331 in a human IgG1 heavy chain, are N and P, respectively.

In one embodiment, in both said first and second heavy chains the amino acid in the position corresponding to position D265 in a human IgG1 heavy chain is hydrophobic or polar amino acid.

The term "hydrophobic" as used herein in relation to an amino acid residue, refers to an amino acid residue selected from the group consisting of; A, C, F, G, H, I, L, M, R, T, V, W, and Y. Thus, in one embodiment, in both said first and second heavy chains the amino acid in the position corresponding to position D265 in a human IgG1 heavy chain is selected from the group of amino acids consisting of; A, C, F, G, H, I, L, M, R, T, V, W and Y.

The term "polar" as used herein in relation to amino acid residues, refers to any amino acid residue selected from the group consisting of; C, D, E, H, K, N, Q, R, S, and T. Thus, in one embodiment, in both said first and second heavy chains the amino acid in the position corresponding to position D265 in a human heavy chain is selected from the group consisting of; C, E, H, K, N, Q, R, S, and T. In one embodiment, in both said first and second heavy chains the amino acid in the position corresponding to position D265 in a human IgG1 heavy chain is selected from the group of amino acids consisting of; A, C, F, G, H, I, L, M, R, T, V, W and Y.

In one embodiment, in both said first and second heavy chains the amino acids in the positions corresponding to position D265 in a human heavy chain is selected from the group consisting of; C, E, H, K, N, Q, R, S, and T.

In another embodiment, in both said first and second heavy chains the amino acid in the position corresponding to position D265 in a human IgG1 heavy chain is aliphatic uncharged, aromatic or acidic amino acids.

The term "aliphatic uncharged" as used herein in relation to amino acid residues, refers to any amino acid residue selected from the group consisting of: A, G, I, L, and V. Thus, in one embodiment, in both said first and second heavy chains the amino acid in the position corresponding to position D265 in a human IgG1 heavy chain is selected from the group consisting of; A, G, I, L, and V.

The term "aromatic" as used herein in relation to amino acid residues, refers to any amino acid residue selected from the group consisting of: F, T, and W. Thus, in one embodiment, in both said first and second heavy chains the amino acid in the position corresponding to position D265 in a human IgG1 heavy chain is selected from the group consisting of; F, T, and W.

The term "acidic" as used herein in relation to amino acid residues, refers to any amino acid residue chosen from the group consisting of: D and E. Thus, in one embodiment, in both said first and second heavy chains the amino acid in the position corresponding to position D265 in a human IgG1 heavy chain are selected from the group consisting of; D and E.

In a particular embodiment, in both said first and second heavy chains the amino acid in the position corresponding to position D265 in a human IgG1 heavy chain is selected from the group consisting of; A, E, F, G, I, L, T, V, and W.

In further embodiment, in at least one of said first and second heavy chains the amino acid in the position corresponding to position N297 in a human IgG1 heavy chain, is not N.

In one embodiment, in at least one of the first and second heavy chains the amino acid in the position corresponding to N297 in a human IgG1 heavy chain, is not N, and the amino acid in the position corresponding to position P331 in a human IgG1 heavy chain, is P.

In one embodiment, in both said first and second heavy chains the amino acid in the position corresponding to positions N297 in a human IgG1 heavy chain, is not N.

In one embodiment, in both the first and second heavy chains the amino acid in the position corresponding to N297 in a human IgG1 heavy chain, is not N, and the amino acid in the position corresponding to position P331 in a human IgG1 heavy chain, is P.

In further embodiment, in at least one of said first and second heavy chains the amino acids in the positions corresponding to positions L234 and L235 in a human IgG1 heavy chain, are not L and L, respectively.

In one embodiment, in at least one of the first and second heavy chains the amino acids in the positions corresponding to L234 and L235 in a human IgG1 heavy chain, are not L and L, respectively, and the amino acids in the positions corresponding to positions N297 and P331 in a human IgG1 heavy chain, are N and P, respectively. In one embodiment, in at least one of said first and second heavy chains the amino acids corresponding to positions L234 and L235 in a human IgG1 heavy chain are selected from the group consisting of; A, C, D, E, F, G, H, I, K, M, N, P, Q, R, S, T, Y, V.

In one embodiment, in at least one of said first and second heavy chains the amino acids in the positions corresponding to positions L234 and L235 in a human IgG1 heavy chain are hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second heavy chains the amino acids in the positions corresponding to positions L234 and L235 in a human IgG1 heavy chain are each selected from the group consisting of; A, C, F, G, H, I, M, R, T, V, W, and Y.

The term "polar" as used herein in relation to amino acid residues, refers to any amino acid residue selected from the group consisting of; C, D, E, H, K, N, Q, R, S, and T. Thus, in one embodiment, in at least one of said first and second heavy chains the amino acids in the positions corresponding to positions L234 and L235 in a human IgG1 heavy chain are each selected from the group of amino acids consisting of; C, D, E, H, K, N, Q, R, S, and T.

In a particular embodiment, in at least one of said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y.

In one embodiment, in both said first and second heavy chains the amino acids in the positions corresponding to positions L234 and L235 in a human IgG1 heavy chain, are not L and L, respectively.

In one embodiment, in both the first and second heavy chains the amino acids in the positions corresponding to L234 and L235 in a human IgG1 heavy chain, are not L and L, respectively, and the amino acids in the positions corresponding to positions N297 and P331 in a human IgG1 heavy chain, are N and P, respectively.

In one embodiment, in both said first and second heavy chains the amino acids in the positions corresponding to L234 and L235 in a human IgG1 heavy chain are hydrophobic or polar amino acids.

In one embodiment, in both said first and second heavy chains the amino acids in the positions corresponding to positions L234 and L235 in a human IgG1 heavy chain are each selected from the group consisting of; A, C, F, G, H, I, M, R, T, V, W, and Y. In one embodiment, in both said first and second heavy chains the amino acids in the positions corresponding to positions L234 and L235 in a human IgG1 heavy chain are each selected from the group of amino acids consisting of; C, D, E, H, K, N, Q, R, S, and T.

In a particular embodiment, in both said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y.

In another embodiment, in at least one of said first and second heavy chains the amino acids in the positions corresponding to positions L234 and L235 in a human IgG1 heavy chain are aliphatic uncharged, aromatic or acidic amino acids.

The term "aliphatic uncharged" as used herein in relation to amino acid residues, refers to any amino acid residue selected from the group consisting of: A, G, I, L, and V. Thus, in one embodiment, in at least one of said first and second heavy chains the amino acids in the positions corresponding to positions L234 and L235 in a human IgG1 heavy chain are each selected from the group consisting of; A, G, I, and V.

The term "aromatic" as used herein in relation to amino acid residues, refers to any amino acid residue selected from the group consisting of: F, T, and W. Thus, in one embodiment, in at least one of said first and second heavy chains the amino acids in the positions corresponding to positions L234 and L235 in a human IgG1 heavy chain are each selected from the group consisting of; F, T, and W.

The term "acidic" as used herein in relation to amino acid residues, refers to any amino acid residue chosen from the group consisting of: D and E. Thus, in one embodiment, in at least one of said first and second heavy chains the amino acids in the positions corresponding to positions L234 and L235 in a human IgG1 heavy chain are each selected from the group consisting of; D and E.

In a particular embodiment, in at least one of said first and second heavy chains the amino acids in the positions corresponding to L234 and L235 are each selected from the group consisting of; A, D, E, F, G, I, T, V, and W.

In one embodiment, in at least one of said first and second heavy chains the amino acids in the positions corresponding to positions L234 and L235 in a human IgG1 heavy chain, are F and E; or A and A, respectively.

In one embodiment, in at least one of the first and second heavy chains the amino acids in the positions corresponding to L234 and L235 in a human IgG1 heavy chain, are F and E; or A and A, respectively, and the amino acids in the positions corresponding to positions N297 and P331 In a human IgG1 heavy chain, are N and P, respectively.

In one embodiment, in both said first and second heavy chains the amino acids in the positions corresponding to positions L234 and L235 in a human IgG1 heavy chain, are F and E; or A and A, respectively.

In one embodiment, in both the first and second heavy chains the amino acids in the positions corresponding to L234 and L235 in a human IgG1 heavy chain, are F and E; or A and A, respectively, and the amino acids in the positions corresponding to positions N297 and P331 in a human IgG1 heavy chain, are N and P, respectively.

In a particular embodiment, in at least one of said first and second heavy chains the amino acids in the positions corresponding to positions L234 and L235 in a human IgG1 heavy chain, are F and E, respectively.

In one embodiment, in both said first and second heavy chains the amino acids in the positions corresponding to positions L234 and L235 in a human IgG1 heavy chain, are F and E, respectively.

In one embodiment, in at least one of said first and second heavy chains at least the amino acids in the positions corresponding to positions L234 and L235 in a human IgG1 heavy chain, are A and A, respectively.

In one embodiment, in both said first and second heavy chains at least the amino acids in the positions corresponding to positions L234 and L235 in a human IgG1 heavy chain, are A and A, respectively.

In one embodiment, in at least one of said first and second heavy chains the amino acids in the positions corresponding to positions L234, L235, and D265 in a human IgG1 heavy chain, are not L, L, and D, respectively.

In one embodiment, in at least one of the first and second heavy chains the amino acids in the positions corresponding to L234, L235, and D265 in a human IgG1 heavy chain, are not L, L and D, respectively, and the amino acids in the positions corresponding to positions N297 and P331 in a human IgG1 heavy chain, are N and P, respectively.

In one embodiment, in at least one of said first and second heavy chains the amino acids corresponding to positions L234 and L235 in a human IgG1 heavy chain are selected from the group consisting of; A, C, D, E, F, G, H, I, K, M, N, P, Q, R, S, T, Y, V, and W, and the amino acid corresponding to position D265 is selected from the group consisting of; A, C, E, F, G, H, I, K, L, M, N, P, Q, R, S, T, Y, V, and W.

In one embodiment, in at least one of said first and second heavy chains the amino acids in the positions corresponding to positions L234, L235 and D265 in a human IgG1 heavy chain are hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second heavy chains the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

The term "polar" as used herein in relation to amino acid residues, refers to any amino acid residue selected from the group consisting of; C, D, E, H, K, N, Q, R, S, and T. Thus, in one embodiment, in at least one of said first and second heavy chains the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in at least one of said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 in a human IgG1 heavy chain is selected from the group consisting of; A, C, E, F, G, H, I, K, L, M, N, Q, R, S, T, V, W, and Y.

In one embodiment, in both said first and second heavy chains the amino acids in the positions corresponding to L234, L235, and D265 in a human IgG1 heavy chain are hydrophobic or polar amino acids.

In one embodiment, in both said first and second heavy chains the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

In one embodiment, in both said first and second heavy chains the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in both said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 In a human IgG1 heavy chain is selected from the group consisting of; A, C, E, F, G, H, I, K, L, M, N, Q, R, S, T, V, W, and Y.

In another embodiment, in at least one of said first and second heavy chains the amino acids in the positions corresponding to positions L234, L235 and D265 in a human IgG1 heavy chain are aliphatic uncharged, aromatic or acidic amino acids.

The term "aliphatic uncharged" as used herein in relation to amino acid residues, refers to any amino acid residue selected from the group consisting of: A, G, I, L, and V. Thus, in one embodiment, in at least one of said first and second heavy chains the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

The term "aromatic" as used herein in relation to amino acid residues, refers to any amino acid residue selected from the group consisting of: F, T, and W. Thus, in one embodiment, in at least one of said first and second heavy chains the amino acids in the positions corresponding to positions L234, L235 and D265 in a human IgG1 heavy chain are each selected from the group consisting of; F, T, and W.

The term "acidic" as used herein in relation to amino acid residues, refers to any amino acid residue chosen from the group consisting of: D and E. Thus, in one embodiment, in at least one of said first and second heavy chains the amino acids in the positions corresponding to positions L234, L235, and D265 in a human IgG1 heavy chain are each selected from the group consisting of; D and E.

In a particular embodiment, in at least one of said first and second heavy chains the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In one embodiment, in both said first and second heavy chains the amino acids in the positions corresponding to positions L234, L235 and D265 in a human IgG1 heavy chain, are not L, L, and D, respectively.

In one embodiment, in both the first and second heavy chains the amino acids in the positions corresponding to L234, L235, and D265 in a human IgG1 heavy chain, are not L, L, and D, respectively, and the amino acids in the positions corresponding to positions N297 and P331 in a human IgG1 heavy chain, are N and P, respectively.

In one embodiment, in both said first and second heavy chains the amino acids in the positions corresponding to L234, L235, and D265 in a human IgG1 heavy chain are aliphatic uncharged, aromatic or acidic amino acids.

In one embodiment, in both said first and second heavy chains the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

In one embodiment, in both said first and second heavy chains the amino acids in the positions corresponding to positions L234, L235, and D265 in a human IgG1 heavy chain are each selected from the group consisting of; D and E.

In a particular embodiment, in both said first and second heavy chains the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In one embodiment, in at least one of said first and second heavy chains the amino acids in the positions corresponding to positions L234, L235, and D265 in a human IgG1 heavy chain, are F, E, and A; or A, A, and A, respectively.

In one embodiment, in at least one of the first and second heavy chains the amino acids in the positions corresponding to L234, L235, and D265 in a human IgG1 heavy chain, are F, E, and A; or A, A, and A, respectively, and the amino acids in the positions corresponding to positions N297 and P331 in a human IgG1 heavy chain, are N and P, respectively.

In one embodiment, in both said first and second heavy chains the amino acids in the positions corresponding to positions L234, L235, and D265 in a human IgG1 heavy chain, are F, E, and A; or A, A, and A, respectively.

In one embodiment, in both the first and second heavy chains the amino acids in the positions corresponding to L234, L235, and D265 in a human IgG1 heavy chain, are F, E, and A; or A, A, and A, respectively, and the amino acids in the positions corresponding to positions N297 and P331 in a human IgG1 heavy chain, are N and P, respectively.

In a particular embodiment, in at least one of said first and second heavy chains the amino acids in the positions corresponding to positions L234, L235, and D265 in a human IgG1 heavy chain, are F, E, and A, respectively.

In one embodiment, in both said first and second heavy chains the amino acids in the positions corresponding to positions L234, L235, and D265 in a human IgG1 heavy chain, are F, E, and A, respectively.

In one embodiment, in at least one of said first and second heavy chains the amino acids in the positions corresponding to positions L234, L235, and D265 in a human IgG1 heavy chain, are A, A, and A, respectively.

In one embodiment, in both said first and second heavy chains the amino acids in the positions corresponding to positions L234, L235, and D265 in a human IgG1 heavy chain, are A, A, and A, respectively.

In another embodiment, in at least one of said first and second heavy chains the amino acids in the positions corresponding to positions L234, L235, D265, N297, and P331 in a human IgG1 heavy chain, are F, E, A, Q, and S, respectively.

In one embodiment, in both said first and second heavy chains the amino acids in the positions corresponding to positions L234, L235, D265, N297, and P331 in a human IgG1 heavy chain, are F, E, A, Q, and S, respectively.

In one embodiment, the antibody according to the invention, comprises a VH sequence as set out in any one of the sequences in the group of: SEQ ID NOs: 107; 59; 245; 299; 285; 55; 185; 179; 237; 177 and 293, a VL sequence as set out in SEQ ID NO:8, and in at least one, or both of the heavy chains the amino acids in positions corresponding to positions L234, L235, and D265 in a human IgG1 heavy chain, are F, E, and A, respectively. Hereby embodiments are provided of anti CD3 antibodies with reduced affinity to human CD3 epsilon compared to a reference antibody comprising the VH and VL sequences as set out in SEQ ID NO:4 and 8, and where the antibodies further comprises a non-activating Fc region.

In a particular embodiment, the antibody according to the invention, comprises a VH sequence as set out in any one of the sequences set out in SEQ ID NOs: 107; 59; 245; 299; 285; 55; 185; 179; 237; 177 and 293, a VL sequence as set out in SEQ ID NO:10, and in at least one, or both of the heavy chains the amino acids in positions corresponding to positions L234, L235, and D265 in a human IgG1 heavy chain, are F, E, and A, respectively. Hereby embodiments are provided of anti CD3 antibodies with reduced affinity to human CD3 epsilon compared to a reference antibody comprising the VH and VL sequences as set out in SEQ ID NO:4 and 8, and where the antibodies further comprises a non-activating Fc region and a VL region that allows for enhanced production.

In another embodiment, the antibody according to the invention, comprises a VH sequence as set out in SEQ ID NOs: 221, a VL sequence as set out in SEQ ID NO:8 or 10, and in at least one, or both of the heavy chains the amino acids in positions corresponding to positions L234, L235, and D265 in a human IgG1 heavy chain, are F, E, and A, respectively.

In one embodiment of the present invention the human IgG1 heavy chain has the IgG1m(f) sequence as set out in SEQ ID NO:407. In a further embodiment the amino acids in positions corresponding to positions L234, L235, and D265 in a human IgG1m(f) as set out in SEQ ID NO:407, are F, E, and A, respectively.

In one embodiment of the present invention the human IgG1 heavy chain has the IgG1m(f) sequence as set out in SEQ ID NO:409.

In one aspect, the antibody according to the invention comprises the human IgLC2/IgLC3 constant domain lambda light chain of SEQ ID NO:408.

In one aspect, the antibodies according to the invention may be modified in the light chain (LC) and/or heavy chain (HC) to Increase the expression level and/or production yield. In one embodiment, the antibodies according to the invention may be modified in the light chain (LC). Such modifications are known in the art and may be performed according to the methods described in e.g. Zheng, L., Goddard, J.-P., Baumann, U., & Reymond, J.-L. (2004). Expression Improvement and mechanistic study of the retro-Diels-Alderase catalytic antibody 10F11 by site-directed mutagenesis. Journal of Molecular Biology, 341(3), 807-14. doi:10.1016/j.jmb.2004.06.014.

In one aspect, the antibodies according to the invention may be modified in the VH region and/or the VL region to modify the affinity of the antibodies, such as to reduce or Increase the affinity of the antibodies. This may be advantageous in some settings and lead to Increased efficacy. In particular low affinity of the CD3 arm may have an impact on the motility of T cells in circulation and at tumor site thus leading to better engagement of T cells with tumor cells, cf. Mølhøj et al, Molecular Immunology 44 (2007). In particular this may be useful in bispecific formats, in which a CD3 antibody is used as one of the binding arms. Modifications that lead to reduced antibody affinity are known in the art, see for example Webster et al. Int J Cancer Suppl. 1988; 3:13-6.

Thus in one embodiment the antibody of the present invention comprises a the variable light chain (VL) region comprising the CDR1, CDR2 and CDR3 having the sequences as set forth in SEQ ID NO: 6, GTN, 7 and a variable heavy chain (VH) region, wherein said VH region comprises the CDR1, CDR2, and CDR3 having the CDR sequences selected from one of the groups consisting of;

a) CDR sequences set forth in SEQ ID NO: 54, 2, 3 [T31M];

b) CDR1, CDR2 and CDR3 sequence set forth in SEQ ID NO: 58, 2, 3 [T31P];

c) CDR1, CDR2 and CDR3 sequences set forth in SEQ ID NO: 1, 106, 3 [N57E];

d) CDR1, CDR2 and CDR3 sequences set forth in SEQ ID NO: 1, 2, 176 [H101G];

e) CDR1, CDR2 and CDR3 sequences set forth in SEQ ID NO: 1, 2, 184 [H101N];

f) CDR1, CDR2 and CDR3 sequences set forth in SEQ ID NO: 1, 2, 220 [G105P];

g) CDR1, CDR2 and CDR3 sequences set forth in SEQ ID NO: 1, 2, 236 [S110A];

h) CDR1, CDR2 and CDR3 sequences set forth in SEQ ID NO: 1, 2, 244 [S110G];

i) CDR1, CDR2 and CDR3 sequences set forth in SEQ ID NO: 1, 2, 284 [Y114M];

j) CDR1, CDR2 and CDR3 sequences set forth in SEQ ID NO: 1, 2, 292 [Y114R]; and k) CDR1, CDR2 and CDR3 sequences set forth in SEQ ID NO: 1, 2, 298 [Y114V].

In another aspect, the present invention provides an antibody binding to human CD3, comprising a binding region comprising a variable light chain (VL) region having the sequence set forth in SEQ ID NO 10 and a variable heavy chain (VH) region the CDR1, CDR2 and CDR3 having the sequences selected from one of the groups consisting of:

a) CDR1, CDR2 and CDR3 sequences set forth in SEQ ID NO: 54, 2, 3 [T31M];

b) CDR1, CDR2 and CDR3 sequence set forth in SEQ ID NO: 58, 2, 3 [T31P];

c) CDR1, CDR2 and CDR3 sequences set forth in SEQ ID NO: 1, 106, 3 [N57E];

d) CDR1, CDR2 and CDR3 sequences set forth in SEQ ID NO: 1, 2, 176 [H101G];

e) CDR1, CDR2 and CDR3 sequences set forth in SEQ ID NO: 1, 2, 184 [H101N];

f) CDR1, CDR2 and CDR3 sequences set forth in SEQ ID NO: 1, 2, 220 [G105P];

g) CDR1, CDR2 and CDR3 sequences set forth in SEQ ID NO: 1, 2, 236 [S110A];

h) CDR1, CDR2 and CDR3 sequences set forth in SEQ ID NO: 1, 2, 244 [S110G];

i) CDR1, CDR2 and CDR3 sequences set forth in SEQ ID NO: 1, 2, 284 [Y114M];

j) CDR1, CDR2 and CDR3 sequences set forth in SEQ ID NO: 1, 2, 292 [Y114R]; and k) CDR1, CDR2 and CDR3 sequences set forth in SEQ ID NO: 1, 2, 298 [Y114V].

Hereby embodiments are provided comprising the T41K mutation in the VL region as set forth in SEQ ID NO:10, thereby allowing Increased production of said antibodies.

In one aspect, the present invention relates to a multispecific antibody comprising at least a first binding region of an antibody according to any aspect or embodiment herein described, and one or more binding regions which binds one or more different targets than the first binding region. Such a multispecific antibody may be a bispecific antibody.

Thus, in one aspect, the present invention relates to a bispecific antibody comprising a first binding region of an antibody according to any aspect or embodiment herein described, and a second binding region which binds a different target than the first binding region.

The term "multispecific antibody" refers to an antibody having specificities for at least two different, such as at least three, typically non-overlapping, epitopes. Such epitopes may be on the same or different targets. If the epitopes are on different targets, such targets may be on the same cell or different cells or cell types.

The term "bispecific antibody" refers to an antibody having specificities for at least two different, typically non-overlapping, epitopes. Such epitopes may be on the same or different targets. If the epitopes are on different targets, such targets may be on the same cell or different cells or cell types.

In one embodiment, the bispecific antibody comprises a first and a second heavy chain.

The embodiments relating to modification of the Fc region and embodiments relating to specific amino acid substitutions are contemplated to be part of any bispecific antibody according to the invention. Thus, in one embodiment, at least one of the first and second heavy chains comprise one or more amino acids modified as defined in any embodiment herein described, such as those described to in relation to providing an inert Fc region. In one embodiment, both said first and second heavy chains comprise one or more amino acids modified as defined in any embodiment herein described, such as those described to in relation to providing an inert Fc region. Accordingly, the bispecific antibody comprises an Fc region modified according to any aspect or embodiment herein described; or at least one of said first and second heavy chains comprise one or more amino acids modified as defined in any aspect or embodiment herein described.

Examples of bispecific antibody molecules which may be used in the present invention comprise (1) a single antibody that has two arms comprising different antigen-binding regions, (ii) a single chain antibody that has specificity to two different epitopes, e.g., via two scFvs linked in tandem by an extra peptide linker; (iii) a dual-variable-domain antibody (DVD-Ig™), where each light chain and heavy chain contains two variable domains in tandem through a short peptide linkage ([40]); (iv) a chemically-linked bispecific (Fab')2 fragment; (v) a TandAb®, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so called "dock and lock" molecule (Dock-and-Lock®), based on the "dimerization and docking domain" in Protein Kinase A, which, when applied to Fabs, can yield a trivalent bispecific binding protein consisting of two Identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, or a bispecific antibody obtained via a controlled Fab arm exchange, e.g. DuoBody® (such as described in [41]) as those described in the present invention.

Examples of different classes of bispecific antibodies Include but are not limited to (1) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, Nanobodies®) wherein different single chain Fv molecules or different diabodies or different heavy-chain antibodies (e.g. domain antibodies, Nanobodies®) are fused to each other or to another protein or carrier molecule fused to heavy-chain constant-domains, Fc-regions or parts thereof.

Examples of IgG-like molecules with complementary CH3 domains molecules include but are not limited to the Triomab® (Trion Pharma/Fresenius Biotech, [42]), the Knobs-into-Holes (Genentech, [43]), CrossMAbs (Roche, [44]) and the electrostatically-matched (Amgen, [45]-[46]; Chugai, [47]; Oncomed, [48]), the LUZ-Y (Genentech, Wranik et al. J. Biol. Chem. 2012, 287(52): 43331-9, doi: 10.1074/jbc.M112.397869. Epub 2012 Nov. 1), DIG-body and PIG-body (Pharmabcine, WO2010134666, WO2014081202), the Strand Exchange Engineered Domain body (SEEDbody)(EMD Serono, [49]), the Biclonics (Merus, WO2013157953), FcAdp (Regeneron, [50]), bispecific IgG1 and IgG2 (Pflzer/Rinat, [51]), Azymetric scaffold (Zymeworks/Merck, [52]), mAb-Fv (Xencor, [53]), bivalent bispecific antibodies (Roche, WO2009080254) and Duo-Body® molecules (Genmab A/S, [41]).

Examples of recombinant IgG-like dual targeting molecules include but are not limited to Dual Targeting (DT)-Ig (GSK/Domantis, WO2009058383), Two-in-one Antibody (Genentech, Bostrom, et al 2009. Science 323, 1610-1614), Cross-linked Mabs (Karmanos Cancer Center), mAb2 (F-Star, [54]), Zybodies™ (Zyngenia, LaFleur et al. MAbs. 2013 March-April; 5(2):208-18), approaches with common light chain (Crucell/Merus, [55]), KABodies (NovImmune, WO2012023053) and CovX-Body® (CovX/Pflzer, Doppalapudi, V. R., et al 2007. Bioorg. Med. Chem. Lett. 17, 501-506).

Examples of IgG fusion molecules include but are not limited to Dual Variable Domain (DVD)-Ig™ (Abbott, [56]), Dual domain double head antibodies (Unilever; Sanofi Aventis, [57]), IgG-like Bispecific (ImClone/Eli Lilly, Lewis et al. Nat Biotechnol. 2014 February; 32(2):191-8), Ts2Ab (MedImmune/AZ, Dimasi et al. J Mol Biol. 2009 Oct. 30; 393(3):672-92) and BsAb (Zymogenetics, WO2010111625), HERCULES (Biogen Idec, [58]), scFv fusion (Novartis), scFv fusion (Changzhou Adam Biotech Inc, [59]) and TvAb (Roche, [59], [60]).

Examples of Fc fusion molecules include but are not limited to ScFv/Fc Fusions (Academic Institution, Pearce et al Biochem Mol Biol Int. 1997 September; 42(6):1179-88), SCORPION (Emergent BloSolutions/Trubion, Blankenship J W, et al. AACR 100 th Annual meeting 2009 (Abstract #5465); Zymogenetics/BMS, WO2010111625), Dual Affinity Retargeting Technology (Fc-DART™) (MacroGenics, [62], [63]) and Dual(ScFv)2-Fab (National Research Center for Antibody Medicine—China).

Examples of Fab fusion bispecific antibodies Include but are not limited to F(ab)2 (Medarex/AMGEN), Dual-Action or Bis-Fab (Genentech), Dock-and-Lock® (DNL) (ImmunoMedics), Bivalent Bispecific (Biotecnol) and Fab-Fv (UCB-Celltech).

Examples of ScFv-, diabody-based and domain antibodies Include but are not limited to Bispecific T Cell Engager (BITE®) (Micromet, Tandem Diabody (Tandab) (Affimed), Dual Affinity Retargeting Technology (DART™) (Macro-Genics), Single-chain Diabody (Academic, Lawrence FEBS Lett. 1998 Apr. 3; 425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August; 88(6):667-75), dual targeting Nanobodies® (Ablynx, Hmila et al., FASEB J. 2010), dual targeting heavy chain only domain antibodies.

It is further contemplated that any monospecific antibody fulfilling the assay conditions herein described may form the basis of a bispecific antibody. I.e. a bispecific antibody wherein one of the binding regions binds CD3 may originate from any monospecific CD3 antibody tested in the functional assays and fulfilling the requirements stated herein. Such a bispecific antibody may be provided by the methods described in [41], which is hereby Incorporated by reference.

In one aspect, the bispecific antibody of the Invention comprises a first Fc-region comprising a first CH3 region, and a second Fc-region comprising a second CH3 region, wherein the sequences of the first and second CH3 regions are different and are such that the heterodimeric Interaction between said first and second CH3 regions is stronger than each of the homodimeric Interactions of said first and second CH3 regions.

More details on these Interactions and how they can be achieved are provided in WO2011131746 and WO2013060867 (Genmab), which are hereby Incorporated by reference.

Thus, in a particular embodiment, each of said first and second heavy chain comprises at least a hinge region, a CH2 and CH3 region, wherein in said first heavy chain at least one of the amino acids in the positions corresponding to a position selected from the group consisting of T366, L368, K370, D399, F405, Y407, and K409 in a human IgG1 heavy chain has been substituted, and in said second heavy chain at least one of the amino acids in the positions corresponding to a position selected from the group consisting of T366, L368, K370, D399, F405, Y407, and K409 in a human IgG1 heavy chain has been substituted, and wherein said first and said second heavy chains are not substituted in the same positions. In this context the term "substituted", refers to that the amino acid in a specific amino acid position has been substituted with another naturally or non-naturally occurring amino acid. Thus, a "substituted" amino acid in a position corresponding to the position in a human IgG1 heavy chain means the amino acid at the particular position is different from the naturally occurring amino acid in an IgG1 heavy chain.

In one embodiment, in said first heavy chain the amino acid in the position corresponding to K409 in a human IgG1 heavy chain is not K, L or M, and optionally the amino acid in the position corresponding to F405 in a human IgG1 heavy chain is F, and in said second heavy chain at least one of the amino acids in the positions corresponding to a position selected from the group consisting of; T366, L368, K370, D399, F405, and Y407 In a human IgG1 heavy chain has been substituted.

In one embodiment, in said first heavy chain the amino acid in the position corresponding to K409 in a human IgG1 heavy chain is not K, L or M, and in said second heavy chain the amino acid in the position corresponding to F405 in a human IgG1 heavy chain is not F and optionally the amino acid in the position corresponding to K409 in a human IgG1 heavy chain is K.

In one embodiment, in said first heavy chain, the amino acid in the position corresponding to F405 in a human IgG1 heavy chain is not F, R, and G, and in said second heavy chain the amino acids in the positions corresponding to a position selected form the group consisting of; T366, L368, K370, D399, Y407, and K409 in a human IgG1 heavy chain has been substituted.

In one embodiment, the amino acid in position corresponding to K409 in a human IgG1 heavy chain is not K, L or M in said first heavy chain, and the amino acid in position corresponding to F405 in a human IgG1 heavy chain is not F.

In a further embodiment, the amino acid in the position corresponding to F405 in a human IgG1 heavy chain is L in said first heavy chain, and the amino acid in the position corresponding to K409 in a human IgG1 heavy chain is R in said second heavy chain, or vice versa.

Thus, in one embodiment, the amino acid in the position corresponding to K409 in a human IgG1 heavy chain is R in the first heavy chain, and the amino acid in the position corresponding to F405 in a human IgG1 heavy chain is L in the second heavy chain.

In a further embodiment, the humanized or chimeric CD3 antibody of the Invention contains in at least one of the first and second heavy chain one or more of the Inactivating substitutions as disclosed in any one of the above embodiments, such as L234F, L235E, and D265A; and that the amino acid in the position corresponding to F405 is not F. In one embodiment the humanized or chimeric CD3 antibody of the invention contains in at least one of the first and second heavy chain one or more of the Inactivating substitutions as disclosed in any one of the above embodiments, such as L234F, L235E, and D265A; and a further substitution in the K409 position, such as K409R. In particular, in one embodiment, the humanized or chimeric CD3 antibody of the invention contains in both the first and second heavy chain one or more of the Inactivating substitutions as disclosed in any one of the above embodiments, such as L234F, L235E, and D265A; and a substitution in the F405 position, such as F405L. In one embodiment the humanized or chimeric CD3 antibody of the invention contains in both the first and second heavy chain one or more of the Inactivating substitutions as disclosed in any one of the above embodiments, such as L234F, L235E, and D265A; and a further substitution in the K409 position, such as K409R. Such antibodies are useful for generating a bispecific antibody.

Accordingly, in a further embodiment, in at least one of the first and second heavy chains the amino acids in the positions corresponding to position L234, L235, and D265 in a human IgG1 heavy chain are F, E, and A, respectively, the amino acid in the position corresponding to F405 in a human IgG1 heavy chain is L in the first heavy chain, and the amino acid in the position corresponding to K409 in a human IgG1 heavy chain is R in the second heavy chain.

In one embodiment, in at least one of the first and second heavy chains the amino acids in the positions corresponding to L234, L235, D265, N297, and P331 in a human IgG1 heavy chain are F, E, A, N, and P respectively, the amino acid in the position corresponding to F405 in a human IgG1 heavy chain is L in the first heavy chain, and the amino acid in the position corresponding to K409 in a human IgG1 heavy chain is R in the second heavy chain.

In an alternative embodiment, in at least one of the first and second heavy chains the amino acids in the positions corresponding to position L234, L235, and D265 in a human IgG1 heavy chain are F, E, and A, respectively, the amino acid in the position corresponding to K409 in a human IgG1 heavy chain is R in the first heavy chain, and the amino acid in the position corresponding to F405 in a human IgG1 heavy chain is L in the second heavy chain.

In one embodiment, in at least one of the first and second heavy chains the amino acids in the positions corresponding to L234, L235, D265, N297, and P331 in a human IgG1 heavy chain are F, E, A, N, and P respectively, the amino acid in the position corresponding to K409 in a human IgG1 heavy chain is R in the first heavy chain, and the amino acid in the position corresponding to F405 in a human IgG1 heavy chain is L in the second heavy chain.

In another embodiment, in both the first and second heavy chains the amino acids in the positions corresponding to position L234, L235, and D265 in a human IgG1 heavy chain are F, E, and A, respectively, the amino acid in the position corresponding to F405 in a human IgG1 heavy chain is L in the first heavy chain, and the amino acid in the position corresponding to K409 in a human IgG1 heavy chain is R in the second heavy chain.

In one embodiment, in both the first and second heavy chains the amino acids in the positions corresponding to L234, L235, D265, N297, and P331 in a human IgG1 heavy chain are F, E, A, N, and P respectively, the amino acid in the position corresponding to F405 in a human IgG1 heavy chain is L in the first heavy chain, and the amino acid in the position corresponding to K409 in a human IgG1 heavy chain is R in the second heavy chain.

In an alternative embodiment, in both the first and second heavy chains the amino acids in the positions corresponding to position L234, L235, and D265 in a human IgG1 heavy chain are F, E, and A, respectively, the amino acid in the position corresponding to K409 in a human IgG1 heavy chain is R in the first heavy chain, and the amino acid in the position corresponding to F405 in a human IgG1 heavy chain is L in the second heavy chain.

In one embodiment, in both the first and second heavy chains the amino acids in the positions corresponding to L234, L235, D265, N297, and P331 in a human IgG1 heavy chain are F, E, A, N, and P respectively, the amino acid in the position corresponding to K409 in a human IgG1 heavy chain is R in the first heavy chain, and the amino acid in the position corresponding to F405 in a human IgG1 heavy chain is L in the second heavy chain.

As described herein, T cell recruitment to specific target cells, such as cancer or tumor cells, provides a way of killing the target cells. T cell mediated killing may be obtained by a bispecific antibody targeting CD3 with the first binding region and another target with the second binding region. Thus, in one embodiment, the first binding region is according to any embodiments described herein for the humanized or chimeric CD3 antibody, and the second binding region binds a different target than the first binding region. It is to be understood that when the antibody is a bispecific antibody, at least one half of the antibody, i.e. one of the pair of heavy and light chains of the antibody, is a humanized or chimeric antibody as herein described. Thus, one half of the bispecific antibody is a humanized or chimeric antibody binding CD3 according to the present invention and the other half may be humanized, chimeric, fully non-human or fully human binding a second target. Thus, in one embodiment, the antibody comprises a first and a second heavy chain, a first and second light chain, wherein said first heavy and said first light chains are humanized or chimeric and are connected via disulfide bridges forming a first binding region; and said second heavy and light chains are fully human and are connected via disulfide bridges forming a second binding region, wherein said first binding region is according to any aspect or embodiment herein described, and said second binding region binds a different target. In one embodiment, the antibody comprises a first and a second heavy chain, a first and second light chain, wherein said first heavy and said first light chains are humanized or chimeric and are connected via disulfide bridges forming a first binding region; and said second heavy and light chains are humanized or chimeric and are connected via disulfide bridges forming a second binding region, wherein said first binding region is according to any aspect or embodiment herein described, and said second binding region binds a different epitope of CD3 than said first binding region.

The term "disulfide bridges" as used herein refers to the covalent bond between two Cysteine residues, i.e. said Interaction may also be designated a Cys-Cys Interaction.

The term "target" as used herein, refers to a molecule to which the binding region of the antibody according to the invention binds. When used in the context of the binding of an antibody the term Includes any antigen towards which the raised antibody is directed.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different target; and wherein in at least one of the first and second heavy chains the amino acids in the positions corresponding to positions L234, L235, and D265 in a human IgG1 heavy chain, are F, E, and A, respectively.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different epitope of CD3 than the first binding region; and wherein in at least one of the first and second heavy chains the amino acids in the positions corresponding to positions L234, L235, and D265 in a human IgG1 heavy chain, are F, E, and A, respectively.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different target; and wherein in both the first and second heavy chains the amino acids in the positions corresponding to positions L234, L235, and D265 in a human IgG1 heavy chain, are F, E, and A, respectively.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different epitope of CD3 than the first binding region; and wherein in both the first and second heavy chains the amino acids in the positions corresponding to positions L234, L235, and D265 in a human IgG1 heavy chain, are F, E, and A, respectively.

In another aspect, the present Invention relates to a method of reducing the binding affinity of an antibody binding to human CD3 compared to a reference antibody comprising a heavy chain variable (VH) region, wherein said VH region comprises the CDR1, CDR2, and CDR3 sequences set forth in SEQ ID NO: 1, 2, 3, which method comprises Introducing a mutation in one of the three CDR sequences of the said reference antibody selected from a mutation in one of the positions selected from the group of T31M, T31P, N57, H101, S110 and Y114, wherein the positions are numbered according to the reference sequence of the SEQ ID NO: 4.

The numbering of the amino acids in the VH regions and the positions to be mutated are according to the amino acids in SEQ ID NO: 4. Numbering are according to a direct numerical numbering scheme from the first amino acid to number 125 in the direction from N-terminus to the C-terminus. The numerical numbering of positions corresponding to SEQ ID NO:4 Is Illustrated in FIG. 2. Further, The CDR regions have been annotated according to the IMGT definitions.

In one embodiment of the invention the method comprises Introducing a T31M or T31P mutation. Position T31 is in accordance to SEQ ID NO:4.

In one embodiment of the invention the method comprises Introducing a mutation in the position N57. Position N57 is in accordance to SEQ ID NO:4. In one embodiment the mutation is N57E In one embodiment of the invention the method comprises Introducing a mutation in the position H101. Position H101 is in accordance to SEQ ID NO: 4. In one embodiment the mutation Is H101G or H101N.

In one embodiment of the invention the method comprises Introducing a mutation in the position Y114. Position Y114 is in accordance to of SEQ ID NO: 4. In one embodiment the mutation is Y114, Y114R or Y114V.

In one embodiment of the invention the method comprises Introducing a mutation in the mutation in the VH CDR3 region corresponding to a position selected from the group of H101, S110 and Y114.

In one embodiment of the invention the method comprises Introducing a mutation in the VH CDR3 region is selected from the group consisting of H101G, H101N, S110A, S110G, Y114M, Y114R and Y114V.

In one embodiment of the invention the method comprises Introducing a mutation, wherein antibody has a binding affinity to human CD3 epsilon peptide with SEQ ID NO: 402 corresponding to a $K_D$ value from $1.6 \times 10^{-8}$ M to $9.9 \times 10^{-8}$ M or from $1.0 \times 10^{-7}$ to $9.9 \times 10^{-7}$ M as determined by Bio-Layer Interferometry.

In one embodiment of the invention the method comprises Introducing a mutation, wherein the antibody has a binding affinity to human CD3 epsilon peptide with SEQ ID NO: 402 corresponding to a $K_D$ value from $1.4 \times 10^{-8}$ to $1.0 \times 10^{-8}$ M or from as $9.9 \times 10^{-8}$ to $1 \times 10^{-8}$ M as determined by Bio-Layer Interferometry.

In one embodiments of the present invention the antibody has a binding affinity to human CD3 epsilon peptide with SEQ ID NO: 402 corresponding to a $K_D$ value from $1.6 \times 10^{-8}$ M to $9.9 \times 10^{-8}$ M or from $1.0 \times 10^{-7}$ to $9.9 \times 10^{-7}$ M as determined by Bio-Layer Interferometry. In another aspect, the present invention relates to a method of Increasing the binding affinity of an antibody binding to human CD3 compared to a reference antibody comprising a heavy chain variable (VH) region, wherein said VH region comprises the CDR1, CDR2, and CDR3 sequences set forth in SEQ ID NO: 1, 2, 3, which method comprises Introducing a mutation in the VH CDR3 corresponding to position G105, wherein the position is numbered according to the reference sequence of the SEQ ID NO: 4.

In one embodiment of the invention the method comprises Introducing a mutation in the position G105. Position G105 is in accordance to SEQ ID NO: 4. In one embodiment the mutation is G105P.

In one embodiment of the invention the method comprises Introducing at most 5 further mutations, at most 4 further mutations, at most 3 further mutations, at most 2 further mutations or at most 1 further mutation into the CDRs of the VH region of the reference antibody as set forth in SEQ ID NO: 1, 2, 3.

In one embodiment of the invention the method of Increased or reduced binding affinity comprises a binding region comprising a heavy chain variable (VH) region, wherein said VH region comprises the CDR1, CDR2, and CDR3 sequences selected from the group consisting of;

a) CDR1, CDR2, and CDR3 sequences set forth in SEQ ID NO: 54, 2, 3 [T31M];

b) CDR1, CDR2, and CDR3 sequences set forth in SEQ ID NO: 58, 2, 3 [T31P];

c) CDR1, CDR2, and CDR3 sequences set forth in SEQ ID NO: 1, 106, 3 [N57E];

d) CDR1, CDR2, and CDR3 sequences set forth in SEQ ID NO: 1, 2, 176 [H101G];

e) CDR1, CDR2, and CDR3 sequences set forth in SEQ ID NO: 1, 2, 184 [H101N];

f) CDR1, CDR2, and CDR3 sequences set forth in SEQ ID NO: 1, 2, 220 [G105P];

g) CDR1, CDR2, and CDR3 sequences set forth in SEQ ID NO: 1, 2, 236 [S110A];

h) CDR1, CDR2, and CDR3 sequences set forth in SEQ ID NO: 1, 2, 244 [S110G];

i) CDR1, CDR2, and CDR3 sequences set forth in SEQ ID NO: 1, 2, 284 [Y114M];

j) CDR1, CDR2, and CDR3 sequences set forth in SEQ ID NO: 1, 2, 292 [Y114R]; and k) CDR1, CDR2, and CDR3 sequences set forth in SEQ ID NO: 1, 2, 298 [Y114V].

In another embodiment of the present invention the method comprises Introducing a mutation in the VH region CDR2 region corresponding to N57E. In a further embodiment of the present invention the method comprises Introducing a mutation in the VH region CDR3 region corresponding to H101G, H101N, G105P, S110A, S110G, Y114M, Y114R or Y114V. In another aspect, the present invention relates to method of reducing or Increasing the binding affinity of an antibody to CD3, wherein said antibody comprises a binding region comprising heavy chain variable (VH) region, wherein said VH region comprises a mutation in one of the three CDR sequences of a reference antibody as set forth by CDR1 SEQ ID: 1, CDR2 SEQ ID: 2 and CDR3 SEQ ID: 3, wherein said antibody comprises a mutation in one of the following positions selected from the group of T31M, T31P, N57, H101, G105, S110 and Y114, wherein the positions are corresponding to the reference sequence of the SEQ ID NO: 4.

In one embodiment of the present invention the method comprises Introducing a mutation in the VH region CDR1 region sequence corresponding to T31M or T31P. In another embodiment of the present invention the method comprises Introducing a mutation in the VH region CDR2 region corresponding to N57E. In a further embodiment of the present invention the method comprises Introducing a mutation in the VH region CDR3 region corresponding to H101G, H101N, G105P, S110A, S110G, Y114M, Y114R or Y114V.

In further aspect, the present invention relates to a method of reducing the binding affinity of an antibody binding to CD3 compared to a reference antibody comprising a heavy chain variable (VH) region, wherein said VH region comprises CDR1, CDR2, and CDR3 having the CDR sequences set forth in SEQ ID NO: 1, 2 and 3, which method comprises Introducing a mutation in one of the VH region CDR1, CDR2 or CDR3 sequences as set forth in SEQ ID NO: 1, 2 or 3.

In one embodiment the present invention the method comprises Introducing a mutation in one of the three CDR regions of the VH region corresponding to one of the following positions: T31, N57, H101, S110 or Y114, wherein the positions are corresponding to the reference sequence of the SEQ ID NO: 4.

In one embodiment of the present invention the method comprises Introducing a mutation in the VH region CDR1 sequence corresponding to position T31, wherein the CDR1 sequence is as set forth in SEQ ID NO 1. When the mutation is represented by X the resulting CDR1 sequence may be presented as GFTFNXYA (SEQ ID NO: 412). In one embodiment the three CDR sequences of the VH region may have the following sequences CDR1 GFTFNXYA (SEQ ID NO: 412), CDR2 IRSKYNNYAT (SEQ ID NO: 2) and CDR3 VRHGNFGNSYVSWFAY (SEO ID NO: 3). In one embodiment the mutation in position T31 in in VH region CDR1 Is a T31M or T31P mutation.

In one embodiment of the present invention the method comprises Introducing a mutation in the VH region CDR2 sequence corresponding to postion N57, wherein the CDR2 sequence is as set forth in SEQ ID NO 2. When the mutation is represented by X the resulting CDR2 sequence may be presented as IRSKYNXYAT (SEQ ID NO: 413). In one embodiment the three CDR sequences of the VH region may have the following sequences CDR1 GFTFNTYA (SEQ ID NO: 1), CDR2 IRSKYNXYAT (SEQ ID NO: 413) and CDR3 VRHGNFGNSYVSWFAY (SEO ID NO: 3). In one embodiment the mutation in position N57 In VH region CDR2 Is a N57E mutation.

In one embodiment of the present invention the method comprises Introducing a mutation in the VH region CDR3 sequence corresponding to postion H101, wherein the CDR3 sequence is as set forth in SEQ ID NO 3. When the mutation is represented by X the resulting CDR3 sequence may be presented as VRXGNFGNSYVSWFAY (SEQ ID NO: 414).

In one embodiment the three CDR sequences of the VH region may have the following sequences CDR1 GFTFN-TYA (SEQ ID NO: 1), CDR2 IRSKYNNYAT (SEQ ID NO: 2) and CDR3 VRXGNFGNSYVSWFAY (SEQ ID NO: 414). In one embodiment the mutation in position H101 in VH region CDR3 is an H101G or an H101N mutation.

In one embodiment of the present invention the method comprises Introducing a mutation in the VH region CDR3 sequence corresponding to postion S110, wherein the CDR3 sequence is as set forth in SEQ ID NO 3. When the mutation is represented by X the resulting CDR3 sequence may be presented as VRHGNFGNSYVXWFAY (SEQ ID NO: 415).

In one embodiment the three CDR sequences of the VH region may have the following sequences CDR1 GFTFN-TYA (SEQ ID NO: 1), CDR2 IRSKYNNYAT (SEQ ID NO: 2) and CDR3 VRHGNFGNSYVXWFAY (SEO ID NO: 415). In one embodiment the mutation in position H101 in VH region CDR3 Is a S110A or a S110G mutation.

In one embodiment of the present invention the method comprises Introducing a mutation in the VH region CDR3 sequence corresponding to position Y114, wherein the CDR3 sequence is as set forth in SEQ ID NO 3. When the mutation is represented by X the resulting CDR3 sequence may be presented as VRHGNFGNSYVSWFAX (SEQ ID NO: 416).

In one embodiment the three CDR sequences of the VH region may have the following sequences CDR1 GFTFN-TYA (SEQ ID NO: 1), CDR2 IRSKYNNYAT (SEQ ID NO: 2) and CDR3 VRHGNFGNSYVSWFAX (SEO ID NO: 416). In one embodiment the mutation in position Y114 in VH region CDR3 Is a Y114M, Y114R or a Y114V mutation.

In one embodiment of the invention the method comprises Introducing at most 3 mutations, at most 2 mutations or at most 1 mutation into the one or more of the three CDRs of the VH region of a reference antibody as set forth in SEQ ID NO: 1, 2, 3.

In one embodiment of the invention the method comprises Introducing at most 10 mutations, at most 9 mutations at, at most 8 mutations, at most 7 mutations, at most 6 mutations, at most 5 mutations, at most 4 mutations, at most 3 mutations, at most 2 mutations or at most 1 mutation into variable heavy chain frame work region of an antibody, wherein said mutations does preferable not alter binding of the antibody to CD3 compared to the same antibody without the mutation(s).

In one embodiment of the present invention the method comprises Introducing a mutation in the VH region CDR1 sequence selected from T31M or T31P. In another embodiment of the present invention the method comprises Introducing a mutation in the VH region CDR2 sequence of N57E. In a further embodiment of the present invention the method comprises Introducing a mutation in the VH region CDR3 sequence selected from the group of: H101G, H101N, S110A, S110G, Y114M, Y114R and Y114V.

In another aspect, the present invention relates to a method of Increasing the binding affinity of an antibody binding to CD3 compared to a reference antibody comprising a heavy chain variable (VH) region, wherein said VH region comprises CDR1, CDR2, and CDR3 having the CDR sequences set forth in SEQ ID NO: 1, 2 and 3, which method comprises Introducing a mutation in one of the VH region CDR1, CDR2 or CDR3 sequences as set forth in SEQ ID NO: 1, 2 or 3.

In one embodiment of the present invention the method comprises Introducing a mutation in the VH region CDR3 sequence corresponding to postion G105, wherein the CDR3 sequence is as set forth in SEQ ID NO 3. When the mutation is represented by X the resulting CDR3 sequence may be presented as VRHGNFXNSYVSWFAY (SEQ ID NO: 417).

In one embodiment the three CDR sequences of the VH region may have the following sequences CDR1 GFTFN-TYA (SEQ ID NO: 1), CDR2 IRSKYNNYAT (SEQ ID NO: 2) and CDR3 VRXGNFGNSYVSWFAY (SEO ID NO: 414). In one embodiment the mutation in position G105 in VH region CDR3 Is a G105P mutation.

Nucleic Acid Constructs, Expression Vectors, and Host Cells

In one aspect, the present invention relates to a nucleic acid construct encoding one or more sequences set out in Table 1. Thus, the present invention relates to a nucleic acid construct encoding any one of the sequences set out in SEQ ID NOs: 107; 221; 59; 245; 299; 285; 55; 185; 179; 237; 177 and 293.

In a further aspect, the invention relates to nucleic acid construct encoding a sequence of a humanized or chimeric CD3 antibody according to the present invention, to expression vectors comprising a nucleic acid construct according to the present invention, to host cells comprising such expression vectors, and to methods of producing such an antibody by culturing such host cells under appropriate conditions whereby the antibody is produced and, optionally, retrieved. Humanized CD3 antibodies may also be denoted as "huCD3".

In one embodiment, the invention provides an expression vector comprising (i) a nucleic acid sequence encoding a heavy chain sequence of a humanized or chimeric antibody according to the invention, (ii) a nucleic acid sequence encoding a light chain sequence of a humanized or chimeric antibody according to the invention, or (iii) both (i) and (ii). Thus, the expression vector comprises one or more nucleic acid constructs or nucleic acid sequences according to any aspect or embodiment herein described.

In one embodiment, the expression vector of the invention comprises a nucleic acid sequence encoding one or more of the heavy chain and light chain CDR sequences wherein the VH CDR sequences are selected from the group consisting of: SEQ ID NOs.: 12, 2, 3; 14, 2, 3; 16, 2, 3; 18, 2, 3; 20, 2, 3; 22, 2, 3; 24, 2, 3; 26, 2, 3; 28, 2, 3; 30, 2, 3; 32, 2, 3; 34, 2, 3; 36, 2, 3; 38, 2, 3; 40, 2, 3; 42, 2, 3; 44, 2, 3; 46, 2, 3; 48, 2, 3; 50, 2, 3; 52, 2, 3; 54, 2, 3; 56, 2, 3; 58, 2, 3; 60, 2, 3; 62, 2, 3; 64, 2, 3; 66, 2, 3; 68, 2, 3; 70, 2, 3; 72, 2, 3; 74, 2, 3; 76, 2, 3; 78, 2, 3; 80, 2, 3; 82, 2, 3; 84, 2, 3; 86, 2, 3; 88, 2, 3; 90, 2, 3; 92, 2, 3; 94, 2, 3; 96, 2, 3; 98, 2, 3; 1, 100, 3; 1, 102, 3; 1, 104, 3; 1, 106, 3; 1, 108, 3; 1, 110, 3; 1, 112, 3; 1, 114, 3; 1, 116, 3; 1, 118, 3; 1, 120, 3; 1, 122, 3; 1, 124, 3; 1, 126, 3; 1, 128, 3; 1, 130, 3; 1, 132, 3; 1, 134, 3; 1, 136, 3; 1, 138, 3; 1, 140, 3; 1, 142, 3; 1, 144, 3; 1, 146, 3; 1, 148, 3; 1, 150, 3; 1, 152, 3; 1, 154, 3; 1, 156, 3; 1, 158, 3; 1: 1, 2, 176; 1, 2, 178; 1, 2, 180; 1, 2, 182; 1, 2, 184; 1, 2, 186; 1, 2, 188; 1, 2, 190; 1, 2, 192; 1, 2, 194; 1, 2, 196; 1, 2, 198; 1, 2, 200; 1, 2, 202; 1, 2, 204; 1, 2, 206; 1, 2, 208; 1, 2, 210; 1, 2, 212; 1, 2, 214; 1, 2, 216; 1, 2, 218; 1, 2, 220; 1, 2, 222; 1, 2, 224; 1, 2, 226; 1, 2, 228; 1, 2, 230; 1, 2, 232; 1, 2, 234; 1, 2, 236; 1, 2, 238; 1, 2, 240; 1, 2, 242; 1, 2, 244; 1, 2, 246; 1, 2, 248; 1, 2, 250; 1, 2, 252; 1, 2, 254; 1, 2, 256; 1, 2, 258; 1, 2, 260; 1, 2, 262; 1, 2, 264; 1, 2, 266; 1, 2, 268; 1, 2, 270; 1, 2, 272; 1, 2, 274; 1, 2, 276; 1, 2, 278; 1, 2, 280; 1, 2, 282; 1, 2, 284; 1, 2, 286; 1, 2, 288; 1, 2, 290; 1, 2, 292; 1, 2, 294; 1, 2, 296; 1, 2, 298 and 1, 2, 300. and wherein the VL CDR sequences are selected from the group consisting of CDR sequences as set forth in SEQ ID NO: 6, GTN, 7;

302, GTN, 7; 304, GTN, 7; 306, GTN, 7; 308, GTN, 7; 310, GTN, 7; 312, GTN, 7; 314, GTN, 7; 316, GTN, 7; 318, GTN, 7; 320, GTN, 7; 322, GTN, 7; 324, GTN, 7; 326, GTN, 7; 328, GTN, 7; 330, GTN, 7; 6, GTN, 332; 6, GTN, 334; 6, GTN, 336; 6, GTN, 338; 6, GTN, 340; 6, GTN, 342; 6, GTN, 344; 6, GTN, 346; 6, GTN, 348; 6, GTN, 350; 6, GTN, 352; 6, GTN, 354; 6, GTN, 356; 6, GTN, 358; 6, GTN, 360; 6, GTN, 362; 6, GTN, 364; 6, GTN, 366; 6, GTN, 368; 6, GTN, 370; 6, GTN, 372; 6, GTN, 374; 6, GTN, 376; 6, GTN, 378; 6, GTN, 380; 6, GTN, 382; 6, GTN, 384; GTN, 386; 6, GTN, 388; 6, GTN, 390; GTN, 392; and 6, GTN, 394.

In one embodiment, the expression vector of the Invention comprises a nucleic acid sequence encoding one or more of the heavy chain and light chain CDR sequences wherein VL region CDR1, CDR2, CDR3 region CDR sequences comprise the CDR sequences as set forth in SEQ ID NO: 6, GTN, 7 and VH region CDR1, CDR2, CDR3 region CDR sequences are selected from the group consisting of: CDR1, CDR2, CDR3 as set forth in SEQ ID NOs.: 54, 2, 3; CDR1, CDR2, CDR3 as set forth in SEQ ID NO: 58, 2, 3; CDR1, CDR2, CDR3 as set forth in SEQ ID NO:1, 106, 3; CDR1, CDR2, CDR3 as set forth in SEQ ID NO: 1, 2, 176; CDR1, CDR2, CDR3 as set forth in SEQ ID NO: 1, 2, 184; CDR1, CDR2, CDR3 as set forth in SEQ ID NO 1, 2, 220; 1, 2, CDR1, CDR2, CDR3 as set forth in SEQ ID NO 236; 1, 2, 244; CDR1, CDR2, CDR3 as set forth in SEQ ID NO 1, 2, 284; CDR1, CDR2, CDR3 as set forth in SEQ ID NO 1, 2, 292 and CDR1, CDR2, CDR3 as set forth in SEQ ID NO 1, 2, 298.

In a particular embodiment, the expression vector comprises a nucleic acid sequence encoding a variant of one or more of the above amino acid sequences, said variant having at most 25 amino acid modifications, such as at most 20, such as at most 15, 14, 13, 12, or 11 amino acid modifications, such as 10, 9, 8, 7, 6, 5, 4, 3, 2, or 1 amino acid modifications, such as deletions or Insertions, preferably substitutions, such as conservative or non-conservative substitutions, or at least 80% identity to any of said sequences, such as at least 85% identity or 90% identity or 95% identity, such as 96% Identity or 97% identity or 98% identity or 99% identity to any of the afore-mentioned amino acid sequences. The present invention also relates to nucleic acid sequences different from the above mentioned nucleic acid sequences but which due to the variance of the genetic code encode the same amino acid sequence as an antibody of the present invention. E.g. the nucleic acid sequence may vary but result in an Identical amino acid sequences as any amino acid sequence herein described. It is well-known for the skilled person how to Identify such further nucleic acid sequences based on the genetic code.

In a further embodiment, the expression vector further comprises a nucleic acid sequence encoding the constant region of a light chain, a heavy chain or both light and heavy chains of an antibody, e.g. a human antibody.

Such expression vectors as described above may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors Include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a humanized or chimeric CD3 antibody-encoding nucleic acid is comprised in a naked DNA or RNA vector, including, for example, a linear expression element (as described in for Instance [64]), a compacted nucleic acid vector (as described in for Instance [65] and/or [66]), a plasmid vector such as pBR322, pUC 19/18, or pUC 118/119, a "midge" minimally-sized nucleic acid vector (as described in for Instance [67]), or as a precipitated nucleic acid vector construct, such as a CaPO$_4^-$-precipitated construct (as described in for Instance [68], [69], [70], and [71]). Such nucleic acid vectors and the usage thereof are well known in the art (see for Instance [72] and [73]).

In one embodiment, the vector is suitable for expression of the humanized or chimeric CD3 antibody in a bacterial cell. Examples of such vectors Include expression vectors such as BlueScript (Stratagene), pIN vectors ([74]), pET vectors (Novagen, Madison WI) and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: [75] and [76]).

A nucleic acid construct and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle-targeting sequences (e. g., nuclear localization sequences, ER retention signals, mitochondrial transit sequences, chloroplast transit sequences), membrane localization/anchor sequences (e. g., stop transfer sequences, GPI anchor sequences), and the like which are well-known in the art.

In an expression vector of the invention, humanized or chimeric CD3 antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker).

Nucleic acid constructs and/or vectors may also comprise an inducible promoter as opposed to a constitutive promoter such as CMV IE (the skilled person will recognize that such terms are actually descriptors of a degree of gene expression under certain conditions).

In one embodiment, the humanized or chimeric CD3 antibody-encoding expression vector is positioned in and/or delivered to the host cell or host animal via a viral vector.

Such expression vectors may be used for recombinant production of humanized or chimeric CD3 antibodies.

In one aspect, the invention provides a host cell comprising an expression vector according to the invention.

In one aspect, the humanized or chimeric CD3 antibodies of any aspect or embodiment described herein are provided by use of recombinant eukaryotic, recombinant prokaryotic, or recombinant microbial host cell which produces the antibody. Accordingly, the invention provides a recombinant eukaryotic, recombinant prokaryotic, or recombinant microbial host cell, which produces a humanized or chimeric CD3 antibody or immunoglobulin as defined herein. Examples of host cells include yeast, bacterial and mammalian cells, such as CHO or HEK-293 cells. For example, in one embodiment, the host cell comprises a nucleic acid sequence stably Integrated into the cellular genome that comprises a sequence coding for expression of a humanized or chimeric CD3 antibody described herein. In another embodiment, the host cell comprises a non-integrated nucleic acid sequence, such as a plasmid, cosmid, phagemid, or linear expression element, which comprises a sequence coding for expression of a humanized or chimeric CD3 antibody described herein.

The term "recombinant host cell" (or simply "host cell"), as used herein, is intended to refer to a cell into which an expression vector or nucleic acid construct or sequence has been Introduced. It should be understood that such terms are intended to refer not only to the particular subject cell, but also to the progeny of such a cell. Because certain modifications may occur in succeeding generations due to either mutation or environmental Influences, such progeny may not, in fact, be Identical to the parent cell, but are still Included within the scope of the term "host cell" as used herein. Recombinant host cells Include, for example, eukaryotic host cells, such as CHO cells, HEK-293 cells, PER.C6, NS0 cells, and lymphocytic cells, and prokaryotic cells such as *E. coli* and other eukaryotic hosts such as plant cells and fungi.

In a further aspect, the invention relates to a method for producing a humanized or chimeric CD3 antibody of the invention, said method comprising the steps of
a) culturing a host cell of the invention as described herein above, and
b) retrieving and/or purifying the antibody of the invention from the culture media.

In a further aspect, the nucleotide sequence encoding a sequence of a humanized or chimeric CD3 antibody further encodes a second moiety, such as a therapeutic polypeptide. Exemplary therapeutic polypeptides are described elsewhere herein. In one embodiment, the invention relates to a method for producing a humanized or chimeric CD3 antibody fusion protein, said method comprising the steps of
a) culturing a host cell comprising an expression vector comprising such a nucleotide sequence, and
b) retrieving and/or purifying the humanized or chimeric CD3 antibody fusion protein from the culture media.

Compositions

In one aspect, the invention provides a composition comprising the antibody or bispecific antibody according to any aspect and embodiment herein described.

In one aspect, the invention provides a pharmaceutical composition comprising the antibody or bispecific antibody as defined in any one of the aspects and embodiments herein described, and a pharmaceutically acceptable carrier.

The pharmaceutical compositions may be formulated with pharmaceutically acceptable carriers or diluents as well as any other known adjuvants and excipients in accordance with conventional techniques such as those disclosed in [77].

The pharmaceutically acceptable carriers or diluents as well as any other known adjuvants and excipients should be suitable for the humanized or chimeric antibody of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also Include diluents, fillers, salts, buffers, detergents (e. g., a nonionic detergent, such as Tween-20 or Tween-80), stabilizers (e.g., sugars or protein-free amino acids), preservatives, tissue fixatives, solubilizers, and/or other materials suitable for Inclusion in a pharmaceutical composition.

The actual dosage levels of the active Ingredients in the pharmaceutical compositions of the present invention may be varied so as to obtain an amount of the active Ingredient which is effective to achieve the desired therapeutic response for a particular patient, composition, and mode of administration, without being toxic to the patient. The selected dosage level will depend upon a variety of pharmacokinetic factors Including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a humanized or chimeric antibody of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by Injection, and include epidermal, Intravenous, Intramuscular, intra-arterial, intrathecal, intracapsular, intraorbital, intracardiac, intradermal, Intraperitoneal, intratendinous, transtracheal, subcutaneous, subcuticular, intra-articular, subcapsular, subarachnoid, intraspinal, intracranial, intrathoracic, epidural and intrasternal Injection and Infusion.

In one embodiment that pharmaceutical composition is administered by Intravenous or subcutaneous Injection or infusion.

In a preferred embodiment the pharmaceutical composition is administered subcutaneous.

Pharmaceutically acceptable carriers include any and all suitable solvents, dispersion media, coatings, antibacterial and antifungal agents, isotonicity agents, antioxidants and absorption-delaying agents, and the like that are physiologically compatible with a humanized or chimeric antibody of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and Injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile Injectable solutions or dispersion. The use of such media and agents for pharmaceutically active substances is known in the art. Except Insofar as any conventional media or agent is Incompatible with the active compound, use thereof in the pharmaceutical compositions of the present invention is contemplated.

When referring to the "active compound" It is contemplated to also refer to the humanized or chimeric antibody according to the present invention.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for Instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The humanized or chimeric antibody of the present invention may be prepared with carriers that will protect the compound against rapid release, such as a controlled release formulation, including Implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-orthoesters, and polylactic acid alone or with a wax, or other materials well known in the art. Methods for the preparation of such formulations are generally known to those skilled in the art (see e.g., [78]).

In one embodiment, the humanized or chimeric antibody of the present invention may be formulated to ensure proper distribution in vivo. Pharmaceutically acceptable carriers for parenteral administration include sterile aqueous solutions or dispersions and sterile powders for the extemporaneous preparation of sterile Injectable solutions or dispersion. The use of such media and agents for pharmaceutically active substances is known in the art. Except Insofar as any conventional media or agent is Incompatible with the active compound, use thereof in the pharmaceutical compositions of the present invention is contemplated. Other active or therapeutic compounds may also be Incorporated into the compositions.

Pharmaceutical compositions for Injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for Instance water, ethanol, polyols (such as glycerol, propylene glycol, polyethylene glycol, and the like), and suitable mixtures thereof, vegetable oils, such as olive oil, and Injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to Include isotonic agents, for example, sugars, polyalcohols such as glycerol, mannitol, sorbitol, or sodium chloride in the composition. Prolonged absorption of the Injectable compositions may be brought about by Including in the composition an agent that delays absorption, for example, monostearate salts and gelatin. Sterile Injectable solutions may be prepared by Incorporating the active compound in the required amount in an appropriate solvent with one or a combination of Ingredients e.g. as enumerated above, as required, followed by sterilization microfiltration. Generally, dispersions are prepared by Incorporating the active compound into a sterile vehicle that contains a basic dispersion medium and the required other Ingredients e.g. from those enumerated above. In the case of sterile powders for the preparation of sterile Injectable solutions, examples of methods of preparation are vacuum drying and freeze-drying (lyophilization) that yield a powder of the active Ingredient plus any additional desired Ingredient from a previously sterile-filtered solution thereof.

Sterile Injectable solutions may be prepared by Incorporating the active compound in the required amount in an appropriate solvent with one or a combination of Ingredients enumerated above, as required, followed by sterilization microfiltration. Generally, dispersions are prepared by Incorporating the active compound into a sterile vehicle that contains a basic dispersion medium and the required other Ingredients from those enumerated above. In the case of sterile powders for the preparation of sterile Injectable solutions, examples of methods of preparation are vacuum-drying and freeze-drying (lyophilization) that yield a powder of the active Ingredient plus any additional desired Ingredient from a previously sterile-filtered solution thereof.

Therapeutic Applications

In another aspect, the present invention relates to a humanized or chimeric antibody, or pharmaceutical composition of the invention as defined in any aspect or embodiment herein described, for use as a medicament.

In another aspect, the present invention relates to a humanized or chimeric antibody, or pharmaceutical composition of the invention as defined in any aspect or embodiment herein described, for use in the treatment of a disease.

In one embodiment of the present invention a bispecific antibody, a composition, a pharmaceutical composition, for use in the treatment of a disease.

In one embodiment of the present invention, bispecific antibody, a composition, a pharmaceutical composition is for use for the treatment of a disease, wherein the disease is cancer, an Infectious disease, or autoimmune diseases.

The humanized or chimeric antibody or pharmaceutical composition of the invention can be used as in the treatment of any cancer wherein the effector mechanisms of cytotoxic T cells are desired. For example, the humanized or chimeric antibody may be administered to cells in culture, e.g., in vitro or ex vivo, or to human subjects, e.g. in vivo, to treat or prevent disorders such as cancer, Inflammatory or autoimmune disorders. As used herein, the term "subject" is typically a human which respond to the humanized or chimeric antibody, or pharmaceutical composition. Subjects may for Instance include human patients having disorders that may be corrected or ameliorated by modulating a target function or by leading to killing of the cell, directly or Indirectly.

In another aspect, the present invention provides methods for treating or preventing a disorder, such as cancer, wherein recruitment of T cells would contribute to the treatment or prevention, which method comprises administration of a therapeutically effective amount of a humanized or chimeric antibody, or pharmaceutical composition of the present invention to a subject in need thereof. The method typically Involves administering to a subject a humanized or chimeric antibody in an amount effective to treat or prevent the disorder.

In one particular aspect, the present invention relates to a method of treatment of cancer comprising administering the humanized or chimeric antibody or pharmaceutical composition of the invention as defined in any aspect and embodiments herein described, to a subject in need thereof.

In another aspect, the present invention relates to the use or the method as defined in any aspect or embodiments herein described wherein the humanized or chimeric antibody is a bispecific antibody specifically binding to both CD3 and a cancer-specific target, or a target that is overexpressed in cancer or associated with cancer, such as HER2, CD19, EpCAM, EGFR, CD66e (or CEA, CEACAM5), CD33, EphA2 or MCSP (or HMW-MAA), CD20 and wherein the disease is cancer, such as breast cancer, prostate cancer, non-small cell lung cancer, bladder cancer, ovarian cancer, gastric cancer, colorectal cancer, esophageal cancer and squamous cell carcinoma of the head & neck, cervical cancer, pancreatic cancer, testis cancer, malignant melanoma, a soft-tissue cancer (e.g., synovial sarcoma), an Indolent or aggressive form of B-cell lymphoma, chronic lymphatic leukemia or acute lymphatic leukemia.

The efficient dosages and dosage regimens for the humanized or chimeric antibody depend on the disease or condition to be treated and may be determined by the persons skilled in the art.

A physician having ordinary skill in the art may readily determine and prescribe the effective amount of the pharmaceutical composition required. For example, the physician could start doses of the humanized or chimeric antibody employed in the pharmaceutical composition at levels lower than that required in order to achieve the desired therapeutic effect and gradually Increase the dosage until the desired effect is achieved. In general, a suitable dose of a composition of the present invention will be that amount of the humanized or chimeric antibody which is the lowest dose effective to produce a therapeutic effect according to a particular dosage regimen. Such an effective dose will generally depend upon the factors described above.

For example, an "effective amount" for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the humanized or chimeric antibody to inhibit cell growth or to induce cytotoxicity by in vitro assays known to the skilled practitioner. A therapeutically effective amount of a therapeutic compound, i.e. a therapeutic humanized or chimeric antibody, or pharmaceutical composition according to the invention, may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An exemplary, non-limiting range for a therapeutically effective amount of a humanized or chimeric antibody of the invention is about 0.001-30 mg/kg, such as about 0.001-20 mg/kg, such as about 0.001-10 mg/kg, such as about 0.001-5 mg/kg, for example about 0.001-2 mg/kg, such as about 0.001-1 mg/kg, for Instance about 0.001, about 0.01, about 0.1, about 1, about 5, about 8, about 10, about 12, about 15, about 18 mg/kg.

Administration may e.g. be Intravenous, Intramuscular, Intraperitoneal, or subcutaneous, and for Instance administered proximal to the site of the target.

Dosage regimens in the above methods of treatment and uses are adjusted to provide the optimum desired response (e.g., a therapeutic response). For example, a single bolus may be administered, several divided doses may be administered over time or the dose may be proportionally reduced or Increased as Indicated by the exigencies of the therapeutic situation.

In one embodiment, the efficacy of the treatment is monitored during the therapy, e.g. at predefined points in time.

If desired, an effective daily dose of a pharmaceutical composition may be administered as two, three, four, five, six or more sub-doses administered separately at appropriate Intervals throughout the day, optionally, in unit dosage forms. In another embodiment, the humanized or chimeric antibody, or pharmaceutical composition is administered by slow continuous infusion over a long period, such as more than 24 hours, in order to minimize any unwanted side effects.

While it is possible for a humanized or chimeric antibody of the present invention to be administered alone, it is preferable to administer the humanized or chimeric antibody as a pharmaceutical composition as described above.

An effective dose of a humanized or chimeric antibody of the invention may also be administered using a weekly, biweekly or triweekly dosing period. The dosing period may be restricted to, e.g., 8 weeks, 12 weeks or until clinical progression has been established. Alternatively, an effective dose of a humanized or chimeric antibody of the invention may be administered every second, third or fourth week.

In one embodiment, the humanized or chimeric antibody may be administered by infusion in a weekly dosage of calculated by mg/m$^2$. Such dosages can, for example, be based on the mg/kg dosages provided above according to the following: dose (mg/kg)×70: 1.8. Such administration may be repeated, e.g., 1 to 8 times, such as 3 to 5 times. The administration may be performed by continuous infusion over a period of from 2 to 24 hours, such as of from 2 to 12 hours. In one embodiment, the humanized or chimeric antibody may be administered by slow continuous infusion over a long period, such as more than 24 hours, in order to reduce toxic side effects.

In one embodiment, the humanized or chimeric antibody may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of humanized or chimeric antibody of the present invention in the blood upon administration by for Instance taking out a biological sample and using anti-idiotypic antibodies which target the binding region of the humanized or chimeric antibodies of the present invention.

In one embodiment, the humanized or chimeric antibody may be administered by maintenance therapy, such as, e.g., once a week for a period of 6 months or more.

A humanized or chimeric antibody may also be administered prophylactically in order to reduce the risk of developing cancer, delay the onset of the occurrence of an event in cancer progression, and/or reduce the risk of recurrence when a cancer is in remission.

Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations Inherent in the art of compounding such an active compound for the treatment of sensitivity in individuals.

A humanized or chimeric antibody may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

Diagnostic Applications

The humanized or chimeric antibody of the invention may also be used for diagnostic purposes, using a composition comprising a humanized or chimeric antibody as described herein. Accordingly, the invention provides diagnostic methods and compositions using the humanized or chimeric antibodies described herein. Such methods and compositions can be used for purely diagnostic purposes, such as detecting or Identifying a disease, as well as for monitoring of the progress of therapeutic treatments, monitoring disease progression, assessing status after treatment, monitoring for recurrence of disease, evaluating risk of developing a disease, and the like.

In one aspect, the present invention relates to a method of diagnosing a disease characterized by Involvement or accumulation of CD3-expression cells, comprising administering the humanized or chimeric antibody according to the invention, the composition according to the invention, or the pharmaceutically composition according to the invention to a subject, optionally wherein said humanized or chimeric antibody is labeled with a detectable agent.

In one aspect, the humanized or chimeric antibody of the present invention is used ex vivo, such as in diagnosing a disease in which cells expressing a specific target of Interest and to which the humanized or chimeric antibody binds, are Indicative of disease or Involved in the pathogenesis, by detecting levels of the target or levels of cells which express the target of Interest on their cell surface in a sample taken from a patient. This may be achieved, for example, by contacting the sample to be tested, optionally along with a control sample, with the humanized or chimeric antibody according to the invention under conditions that allow for binding of the antibody to the target. Complex formation can then be detected (e.g., using an ELISA). When using a control sample along with the test sample, the level of humanized or chimeric antibody or antibody-target complex is analyzed in both samples and a statistically significant higher level of humanized or chimeric antibody or antibody-target complex in the test sample Indicates a higher level of the target in the test sample compared with the control sample.

Examples of conventional immunoassays in which humanized or chimeric antibodies of the present invention can be used Include, without limitation, ELISA, RIA, FACS assays, plasmon resonance assays, chromatographic assays, tissue immunohistochemistry, Western blot, and/or immunoprecipitation.

Accordingly, in one embodiment, the present invention relates to a method of diagnosing a disease characterized by Involvement or accumulation of CD3-expressing cells, comprising administering an antibody, bispecific antibody, composition or pharmaceutical composition according to any aspect or embodiment herein described, to a subject, optionally wherein the antibody is labeled with a detectable label.

In one embodiment, the invention relates to a method for detecting the presence of a target, or a cell expressing the target, in a sample comprising:

contacting the sample with a humanized or chimeric antibody of the invention under conditions that allow for binding of the humanized or chimeric antibody to the target in the sample; and analyzing whether a complex has been formed. Typically, the sample is a biological sample.

In one embodiment, the sample is a tissue sample known or suspected of containing a specific target and/or cells expressing the target. For example, in situ detection of the target expression may be accomplished by removing a histological specimen from a patient, and providing the humanized or chimeric antibody of the present invention to such a specimen. The humanized or chimeric antibody may be provided by applying or by overlaying the humanized or chimeric antibody to the specimen, which is then detected using suitable means. It is then possible to determine not only the presence of the target or target-expressing cells, but also the distribution of the target or target-expressing cells in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In the above assays, the humanized or chimeric antibody can be labeled with a detectable substance to allow bound antibody to be detected. Alternatively, bound (primary) specific humanized or chimeric antibody may be detected by an antibody which is labeled with a detectable substance and which binds to the primary specific humanized or chimeric antibody. Furthermore, in the above assays, a diagnostic composition comprising an antibody or bispecific antibody according to any aspect or embodiments herein described may be used. Thus, in one aspect, the present invention relates to a diagnostic composition comprising an antibody or bispecific antibody according to any aspect or embodiment herein described.

The level of target in a sample can also be estimated by a competition immunoassay utilizing target standards labeled with a detectable substance and an unlabeled target-specific humanized or chimeric antibody. In this type of assay, the biological sample, the labeled target standard(s) and the target-specific humanized or chimeric antibody are combined, and the amount of labeled target standard bound to the unlabeled target-specific humanized or chimeric antibody is determined. The amount of target in the biological sample is Inversely proportional to the amount of labeled target standard bound to the target-specific humanized or chimeric antibody.

Suitable labels for the target-specific humanized or chimeric antibody, secondary antibody and/or target standard used in in vitro diagnostic techniques include, without limitation, various enzymes, prosthetic groups, fluorescent materials, luminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material Includes luminol; and examples of suitable radioactive material Include $^{125}I$, $^{131}I$, $^{35}S$, and $^3H$.

In one aspect, the target-specific humanized or chimeric antibody of the invention is used in the in vivo Imaging of target-expressing tissues such as tumors. For in vivo methods, antibody fragments such as, e.g., $(Fab')_2$, Fab and Fab' fragments, are particularly advantageous because of their rapid distribution kinetics.

In vivo Imaging can be performed by any suitable technique. For example, a target-specific humanized or chimeric antibody (e.g., an antibody or a fragment) labeled with $^{99}Tc$, $^{131}I$, $^{111}In$ or other gamma-ray emitting Isotope may be used to image target-specific antibody accumulation or distribution in target-expressing tissues such as tumors with a gamma scintillation camera (e.g., an Elscint Apex 409ECT device), typically using low-energy, high resolution collimator or a low-energy all-purpose collimator. Alternatively, labeling with $^{89}Zr$, $^{76}Br$, $^{18}F$ or other positron-emitting radionuclide may be used to image target-specific humanized or chimeric antibody, or antibody fragment distribution in tumors using positron emission tomography (PET). The images obtained by the use of such techniques may be used to assess biodistribution of target in a patient, mammal, or tissue, for example in the context of using target as a biomarker for the presence of cancer/tumor cells. Variations on this technique may include the use of magnetic resonance Imaging (MRI) to improve Imaging over gamma camera techniques. Conventional immunoscintiography methods and principles are described in, e.g., [79], [80], and [81]. Moreover, such images may also, or alternatively, serve as the basis for surgical techniques to remove tumors. Furthermore, such in vivo Imaging techniques may allow for the Identification and localization of a tumor in a situation where a patient is Identified as having a tumor (due to the presence of other biomarkers, metastases, etc.), but the tumor cannot be Identified by traditional analytical techniques. All of these methods are features of the present invention.

The in vivo Imaging and other diagnostic methods provided by the present invention are particularly useful in the detection of micrometastases in a human patient (e.g., a patient not previously diagnosed with cancer or a patient in a period of recovery/remission from a cancer).

In one embodiment, the present invention provides an in vivo Imaging method wherein a target-specific humanized or chimeric antibody of the present invention is conjugated to a detection-promoting radio-opaque agent, the conjugated humanized or chimeric antibody is administered to a host, such as by Injection into the bloodstream, and the presence and location of the labeled humanized or chimeric antibody in the host is assayed. Through this technique and any other diagnostic method provided herein, the present invention provides a method for screening for the presence of disease-related cells in a human patient or a biological sample taken from a human patient and/or for assessing the distribution of target-specific humanized or chimeric antibody prior to target-specific ADC therapy.

For diagnostic Imaging, radioisotopes may be bound to a target-specific humanized or chimeric antibody either directly or Indirectly by using an Intermediary functional group. Useful Intermediary functional groups include chelators, such as ethylenediaminetetraacetic acid and diethylenetriaminepentaacetic acid (see for Instance [82]).

In addition to radioisotopes and radio-opaque agents, diagnostic methods may be performed using target-specific antibodies that are conjugated to dyes (such as with the biotin-streptavidin complex), contrast agents, fluorescent compounds or molecules and enhancing agents (e.g. paramagnetic Ions) for magnetic resonance Imaging (MRI) (see, e.g., [83], which describes MRI techniques and the preparation of antibodies conjugated to a MRI enhancing agent). Such diagnostic/detection agents may be selected from agents for use in MRI, and fluorescent compounds. In order to load a target-specific humanized or chimeric antibody with radioactive metals or paramagnetic ions, it may be necessary to react it with a reagent having a long tall to which a multiplicity of chelating groups are attached for binding the Ions. Such a tall may be a polymer such as a polylysine, polysaccharide, or another derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to target-specific humanized or chimeric antibodies using standard chemistries.

Thus, the present invention provides a diagnostic target-specific humanized or chimeric antibody, wherein the target-specific humanized or chimeric antibody is conjugated to a contrast agent (such as for magnetic resonance Imaging, computed tomography, or ultrasound contrast-enhancing agent) or a radionuclide that may be, for example, a gamma-, beta-, alpha-, Auger electron-, or positron-emitting Isotope.

In one aspect, the present invention relates to a diagnostic composition comprising an antibody or bispecific antibody according to the invention.

In a further aspect, the invention relates to a kit for detecting the presence of target antigen or a cell expressing the target, in a sample, comprising:
    a target-specific humanized or chimeric antibody of the invention; and
    instructions for use of the kit.

Thus, in one aspect, the present invention provides a kit for detecting the presence of a CD3 antigen, or a cell expressing CD3, in a sample comprising the steps of;
    a) contacting the sample with an antibody or bispecific antibody according to the invention, under conditions that allow for formation of a complex between the antibody or bispecific antibody and CD3; and
    b) analyzing whether a complex has been formed.

In one embodiment, the present invention provides a kit for diagnosis of cancer comprising a container comprising a target-specific humanized or chimeric antibody, and one or more reagents for detecting binding of the target-specific humanized or chimeric antibody to the target. Reagents may Include, for example, fluorescent tags, enzymatic tags, or other detectable tags. The reagents may also Include secondary or tertiary antibodies or reagents for enzymatic reactions, wherein the enzymatic reactions produce a product that may be visualized. In one embodiment, the present invention provides a diagnostic kit comprising one or more target-specific humanized or chimeric antibodies of the present invention in labeled or unlabeled form in suitable container(s), reagents for the Incubations for an Indirect assay, and substrates or derivatizing agents for detection in such an assay, depending on the nature of the label. Control reagent(s) and Instructions for use also may be included.

Diagnostic kits may also be supplied for use with a target-specific humanized or chimeric antibody, such as a labeled target-specific antibody, for the detection of the presence of the target in a tissue sample or host. In such diagnostic kits, as well as in kits for therapeutic uses described elsewhere herein, a target-specific humanized or chimeric antibody typically may be provided in a lyophilized form in a container, either alone or in conjunction with additional antibodies specific for a target cell or peptide. Typically, a pharmaceutically acceptable carrier (e.g., an inert diluent) and/or components thereof, such as a Tris, phosphate, or carbonate buffer, stabilizers, preservatives, biocides, inert proteins, e.g., serum albumin, or the like, also are included (typically in a separate container for mixing) and additional reagents (also typically in separate container(s)). In certain kits, a secondary antibody capable of binding to the target-specific humanized or chimeric antibody, which typically is present in a separate container, is also included. The second antibody is typically conjugated to a label and formulated in a manner similar to the target-specific humanized or chimeric antibody of the present invention. Using the methods described above and elsewhere herein, target-specific humanized or chimeric antibodies may be used to define subsets of cancer/tumor cells and characterize such cells and related tumor tissues.

Anti-Idiotypic Antibodies

In a further aspect, the invention relates to an anti-idiotypic antibody which binds to a humanized or chimeric antibody of the invention as described herein. In one embodiment the invention relates to an anti-idiotypic antibody which binds to an antibody of any one of claims or a bispecific antibody according to the invention.

An anti-idiotypic (Id) antibody is an antibody which recognizes unique determinants generally associated with the antigen-binding site of an antibody. An anti-Id antibody may be prepared by Immunizing an animal of the same species and genetic type as the source of a CD3 monoclonal antibody with the monoclonal antibody to which an anti-Id is being prepared. The Immunized animal typically can recognize and respond to the idiotypic determinants of the Immunizing antibody by producing an antibody to these idiotypic determinants (the anti-Id antibody). Such antibodies are described in for Instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically Identical to the original monoclonal antibody, which Induced the anti-Id antibody. Thus, by using antibodies to the idiotypic determinants of a monoclonal antibody, it is possible to Identify other clones expressing antibodies of Identical specificity. Anti-Id antibodies may be varied (thereby producing anti-Id antibody variants) and/or derivatized by any suitable technique, such as those described elsewhere herein with respect to CD3-specific antibodies of the present invention. For example, a monoclonal anti-Id antibody may be coupled to a carrier such as keyhole limpet hemocyanin (KLH) and used to Immunize BALB/c mice. Sera from these mice typically will contain anti-anti-Id antibodies that have the binding properties similar, if not Identical, to an original/parent CD3 antibody.

TABLE 1

| SEQ ID NO: | Clone name | Sequence |
|---|---|---|
| SEQ ID NO: 1 | VH-huCD3-H1 CDR1 | GFTFNTYA |
| SEQ ID NO: 2 | VH-huCD3-H1 CDR2 | IRSKYNNYAT |
| SEQ ID NO: 3 | VH-huCD3-H1 CDR3 | VRHGNFGNSYVSWFAY |
| SEQ ID NO: 4 | VH-huCD3-H1 | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 5 | VH-huCD3-H1 | GAAGTGAAGCTGGTGGAATCTGGCGGCGGACTGGTGCAGCCTG GCGGGATCTCTGAGACTGAGCTGTGCCGCCAGCGGCTTCACCTTCA ACACCTACGCCATGAACTGGGTGCGCCAGGCCCCTGGCAAAGGC CTGGAATGGGTGGCCCGGATCAGAAGCAAGTACAACAATTACGC CACCTACTACGCCGACAGCGTGAAGGACCGGTTCACCATCAGCC GGGACGACAGCAAGAGCAGCCTGTACCTGCAGATGAACAACCTG AAAACCGAGGACACCGCCATGTACTACTGCGTGCGGCACGGCAA CTTCGGCAACAGCTATGTGTCTTGGTTTGCCTACTGGGGCCAGGG CACCCTCGTGACAGTGTCTAGC |
| SEQ ID NO: 6 | VL-huCD3-L1 CDR1 | TGAVTTSNY |
|  | VL-huCD3-L1 CDR2 | GTN |
| SEQ ID NO: 7 | VL-huCD3-L1 CDR3 | ALWYSNLWV |
| SEQ ID NO: 8 | VL-huCD3-L1 | QAVVTQEPSFSVSPGGTVTLTCRSSTGAVTTSNYANWVQQTPGQA FRGLIGGTNKRAPGVPARFSGSLIGDKAALTITGAQADDESIYFCALW YSNLWVFGGGTKLTVL |
| SEQ ID NO: 9 | VL-huCD3-L1 | CAGGCCGTCGTGACCCAGGAACCCAGCTTTTCCGTGTCTCCTGGC GGCACCGTGACCCTGACCTGCAGATCTTCTACAGGCGCCGTGACC ACCAGCAACTACGCCAACTGGGTGCAGCAGACACCCGGCCAGGC CTTTAGAGGACTGATCGGCGGCACCAACAAGAGGGCACCTGGCG TGCCAGCCAGATTCAGCGGCAGCCTGATCGGAGATAAGGCCGCC CTGACAATCACTGGCGCCCAGGCTGACGACGAGAGCATCTACTTT TGCGCCCTGTGGTACAGCAACCTGTGGGTGTTCGGCGGAGGCAC CAAGCTGACAGTGCTG |
| SEQ ID NO: 6 | VL-huCD3-L1-T41K CDR1 | TGAVTTSNY |
|  | VL-huCD3-L1-T41K CDR2 | GTN |
| SEQ ID NO: 7 | VL-huCD3-L1-T41K CDR3 | ALWYSNLWV |
| SEQ ID NO: 10 | VL-huCD3-L1-T41K | QAVVTQEPSFSVSPGGTVTLTCRSSTGAVTTSNYANWVQQKPGQA FRGLIGGTNKRAPGVPARFSGSLIGDKAALTITGAQADDESIYFCALW YSNLWVFGGGTKLTVL |
| SEQ ID NO: 11 | VL-huCD3-L1-T41K | CAGGCCGTCGTGACCCAGGAACCCAGCTTTTCCGTGTCTCCTGGC GGCACCGTGACCCTGACCTGCAGATCTTCTACAGGCGCCGTGACC ACCAGCAACTACGCCAACTGGGTGCAGCAGAAGCCCGGCCAGGC CTTTAGAGGACTGATCGGCGGCACCAACAAGAGGGCACCTGGCG TGCCAGCCAGATTCAGCGGCAGCCTGATCGGAGATAAGGCCGCC CTGACAATCACTGGCGCCCAGGCTGACGACGAGAGCATCTACTTT TGCGCCCTGTGGTACAGCAACCTGTGGGTGTTCGGCGGAGGCAC CAAGCTGACCGTCCTA |
| SEQ ID NO: 12 | HC_N30A CDR1 | GFTFATYA |
| SEQ ID NO: 2 | HC_N30A CDR2 | IRSKYNNYAT |
| SEQ ID NO: 3 | HC_N30A CDR3 | VRHGNFGNSYVSWFAY |
| SEQ ID NO: 13 | HC_N30A | EVKLVESGGGLVQPGGSLRLSCAASGFTFATYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 14 | HC_N30C CDR1 | GFTFCTYA |
| SEQ ID NO: 2 | HC_N30C CDR2 | IRSKYNNYAT |
| SEQ ID NO: 3 | HC_N30C CDR3 | VRHGNFGNSYVSWFAY |

TABLE 1-continued

| | | Sequences |
| --- | --- | --- |
| SEQ ID NO: | Clone name | Sequence |
| SEQ ID NO: 15 | HC_N30C | EVKLVESGGGLVQPGGSLRLSCAASGFTFCTYAMNWVRQAPGKGL<br>EWVARIRSKYNNYATYYADSVKDRFTISRDDSKSSLYLQMNNLKTED<br>TAMYYCVRHGNFGNSYVSWFAYWGQGTLVTVSS |
| SEQ ID NO: 16 | HC_N30D CDR1 | GFTFDTYA |
| SEQ ID NO: 2 | HC_N30D CDR2 | IRSKYNNYAT |
| SEQ ID NO: 3 | HC_N30D CDR3 | VRHGNFGNSYVSWFAY |
| SEQ ID NO: 17 | HC_N30D | EVKLVESGGGLVQPGGSLRLSCAASGFTFDTYAMNWVRQAPGKGL<br>EWVARIRSKYNNYATYYADSVKDRFTISRDDSKSSLYLQMNNLKTED<br>TAMYYCVRHGNFGNSYVSWFAYWGQGTLVTVSS |
| SEQ ID NO: 18 | HC_N30F CDR1 | GFTFFFTYA |
| SEQ ID NO: 2 | HC_N30F CDR2 | IRSKYNNYAT |
| SEQ ID NO: 3 | HC_N30F CDR3 | VRHGNFGNSYVSWFAY |
| SEQ ID NO: 19 | HC_N30F | EVKLVESGGGLVQPGGSLRLSCAASGFTFFTYAMNWVRQAPGKGL<br>EWVARIRSKYNNYATYYADSVKDRFTISRDDSKSSLYLQMNNLKTED<br>TAMYYCVRHGNFGNSYVSWFAYWGQGTLVTVSS |
| SEQ ID NO: 20 | HC_N30G CDR1 | GFTFGTYA |
| SEQ ID NO: 2 | HC_N30G CDR2 | IRSKYNNYAT |
| SEQ ID NO: 3 | HC_N30G CDR3 | VRHGNFGNSYVSWFAY |
| SEQ ID NO: 21 | HC_N30G | EVKLVESGGGLVQPGGSLRLSCAASGFTFGTYAMNWVRQAPGKGL<br>EWVARIRSKYNNYATYYADSVKDRFTISRDDSKSSLYLQMNNLKTED<br>TAMYYCVRHGNFGNSYVSWFAYWGQGTLVTVSS |
| SEQ ID NO: 22 | HC_N30H CDR1 | GFTFHTYA |
| SEQ ID NO: 2 | HC_N30H CDR2 | IRSKYNNYAT |
| SEQ ID NO: 3 | HC_N30H CDR3 | VRHGNFGNSYVSWFAY |
| SEQ ID NO: 23 | HC_N30H | EVKLVESGGGLVQPGGSLRLSCAASGFTFHTYAMNWVRQAPGKGL<br>EWVARIRSKYNNYATYYADSVKDRFTISRDDSKSSLYLQMNNLKTED<br>TAMYYCVRHGNFGNSYVSWFAYWGQGTLVTVSS |
| SEQ ID NO: 24 | HC_N30K CDR1 | GFTFKTYA |
| SEQ ID NO: 2 | HC_N30K CDR2 | IRSKYNNYAT |
| SEQ ID NO: 3 | HC_N30K CDR3 | VRHGNFGNSYVSWFAY |
| SEQ ID NO: 25 | HC_N30K | EVKLVESGGGLVQPGGSLRLSCAASGFTFKTYAMNWVRQAPGKGL<br>EWVARIRSKYNNYATYYADSVKDRFTISRDDSKSSLYLQMNNLKTED<br>TAMYYCVRHGNFGNSYVSWFAYWGQGTLVTVSS |
| SEQ ID NO: 26 | HC_N30L CDR1 | GFTFLTYA |
| SEQ ID NO: 2 | HC_N30L CDR2 | IRSKYNNYAT |
| SEQ ID NO: 3 | HC_N30L CDR3 | VRHGNFGNSYVSWFAY |
| SEQ ID NO: 27 | HC_N30L | EVKLVESGGGLVQPGGSLRLSCAASGFTFLTYAMNWVRQAPGKGLE<br>WVARIRSKYNNYATYYADSVKDRFTISRDDSKSSLYLQMNNLKTEDT<br>AMYYCVRHGNFGNSYVSWFAYWGQGTLVTVSS |
| SEQ ID NO: 28 | HC_N30P CDR1 | GFTFPTYA |
| SEQ ID NO: 2 | HC_N30P CDR2 | IRSKYNNYAT |
| SEQ ID NO: 3 | HC_N30P CDR3 | VRHGNFGNSYVSWFAY |
| SEQ ID NO: 29 | HC_N30P | EVKLVESGGGLVQPGGSLRLSCAASGFTFPTYAMNWVRQAPGKGL<br>EWVARIRSKYNNYATYYADSVKDRFTISRDDSKSSLYLQMNNLKTED<br>TAMYYCVRHGNFGNSYVSWFAYWGQGTLVTVSS |
| SEQ ID NO: 30 | HC_N30Q CDR1 | GFTFQTYA |

TABLE 1-continued

| | | Sequences |
|---|---|---|
| SEQ ID NO: | Clone name | Sequence |
| SEQ ID NO: 2 | HC_N30Q CDR2 | IRSKYNNYAT |
| SEQ ID NO: 3 | HC_N30Q CDR3 | VRHGNFGNSYVSWFAY |
| SEQ ID NO: 31 | HC_N30Q | EVKLVESGGGLVQPGGSLRLSCAASGFTFQTYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 32 | HC_N30R CDR1 | GFTFRTYA |
| SEQ ID NO: 2 | HC_N30R CDR2 | IRSKYNNYAT |
| SEQ ID NO: 3 | HC_N30R CDR3 | VRHGNFGNSYVSWFAY |
| SEQ ID NO: 33 | HC_N30R | EVKLVESGGGLVQPGGSLRLSCAASGFTFRTYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 34 | HC_N30T CDR1 | GFTFTTYA |
| SEQ ID NO: 2 | HC_N30T CDR2 | IRSKYNNYAT |
| SEQ ID NO: 3 | HC_N30T CDR3 | VRHGNFGNSYVSWFAY |
| SEQ ID NO: 35 | HC_N30T | EVKLVESGGGLVQPGGSLRLSCAASGFTFTTYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 36 | HC_N30V CDR1 | GFTFVTYA |
| SEQ ID NO: 2 | HC_N30V CDR2 | IRSKYNNYAT |
| SEQ ID NO: 3 | HC_N30V CDR3 | VRHGNFGNSYVSWFAY |
| SEQ ID NO: 37 | HC_N30V | EVKLVESGGGLVQPGGSLRLSCAASGFTFVTYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 38 | HC_N30W CDR1 | GFTFWTYA |
| SEQ ID NO: 2 | HC_N30W CDR2 | IRSKYNNYAT |
| SEQ ID NO: 3 | HC_N30W CDR3 | VRHGNFGNSYVSWFAY |
| SEQ ID NO: 39 | HC_N30W | EVKLVESGGGLVQPGGSLRLSCAASGFTFWTYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 40 | HC_T31A CDR1 | GFTFNAYA |
| SEQ ID NO: 2 | HC_T31A CDR2 | IRSKYNNYAT |
| SEQ ID NO: 3 | HC_T31A CDR3 | VRHGNFGNSYVSWFAY |
| SEQ ID NO: 41 | HC_T31A | EVKLVESGGGLVQPGGSLRLSCAASGFTFNAYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 42 | HC_T31C CDR1 | GFTFNCYA |
| SEQ ID NO: 2 | HC_T31C CDR2 | IRSKYNNYAT |
| SEQ ID NO: 3 | HC_T31C CDR3 | VRHGNFGNSYVSWFAY |
| SEQ ID NO: 43 | HC_T31C | EVKLVESGGGLVQPGGSLRLSCAASGFTFNCYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 44 | HC_T31D CDR1 | GFTFNDYA |
| SEQ ID NO: 2 | HC_T31D CDR2 | IRSKYNNYAT |
| SEQ ID NO: 3 | HC_T31D CDR3 | VRHGNFGNSYVSWFAY |

TABLE 1-continued

| | | Sequences |
|---|---|---|
| SEQ ID NO: | Clone name | Sequence |
| SEQ ID NO: 45 | HC_T31D | EVKLVESGGGLVQPGGSLRLSCAASGFTFNDYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 46 | HC_T31E CDR1 | GFTFNEYA |
| SEQ ID NO: 2 | HC_T31E CDR2 | IRSKYNNYAT |
| SEQ ID NO: 3 | HC_T31E CDR3 | VRHGNFGNSYVSWFAY |
| SEQ ID NO: 47 | HC_T31E | EVKLVESGGGLVQPGGSLRLSCAASGFTFNEYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 48 | HC_T31F CDR1 | GFTFNFYA |
| SEQ ID NO: 2 | HC_T31F CDR2 | IRSKYNNYAT |
| SEQ ID NO: 3 | HC_T31F CDR3 | VRHGNFGNSYVSWFAY |
| SEQ ID NO: 49 | HC_T31F | EVKLVESGGGLVQPGGSLRLSCAASGFTFNFYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 50 | HC_T31H CDR1 | GFTFNHYA |
| SEQ ID NO: 2 | HC_T31H CDR2 | IRSKYNNYAT |
| SEQ ID NO: 3 | HC_T31H CDR3 | VRHGNFGNSYVSWFAY |
| SEQ ID NO: 51 | HC_T31H | EVKLVESGGGLVQPGGSLRLSCAASGFTFNHYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 52 | HC_T31L CDR1 | GFTFNLYA |
| SEQ ID NO: 2 | HC_T31L CDR2 | IRSKYNNYAT |
| SEQ ID NO: 3 | HC_T31L CDR3 | VRHGNFGNSYVSWFAY |
| SEQ ID NO: 53 | HC_T31L | EVKLVESGGGLVQPGGSLRLSCAASGFTFNLYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 54 | HC_T31M CDR1 | GFTFNMYA |
| SEQ ID NO: 2 | HC_T31M CDR2 | IRSKYNNYAT |
| SEQ ID NO: 3 | HC_T31M CDR3 | VRHGNFGNSYVSWFAY |
| SEQ ID NO: 55 | HC_T31M | EVKLVESGGGLVQPGGSLRLSCAASGFTFNMYAMNWVRQAPGKG LEWVARIRSKYNNYATYYADSVKDRFTISRDDSKSSLYLQMNNLKTE DTAMYYCVRHGNFGNSYVSWFAYWGQGTLVTVSS |
| SEQ ID NO: 56 | HC_T31N CDR1 | GFTFNNYA |
| SEQ ID NO: 2 | HC_T31N CDR2 | IRSKYNNYAT |
| SEQ ID NO: 3 | HC_T31N CDR3 | VRHGNFGNSYVSWFAY |
| SEQ ID NO: 57 | HC_T31N | EVKLVESGGGLVQPGGSLRLSCAASGFTFNNYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 58 | HC_T31P CDR1 | GFTFNPYA |
| SEQ ID NO: 2 | HC_T31P CDR2 | IRSKYNNYAT |
| SEQ ID NO: 3 | HC_T31P CDR3 | VRHGNFGNSYVSWFAY |
| SEQ ID NO: 59 | HC_T31P | EVKLVESGGGLVQPGGSLRLSCAASGFTFNPYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 60 | HC_T31Q CDR1 | GFTFNQYA |

TABLE 1-continued

| | | Sequences |
|---|---|---|
| SEQ ID NO: | Clone name | Sequence |
| SEQ ID NO: 2 | HC_T31Q CDR2 | IRSKYNNYAT |
| SEQ ID NO: 3 | HC_T31Q CDR3 | VRHGNFGNSYVSWFAY |
| SEQ ID NO: 61 | HC_T31Q | EVKLVESGGGLVQPGGSLRLSCAASGFTFNQYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 62 | HC_T31W CDR1 | GFTFNWYA |
| SEQ ID NO: 2 | HC_T31W CDR2 | IRSKYNNYAT |
| SEQ ID NO: 3 | HC_T31W CDR3 | VRHGNFGNSYVSWFAY |
| SEQ ID NO: 63 | HC_T31W | EVKLVESGGGLVQPGGSLRLSCAASGFTFNWYAMNWVRQAPGKG LEWVARIRSKYNNYATYYADSVKDRFTISRDDSKSSLYLQMNNLKTE DTAMYYCVRHGNFGNSYVSWFAYWGQGTLVTVSS |
| SEQ ID NO: 64 | HC_T31Y CDR1 | GFTFNYYA |
| SEQ ID NO: 2 | HC_T31Y CDR2 | IRSKYNNYAT |
| SEQ ID NO: 3 | HC_T31Y CDR3 | VRHGNFGNSYVSWFAY |
| SEQ ID NO: 65 | HC_T31Y | EVKLVESGGGLVQPGGSLRLSCAASGFTFNYYAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 66 | HC_Y32A CDR1 | GFTFNTAA |
| SEQ ID NO: 2 | HC_Y32A CDR2 | IRSKYNNYAT |
| SEQ ID NO: 3 | HC_Y32A CDR3 | VRHGNFGNSYVSWFAY |
| SEQ ID NO: 67 | HC_Y32A | EVKLVESGGGLVQPGGSLRLSCAASGFTFNTAAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 68 | HC_Y32C CDR1 | GFTFNTCA |
| SEQ ID NO: 2 | HC_Y32C CDR2 | IRSKYNNYAT |
| SEQ ID NO: 3 | HC_Y32C CDR3 | VRHGNFGNSYVSWFAY |
| SEQ ID NO: 69 | HC_Y32C | EVKLVESGGGLVQPGGSLRLSCAASGFTFNTCAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 70 | HC_Y32F CDR1 | GFTFNTFA |
| SEQ ID NO: 2 | HC_Y32F CDR2 | IRSKYNNYAT |
| SEQ ID NO: 3 | HC_Y32F CDR3 | VRHGNFGNSYVSWFAY |
| SEQ ID NO: 71 | HC_Y32F | EVKLVESGGGLVQPGGSLRLSCAASGFTFNTFAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 72 | HC_Y32G CDR1 | GFTFNTGA |
| SEQ ID NO: 2 | HC_Y32G CDR2 | IRSKYNNYAT |
| SEQ ID NO: 3 | HC_Y32G CDR3 | VRHGNFGNSYVSWFAY |
| SEQ ID NO: 73 | HC_Y32G | EVKLVESGGGLVQPGGSLRLSCAASGFTFNTGAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 74 | HC_Y32H CDR1 | GFTFNTHA |
| SEQ ID NO: 2 | HC_Y32H CDR2 | IRSKYNNYAT |
| SEQ ID NO: 3 | HC_Y32H CDR3 | VRHGNFGNSYVSWFAY |

TABLE 1-continued

| Sequences | | |
| --- | --- | --- |
| SEQ ID NO: | Clone name | Sequence |
| SEQ ID NO: 75 | HC_Y32H | EVKLVESGGGLVQPGGSLRLSCAASGFTFNTHAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 76 | HC_Y32I CDR1 | GFTFNTIA |
| SEQ ID NO: 2 | HC_Y32I CDR2 | IRSKYNNYAT |
| SEQ ID NO: 3 | HC_Y32I CDR3 | VRHGNFGNSYVSWFAY |
| SEQ ID NO: 77 | HC_Y32I | EVKLVESGGGLVQPGGSLRLSCAASGFTFNTIAMNWVRQAPGKGLE WVARIRSKYNNYATYYADSVKDRFTISRDDSKSSLYLQMNNLKTEDT AMYYCVRHGNFGNSYVSWFAYWGQGTLVTVSS |
| SEQ ID NO: 78 | HC_Y32K CDR1 | GFTFNTKA |
| SEQ ID NO: 2 | HC_Y32K CDR2 | IRSKYNNYAT |
| SEQ ID NO: 3 | HC_Y32K CDR3 | VRHGNFGNSYVSWFAY |
| SEQ ID NO: 79 | HC_Y32K | EVKLVESGGGLVQPGGSLRLSCAASGFTFNTKAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 80 | HC_Y32L CDR1 | GFTFNTLA |
| SEQ ID NO: 2 | HC_Y32L CDR2 | IRSKYNNYAT |
| SEQ ID NO: 3 | HC_Y32L CDR3 | VRHGNFGNSYVSWFAY |
| SEQ ID NO: 81 | HC_Y32L | EVKLVESGGGLVQPGGSLRLSCAASGFTFNTLAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 82 | HC_Y32M CDR1 | GFTFNTMA |
| SEQ ID NO: 2 | HC_Y32M CDR2 | IRSKYNNYAT |
| SEQ ID NO: 3 | HC_Y32M CDR3 | VRHGNFGNSYVSWFAY |
| SEQ ID NO: 83 | HC_Y32M | EVKLVESGGGLVQPGGSLRLSCAASGFTFNTMAMNWVRQAPGKG LEWVARIRSKYNNYATYYADSVKDRFTISRDDSKSSLYLQMNNLKTE DTAMYYCVRHGNFGNSYVSWFAYWGQGTLVTVSS |
| SEQ ID NO: 84 | HC_Y32N CDR1 | GFTFNTNA |
| SEQ ID NO: 2 | HC_Y32N CDR2 | IRSKYNNYAT |
| SEQ ID NO: 3 | HC_Y32N CDR3 | VRHGNFGNSYVSWFAY |
| SEQ ID NO: 85 | HC_Y32N | EVKLVESGGGLVQPGGSLRLSCAASGFTFNTNAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 86 | HC_Y32P CDR1 | GFTFNTPA |
| SEQ ID NO: 2 | HC_Y32P CDR2 | IRSKYNNYAT |
| SEQ ID NO: 3 | HC_Y32P CDR3 | VRHGNFGNSYVSWFAY |
| SEQ ID NO: 87 | HC_Y32P | EVKLVESGGGLVQPGGSLRLSCAASGFTFNTPAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 88 | HC_Y32Q CDR1 | GFTFNTQA |
| SEQ ID NO: 2 | HC_Y32Q CDR2 | IRSKYNNYAT |
| SEQ ID NO: 3 | HC_Y32Q CDR3 | VRHGNFGNSYVSWFAY |
| SEQ ID NO: 89 | HC_Y32Q | EVKLVESGGGLVQPGGSLRLSCAASGFTFNTQAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 90 | HC_Y32R CDR1 | GFTFNTRA |

TABLE 1-continued

Sequences

| SEQ ID NO: | Clone name | Sequence |
|---|---|---|
| SEQ ID NO: 2 | HC_Y32R CDR2 | IRSKYNNYAT |
| SEQ ID NO: 3 | HC_Y32R CDR3 | VRHGNFGNSYVSWFAY |
| SEQ ID NO: 91 | HC_Y32R | EVKLVESGGGLVQPGGSLRLSCAASGFTFNTRAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 92 | HC_Y32S CDR1 | GFTFNTSA |
| SEQ ID NO: 2 | HC_Y32S CDR2 | IRSKYNNYAT |
| SEQ ID NO: 3 | HC_Y32S CDR3 | VRHGNFGNSYVSWFAY |
| SEQ ID NO: 93 | HC_Y32S | EVKLVESGGGLVQPGGSLRLSCAASGFTFNTSAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 94 | HC_Y32T CDR1 | GFTFNTTA |
| SEQ ID NO: 2 | HC_Y32T CDR2 | IRSKYNNYAT |
| SEQ ID NO: 3 | HC_Y32T CDR3 | VRHGNFGNSYVSWFAY |
| SEQ ID NO: 95 | HC_Y32T | EVKLVESGGGLVQPGGSLRLSCAASGFTFNTTAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 96 | HC_Y32V CDR1 | GFTFNTVA |
| SEQ ID NO: 2 | HC_Y32V CDR2 | IRSKYNNYAT |
| SEQ ID NO: 3 | HC_Y32V CDR3 | VRHGNFGNSYVSWFAY |
| SEQ ID NO: 97 | HC_Y32V | EVKLVESGGGLVQPGGSLRLSCAASGFTFNTVAMNWVRQAPGKGL EWVARIRSKYNNYATYYADSVKDRFTISRDDSKSSLYLQMNNLKTED TAMYYCVRHGNFGNSYVSWFAYWGQGTLVTVSS |
| SEQ ID NO: 98 | HC_Y32W CDR1 | GFTFNTWA |
| SEQ ID NO: 2 | HC_Y32W CDR2 | IRSKYNNYAT |
| SEQ ID NO: 3 | HC_Y32W CDR3 | VRHGNFGNSYVSWFAY |
| SEQ ID NO: 99 | HC_Y32W | EVKLVESGGGLVQPGGSLRLSCAASGFTFNTWAMNWVRQAPGKG LEWVARIRSKYNNYATYYADSVKDRFTISRDDSKSSLYLQMNNLKTE DTAMYYCVRHGNFGNSYVSWFAYWGQGTLVTVSS |
| SEQ ID NO: 1 | HC_N57A CDR1 | GFTFNTYA |
| SEQ ID NO: 100 | HC_N57A CDR2 | IRSKYNAYAT |
| SEQ ID NO: 3 | HC_N57A CDR3 | VRHGNFGNSYVSWFAY |
| SEQ ID NO: 101 | HC_N57A | EVKLVESGGGLVQPGGSLRLSCAASGFTFNTYAMNWVRQAPGKGL EWVARIRSKYNAYATYYADSVKDRFTISRDDSKSSLYLQMNNLKTED TAMYYCVRHGNFGNSYVSWFAYWGQGTLVTVSS |
| SEQ ID NO: 1 | HC_N57C CDR1 | GFTFNTYA |
| SEQ ID NO: 102 | HC_N57C CDR2 | IRSKYNCYAT |
| SEQ ID NO: 3 | HC_N57C CDR3 | VRHGNFGNSYVSWFAY |
| SEQ ID NO: 103 | HC_N57C | EVKLVESGGGLVQPGGSLRLSCAASGFTFNTYAMNWVRQAPGKGL EWVARIRSKYNCYATYYADSVKDRFTISRDDSKSSLYLQMNNLKTED TAMYYCVRHGNFGNSYVSWFAYWGQGTLVTVSS |
| SEQ ID NO: 1 | HC_N57D CDR1 | GFTFNTYA |
| SEQ ID NO: 104 | HC_N57D CDR2 | IRSKYNDYAT |
| SEQ ID NO: 3 | HC_N57D CDR3 | VRHGNFGNSYVSWFAY |

TABLE 1-continued

| | | Sequences |
|---|---|---|
| SEQ ID NO: | Clone name | Sequence |
| SEQ ID NO: 105 | HC_N57D | EVKLVESGGGLVQPGGSLRLSCAASGFTFNTYAMNWVRQAPGKGL EWVARIRSKYNDYATYYADSVKDRFTISRDDSKSSLYLQMNNLKTED TAMYYCVRHGNFGNSYVSWFAYWGQGTLVTVSS |
| SEQ ID NO: 1 | HC_N57E CDR1 | GFTFNTYA |
| SEQ ID NO: 106 | HC_N57E CDR2 | IRSKYNEYAT |
| SEQ ID NO: 3 | HC_N57E CDR3 | VRHGNFGNSYVSWFAY |
| SEQ ID NO: 107 | HC_N57E | EVKLVESGGGLVQPGGSLRLSCAASGFTFNTYAMNWVRQAPGKGL EWVARIRSKYNEYATYYADSVKDRFTISRDDSKSSLYLQMNNLKTED TAMYYCVRHGNFGNSYVSWFAYWGQGTLVTVSS |
| SEQ ID NO: 1 | HC_N57F CDR1 | GFTFNTYA |
| SEQ ID NO: 108 | HC_N57F CDR2 | IRSKYNFYAT |
| SEQ ID NO: 3 | HC_N57F CDR3 | VRHGNFGNSYVSWFAY |
| SEQ ID NO: 109 | HC_N57F | EVKLVESGGGLVQPGGSLRLSCAASGFTFNTYAMNWVRQAPGKGL EWVARIRSKYNFYATYYADSVKDRFTISRDDSKSSLYLQMNNLKTED TAMYYCVRHGNFGNSYVSWFAYWGQGTLVTVSS |
| SEQ ID NO: 1 | HC_N57G CDR1 | GFTFNTYA |
| SEQ ID NO: 110 | HC_N57G CDR2 | IRSKYNGYAT |
| SEQ ID NO: 3 | HC_N57G CDR3 | VRHGNFGNSYVSWFAY |
| SEQ ID NO: 111 | HC_N57G | EVKLVESGGGLVQPGGSLRLSCAASGFTFNTYAMNWVRQAPGKGL EWVARIRSKYNGYATYYADSVKDRFTISRDDSKSSLYLQMNNLKTED TAMYYCVRHGNFGNSYVSWFAYWGQGTLVTVSS |
| SEQ ID NO: 1 | HC_N57I CDR1 | GFTFNTYA |
| SEQ ID NO: 112 | HC_N57I CDR2 | IRSKYNIYAT |
| SEQ ID NO: 3 | HC_N57I CDR3 | VRHGNFGNSYVSWFAY |
| SEQ ID NO: 113 | HC_N57I | EVKLVESGGGLVQPGGSLRLSCAASGFTFNTYAMNWVRQAPGKGL EWVARIRSKYNIYATYYADSVKDRFTISRDDSKSSLYLQMNNLKTEDT AMYYCVRHGNFGNSYVSWFAYWGQGTLVTVSS |
| SEQ ID NO: 1 | HC_N57K CDR1 | GFTFNTYA |
| SEQ ID NO: 114 | HC_N57K CDR2 | IRSKYNKYAT |
| SEQ ID NO: 3 | HC_N57K CDR3 | VRHGNFGNSYVSWFAY |
| SEQ ID NO: 115 | HC_N57K | EVKLVESGGGLVQPGGSLRLSCAASGFTFNTYAMNWVRQAPGKGL EWVARIRSKYNKYATYYADSVKDRFTISRDDSKSSLYLQMNNLKTED TAMYYCVRHGNFGNSYVSWFAYWGQGTLVTVSS |
| SEQ ID NO: 1 | HC_N57L CDR1 | GFTFNTYA |
| SEQ ID NO: 116 | HC_N57L CDR2 | IRSKYNLYAT |
| SEQ ID NO: 3 | HC_N57L CDR3 | VRHGNFGNSYVSWFAY |
| SEQ ID NO: 117 | HC_N57L | EVKLVESGGGLVQPGGSLRLSCAASGFTFNTYAMNWVRQAPGKGL EWVARIRSKYNLYATYYADSVKDRFTISRDDSKSSLYLQMNNLKTED TAMYYCVRHGNFGNSYVSWFAYWGQGTLVTVSS |
| SEQ ID NO: 1 | HC_N57M CDR1 | GFTFNTYA |
| SEQ ID NO: 118 | HC_N57M CDR2 | IRSKYNMYAT |
| SEQ ID NO: 3 | HC_N57M CDR3 | VRHGNFGNSYVSWFAY |
| SEQ ID NO: 119 | HC_N57M | EVKLVESGGGLVQPGGSLRLSCAASGFTFNTYAMNWVRQAPGKGL EWVARIRSKYNMYATYYADSVKDRFTISRDDSKSSLYLQMNNLKTED TAMYYCVRHGNFGNSYVSWFAYWGQGTLVTVSS |
| SEQ ID NO: 1 | HC_N57P CDR1 | GFTFNTYA |

TABLE 1-continued

| | Sequences | |
|---|---|---|
| SEQ ID NO: | Clone name | Sequence |
| SEQ ID NQ: 120 | HC_N57P CDR2 | IRSKYNPYAT |
| SEQ ID NO: 3 | HC_N57P CDR3 | VRHGNFGNSYVSWFAY |
| SEQ ID NO: 121 | HC_N57P | EVKLVESGGGLVQPGGSLRLSCAASGFTFNTYAMNWVRQAPGKGL EWVARIRSKYNPYATYYADSVKDRFTISRDDSKSSLYLQMNNLKTED TAMYYCVRHGNFGNSYVSWFAYWGQGTLVTVSS |
| SEQ ID NO: 1 | HC_N57Q CDR1 | GFTFNTYA |
| SEQ ID NO: 122 | HC_N57Q CDR2 | IRSKYNQYAT |
| SEQ ID NO: 3 | HC_N57Q CDR3 | VRHGNFGNSYVSWFAY |
| SEQ ID NO: 123 | HC_N57Q | EVKLVESGGGLVQPGGSLRLSCAASGFTFNTYAMNWVRQAPGKGL EWVARIRSKYNQYATYYADSVKDRFTISRDDSKSSLYLQMNNLKTED TAMYYCVRHGNFGNSYVSWFAYWGQGTLVTVSS |
| SEQ ID NO: 1 | HC_N57R CDR1 | GFTFNTYA |
| SEQ ID NO: 124 | HC_N57R CDR2 | IRSKYNRYAT |
| SEQ ID NO: 3 | HC_N57R CDR3 | VRHGNFGNSYVSWFAY |
| SEQ ID NO: 125 | HC_N57R | EVKLVESGGGLVQPGGSLRLSCAASGFTFNTYAMNWVRQAPGKGL EWVARIRSKYNRYATYYADSVKDRFTISRDDSKSSLYLQMNNLKTED TAMYYCVRHGNFGNSYVSWFAYWGQGTLVTVSS |
| SEQ ID NO: 1 | HC_N57T CDR1 | GFTFNTYA |
| SEQ ID NO: 126 | HC_N57T CDR2 | IRSKYNTYAT |
| SEQ ID NO: 3 | HC_N57T CDR3 | VRHGNFGNSYVSWFAY |
| SEQ ID NO: 127 | HC_N57T | EVKLVESGGGLVQPGGSLRLSCAASGFTFNTYAMNWVRQAPGKGL EWVARIRSKYNTYATYYADSVKDRFTISRDDSKSSLYLQMNNLKTED TAMYYCVRHGNFGNSYVSWFAYWGQGTLVTVSS |
| SEQ ID NO: 1 | HC_N57V CDR1 | GFTFNTYA |
| SEQ ID NO: 128 | HC_N57V CDR2 | IRSKYNVYAT |
| SEQ ID NO: 3 | HC_N57V CDR3 | VRHGNFGNSYVSWFAY |
| SEQ ID NO: 129 | HC_N57V | EVKLVESGGGLVQPGGSLRLSCAASGFTFNTYAMNWVRQAPGKGL EWVARIRSKYNVYATYYADSVKDRFTISRDDSKSSLYLQMNNLKTED TAMYYCVRHGNFGNSYVSWFAYWGQGTLVTVSS |
| SEQ ID NO: 1 | HC_N57W CDR1 | GFTFNTYA |
| SEQ ID NQ: 130 | HC_N57W CDR2 | IRSKYNWYAT |
| SEQ ID NO: 3 | HC_N57W CDR3 | VRHGNFGNSYVSWFAY |
| SEQ ID NO: 131 | HC_N57W | EVKLVESGGGLVQPGGSLRLSCAASGFTFNTYAMNWVRQAPGKGL EWVARIRSKYNWYATYYADSVKDRFTISRDDSKSSLYLQMNNLKTE DTAMYYCVRHGNFGNSYVSWFAYWGQGTLVTVSS |
| SEQ ID NO: 1 | HC_N57Y CDR1 | GFTFNTYA |
| SEQ ID NO: 132 | HC_N57Y CDR2 | IRSKYNYYAT |
| SEQ ID NO: 3 | HC_N57Y CDR3 | VRHGNFGNSYVSWFAY |
| SEQ ID NO: 133 | HC_N57Y | EVKLVESGGGLVQPGGSLRLSCAASGFTFNTYAMNWVRQAPGKGL EWVARIRSKYNYYATYYADSVKDRFTISRDDSKSSLYLQMNNLKTED TAMYYCVRHGNFGNSYVSWFAYWGQGTLVTVSS |
| SEQ ID NO: 1 | HC_A59C CDR1 | GFTFNTYA |
| SEQ ID NO: 134 | HC_A59C CDR2 | IRSKYNNYCT |
| SEQ ID NO: 3 | HC_A59C CDR3 | VRHGNFGNSYVSWFAY |

TABLE 1-continued

| Sequences | | |
|---|---|---|
| SEQ ID NO: | Clone name | Sequence |
| SEQ ID NO: 135 | HC_A59C | EVKLVESGGGLVQPGGSLRLSCAASGFTFNTYAMNWVRQAPGKGL<br>EWVARIRSKYNNYCTYYADSVKDRFTISRDDSKSSLYLQMNNLKTED<br>TAMYYCVRHGNFGNSYVSWFAYWGQGTLVTVSS |
| SEQ ID NO: 1 | HC_A59D CDR1 | GFTFNTYA |
| SEQ ID NO: 136 | HC_A59D CDR2 | IRSKYNNYDT |
| SEQ ID NO: 3 | HC_A59D CDR3 | VRHGNFGNSYVSWFAY |
| SEQ ID NO: 137 | HC_A59D | EVKLVESGGGLVQPGGSLRLSCAASGFTFNTYAMNWVRQAPGKGL<br>EWVARIRSKYNNYDTYYADSVKDRFTISRDDSKSSLYLQMNNLKTED<br>TAMYYCVRHGNFGNSYVSWFAYWGQGTLVTVSS |
| SEQ ID NO: 1 | HC_A59E CDR1 | GFTFNTYA |
| SEQ ID NO: 138 | HC_A59E CDR2 | IRSKYNNYET |
| SEQ ID NO: 3 | HC_A59E CDR3 | VRHGNFGNSYVSWFAY |
| SEQ ID NO: 139 | HC_A59E | EVKLVESGGGLVQPGGSLRLSCAASGFTFNTYAMNWVRQAPGKGL<br>EWVARIRSKYNNYETYYADSVKDRFTISRDDSKSSLYLQMNNLKTED<br>TAMYYCVRHGNFGNSYVSWFAYWGQGTLVTVSS |
| SEQ ID NO: 1 | HC_A59F CDR1 | GFTFNTYA |
| SEQ ID NQ: 140 | HC_A59F CDR2 | IRSKYNNYFT |
| SEQ ID NO: 3 | HC_A59F CDR3 | VRHGNFGNSYVSWFAY |
| SEQ ID NO: 141 | HC_A59F | EVKLVESGGGLVQPGGSLRLSCAASGFTFNTYAMNWVRQAPGKGL<br>EWVARIRSKYNNYFTYYADSVKDRFTISRDDSKSSLYLQMNNLKTED<br>TAMYYCVRHGNFGNSYVSWFAYWGQGTLVTVSS |
| SEQ ID NO: 1 | HC_A59G CDR1 | GFTFNTYA |
| SEQ ID NO: 142 | HC_A59G CDR2 | IRSKYNNYGT |
| SEQ ID NO: 3 | HC_A59G CDR3 | VRHGNFGNSYVSWFAY |
| SEQ ID NO: 143 | HC_A59G | EVKLVESGGGLVQPGGSLRLSCAASGFTFNTYAMNWVRQAPGKGL<br>EWVARIRSKYNNYGTYYADSVKDRFTISRDDSKSSLYLQMNNLKTED<br>TAMYYCVRHGNFGNSYVSWFAYWGQGTLVTVSS |
| SEQ ID NO: 1 | HC_A59H CDR1 | GFTFNTYA |
| SEQ ID NO: 144 | HC_A59H CDR2 | IRSKYNNYHT |
| SEQ ID NO: 3 | HC_A59H CDR3 | VRHGNFGNSYVSWFAY |
| SEQ ID NO: 145 | HC_A59H | EVKLVESGGGLVQPGGSLRLSCAASGFTFNTYAMNWVRQAPGKGL<br>EWVARIRSKYNNYHTYYADSVKDRFTISRDDSKSSLYLQMNNLKTED<br>TAMYYCVRHGNFGNSYVSWFAYWGQGTLVTVSS |
| SEQ ID NO: 1 | HC_A59I CDR1 | GFTFNTYA |
| SEQ ID NO: 146 | HC_A59I CDR2 | IRSKYNNYIT |
| SEQ ID NO: 3 | HC_A59I CDR3 | VRHGNFGNSYVSWFAY |
| SEQ ID NO: 147 | HC_A59I | EVKLVESGGGLVQPGGSLRLSCAASGFTFNTYAMNWVRQAPGKGL<br>EWVARIRSKYNNYITYYADSVKDRFTISRDDSKSSLYLQMNNLKTEDT<br>AMYYCVRHGNFGNSYVSWFAYWGQGTLVTVSS |
| SEQ ID NO: 1 | HC_A59K CDR1 | GFTFNTYA |
| SEQ ID NO: 148 | HC_A59K CDR2 | IRSKYNNYKT |
| SEQ ID NO: 3 | HC_A59K CDR3 | VRHGNFGNSYVSWFAY |
| SEQ ID NO: 149 | HC_A59K | EVKLVESGGGLVQPGGSLRLSCAASGFTFNTYAMNWVRQAPGKGL<br>EWVARIRSKYNNYKTYYADSVKDRFTISRDDSKSSLYLQMNNLKTED<br>TAMYYCVRHGNFGNSYVSWFAYWGQGTLVTVSS |
| SEQ ID NO: 1 | HC_A59L CDR1 | GFTFNTYA |

TABLE 1-continued

| | | Sequences |
|---|---|---|
| SEQ ID NO: | Clone name | Sequence |
| SEQ ID NO: 150 | HC_A59L CDR2 | IRSKYNNYLT |
| SEQ ID NO: 3 | HC_A59L CDR3 | VRHGNFGNSYVSWFAY |
| SEQ ID NO: 151 | HC_A59L | EVKLVESGGGLVQPGGSLRLSCAASGFTFNTYAMNWVRQAPGKGL EWVARIRSKYNNYLTYYADSVKDRFTISRDDSKSSLYLQMNNLKTED TAMYYCVRHGNFGNSYVSWFAYWGQGTLVTVSS |
| SEQ ID NO: 1 | HC_A59M CDR1 | GFTFNTYA |
| SEQ ID NO: 152 | HC_A59M CDR2 | IRSKYNNYMT |
| SEQ ID NO: 3 | HC_A59M CDR3 | VRHGNFGNSYVSWFAY |
| SEQ ID NO: 153 | HC_A59M | EVKLVESGGGLVQPGGSLRLSCAASGFTFNTYAMNWVRQAPGKGL EWVARIRSKYNNYMTYYADSVKDRFTISRDDSKSSLYLQMNNLKTE DTAMYYCVRHGNFGNSYVSWFAYWGQGTLVTVSS |
| SEQ ID NO: 1 | HC_A59N CDR1 | GFTFNTYA |
| SEQ ID NO: 154 | HC_A59N CDR2 | IRSKYNNYNT |
| SEQ ID NO: 3 | HC_A59N CDR3 | VRHGNFGNSYVSWFAY |
| SEQ ID NO: 155 | HC_A59N | EVKLVESGGGLVQPGGSLRLSCAASGFTFNTYAMNWVRQAPGKGL EWVARIRSKYNNYNTYYADSVKDRFTISRDDSKSSLYLQMNNLKTED TAMYYCVRHGNFGNSYVSWFAYWGQGTLVTVSS |
| SEQ ID NO: 1 | HC_A59P CDR1 | GFTFNTYA |
| SEQ ID NO: 156 | HC_A59P CDR2 | IRSKYNNYPT |
| SEQ ID NO: 3 | HC_A59P CDR3 | VRHGNFGNSYVSWFAY |
| SEQ ID NO: 157 | HC_A59P | EVKLVESGGGLVQPGGSLRLSCAASGFTFNTYAMNWVRQAPGKGL EWVARIRSKYNNYPTYYADSVKDRFTISRDDSKSSLYLQMNNLKTED TAMYYCVRHGNFGNSYVSWFAYWGQGTLVTVSS |
| SEQ ID NO: 1 | HC_A59Q CDR1 | GFTFNTYA |
| SEQ ID NO: 158 | HC_A59Q CDR2 | IRSKYNNYQT |
| SEQ ID NO: 3 | HC_A59Q CDR3 | VRHGNFGNSYVSWFAY |
| SEQ ID NO: 159 | HC_A59Q | EVKLVESGGGLVQPGGSLRLSCAASGFTFNTYAMNWVRQAPGKGL EWVARIRSKYNNYQTYYADSVKDRFTISRDDSKSSLYLQMNNLKTED TAMYYCVRHGNFGNSYVSWFAYWGQGTLVTVSS |
| SEQ ID NO: 1 | HC_A59R CDR1 | GFTFNTYA |
| SEQ ID NO: 160 | HC_A59R CDR2 | IRSKYNNYRT |
| SEQ ID NO: 3 | HC_A59R CDR3 | VRHGNFGNSYVSWFAY |
| SEQ ID NO: 161 | HC_A59R | EVKLVESGGGLVQPGGSLRLSCAASGFTFNTYAMNWVRQAPGKGL EWVARIRSKYNNYRTYYADSVKDRFTISRDDSKSSLYLQMNNLKTED TAMYYCVRHGNFGNSYVSWFAYWGQGTLVTVSS |
| SEQ ID NO: 1 | HC_A59S CDR1 | GFTFNTYA |
| SEQ ID NO: 162 | HC_A59S CDR2 | IRSKYNNYST |
| SEQ ID NO: 3 | HC_A59S CDR3 | VRHGNFGNSYVSWFAY |
| SEQ ID NO: 163 | HC_A59S | EVKLVESGGGLVQPGGSLRLSCAASGFTFNTYAMNWVRQAPGKGL EWVARIRSKYNNYSTYYADSVKDRFTISRDDSKSSLYLQMNNLKTED TAMYYCVRHGNFGNSYVSWFAYWGQGTLVTVSS |
| SEQ ID NO: 1 | HC_A59V CDR1 | GFTFNTYA |
| SEQ ID NO: 164 | HC_A59V CDR2 | IRSKYNNYVT |
| SEQ ID NO: 3 | HC_A59V CDR3 | VRHGNFGNSYVSWFAY |

TABLE 1-continued

| | | Sequences |
|---|---|---|
| SEQ ID NO: | Clone name | Sequence |
| SEQ ID NO: 165 | HC_A59V | EVKLVESGGGLVQPGGSLRLSCAASGFTFNTYAMNWVRQAPGKGL EWVARIRSKYNNYVTYYADSVKDRFTISRDDSKSSLYLQMNNLKTED TAMYYCVRHGNFGNSYVSWFAYWGQGTLVTVSS |
| SEQ ID NO: 1 | HC_A59W CDR1 | GFTFNTYA |
| SEQ ID NO: 166 | HC_A59W CDR2 | IRSKYNNYWT |
| SEQ ID NO: 3 | HC_A59W CDR3 | VRHGNFGNSYVSWFAY |
| SEQ ID NO: 167 | HC_A59W | EVKLVESGGGLVQPGGSLRLSCAASGFTFNTYAMNWVRQAPGKGL EWVARIRSKYNNYWTYYADSVKDRFTISRDDSKSSLYLQMNNLKTE DTAMYYCVRHGNFGNSYVSWFAYWGQGTLVTVSS |
| SEQ ID NO: 1 | HC_A59Y CDR1 | GFTFNTYA |
| SEQ ID NO: 168 | HC_A59Y CDR2 | IRSKYNNYYT |
| SEQ ID NO: 3 | HC_A59Y CDR3 | VRHGNFGNSYVSWFAY |
| SEQ ID NO: 169 | HC_A59Y | EVKLVESGGGLVQPGGSLRLSCAASGFTFNTYAMNWVRQAPGKGL EWVARIRSKYNNYYTYYADSVKDRFTISRDDSKSSLYLQMNNLKTED TAMYYCVRHGNFGNSYVSWFAYWGQGTLVTVSS |
| SEQ ID NO: 1 | HC_H101A CDR1 | GFTFNTYA |
| SEQ ID NO: 2 | HC_H101A CDR2 | IRSKYNNYAT |
| SEQ ID NQ: 170 | HC_H101A CDR3 | VRAGNFGNSYVSWFAY |
| SEQ ID NO: 171 | HC_H101A | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRAGNFGNSYVSWFAYWGQGTLVTVSS |
| SEQ ID NO: 1 | HC_H101C CDR1 | GFTFNTYA |
| SEQ ID NO: 2 | HC_H101C CDR2 | IRSKYNNYAT |
| SEQ ID NO: 172 | HC_H101C CDR3 | VRCGNFGNSYVSWFAY |
| SEQ ID NO: 173 | HC_H101C | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRCGNFGNSYVSWFAYWGQGTLVTVSS |
| SEQ ID NO: 1 | HC_H101F CDR1 | GFTFNTYA |
| SEQ ID NO: 2 | HC_H101F CDR2 | IRSKYNNYAT |
| SEQ ID NO: 174 | HC_H101F CDR3 | VRFGNFGNSYVSWFAY |
| SEQ ID NO: 175 | HC_H101F | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRFGNFGNSYVSWFAYWGQGTLVTVSS |
| SEQ ID NO: 1 | HC_H101G CDR1 | GFTFNTYA |
| SEQ ID NO: 2 | HC_H101G CDR2 | IRSKYNNYAT |
| SEQ ID NO: 176 | HC_H101G CDR3 | VRGGNFGNSYVSWFAY |
| SEQ ID NO: 177 | HC_H101G | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRGGNFGNSYVSWFAYWGQGTLVTVSS |
| SEQ ID NO: 1 | HC_H101I CDR1 | GFTFNTYA |
| SEQ ID NO: 2 | HC_H101I CDR2 | IRSKYNNYAT |
| SEQ ID NO: 178 | HC_H101I CDR3 | VRIGNFGNSYVSWFAY |
| SEQ ID NO: 179 | HC_H101I | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRIGNFGNSYVSWFAYWGQGTLVTVSS |
| SEQ ID NO: 1 | HC_H101K CDR1 | GFTFNTYA |

TABLE 1-continued

| | | Sequences |
|---|---|---|
| SEQ ID NO: | Clone name | Sequence |
| SEQ ID NO: 2 | HC_H101K CDR2 | IRSKYNNYAT |
| SEQ ID NO: 180 | HC_H101K CDR3 | VRKGNFGNSYVSWFAY |
| SEQ ID NO: 181 | HC_H101K | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRKGNFGNSYVSWFAYWGQGTLVTVSS |
| SEQ ID NO: 1 | HC_H101L CDR1 | GFTFNTYA |
| SEQ ID NO: 2 | HC_H101L CDR2 | IRSKYNNYAT |
| SEQ ID NO: 182 | HC_H101L CDR3 | VRLGNFGNSYVSWFAY |
| SEQ ID NO: 183 | HC_H101L | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRLGNFGNSYVSWFAYWGQGTLVTVSS |
| SEQ ID NO: 1 | HC_H101N CDR1 | GFTFNTYA |
| SEQ ID NO: 2 | HC_H101N CDR2 | IRSKYNNYAT |
| SEQ ID NO: 184 | HC_H101N CDR3 | VRNGNFGNSYVSWFAY |
| SEQ ID NO: 185 | HC_H101N | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRNGNFGNSYVSWFAYWGQGTLVTVSS |
| SEQ ID NO: 1 | HC_H101P CDR1 | GFTFNTYA |
| SEQ ID NO: 2 | HC_H101P CDR2 | IRSKYNNYAT |
| SEQ ID NO: 186 | HC_H101P CDR3 | VRPGNFGNSYVSWFAY |
| SEQ ID NO: 187 | HC_H101P | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRPGNFGNSYVSWFAYWGQGTLVTVSS |
| SEQ ID NO: 1 | HC_H101Q CDR1 | GFTFNTYA |
| SEQ ID NO: 2 | HC_H101Q CDR2 | IRSKYNNYAT |
| SEQ ID NO: 188 | HC_H101Q CDR3 | VRQGNFGNSYVSWFAY |
| SEQ ID NO: 189 | HC_H101Q | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRQGNFGNSYVSWFAYWGQGTLVTVSS |
| SEQ ID NO: 1 | HC_H101R CDR1 | GFTFNTYA |
| SEQ ID NO: 2 | HC_H101R CDR2 | IRSKYNNYAT |
| SEQ ID NQ: 190 | HC_H101R CDR3 | VRRGNFGNSYVSWFAY |
| SEQ ID NO: 191 | HC_H101R | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRRGNFGNSYVSWFAYWGQGTLVTVSS |
| SEQ ID NO: 1 | HC_H101S CDR1 | GFTFNTYA |
| SEQ ID NO: 2 | HC_H101S CDR2 | IRSKYNNYAT |
| SEQ ID NO: 192 | HC_H101S CDR3 | VRSGNFGNSYVSWFAY |
| SEQ ID NO: 193 | HC_H101S | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRSGNFGNSYVSWFAYWGQGTLVTVSS |
| SEQ ID NO: 1 | HC_H101T CDR1 | GFTFNTYA |
| SEQ ID NO: 2 | HC_H101T CDR2 | IRSKYNNYAT |
| SEQ ID NO: 194 | HC_H101T CDR3 | VRTGNFGNSYVSWFAY |

TABLE 1-continued

| | | Sequences |
| --- | --- | --- |
| SEQ ID NO: | Clone name | Sequence |
| SEQ ID NO: 195 | HC_H101T | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRTGNFGNSYVSWFAYWGQGTLVTVSS |
| SEQ ID NO: 1 | HC_H101V CDR1 | GFTFNTYA |
| SEQ ID NO: 2 | HC_H101V CDR2 | IRSKYNNYAT |
| SEQ ID NO: 196 | HC_H101V CDR3 | VRVGNFGNSYVSWFAY |
| SEQ ID NO: 197 | HC_H101V | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRVGNFGNSYVSWFAYWGQGTLVTVSS |
| SEQ ID NO: 1 | HC_H101W CDR1 | GFTFNTYA |
| SEQ ID NO: 2 | HC_H101W CDR2 | IRSKYNNYAT |
| SEQ ID NO: 198 | HC_H101W CDR3 | VRWGNFGNSYVSWFAY |
| SEQ ID NO: 199 | HC_H101W | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRWGNFGNSYVSWFAYWGQGTLVTVSS |
| SEQ ID NO: 1 | HC_H101Y CDR1 | GFTFNTYA |
| SEQ ID NO: 2 | HC_H101Y CDR2 | IRSKYNNYAT |
| SEQ ID NQ: 200 | HC_H101Y CDR3 | VRYGNFGNSYVSWFAY |
| SEQ ID NO: 201 | HC_H101Y | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRYGNFGNSYVSWFAYWGQGTLVTVSS |
| SEQ ID NO: 1 | HC_G105A CDR1 | GFTFNTYA |
| SEQ ID NO: 2 | HC_G105A CDR2 | IRSKYNNYAT |
| SEQ ID NO: 202 | HC_G105A CDR3 | VRHGNFANSYVSWFAY |
| SEQ ID NO: 203 | HC_G105A | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFANSYVSWFAYWGQGTLVTVSS |
| SEQ ID NO: 1 | HC_G105C CDR1 | GFTFNTYA |
| SEQ ID NO: 2 | HC_G105C CDR2 | IRSKYNNYAT |
| SEQ ID NO: 204 | HC_G105C CDR3 | VRHGNFCNSYVSWFAY |
| SEQ ID NO: 205 | HC_G105C | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFCNSYVSWFAYWGQGTLVTVSS |
| SEQ ID NO: 1 | HC_G105E CDR1 | GFTFNTYA |
| SEQ ID NO: 2 | HC_G105E CDR2 | IRSKYNNYAT |
| SEQ ID NO: 206 | HC_G105E CDR3 | VRHGNFENSYVSWFAY |
| SEQ ID NO: 207 | HC_G105E | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFENSYVSWFAYWGQGTLVTVSS |
| SEQ ID NO: 1 | HC_G105F CDR1 | GFTFNTYA |
| SEQ ID NO: 2 | HC_G105F CDR2 | IRSKYNNYAT |
| SEQ ID NO: 208 | HC_G105F CDR3 | VRHGNFFNSYVSWFAY |
| SEQ ID NO: 209 | HC_G105F | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFFNSYVSWFAYWGQGTLVTVSS |
| SEQ ID NO: 1 | HC_G105H CDR1 | GFTFNTYA |

TABLE 1-continued

| SEQ ID NO: | Clone name | Sequence |
|---|---|---|
| SEQ ID NO: 2 | HC_G105H CDR2 | IRSKYNNYAT |
| SEQ ID NQ: 210 | HC_G105H CDR3 | VRHGNFHNSYVSWFAY |
| SEQ ID NO: 211 | HC_G105H | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFHNSYVSWFAYWGQGTLVTVSS |
| SEQ ID NO: 1 | HC_G105I CDR1 | GFTFNTYA |
| SEQ ID NO: 2 | HC_G105I CDR2 | IRSKYNNYAT |
| SEQ ID NO: 212 | HC_G105I CDR3 | VRHGNFINSYVSWFAY |
| SEQ ID NO: 213 | HC_G105I | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFINSYVSWFAYWGQGTLVTVSS |
| SEQ ID NO: 1 | HC_G105L CDR1 | GFTFNTYA |
| SEQ ID NO: 2 | HC_G105L CDR2 | IRSKYNNYAT |
| SEQ ID NO: 214 | HC_G105L CDR3 | VRHGNFLNSYVSWFAY |
| SEQ ID NO: 215 | HC_G105L | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFLNSYVSWFAYWGQGTLVTVSS |
| SEQ ID NO: 1 | HC_G105M CDR1 | GFTFNTYA |
| SEQ ID NO: 2 | HC_G105M CDR2 | IRSKYNNYAT |
| SEQ ID NO: 216 | HC_G105M CDR3 | VRHGNFMNSYVSWFAY |
| SEQ ID NO: 217 | HC_G105M | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFMNSYVSWFAYWGQGTLVTVSS |
| SEQ ID NO: 1 | HC_G105N CDR1 | GFTFNTYA |
| SEQ ID NO: 2 | HC_G105N CDR2 | IRSKYNNYAT |
| SEQ ID NO: 218 | HC_G105N CDR3 | VRHGNFNNSYVSWFAY |
| SEQ ID NO: 219 | HC_G105N | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFNNSYVSWFAYWGQGTLVTVSS |
| SEQ ID NO: 1 | HC_G105P CDR1 | GFTFNTYA |
| SEQ ID NO: 2 | HC_G105P CDR2 | IRSKYNNYAT |
| SEQ ID NO: 220 | HC_G105P CDR3 | VRHGNFPNSYVSWFAY |
| SEQ ID NO: 221 | HC_G105P | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFPNSYVSWFAYWGQGTLVTVSS |
| SEQ ID NO: 1 | HC_G105Q CDR1 | GFTFNTYA |
| SEQ ID NO: 2 | HC_G105Q CDR2 | IRSKYNNYAT |
| SEQ ID NO: 222 | HC_G105Q CDR3 | VRHGNFQNSYVSWFAY |
| SEQ ID NO: 223 | HC_G105Q | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFQNSYVSWFAYWGQGTLVTVSS |
| SEQ ID NO: 1 | HC_G105R CDR1 | GFTFNTYA |
| SEQ ID NO: 2 | HC_G105R CDR2 | IRSKYNNYAT |
| SEQ ID NO: 224 | HC_G105R CDR3 | VRHGNFRNSYVSWFAY |

TABLE 1-continued

| SEQ ID NO: | Clone name | Sequence |
|---|---|---|
| SEQ ID NO: 225 | HC_G105R | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFRNSYVSWFAYWGQGTLVTVSS |
| SEQ ID NO: 1 | HC_G105S CDR1 | GFTFNTYA |
| SEQ ID NO: 2 | HC_G105S CDR2 | IRSKYNNYAT |
| SEQ ID NO: 226 | HC_G105S CDR3 | VRHGNFSNSYVSWFAY |
| SEQ ID NO: 227 | HC_G105S | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFSNSYVSWFAYWGQGTLVTVSS |
| SEQ ID NO: 1 | HC_G105T CDR1 | GFTFNTYA |
| SEQ ID NO: 2 | HC_G105T CDR2 | IRSKYNNYAT |
| SEQ ID NO: 228 | HC_G105T CDR3 | VRHGNFTNSYVSWFAY |
| SEQ ID NO: 229 | HC_G105T | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFTNSYVSWFAYWGQGTLVTVSS |
| SEQ ID NO: 1 | HC_G105V CDR1 | GFTFNTYA |
| SEQ ID NO: 2 | HC_G105V CDR2 | IRSKYNNYAT |
| SEQ ID NO: 230 | HC_G105V CDR3 | VRHGNFVNSYVSWFAY |
| SEQ ID NO: 231 | HC_G105V | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFVNSYVSWFAYWGQGTLVTVSS |
| SEQ ID NO: 1 | HC_G105W CDR1 | GFTFNTYA |
| SEQ ID NO: 2 | HC_G105W CDR2 | IRSKYNNYAT |
| SEQ ID NO: 232 | HC_G105W CDR3 | VRHGNFWNSYVSWFAY |
| SEQ ID NO: 233 | HC_G105W | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFWNSYVSWFAYWGQGTLVTVSS |
| SEQ ID NO: 1 | HC_G105Y CDR1 | GFTFNTYA |
| SEQ ID NO: 2 | HC_G105Y CDR2 | IRSKYNNYAT |
| SEQ ID NO: 234 | HC_G105Y CDR3 | VRHGNFYNSYVSWFAY |
| SEQ ID NO: 235 | HC_G105Y | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFYNSYVSWFAYWGQGTLVTVSS |
| SEQ ID NO: 1 | HC_S110A CDR1 | GFTFNTYA |
| SEQ ID NO: 2 | HC_S110A CDR2 | IRSKYNNYAT |
| SEQ ID NO: 236 | HC_S110A CDR3 | VRHGNFGNSYVAWFAY |
| SEQ ID NO: 237 | HC_S110A | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVAWFAYWGQGTLVTVSS |
| SEQ ID NO: 1 | HC_S110C CDR1 | GFTFNTYA |
| SEQ ID NO: 2 | HC_S110C CDR2 | IRSKYNNYAT |
| SEQ ID NO: 238 | HC_S110C CDR3 | VRHGNFGNSYVCWFAY |
| SEQ ID NO: 239 | HC_S110C | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVCWFAYWGQGTLVTVSS |
| SEQ ID NO: 1 | HC_S110E CDR1 | GFTFNTYA |

TABLE 1-continued

| | | Sequences |
|---|---|---|
| SEQ ID NO: | Clone name | Sequence |
| SEQ ID NO: 2 | HC_S110E CDR2 | IRSKYNNYAT |
| SEQ ID NO: 240 | HC_S110E CDR3 | VRHGNFGNSYVEWFAY |
| SEQ ID NO: 241 | HC_S110E | EVKLVESGGGLVQPGGSLRLSCAASGFTFNTYAMNWVRQAPGKGL<br>EWVARIRSKYNNYATYYADSVKDRFTISRDDSKSSLYLQMNNLKTED<br>TAMYYCVRHGNFGNSYVEWFAYWGQGTLVTVSS |
| SEQ ID NO: 1 | HC_S110F CDR1 | GFTFNTYA |
| SEQ ID NO: 2 | HC_S110F CDR2 | IRSKYNNYAT |
| SEQ ID NO: 242 | HC_S110F CDR3 | VRHGNFGNSYVFWFAY |
| SEQ ID NO: 243 | HC_S110F | EVKLVESGGGLVQPGGSLRLSCAASGFTFNTYAMNWVRQAPGKGL<br>EWVARIRSKYNNYATYYADSVKDRFTISRDDSKSSLYLQMNNLKTED<br>TAMYYCVRHGNFGNSYVFWFAYWGQGTLVTVSS |
| SEQ ID NO: 1 | HC_S110G CDR1 | GFTFNTYA |
| SEQ ID NO: 2 | HC_S110G CDR2 | IRSKYNNYAT |
| SEQ ID NO: 244 | HC_S110G CDR3 | VRHGNFGNSYVGWFAY |
| SEQ ID NO: 245 | HC_S110G | EVKLVESGGGLVQPGGSLRLSCAASGFTFNTYAMNWVRQAPGKGL<br>EWVARIRSKYNNYATYYADSVKDRFTISRDDSKSSLYLQMNNLKTED<br>TAMYYCVRHGNFGNSYVGWFAYWGQGTLVTVSS |
| SEQ ID NO: 1 | HC_S110H CDR1 | GFTFNTYA |
| SEQ ID NO: 2 | HC_S110H CDR2 | IRSKYNNYAT |
| SEQ ID NO: 246 | HC_S110H CDR3 | VRHGNFGNSYVHWFAY |
| SEQ ID NO: 247 | HC_S110H | EVKLVESGGGLVQPGGSLRLSCAASGFTFNTYAMNWVRQAPGKGL<br>EWVARIRSKYNNYATYYADSVKDRFTISRDDSKSSLYLQMNNLKTED<br>TAMYYCVRHGNFGNSYVHWFAYWGQGTLVTVSS |
| SEQ ID NO: 1 | HC_S110K CDR1 | GFTFNTYA |
| SEQ ID NO: 2 | HC_S110K CDR2 | IRSKYNNYAT |
| SEQ ID NO: 248 | HC_S110K CDR3 | VRHGNFGNSYVKWFAY |
| SEQ ID NO: 249 | HC_S110K | EVKLVESGGGLVQPGGSLRLSCAASGFTFNTYAMNWVRQAPGKGL<br>EWVARIRSKYNNYATYYADSVKDRFTISRDDSKSSLYLQMNNLKTED<br>TAMYYCVRHGNFGNSYVKWFAYWGQGTLVTVSS |
| SEQ ID NO: 1 | HC_S110L CDR1 | GFTFNTYA |
| SEQ ID NO: 2 | HC_S110L CDR2 | IRSKYNNYAT |
| SEQ ID NO: 250 | HC_S110L CDR3 | VRHGNFGNSYVLWFAY |
| SEQ ID NO: 251 | HC_S110L | EVKLVESGGGLVQPGGSLRLSCAASGFTFNTYAMNWVRQAPGKGL<br>EWVARIRSKYNNYATYYADSVKDRFTISRDDSKSSLYLQMNNLKTED<br>TAMYYCVRHGNFGNSYVLWFAYWGQGTLVTVSS |
| SEQ ID NO: 1 | HC_S110N CDR1 | GFTFNTYA |
| SEQ ID NO: 2 | HC_S110N CDR2 | IRSKYNNYAT |
| SEQ ID NO: 252 | HC_S110N CDR3 | VRHGNFGNSYVNWFAY |
| SEQ ID NO: 253 | HC_S110N | EVKLVESGGGLVQPGGSLRLSCAASGFTFNTYAMNWVRQAPGKGL<br>EWVARIRSKYNNYATYYADSVKDRFTISRDDSKSSLYLQMNNLKTED<br>TAMYYCVRHGNFGNSYVNWFAYWGQGTLVTVSS |
| SEQ ID NO: 1 | HC_S110P CDR1 | GFTFNTYA |
| SEQ ID NO: 2 | HC_S110P CDR2 | IRSKYNNYAT |
| SEQ ID NO: 254 | HC_S110P CDR3 | VRHGNFGNSYVPWFAY |

TABLE 1-continued

| Sequences | | |
|---|---|---|
| SEQ ID NO: | Clone name | Sequence |
| SEQ ID NO: 255 | HC_S110P | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVPWFAYWGQGTLVTVSS |
| SEQ ID NO: 1 | HC_S110Q CDR1 | GFTFNTYA |
| SEQ ID NO: 2 | HC_S110Q CDR2 | IRSKYNNYAT |
| SEQ ID NO: 256 | HC_S110Q CDR3 | VRHGNFGNSYVQWFAY |
| SEQ ID NO: 257 | HC_S110Q | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVQWFAYWGQGTLVTVSS |
| SEQ ID NO: 1 | HC_S110R CDR1 | GFTFNTYA |
| SEQ ID NO: 2 | HC_S110R CDR2 | IRSKYNNYAT |
| SEQ ID NO: 258 | HC_S110R CDR3 | VRHGNFGNSYVRWFAY |
| SEQ ID NO: 259 | HC_S110R | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVRWFAYWGQGTLVTVSS |
| SEQ ID NO: 1 | HC_S110T CDR1 | GFTFNTYA |
| SEQ ID NO: 2 | HC_S110T CDR2 | IRSKYNNYAT |
| SEQ ID NO: 260 | HC_S110T CDR3 | VRHGNFGNSYVTWFAY |
| SEQ ID NO: 261 | HC_S110T | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVTWFAYWGQGTLVTVSS |
| SEQ ID NO: 1 | HC_S110W CDR1 | GFTFNTYA |
| SEQ ID NO: 2 | HC_S110W CDR2 | IRSKYNNYAT |
| SEQ ID NO: 262 | HC_S110W CDR3 | VRHGNFGNSYVWWFAY |
| SEQ ID NO: 263 | HC_S110W | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVWWFAYWGQGTLVTVSS |
| SEQ ID NO: 1 | HC_S110Y CDR1 | GFTFNTYA |
| SEQ ID NO: 2 | HC_S110Y CDR2 | IRSKYNNYAT |
| SEQ ID NO: 264 | HC_S110Y CDR3 | VRHGNFGNSYVYWFAY |
| SEQ ID NO: 265 | HC_S110Y | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVYWFAYWGQGTLVTVSS |
| SEQ ID NO: 1 | HC_Y114A CDR1 | GFTFNTYA |
| SEQ ID NO: 2 | HC_Y114A CDR2 | IRSKYNNYAT |
| SEQ ID NO: 266 | HC_Y114A CDR3 | VRHGNFGNSYVSWFAA |
| SEQ ID NO: 267 | HC_Y114A | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAAWGQGTLVTVSS |
| SEQ ID NO: 1 | HC_Y114C CDR1 | GFTFNTYA |
| SEQ ID NO: 2 | HC_Y114C CDR2 | IRSKYNNYAT |
| SEQ ID NO: 268 | HC_Y114C CDR3 | VRHGNFGNSYVSWFAC |
| SEQ ID NO: 269 | HC_Y114C | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFACWGQGTLVTVSS |
| SEQ ID NO: 1 | HC_Y114E CDR1 | GFTFNTYA |

TABLE 1-continued

| | | Sequences |
|---|---|---|
| SEQ ID NO: | Clone name | Sequence |
| SEQ ID NO: 2 | HC_Y114E CDR2 | IRSKYNNYAT |
| SEQ ID NQ: 270 | HC_Y114E CDR3 | VRHGNFGNSYVSWFAE |
| SEQ ID NO: 271 | HC_Y114E | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAEWGQGTLVTVSS |
| SEQ ID NO: 1 | HC_Y114F CDR1 | GFTFNTYA |
| SEQ ID NO: 2 | HC_Y114F CDR2 | IRSKYNNYAT |
| SEQ ID NO: 272 | HC_Y114F CDR3 | VRHGNFGNSYVSWFAF |
| SEQ ID NO: 273 | HC_Y114F | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAFWGQGTLVTVSS |
| SEQ ID NO: 1 | HC_Y114G CDR1 | GFTFNTYA |
| SEQ ID NO: 2 | HC_Y114G CDR2 | IRSKYNNYAT |
| SEQ ID NO: 274 | HC_Y114G CDR3 | VRHGNFGNSYVSWFAG |
| SEQ ID NO: 275 | HC_Y114G | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAGWGQGTLVTVSS |
| SEQ ID NO: 1 | HC_Y114H CDR1 | GFTFNTYA |
| SEQ ID NO: 2 | HC_Y114H CDR2 | IRSKYNNYAT |
| SEQ ID NO: 276 | HC_Y114H CDR3 | VRHGNFGNSYVSWFAH |
| SEQ ID NO: 277 | HC_Y114H | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAHWGQGTLVTVSS |
| SEQ ID NO: 1 | HC_Y114I CDR1 | GFTFNTYA |
| SEQ ID NO: 2 | HC_Y114I CDR2 | IRSKYNNYAT |
| SEQ ID NO: 278 | HC_Y114I CDR3 | VRHGNFGNSYVSWFAI |
| SEQ ID NO: 279 | HC_Y114I | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAIWGQGTLVTVSS |
| SEQ ID NO: 1 | HC_Y114K CDR1 | GFTFNTYA |
| SEQ ID NO: 2 | HC_Y114K CDR2 | IRSKYNNYAT |
| SEQ ID NO: 280 | HC_Y114K CDR3 | VRHGNFGNSYVSWFAK |
| SEQ ID NO: 281 | HC_Y114K | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAKWGQGTLVTVSS |
| SEQ ID NO: 1 | HC_Y114L CDR1 | GFTFNTYA |
| SEQ ID NO: 2 | HC_Y114L CDR2 | IRSKYNNYAT |
| SEQ ID NO: 282 | HC_Y114L CDR3 | VRHGNFGNSYVSWFAL |
| SEQ ID NO: 283 | HC_Y114L | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFALWGQGTLVTVSS |
| SEQ ID NO: 1 | HC_Y114M CDR1 | GFTFNTYA |
| SEQ ID NO: 2 | HC_Y114M CDR2 | IRSKYNNYAT |
| SEQ ID NO: 284 | HC_Y114M CDR3 | VRHGNFGNSYVSWFAM |

TABLE 1-continued

| | | Sequences |
| --- | --- | --- |
| SEQ ID NO: | Clone name | Sequence |
| SEQ ID NO: 285 | HC_Y114M | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAMWGQGTLVTVSS |
| SEQ ID NO: 1 | HC_Y114N CDR1 | GFTFNTYA |
| SEQ ID NO: 2 | HC_Y114N CDR2 | IRSKYNNYAT |
| SEQ ID NO: 286 | HC_Y114N CDR3 | VRHGNFGNSYVSWFAN |
| SEQ ID NO: 287 | HC_Y114N | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFANWGQGTLVTVSS |
| SEQ ID NO: 1 | HC_Y114P CDR1 | GFTFNTYA |
| SEQ ID NO: 2 | HC_Y114P CDR2 | IRSKYNNYAT |
| SEQ ID NO: 288 | HC_Y114P CDR3 | VRHGNFGNSYVSWFAP |
| SEQ ID NO: 289 | HC_Y114P | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAPWGQGTLVTVSS |
| SEQ ID NO: 1 | HC_Y114Q CDR1 | GFTFNTYA |
| SEQ ID NO: 2 | HC_Y114Q CDR2 | IRSKYNNYAT |
| SEQ ID NO: 290 | HC_Y114Q CDR3 | VRHGNFGNSYVSWFAQ |
| SEQ ID NO: 291 | HC_Y114Q | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAQWGQGTLVTVSS |
| SEQ ID NO: 1 | HC_Y114R CDR1 | GFTFNTYA |
| SEQ ID NO: 2 | HC_Y114R CDR2 | IRSKYNNYAT |
| SEQ ID NO: 292 | HC_Y114R CDR3 | VRHGNFGNSYVSWFAR |
| SEQ ID NO: 293 | HC_Y114R | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFARWGQGTLVTVSS |
| SEQ ID NO: 1 | HC_Y114S CDR1 | GFTFNTYA |
| SEQ ID NO: 2 | HC_Y114S CDR2 | IRSKYNNYAT |
| SEQ ID NO: 294 | HC_Y114S CDR3 | VRHGNFGNSYVSWFAS |
| SEQ ID NO: 295 | HC_Y114S | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFASWGQGTLVTVSS |
| SEQ ID NO: 1 | HC_Y114T CDR1 | GFTFNTYA |
| SEQ ID NO: 2 | HC_Y114T CDR2 | IRSKYNNYAT |
| SEQ ID NO: 296 | HC_Y114T CDR3 | VRHGNFGNSYVSWFAT |
| SEQ ID NO: 297 | HC_Y114T | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFATWGQGTLVTVSS |
| SEQ ID NO: 1 | HC_Y114V CDR1 | GFTFNTYA |
| SEQ ID NO: 2 | HC_Y114V CDR2 | IRSKYNNYAT |
| SEQ ID NO: 298 | HC_Y114V CDR3 | VRHGNFGNSYVSWFAV |
| SEQ ID NO: 299 | HC_Y114V | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAVWGQGTLVTVSS |
| SEQ ID NO: 1 | HC_Y114W CDR1 | GFTFNTYA |

TABLE 1-continued

| | | Sequences |
| SEQ ID NO: | Clone name | Sequence |
| --- | --- | --- |
| SEQ ID NO: 2 | HC_Y114W CDR2 | IRSKYNNYAT |
| SEQ ID NO: 300 | HC_Y114W CDR3 | VRHGNFGNSYVSWFAW |
| SEQ ID NO: 301 | HC_Y114W | EVKLVESGGGLVQPGGSLRLSCAASGFTFNTYAMNWVRQAPGKGL EWVARIRSKYNNYATYYADSVKDRFTISRDDSKSSLYLQMNNLKTED TAMYYCVRHGNFGNSYVSWFAWWGQGTLVTVSS |
| SEQ ID NO: 302 | LC_T31A CDR1 | TGAVTASNY |
| | LC_T31A CDR2 | GTN |
| SEQ ID NO: 7 | LC_T31A CDR3 | ALWYSNLWV |
| SEQ ID NO: 303 | LC_T31A | QAVVTQEPSFSVSPGGTVTLTCRSSTGAVTASNYANWVQQKPGQA FRGLIGGTNKRAPGVPARFSGSLIGDKAALTITGAQADDESIYFCALW YSNLWVFGGGTKLTVL |
| SEQ ID NO: 304 | LC_T31D CDR1 | TGAVTDSNY |
| | LC_T31D CDR2 | GTN |
| SEQ ID NO: 7 | LC_T31D CDR3 | ALWYSNLWV |
| SEQ ID NO: 305 | LC_T31D | QAVVTQEPSFSVSPGGTVTLTCRSSTGAVTDSNYANWVQQKPGQA FRGLIGGTNKRAPGVPARFSGSLIGDKAALTITGAQADDESIYFCALW YSNLWVFGGGTKLTVL |
| SEQ ID NO: 306 | LC_T31E CDR1 | TGAVTESNY |
| | LC_T31E CDR2 | GTN |
| SEQ ID NO: 7 | LC_T31E CDR3 | ALWYSNLWV |
| SEQ ID NO: 307 | LC_T31E | QAVVTQEPSFSVSPGGTVTLTCRSSTGAVTESNYANWVQQKPGQA FRGLIGGTNKRAPGVPARFSGSLIGDKAALTITGAQADDESIYFCALW YSNLWVFGGGTKLTVL |
| SEQ ID NO: 308 | LC_T31F CDR1 | TGAVTFSNY |
| | LC_T31F CDR2 | GTN |
| SEQ ID NO: 7 | LC_T31F CDR3 | ALWYSNLWV |
| SEQ ID NO: 309 | LC_T31F | QAVVTQEPSFSVSPGGTVTLTCRSSTGAVTFSNYANWVQQKPGQA FRGLIGGTNKRAPGVPARFSGSLIGDKAALTITGAQADDESIYFCALW YSNLWVFGGGTKLTVL |
| SEQ ID NO: 310 | LC_T31G CDR1 | TGAVTGSNY |
| | LC_T31G CDR2 | GTN |
| SEQ ID NO: 7 | LC_T31G CDR3 | ALWYSNLWV |
| SEQ ID NO: 311 | LC_T31G | QAVVTQEPSFSVSPGGTVTLTCRSSTGAVTGSNYANWVQQKPGQA FRGLIGGTNKRAPGVPARFSGSLIGDKAALTITGAQADDESIYFCALW YSNLWVFGGGTKLTVL |
| SEQ ID NO: 312 | LC_T31H CDR1 | TGAVTHSNY |
| | LC_T31H CDR2 | GTN |
| SEQ ID NO: 7 | LC_T31H CDR3 | ALWYSNLWV |
| SEQ ID NO: 313 | LC_T31H | QAVVTQEPSFSVSPGGTVTLTCRSSTGAVTHSNYANWVQQKPGQA FRGLIGGTNKRAPGVPARFSGSLIGDKAALTITGAQADDESIYFCALW YSNLWVFGGGTKLTVL |
| | LC_T31I CDR2 | GTN |
| SEQ ID NO: 314 | LC_T31K CDR1 | TGAVTKSNY |
| | LC_T31K CDR2 | GTN |
| SEQ ID NO: 7 | LC_T31K CDR3 | ALWYSNLWV |

TABLE 1-continued

| | Sequences | |
| --- | --- | --- |
| SEQ ID NO: | Clone name | Sequence |
| SEQ ID NO: 315 | LC_T31K | QAVVTQEPSFSVSPGGTVTLTCRSSTGAVTKSNYANWVQQKPGQA<br>FRGLIGGTNKRAPGVPARFSGSLIGDKAALTITGAQADDESIYFCALW<br>YSNLWVFGGGTKLTVL |
| SEQ ID NO: 316 | LC_T31L CDR1 | TGAVTLSNY |
| | LC_T31L CDR2 | GTN |
| SEQ ID NO: 7 | LC_T31L CDR3 | ALWYSNLWV |
| SEQ ID NO: 317 | LC_T31L | QAVVTQEPSFSVSPGGTVTLTCRSSTGAVTLSNYANWVQQKPGQA<br>FRGLIGGTNKRAPGVPARFSGSLIGDKAALTITGAQADDESIYFCALW<br>YSNLWVFGGGTKLTVL |
| SEQ ID NO: 318 | LC_T31M CDR1 | TGAVTMSNY |
| | LC_T31M CDR2 | GTN |
| SEQ ID NO: 7 | LC_T31M CDR3 | ALWYSNLWV |
| SEQ ID NO: 319 | LC_T31M | QAVVTQEPSFSVSPGGTVTLTCRSSTGAVTMSNYANWVQQKPGQ<br>AFRGLIGGTNKRAPGVPARFSGSLIGDKAALTITGAQADDESIYFCAL<br>WYSNLWVFGGGTKLTVL |
| SEQ ID NO: 320 | LC_T31N CDR1 | TGAVTNSNY |
| | LC_T31N CDR2 | GTN |
| SEQ ID NO: 7 | LC_T31N CDR3 | ALWYSNLWV |
| SEQ ID NO: 321 | LC_T31N | QAVVTQEPSFSVSPGGTVTLTCRSSTGAVTNSNYANWVQQKPGQA<br>FRGLIGGTNKRAPGVPARFSGSLIGDKAALTITGAQADDESIYFCALW<br>YSNLWVFGGGTKLTVL |
| SEQ ID NO: 322 | LC_T31P CDR1 | TGAVTPSNY |
| | LC_T31P CDR2 | GTN |
| SEQ ID NO: 7 | LC_T31P CDR3 | ALWYSNLWV |
| SEQ ID NO: 323 | LC_T31P | QAVVTQEPSFSVSPGGTVTLTCRSSTGAVTPSNYANWVQQKPGQA<br>FRGLIGGTNKRAPGVPARFSGSLIGDKAALTITGAQADDESIYFCALW<br>YSNLWVFGGGTKLTVL |
| SEQ ID NO: 324 | LC_T31Q CDR1 | TGAVTQSNY |
| | LC_T31Q CDR2 | GTN |
| SEQ ID NO: 7 | LC_T31Q CDR3 | ALWYSNLWV |
| SEQ ID NO: 325 | LC_T31Q | QAVVTQEPSFSVSPGGTVTLTCRSSTGAVTQSNYANWVQQKPGQA<br>FRGLIGGTNKRAPGVPARFSGSLIGDKAALTITGAQADDESIYFCALW<br>YSNLWVFGGGTKLTVL |
| SEQ ID NO: 326 | LC_T31R CDR1 | TGAVTRSNY |
| | LC_T31R CDR2 | GTN |
| SEQ ID NO: 7 | LC_T31R CDR3 | ALWYSNLWV |
| SEQ ID NO: 327 | LC_T31R | QAVVTQEPSFSVSPGGTVTLTCRSSTGAVTRSNYANWVQQKPGQA<br>FRGLIGGTNKRAPGVPARFSGSLIGDKAALTITGAQADDESIYFCALW<br>YSNLWVFGGGTKLTVL |
| | LC_T31S CDR2 | GTN |
| SEQ ID NO: 328 | LC_T31V CDR1 | TGAVTVSNY |
| | LC_T31V CDR2 | GTN |
| SEQ ID NO: 7 | LC_T31V CDR3 | ALWYSNLWV |
| SEQ ID NO: 329 | LC_T31V | QAVVTQEPSFSVSPGGTVTLTCRSSTGAVTVSNYANWVQQKPGQA<br>FRGLIGGTNKRAPGVPARFSGSLIGDKAALTITGAQADDESIYFCALW<br>YSNLWVFGGGTKLTVL |

TABLE 1-continued

| | | Sequences |
| --- | --- | --- |
| SEQ ID NO: | Clone name | Sequence |
| SEQ ID NO: 330 | LC_T31Y CDR1 | TGAVTYSNY |
| | LC_T31Y CDR2 | GTN |
| SEQ ID NO: 7 | LC_T31Y CDR3 | ALWYSNLWV |
| SEQ ID NO: 331 | LC_T31Y | QAVVTQEPSFSVSPGGTVTLTCRSSTGAVTYSNYANWVQQKPGQA<br>FRGLIGGTNKRAPGVPARFSGSLIGDKAALTITGAQADDESIYFCALW<br>YSNLWVFGGGTKLTVL |
| SEQ ID NO: 6 | LC_L92A CDR1 | TGAVTTSNY |
| | LC_L92A CDR2 | GTN |
| SEQ ID NO: 332 | LC_L92A CDR3 | AAWYSNLWV |
| SEQ ID NO: 333 | LC_L92A | QAVVTQEPSFSVSPGGTVTLTCRSSTGAVTTSNYANWVQQKPGQA<br>FRGLIGGTNKRAPGVPARFSGSLIGDKAALTITGAQADDESIYFCAA<br>WYSNLWVFGGGTKLTVL |
| SEQ ID NO: 6 | LC_L92C CDR1 | TGAVTTSNY |
| | LC_L92C CDR2 | GTN |
| SEQ ID NO: 334 | LC_L92C CDR3 | ACWYSNLWV |
| SEQ ID NO: 335 | LC_L92C | QAVVTQEPSFSVSPGGTVTLTCRSSTGAVTTSNYANWVQQKPGQA<br>FRGLIGGTNKRAPGVPARFSGSLIGDKAALTITGAQADDESIYFCAC<br>WYSNLWVFGGGTKLTVL |
| SEQ ID NO: 6 | LC_L92D CDR1 | TGAVTTSNY |
| | LC_L92D CDR2 | GTN |
| SEQ ID NO: 336 | LC_L92D CDR3 | ADWYSNLWV |
| SEQ ID NO: 337 | LC_L92D | QAVVTQEPSFSVSPGGTVTLTCRSSTGAVTTSNYANWVQQKPGQA<br>FRGLIGGTNKRAPGVPARFSGSLIGDKAALTITGAQADDESIYFCAD<br>WYSNLWVFGGGTKLTVL |
| SEQ ID NO: 6 | LC_L92E CDR1 | TGAVTTSNY |
| | LC_L92E CDR2 | GTN |
| SEQ ID NO: 338 | LC_L92E CDR3 | AEWYSNLWV |
| SEQ ID NO: 339 | LC_L92E | QAVVTQEPSFSVSPGGTVTLTCRSSTGAVTTSNYANWVQQKPGQA<br>FRGLIGGTNKRAPGVPARFSGSLIGDKAALTITGAQADDESIYFCAEW<br>YSNLWVFGGGTKLTVL |
| SEQ ID NO: 6 | LC_L92F CDR1 | TGAVTTSNY |
| | LC_L92F CDR2 | GTN |
| SEQ ID NO: 340 | LC_L92F CDR3 | AFWYSNLWV |
| SEQ ID NO: 341 | LC_L92F | QAVVTQEPSFSVSPGGTVTLTCRSSTGAVTTSNYANWVQQKPGQA<br>FRGLIGGTNKRAPGVPARFSGSLIGDKAALTITGAQADDESIYFCAFW<br>YSNLWVFGGGTKLTVL |
| SEQ ID NO: 6 | LC_L92G CDR1 | TGAVTTSNY |
| | LC_L92G CDR2 | GTN |
| SEQ ID NO: 342 | LC_L92G CDR3 | AGWYSNLWV |
| SEQ ID NO: 343 | LC_L92G | QAVVTQEPSFSVSPGGTVTLTCRSSTGAVTTSNYANWVQQKPGQA<br>FRGLIGGTNKRAPGVPARFSGSLIGDKAALTITGAQADDESIYFCAG<br>WYSNLWVFGGGTKLTVL |
| SEQ ID NO: 6 | LC_L921 CDR1 | TGAVTTSNY |
| | LC_L921 CDR2 | GTN |
| SEQ ID NO: 344 | LC_L921 CDR3 | AIWYSNLWV |

TABLE 1-continued

| | | Sequences |
|---|---|---|
| SEQ ID NO: | Clone name | Sequence |
| SEQ ID NO: 345 | LC_L921 | QAVVTQEPSFSVSPGGTVTLTCRSSTGAVTTSNYANWVQQKPGQA<br>FRGLIGGTNKRAPGVPARFSGSLIGDKAALTITGAQADDESIYFCAIW<br>YSNLWVFGGGTKLTVL |
| SEQ ID NO: 6 | LC_L92K CDR1 | TGAVTTSNY |
| | LC_L92K CDR2 | GTN |
| SEQ ID NO: 346 | LC_L92K CDR3 | AKWYSNLWV |
| SEQ ID NO: 347 | LC_L92K | QAVVTQEPSFSVSPGGTVTLTCRSSTGAVTTSNYANWVQQKPGQA<br>FRGLIGGTNKRAPGVPARFSGSLIGDKAALTITGAQADDESIYFCAK<br>WYSNLWVFGGGTKLTVL |
| SEQ ID NO: 6 | LC_L92M CDR1 | TGAVTTSNY |
| | LC_L92M CDR2 | GTN |
| SEQ ID NO: 348 | LC_L92M CDR3 | AMWYSNLWV |
| SEQ ID NO: 349 | LC_L92M | QAVVTQEPSFSVSPGGTVTLTCRSSTGAVTTSNYANWVQQKPGQA<br>FRGLIGGTNKRAPGVPARFSGSLIGDKAALTITGAQADDESIYFCAM<br>WYSNLWVFGGGTKLTVL |
| SEQ ID NO: 6 | LC_L92N CDR1 | TGAVTTSNY |
| | LC_L92N CDR2 | GTN |
| SEQ ID NO: 350 | LC_L92N CDR3 | ANWYSNLWV |
| SEQ ID NO: 351 | LC_L92N | QAVVTQEPSFSVSPGGTVTLTCRSSTGAVTTSNYANWVQQKPGQA<br>FRGLIGGTNKRAPGVPARFSGSLIGDKAALTITGAQADDESIYFCAN<br>WYSNLWVFGGGTKLTVL |
| SEQ ID NO: 6 | LC_L92P CDR1 | TGAVTTSNY |
| | LC_L92P CDR2 | GTN |
| SEQ ID NO: 352 | LC_L92P CDR3 | APWYSNLWV |
| SEQ ID NO: 353 | LC_L92P | QAVVTQEPSFSVSPGGTVTLTCRSSTGAVTTSNYANWVQQKPGQA<br>FRGLIGGTNKRAPGVPARFSGSLIGDKAALTITGAQADDESIYFCAP<br>WYSNLWVFGGGTKLTVL |
| SEQ ID NO: 6 | LC_L92R CDR1 | TGAVTTSNY |
| | LC_L92R CDR2 | GTN |
| SEQ ID NO: 354 | LC_L92R CDR3 | ARWYSNLWV |
| SEQ ID NO: 355 | LC_L92R | QAVVTQEPSFSVSPGGTVTLTCRSSTGAVTTSNYANWVQQKPGQA<br>FRGLIGGTNKRAPGVPARFSGSLIGDKAALTITGAQADDESIYFCAR<br>WYSNLWVFGGGTKLTVL |
| SEQ ID NO: 6 | LC_L92S CDR1 | TGAVTTSNY |
| | LC_L92S CDR2 | GTN |
| SEQ ID NO: 356 | LC_L92S CDR3 | ASWYSNLWV |
| SEQ ID NO: 357 | LC_L92S | QAVVTQEPSFSVSPGGTVTLTCRSSTGAVTTSNYANWVQQKPGQA<br>FRGLIGGTNKRAPGVPARFSGSLIGDKAALTITGAQADDESIYFCASW<br>YSNLWVFGGGTKLTVL |
| SEQ ID NO: 6 | LC_L92T CDR1 | TGAVTTSNY |
| | LC_L92T CDR2 | GTN |
| SEQ ID NO: 358 | LC_L92T CDR3 | ATWYSNLWV |
| SEQ ID NO: 359 | LC_L92T | QAVVTQEPSFSVSPGGTVTLTCRSSTGAVTTSNYANWVQQKPGQA<br>FRGLIGGTNKRAPGVPARFSGSLIGDKAALTITGAQADDESIYFCATW<br>YSNLWVFGGGTKLTVL |

TABLE 1-continued

| | | Sequences |
|---|---|---|
| SEQ ID NO: | Clone name | Sequence |
| SEQ ID NO: 6 | LC_L92V CDR1 | TGAVTTSNY |
| | LC_L92V CDR2 | GTN |
| SEQ ID NO: 360 | LC_L92V CDR3 | AVWYSNLWV |
| SEQ ID NO: 361 | LC_L92V | QAVVTQEPSFSVSPGGTVTLTCRSSTGAVTTSNYANWVQQKPGQA<br>FRGLIGGTNKRAPGVPARFSGSLIGDKAALTITGAQADDESIYFCAV<br>WYSNLWVFGGGTKLTVL |
| SEQ ID NO: 6 | LC_L92W CDR1 | TGAVTTSNY |
| | LC_L92W CDR2 | GTN |
| SEQ ID NO: 362 | LC_L92W CDR3 | AWWYSNLWV |
| SEQ ID NO: 363 | LC_L92W | QAVVTQEPSFSVSPGGTVTLTCRSSTGAVTTSNYANWVQQKPGQA<br>FRGLIGGTNKRAPGVPARFSGSLIGDKAALTITGAQADDESIYFCAW<br>WYSNLWVFGGGTKLTVL |
| SEQ ID NO: 6 | LC_L92Y CDR1 | TGAVTTSNY |
| | LC_L92Y CDR2 | GTN |
| SEQ ID NO: 364 | LC_L92Y CDR3 | AYWYSNLWV |
| SEQ ID NO: 365 | LC_L92Y | QAVVTQEPSFSVSPGGTVTLTCRSSTGAVTTSNYANWVQQKPGQA<br>FRGLIGGTNKRAPGVPARFSGSLIGDKAALTITGAQADDESIYFCAYW<br>YSNLWVFGGGTKLTVL |
| SEQ ID NO: 6 | LC_L97D CDR1 | TGAVTTSNY |
| | LC_L97D CDR2 | GTN |
| SEQ ID NO: 366 | LC_L97D CDR3 | ALWYSNDWV |
| SEQ ID NO: 367 | LC_L97D | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNDWVFGGGTKLTVL |
| SEQ ID NO: 6 | LC_L97E CDR1 | TGAVTTSNY |
| | LC_L97E CDR2 | GTN |
| SEQ ID NO: 368 | LC_L97E CDR3 | ALWYSNEWV |
| SEQ ID NO: 369 | LC_L97E | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNEWVFGGGTKLTVL |
| SEQ ID NO: 6 | LC_L97F CDR1 | TGAVTTSNY |
| | LC_L97F CDR2 | GTN |
| SEQ ID NO: 370 | LC_L97F CDR3 | ALWYSNFWV |
| SEQ ID NO: 371 | LC_L97F | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNFWVFGGGTKLTVL |
| SEQ ID NO: 6 | LC_L97G CDR1 | TGAVTTSNY |
| | LC_L97G CDR2 | GTN |
| SEQ ID NO: 372 | LC_L97G CDR3 | ALWYSNGWV |
| SEQ ID NO: 373 | LC_L97G | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNGWVFGGGTKLTVL |
| SEQ ID NO: 6 | LC_L97H CDR1 | TGAVTTSNY |
| | LC_L97H CDR2 | GTN |
| SEQ ID NO: 374 | LC_L97H CDR3 | ALWYSNHWV |

TABLE 1-continued

| | | Sequences |
|---|---|---|
| SEQ ID NO: | Clone name | Sequence |
| SEQ ID NO: 375 | LC_L97H | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNHWVFGGGTKLTVL |
| SEQ ID NO: 6 | LC_L97K CDR1 | TGAVTTSNY |
| | LC_L97K CDR2 | GTN |
| SEQ ID NO: 376 | LC_L97K CDR3 | ALWYSNKWV |
| SEQ ID NO: 377 | LC_L97K | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNKWVFGGGTKLTVL |
| SEQ ID NO: 6 | LC_L97M CDR1 | TGAVTTSNY |
| | LC_L97M CDR2 | GTN |
| SEQ ID NO: 378 | LC_L97M CDR3 | ALWYSNMWV |
| SEQ ID NO: 379 | LC_L97M | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNMWVFGGGTKLTVL |
| SEQ ID NO: 6 | LC_L97N CDR1 | TGAVTTSNY |
| | LC_L97N CDR2 | GTN |
| SEQ ID NO: 380 | LC_L97N CDR3 | ALWYSNNWV |
| SEQ ID NO: 381 | LC_L97N | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNNWVFGGGTKLTVL |
| SEQ ID NO: 6 | LC_L97P CDR1 | TGAVTTSNY |
| | LC_L97P CDR2 | GTN |
| SEQ ID NO: 382 | LC_L97P CDR3 | ALWYSNPWV |
| SEQ ID NO: 383 | LC_L97P | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNPWVFGGGTKLTVL |
| SEQ ID NO: 6 | LC_L97Q CDR1 | TGAVTTSNY |
| | LC_L97Q CDR2 | GTN |
| SEQ ID NO: 384 | LC_L97Q CDR3 | ALWYSNQWV |
| SEQ ID NO: 385 | LC_L97Q | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNQWVFGGGTKLTVL |
| | LC_L97R CDR2 | GTN |
| SEQ ID NO: 6 | LC_L97S CDR1 | TGAVTTSNY |
| | LC_L97S CDR2 | GTN |
| SEQ ID NO: 386 | LC_L97S CDR3 | ALWYSNSWV |
| SEQ ID NO: 387 | LC_L97S | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNSWVFGGGTKLTVL |
| SEQ ID NO: 6 | LC_L97T CDR1 | TGAVTTSNY |
| | LC_L97T CDR2 | GTN |
| SEQ ID NO: 388 | LC_L97T CDR3 | ALWYSNTWV |
| SEQ ID NO: 389 | LC_L97T | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNTWVFGGGTKLTVL |

TABLE 1-continued

Sequences

| SEQ ID NO: | Clone name | Sequence |
|---|---|---|
| SEQ ID NO: 6 | LC_L97V CDR1 | TGAVTTSNY |
| | LC_L97V CDR2 | GTN |
| SEQ ID NO: 390 | LC_L97V CDR3 | ALWYSNVWV |
| SEQ ID NO: 391 | LC_L97V | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNVWVFGGGTKLTVL |
| SEQ ID NO: 6 | LC_L97W CDR1 | TGAVTTSNY |
| | LC_L97W CDR2 | GTN |
| SEQ ID NO: 392 | LC_L97W CDR3 | ALWYSNWWV |
| SEQ ID NO: 393 | LC_L97W | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNWWVFGGGTKLTVL |
| SEQ ID NO: 6 | LC_L97Y CDR1 | TGAVTTSNY |
| | LC_L97Y CDR2 | GTN |
| SEQ ID NO: 394 | LC_L97Y CDR3 | ALWYSNYWV |
| SEQ ID NO: 395 | LC_L97Y | QAVVTQEPSFSVSPGGTVTLTCRSSTGAVTTSNYANWVQQKPGQA<br>FRGLIGGTNKRAPGVPARFSGSLIGDKAALTITGAQADDESIYFCALW<br>YSNYWVFGGGTKLTVL |
| SEQ ID NO: 396 | Mature huTRA | KTTQPNSMESNEEEPVHLPCNHSTISGTDYIHWYRQLPSQGPEYVIH<br>GLTSNVNNRMASLAIAEDRKSSTLILHRATLRDAAVYYCILPLAGGTS<br>YGKLTFGQGTILTVHPNIQNPDPAVYQLRDSKSSDKSVCLFTDFDSQ<br>TNVSQSKDSDVYITDKTVLDMRSMDFKSNSAVAWSNKSDFACANA<br>FNNSIIPEDTFFPSPESSCDVKLVEKSFETDTNLNFQNLSVIGFRILLLK<br>VAGFNLLMTLRLWSS |
| SEQ ID NO: 397 | Mature huTRB | GVSQSPRYKVAKRGQDVALRCDPISGHVSLFWYQQALGQGPEFLTY<br>FQNEAQLDKSGLPSDRFFAERPEGSVSTLKIQRTQQEDSAVYLCASSL<br>GQAYEQYFGPGTRLTVTEDLNKVFPPEVAVFEPSEAEISHTQKATLVC<br>LATGFFPDHVELSWWVNGKEVHSGVSTDPQPLKEQPALNDSRYCLS<br>SRLRVSATFWQNPRNHFRCQVQFYGLSENDEWTQDRAKPVTQIVS<br>AEAWGRADCGFTSVSYQQGVLSATILYEILLGKATLYAVLVSALVLM<br>AMVKRKDF |
| SEQ ID NO: 398 | Mature huCD3δ | FKIPIEELEDRVFVNCNTSITWVEGTVGTLLSDITRLDLGKRILDPRGIY<br>RCNGTDIYKDKESTVQVHYRMCQSCVELDPATVAGIIVTDVIATLLLA<br>LGVFCFAGHETGRLSGAADTQALLRNDQVYQPLRDRDDAQYSHLG<br>GNWARNK |
| SEQ ID NO: 399 | Mature huCD3ε | QDGNEEMGGITQTPYKVSISGTTVILTCPQYPGSEILWQHNDKNIGG<br>DEDDKNIGSDEDHLSLKEFSELEQSGYYVCYPRGSKPEDANFYLYLRA<br>RVCENCMEMDVMSVATIVIVDICITGGLLLLVYYWSKNRKAKAKPVT<br>RGAGAGGRQRGQNKERPPPVPNPDYEPIRKGQRDLYSGLNQRRI |
| SEQ ID NQ: 400 | Mature huCD3γ | QSIKGNHLVKVYDYQEDGSVLLTCDAEAKNITWFKDGKMIGFLTED<br>KKKWNLGSNAKDPRGMYQCKGSQNKSKPLQVYYRMCQNCIELNA<br>ATISGFLFAEIVSIFVLAVGVYFIAGQDGVRQSRASDKQTLLPNDQLY<br>QPLKDREDDQYSHLQGNQLRRN |
| SEQ ID NO: 401 | Mature huCD3ζ | QSFGLLDPKLCYLLDGILFIYGVILTALFLRVKFSRSADAPAYQQGQNQ<br>LYNELNLGRREEYDVLDKRRGRDPEMGGKPQRRKNPQEGLYNELQ<br>KDKMAEAYSEIGMKGERRRGKGHDGLYQGLSTATKDTYDALHMQ<br>ALPPR |
| SEQ ID NO: 402 | Mature CD3ε27-GSKa | QDGNEEMGGITQTPYKVSISGTTVILTGGGGSGGGGSGGGGSEIVL<br>TQSPATLSLSPGERATLSCRASQSVSSYLAWYQQKPGQAPRLLIYDAS<br>NRATGIPARFSGSGSGTDFTLTISSLEPEDFAVYYCQQRSNWPITFGQ<br>GTRLEIKRTVAAPSVFIFPPSDEQLKSGTASVVCLLNNFYPREAKVQW<br>KVDNALQSGNSQESVTEQDSKDSTYSLSSTLTLSKADYEKHKVYACE<br>VTHQGLSSPVTKSFNRGE |
| SEQ ID NO: 403 | Mature cyno CD3ε<br>(epsilon) | QDGNEEMGSITQTPYQVSISGTTVILTCSQHLGSEAQWQHNGKNK<br>EDSGDRLFLPEFSEMEQSGYYVCYPRGSNPEDASHHLYLKARVCENC<br>MEMDVMAVATIVIVDICITLGLLLLVYYWSKNRKAKAKPVTRGAGA<br>GGRQRGQNKERPPPVPNPDYEPIRKGQQDLYSGLNQRRI |

TABLE 1-continued

| SEQ ID NO: | Clone name | Sequence |
|---|---|---|
| SEQ ID NO: 404 | Mature rhesus CD3ε (epsilon) | QDGNEEMGSITQTPYHVSISGTTVILTCSQHLGSEVQWQHNGKNKE DSGDRLFLPEFSEMEQSGYYVCYPRGSNPEDASHHLYLKARVCENC MEMDVMAVATIVIVDICITLGLLLLVYYWSKNRKAKAKPVTRGAGA GGRQRGQNKERPPPVPNPDYEPIRKGQQDLYSGLNQRRI |
| SEQ ID NO: 405 | Parent murine VH | EVKLLESGGGLVQPKGSLKLSC AASGFTFNTYAMNWVRQAPGKG LEWVARIRSKYNNYATYYADSV KDRFTISRDDSQSILYLQMNNL KTEDTAMYYCVRHGNFGNSYVS WFAYWGQGTLVTVSA |
| SEQ ID NO: 406 | Parent murine VL | QAVVTQESALTTSPGETVTLTC RSSTGAVTTSNYANWVQEKPDH LFTGLIGGTNKRAPGVPARFSG SLIGDKAALTITGAQTEDEAIY FCALWYSNLWVFGGGTKLTVL |
| SEQ ID NO: 407 | IgG1m(f) heavy chain constant region | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKRVEPKSCDKTHTCPPCPAPELLGGPSVFLFPPKPKDTLMISRTP EVTCVVVDVSHEDPEVKFNWYVDGVEVHNAKTKPREEQYNSTYR WSVLTVLHQDWLNGKEYKCKVSNKALPAPIEKTISKAKGQPREPQ VYTLPPSREEMTKNQVSLTCLVKGFYPSDIAVEWESNGQPENNYK TTPPVLDSDGSFFLYSKLTVDKSRWQQGNVFSCSVMHEALHNHYT QKSLSLSPGK |
| SEQ ID NO: 408 | Human IgLC2/IgLC3 constant domain | GQPKAAPSVTLFPPSSEELQANKATLVCLISDFYPGAVTVAWKADS SPVKAGVETTTPSKQSNNKYAASSYLSLTPEQWKSHRSYSCQVTHE GSTVEKTVAPTECS |
| SEQ ID NO: 409 | IgG1m(f) heavy chain constant region with FEA mutations | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KRVEPKSCDKTHTCPPCPAPEFEGGPSVFLFPPKPKDTLMISRTPEVT CVVVAVSHEDPEVKFNWYVDGVEVHNAKTKPREEQYNSTYRVVSV LTVLHQDWLNGKEYKCKVSNKALPAPIEKTISKAKGQPREPQVYTLP PSREEMTKNQVSLTCLVKGFYPSDIAVEWESNGQPENNYKTTPPVL DSDGSFFLYSKLTVDKSRWQQGNVFSCSVMHEALHNHYTQKSLSLS PGK |
| SEQ ID NO: 410 | Primer CMV P f (MAR5) | GCTTCGCGATGTACGGGCCAGATATAC |
| SEQ ID NO: 411 | TK pA r(MAR1) | GGATACCCCCTAGAGCCCCAGCTGCGCAGATCTGCTATG GC |

The CDR regions have been annotated according to the IMGT definitions.

EXAMPLES

Example 1—Generation of Humanized CD3 Antibodies and Non-Activating Antibody Variants Humanization of CD3 Antibodies Humanization of a murine CD3 antibody (U.S. Pat. No. 8,236,308, described herein as IgG1-CD3) was performed by Antitope (Cambridge, UK) using their Improved version of the germline humanization (CDR-grafting) technology (EP 0 629 240). Using this technology, 1 different VH chain (SEQ ID NO:4) and 2 different VL chains (SEQ ID NO:8, 10) were designed. By combining these 1 VH with the 2 VL chains, 2 different antibodies were generated. The humanized variants are described herein as huCD3. Thus, humanized variants comprising a VH and a VL according to the Invention, are described as, e.g., IgG1-huCD3-H1L1 meaning that said specific variant is of the IgG1 isotype, is a humanized CD3 and comprises the VH amino acid sequence termed "H1" and is defined according to SEQ ID NO:4, and the VL amino acid sequence termed "L1" and is defined according to SEQ ID NO: 8. Thus, H1 refers to the variable heavy chain region VH1, L1 refers to the variable light chain region VL1, and so forth.

In particular, the variants IgG1-huCD3-H1L1 (humanized CD3 comprising the VH1 sequence set forth in SEQ ID NO:4 and the VL1 sequence set forth in SEQ ID NO:8), IgG1-huCD3-L1-T41K (humanized CD3 comprising the VH1 sequence set forth in SEQ ID NO:4 and the VL sequence set forth in SEQ ID NO:10.

b12 Antibody

In some of the examples the antibody b12, a HIV-1 gp120 specific antibody (Barbas, C F. J Mol Biol. 1993 Apr. 5; 230(3):812-23) was used as a negative control, and is termed "IgG1-b12".

Expression

Antibodies were expressed as IgG1,κ or IgG1,λ with or without the non-activating mutations described below and with a mutation in the CH3 domain enabling the generation of bispecific antibodies by the method described below. Plasmid DNA mixtures encoding both heavy and light chain of antibodies were transiently transfected to Freestyle HEK293F cells (Invitrogen, US) using 293fectin (Invitrogen, US) essentially as described by the manufacturer.

Purification of Antibodies

Culture supernatant was filtered over 0.2 μm dead-end filters, loaded on 5 mL MabSelect SuRe columns (GE Health Care) and eluted with 0.1 M sodium citrate-NaOH, pH 3. The eluate was Immediately neutralized with 2M Tris-HCl, pH 9 and dialyzed overnight to 12.6 mM NaH2PO4, 140 mM NaCl, pH 7.4 (B.Braun). Alternatively, subsequent to purification, the eluate was loaded on a HiPrep Desalting column and the antibody was exchanged into 12.6 mM NaH2PO4, 140 mM NaCl, pH 7.4 (B.Braun) buffer. After dialysis or exchange of buffer, samples were sterile filtered over 0.2 μm dead-end filters. Purity was determined by SDS-PAGE and concentration was measured by absorbance at 280 nm. Purified antibodies were stored at 2-8° C.

Example 2: Generation of Mutant Library

Point mutations were generated by random mutagenesis performed using the Quick change mutagenesis kit (Stratagene, according to the manufacturer's Instructions and the HC (p33HGTE-huCD3-H1) and LC (p33L-huCD3-L1-T41K) expression plasmids as templates. The HC plasmid encodes for the monovalent UniBody-TE format as described in WO2011110642. Each selected position was randomized by using primers containing a NNS codon at the selected position (N=G, A, T or C and S=G or C). Mutant libraries were transformed to OneShot DH5alpha (Invitrogen) according to manufacturer's Instructions.

Colony Picking and LEE PCR

For each mutated position 96 clones were Individually picked into 50 μL LEE (linear expression element) PCR buffer (5 μL 10× AccuPrime PCR buffer 1, 44.6 μL water (B.Braun), 0.1 μL CMV P f (MAR5) and 0.1 μL Tk pA r (MAR1) primers (100 μM stock), 0.2 μL Accuprime Taq (Invitrogen) to amplify the expression cassette from the expression plasmid (promoter up to poly A). LEE PCRs were performed by Incubating the mixtures 2' 94° C., [30" 94° C., 30" 55 0C, 5' 68° C.]35x, 10' 72° C. and storage at 4° C. until further use.

Each library (12) of 96 colonies was sequenced using Sanger sequencing (Beckman Coulter Genomics, UK).

TABLE 2

| Primer sequences for LEE PCR | |
| --- | --- |
| Primer name | Primer Sequence |
| CMV P f (MAR5) | GCTTCGCGATGTACGGGCCAGATATAC |
| TK pA r (MAR1) | GGATACCCCCTAGAGCCCCAGCTGCGC AGATCTGCTATGGC |

Example 3: Expression of Mutant Library and IgG Quantification

Of each mutant (12×96 in total) 1.11 μL HC and 1.11 μL LC LEE PCR product were diluted in 2.78 μL water. The 5 μL DNA dilution was used to transfect a single well in a 96 well plate.

Per well 0.4 μL ExpiFectamine™ 293 (Invitrogen, US) and 4.6 μL Opti-MEM (Gibco, US) were mixed and Incubated for 5 minutes at room temperature. Next, the Fectin/Opti-MEM mix was added to the 5 μL DNA dilution and Incubated for 30 minutes at room temperature. Finally, 8.3 μL of the Fectin/Opti-MEM/DNA mix was added to 117.5 μL Exp1293F™ cells. During all procedures, the plates with Exp1293F™ cells were shaken to keep the cells in suspension. After transfection, cells were Incubated at 37° C./8% CO2 for 5 days.

Five days post transfection, the supernatant was harvested. Antibody concentration in supernatant was measured by BioLayer Interferometry using the Octet RED (ForteBio, US).

Example 4: Generation of CD3/TCR-LC13 Screening Library

Freestyle 293-F cells (Invitrogen, US) were co-transfected with expression constructs encoding the human alpha and beta chains of the TCR (SEQ ID NO: 396 and SEQ ID NO: 397 respectively), human CD3δ (SEQ ID NO: 398), human CD3Σ (SEQ ID NO: 399), human CD3γ (SEQ ID NO: 400) and human CD3 (SEQ ID NO: 401). The signal peptide sequence is excluded in these sequences. Transfection was performed according to manufacturer's Instructions (Invitrogen, US). One day post transfection, cells were frozen until further use.

Example 5: Screening of Affinity Mutants

Homogeneous Assay (Dose Response)

Based on the sequence data, mutants were selected where sequence traces showed high PHRED scores, Indicative for the absence of multiple mutations. Per mutation, multiple redundant clones were selected when available.

The binding of recombinantly produced UniBody molecules in cell culture supernatant was determined by homogeneous antigen specific binding assays using Fluorometric Micro volume Assay Technology (FMAT; Applied Biosystems, Foster City, CA, USA). In the assay test design samples were analyzed in dose response for binding of antibodies or monovalent antibody molecules to CD3/TCR-LC13 (Freestyle 293-F cells transiently expressed human CD3 and human T cell receptor (TCR); produced as described above) and Freestyle 293-F wild-type cells (negative control which does not express human TCR). IgG levels for sample normalization prior to dose response binding were measured using an Octet Instrument (Fortebio, Menlo Park, USA).

Dilution series of samples were added to the cells to allow binding to CD3. Subsequently, binding of monovalent antibody molecules was detected using a fluorescent conjugate (Goat anti-Human IgG Fc gamma-Alexa647; Jackson ImmunoResearch). The CD3 specific humanized mouse antibody IgG1-HuM291-F405L (produced in Freestyle 293-F cells) and monovalent antibody UniTE-huCD3-H1L1-LT41K were used as a positive control and Chrom-Pure Human IgG, whole molecule (Jackson ImmunoResearch) was used as negative control. The samples were scanned using an Applied Biosystems 8200 Cellular Detection System (8200 CDS) and total fluorescence over sample concentration was used as read-out. Samples were stated positive when counts were higher than 50 and counts x fluorescence (total florescence) was at least three times higher than the negative control.

Heatmap

From the Homogeneous Dose Response screen, the binding curves were fitted using a 4 parameter sigmoidal model. From the fit, the maximal binding for every mutant was determined. Per mutant, the average maximal binding was calculated, and depicted as a ratio between average maximal over wt binding as shown in FIG. 1.

Alignment

Selected HC mutants generated in these libraries are aligned and depicted in FIG. 2. The CDR regions have been annotated according to the IMGT definitions. Numbering of the sequence is annotated according to a direct numbering scheme.

Example 6—Generation of Bispecific Antibodies by 2-MEA-Induced Fab-Arm Exchange The bispecific antibodies according to the invention may be generated by use of the methods disclosed in WO2011131746 and WO2013060867 (Genmab).

By way of example a mutation in position F405L may be introduced in one parental antibody of IgG1 isotype, and a mutation in position K409R may be introduced in the other parental antibody of IgG1 isotype.

These two parental antibodies, each at a final concentration of 0.5 mg/mL (equimolar concentration), may be incubated under reducing conditions with 25 mM 2-mercapto-ethylamine-HCl (2-MEA) in a total volume of 100 μL Tris-EDTA (TE) at 37° C. for 90 min. The reduction reaction is stopped when the reducing agent 2-MEA is removed by using spin columns (Microcon centrifugal filters, 30 k, Millipore) according to the manufacturer's protocol.

The bispecific antibodies may be filtered over 0.2 μm dead-end filters and the absorbance at 280 nm (A280) of the bispecific antibodies may be measured to determine the final concentration thereof.

Example 7: Binding Data

For all binding assays below a selected panel of heavy chain variants of huCD3-H1L1 were tested in different formats:

TABLE 3

| Selected affinity variants of huCD3-H1L1 in monovalent antibody-TE format Selected UniTE-huCD3 HC affinity variants |
| --- |
| UniTE-huCD3-H1L1-LT41K (WT) |
| UniTE-huCD3-H1L1-T31M-LT41K |
| UniTE-huCD3-H1L1-T31P-LT41K |
| UniTE-huCD3-H1L1-Y32A-LT41K |
| UniTE-huCD3-H1L1-N57E-LT41K |
| UniTE-huCD3-H1L1-H101F-LT41K |
| UniTE-huCD3-H1L1-H101G-LT41K |
| UniTE-huCD3-H1L1-H101I-LT41K |
| UniTE-huCD3-H1L1-H101K-LT41K |
| UniTE-huCD3-H1L1-H101L-LT41K |
| UniTE-huCD3-H1L1-H101N-LT41K |
| UniTE-huCD3-H1L1-G105P-LT41K |
| UniTE-huCD3-H1L1-S110A-LT41K |
| UniTE-huCD3-H1L1-S110G-LT41K |
| UniTE-huCD3-H1L1-Y114M-LT41K |
| UniTE-huCD3-H1L1-Y114R-LT41K |
| UniTE-huCD3-H1L1-Y114V-LT41K |

Octet Binding Affinity Determination of the CD3 Affinity Mutants in Monovalent Antibody-TE Format Affinities of a selected panel of affinity VH variants (Table 3) were determined using Bio-Layer Interferometry on a ForteBio Octet HTX. Anti-human Fc Capture (AHC) biosensors (ForteBio, Portsmouth, UK; cat no. 18-5060) were loaded for 600 s with the CD3 affinity mutants in monovalent antibody-TE format (2 μg/mL), aiming at a loading response of 0.4 nm. Antibodies of the UniBody-TE format were used to specifically measure the monovalent interaction affinity between the CD3 affinity mutants and the CD3ε27-GSKa ligand. After a baseline (150 s) the association (1000 s) and dissociation (1000 s) of CD3ε27-GSKa (100 and 1000 nM) was determined. The CD3ε27-GSKa protein consists of the human CD3ε peptide (aa1-27) fused to the N-terminus of a kappa LC (SEQ ID NO: 402). For calculations, the theoretical molecular mass of CD3ε27-GSKa based on the amino acid sequence was used, i.e. 27.1 kDa. Experiments were carried out while shaking at 1000 rpm and at 30° C.

Data was analyzed with ForteBio Data Analysis Software v8.1, using the 1:1 model and a global full fit with 1000 s association time and 200 s dissociation time. Data traces were corrected by subtraction of a reference curve (CD3 affinity mutant without CD3ε27-GSKa), the Y-axis was aligned to the last 5 s of the baseline, and interstep correction as well as Savitzky-Golay filtering was applied.

TABLE 4

| Equilibrium dissociation constant (KD) for selected variants | | |
| --- | --- | --- |
| Antibody ID | KD (M) | 1/KD (M$^{-1}$) |
| UniTE-huCD3-H1L1-N57E-LT41K | $2.4 \times 10^{-8}$ | $4.1 \times 10^7$ |
| uniTE-huCD3-H1L1-LT41K | $3.4 \times 10^{-8}$ | $3.0 \times 10^7$ |
| UniTE-huCD3-H1L1-G105P-LT41K | $3.5 \times 10^{-8}$ | $2.8 \times 10^7$ |
| UniTE-huCD3-H1L1-T31P-LT41K | $4.9 \times 10^{-8}$ | $2.0 \times 10^7$ |
| UniTE-huCD3-H1L1-S110G-LT41K | $6.1 \times 10^{-8}$ | $1.6 \times 10^7$ |
| UniTE-huCD3-H1L1-Y114V-LT41K | $7.5 \times 10^{-8}$ | $1.3 \times 10^7$ |
| UniTE-huCD3-H1L1-Y114M-LT41K | $7.6 \times 10^{-8}$ | $1.3 \times 10^7$ |
| UniTE-huCD3-H1L1-T31M-LT41K | $2.0 \times 10^{-7}$ | $5.1 \times 10^6$ |
| UniTE-huCD3-H1L1-H101N-LT41K | $2.0 \times 10^{-7}$ | $5.1 \times 10^6$ |
| UniTE-huCD3-H1L1-H101I-LT41K | $2.2 \times 10^{-7}$ | $4.6 \times 10^6$ |
| UniTE-huCD3-H1L1-S110A-LT41K | $3.2 \times 10^{-7}$ | $3.1 \times 10^6$ |
| UniTE-huCD3-H1L1-H101G-LT41K | $9.7 \times 10^{-7}$ | $1.0 \times 10^6$ |
| UniTE-huCD3-H1L1-H101L-LT41K | nd | nd |
| UniTE-huCD3-H1L1-Y32A-LT41K | nd | nd |
| UniTE-huCD3-H1L1-H101K-LT41K | nd | nd |
| UniTE-huCD3-H1L1-T31A-LT41K | nd | nd |
| UniTE-huCD3-H1L1-H101F-LT41K | nd | nd |
| UniTE-huCD3-H1L1-Y114R-LT41K | nd | nd | nd = not determined

T Cell Binding of Affinity Variants of Humanized CD3 (UniTE-huCD3-H1L1-LT41K) on Flow Cytometry (FACS)

Figure 4:
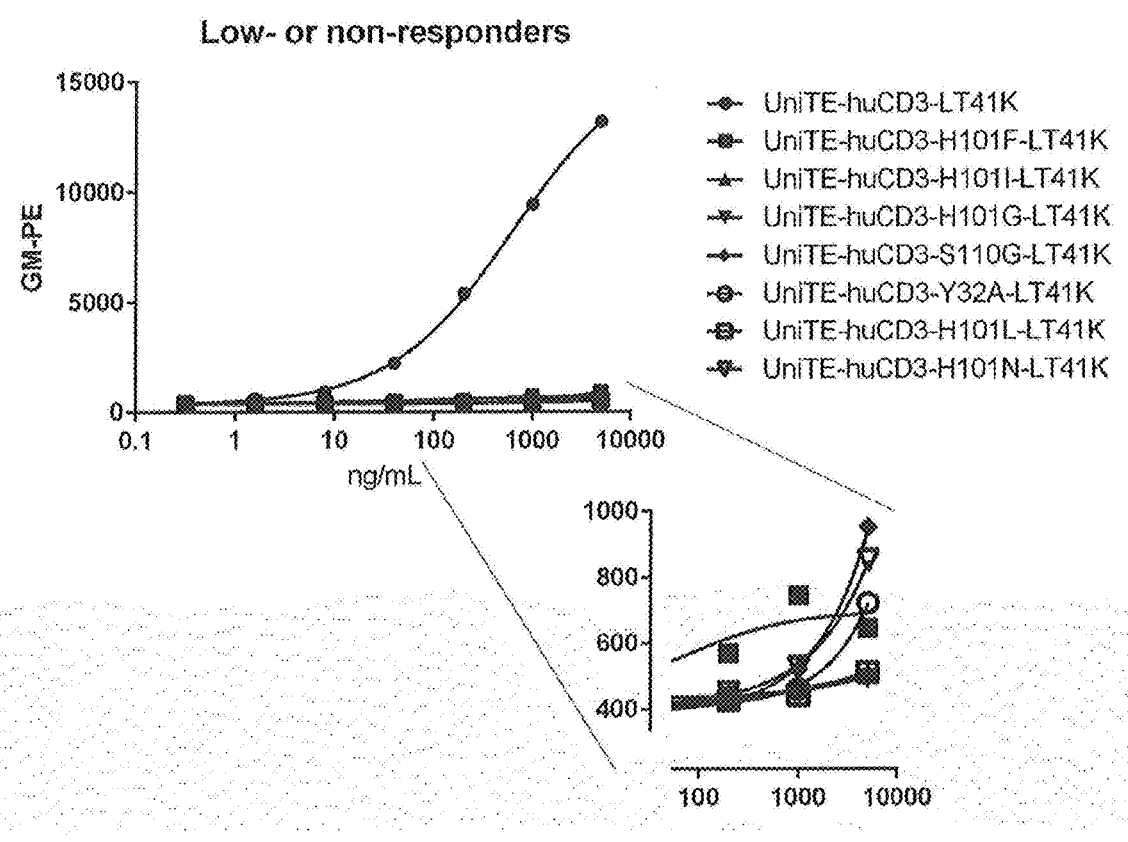
FIG. 4: T cell binding curves of selected VH affinity variants of humanized CD3 (UniTE-huCD3-H1L1-T41K) antibodies as determined by flow cytometry showing a very low, undetectable T cell binding.

T cell binding of purified VH affinity variants of humanized CD3 (IgG1-huCD3-H1L1) antibodies was determined using Fluorescence-Activated Cell Sorting on a FACSCanto 752 (BD Biosciences). T cells were Isolated from a buffy coat fraction of anti-coagulated human donor blood samples and resuspended in PBS/0.1% BSA/0.02% azide at 1.8× 10E6 cells/mL. 50 μL of T cell suspension and 50 μL of the antibody dilutions were combined in a 96 well plate on ice, Incubated for 30 min at 4° C. and washed twice with PBS/0.1% BSA/0.02% azide. Next, 50 μL of secondary antibody, R-Phycoerythrin (PE)-conjugated goat-anti-human IgG F(ab')2 (109-116-098, Jackson ImmunoResearch Laboratories, Inc., West Grove, PA) diluted 1/200 in PBS/0.1% BSA/0.02% azide, was added for staining, the mixture was Incubated for 30 min at 4° C. and subsequently washed twice with PBS/0.1% BSA/0.02% azide. The cells were resuspended in 120 µL PBS/0.1% BSA/0.02% azide and PE geometric Mean Fluorescence Intensity was measured. Binding curves were analyzed using non-linear regression (sigmoidal dose-response with variable slope) using Graph-Pad Prism V5.04 software (GraphPad Software, San Diego, CA, USA) and apparent affinity (KD) was derived from the concentration at half-maximal binding. FIG. 4 shows binding curves of affinity variants of humanized CD3 (UniTE-huCD3-H1L1-LT41K) and FIG. 5 shows the binding curves of low affinity variants of humanized CD3 (UniTE-huCD3-H1L1-LT41K).

TABLE 5

Summary of binding data of CD3 affinity
mutants in monovalent antibody-TE format

| antibody ID | Tcell binding average at 5000ng/ml (Geometric MFI) | Max CD3/ TCRLC13 (RFU) | KD (M) |
|---|---|---|---|
| UniTE-huCD3-H1L1-LT41K | 13206 | 2030549 | $3.4 \times 10^{-8}$ |
| UniTE-huCD3-H1L1-G105P-LT41K | 10526 | 2628228 | $3.5 \times 10^{-8}$ |
| UniTE-huCD3-H1L1-T31A-LT41K | 10240 | 1836187 | |
| UniTE-huCD3-H1L1-N57E-LT41K | 8492 | 1788851 | $2.4 \times 10^{-8}$ |
| UniTE-huCD3-H1L1-Y114R-LT41K | 6197 | 1599412 | |
| UniTE-huCD3-H1L1-Y114V-LT41K | 6025 | 1807485 | $7.5 \times 10^{-8}$ |
| UniTE-huCD3-H1L1-T31P-LT41K | 4286 | 1718317 | $4.9 \times 10^{-8}$ |
| UniTE-huCD3-H1L1-Y114M-LT41K | 3830 | 1771714 | $7.6 \times 10^{-8}$ |
| UniTE-huCD3-H1L1-T31M-LT41K | 1919 | 1539506 | $2.0 \times 10^{-7}$ |
| UniTE-huCD3-H1L1-S110A-LT41K | 1660 | 1411016 | $3.2 \times 10^{-7}$ |
| UniTE-huCD3-H1L1-H101K-LT41K | 1321 | 893765 | |
| UniTE-huCD3-H1L1-S110G-LT41K | 949 | 385873 | $6.1 \times 10^{-8}$ |
| UniTE-huCD3-H1L1-H101N-LT41K | 848 | 1060228 | $2.0 \times 10^{-7}$ |

TABLE 5-continued

Summary of binding data of CD3 affinity
mutants in monovalent antibody-TE format

| antibody ID | Tcell binding average at 5000ng/ml (Geometric MFI) | Max CD3/ TCRLC13 (RFU) | KD (M) |
|---|---|---|---|
| UniTE-huCD3-H1L1-Y32A-LT41K | 719 | 541497 | |
| UniTE-huCD3-H1L1-H101F-LT41K | 641 | | |
| UniTE-huCD3-H1L1-H101I-LT41K | 511 | 603683 | $2.2 \times 10^{-7}$ |
| UniTE-huCD3-H1L1-H101L-LT41K | 509 | 812768 | |
| UniTE-huCD3-H1L1-H101G-LT41K | 492 | 139712 | $9.7 \times 10^{-7}$ |

For all binding assays below a selected panel of preferred heavy chain variants was tested (see Table 5)

Octet Binding Affinity Determination of IgG1-huCD3-H1L1-FEAL Affinity Mutants

Affinities of selected CD3 affinity variants in an IgG1-huCD3-H1L1-FEAL format were determined using Bio-Layer Interferometry on a ForteBio Octet HTX (ForteBio, UK) (Table 6). Anti-human Fc capture biosensors (cat: 18-5060, ForteBio, UK) were loaded for 600 s with hIgG (1 µg/mL). After a baseline (200 s) the association (1000 s) and dissociation (2000 s) of CD3ε27-GSKa was determined, using a CD3ε27-GSKa concentration range of 27.11 µg/mL-0.04 µg mL (1000 nM-1.4 nM) with three-fold dilution steps (sample diluent, cat: 18-5028, ForteBio, UK). For calculations, the theoretical molecular mass of CD3ε27-GSKa based on the amino acid sequence was used, i.e. 27.11 kDa. Experiments were carried out while shaking at 1000 rpm and at 30° C. Each antibody was tested in at at least two independent experiments (Table 6).

Data was analyzed with ForteBio Data Analysis Software v8.1, using the 1:1 model and a global full fit with 1000 s association time and 100 s dissociation time. Data traces were corrected by subtraction of a reference curve (antibody without CD3ε27-GSKa), the Y-axis was aligned to the last 10 s of the baseline, and interstep correction as well as Savitzky-Golay filtering was applied. Data traces with a response <0.05 nm were excluded from analysis.

TABLE 6

| Average | <KD> (nM) | SDEV | SEM | CV | <Kon> | SDEV | SEM | CV | <Kdis> | SDEV | SEM | CV | pKD | n |
|---|---|---|---|---|---|---|---|---|---|---|---|---|---|---|
| IgG1-huCD3-G105P-FEAL | 5 | 2 | 1 | 45 | 4.7E+05 | 9.7E+04 | 5.6E+04 | 21 | 2.5E-03 | 1.0E-03 | 5.8E-04 | 40 | 8.3 | 3 |
| IgG1-huCD3-FEAL | 15 | 6 | 3 | 37 | 2.7E+05 | 5.1E+04 | 2.9E+04 | 19 | 4.0E-03 | 1.6E-03 | 9.1E-04 | 39 | 7.8 | 3 |
| IgG1-huCD3-Y114V-FEAL | 29 | 8 | 4 | 26 | 2.2E+05 | 3.3E+04 | 1.9E+04 | 15 | 6.3E-03 | 9.7E-04 | 5.6E-04 | 15 | 7.5 | 3 |
| IgG1-huCD3-T31P-FEAL | 42 | 9 | 4 | 21 | 1.9E+05 | 3.8E+04 | 1.6E+04 | 20 | 7.8E-03 | 1.3E-03 | 5.3E-04 | 17 | 7.4 | 6 |
| IgG1-huCD3-Y114M-FEAL | 42 | 14 | 8 | 33 | 2.6E+05 | 6.2E+04 | 3.6E+04 | 24 | 1.0E-02 | 1.5E-03 | 8.7E-04 | 15 | 7.4 | 3 |
| IgG1-huCD3-H101N-FEAL | 45 | 13 | 7 | 29 | 4.8E+05 | 2.2E+05 | 1.2E+05 | 45 | 2.0E-02 | 3.1E-03 | 1.8E-03 | 16 | 7.3 | 3 |
| IgG1-huCD3-Y114R-FEAL | 46 | 10 | 6 | 22 | 1.5E+05 | 4.1E+04 | 2.4E+04 | 27 | 6.8E-03 | 4.1E-04 | 2.4E-04 | 6 | 7.3 | 3 |
| IgG1-huCD3-S110A-FEAL | 72 | 15 | 6 | 21 | 1.8E+05 | 2.5E+04 | 1.0E+04 | 14 | 1.3E-02 | 1.6E-03 | 6.4E-04 | 12 | 7.1 | 6 |
| IgG1-huCD3-N57E-FEAL | 91 | 30 | 17 | 33 | 2.1E+05 | 2.8E+04 | 1.6E+04 | 13 | 1.9E-02 | 4.0E-03 | 2.3E-03 | 21 | 7.0 | 3 |
| IgG1-huCD3-T31M-FEAL | 99 | 23 | 13 | 23 | 1.9E+05 | 2.5E+04 | 1.5E+04 | 14 | 1.8E-02 | 2.6E-03 | 1.5E-03 | 14 | 7.0 | 3 |
| IgG1-huCD3-Y32A-FEAL | 105 | 31 | 22 | 29 | 2.2E+05 | 1.1E+05 | 7.5E+04 | 48 | 2.2E-02 | 4.4E-03 | 3.1E-03 | 20 | 7.0 | 2 |

TABLE 6-continued

| Average | <KD> (nM) | SDEV | SEM | CV | <Kon> | SDEV | SEM | CV | <Kdis> | SDEV | SEM | CV | pKD | n |
|---|---|---|---|---|---|---|---|---|---|---|---|---|---|---|
| IgG1-huCD3-H101L-FEAL | 107 | 39 | 23 | 37 | 2.7E+05 | 4.3E+04 | 2.5E+04 | 16 | 2.8E-02 | 7.5E-03 | 4.4E-03 | 27 | 7.0 | 3 |
| IgG1-huCD3-H101K-FEAL | 120 | 94 | 55 | 79 | 2.2E+05 | 1.9E+05 | 1.1E+05 | 84 | 1.7E-02 | 9.8E-03 | 5.7E-03 | 58 | 6.9 | 3 |
| IgG1-huCD3-S110G-FEAL | 153 | 120 | 70 | 79 | 3.8E+05 | 4.2E+05 | 2.4E+05 | 112 | 2.6E-02 | 8.3E-03 | 4.8E-03 | 32 | 6.8 | 3 |
| IgG1-huCD3-H101G-FEAL | 683 | 169 | 97 | 25 | 3.0E+04 | 9.2E+03 | 5.3E+03 | 30 | 2.0E-02 | 8.5E-04 | 4.9E-04 | 4 | 6.2 | 3 |
| IgG1-huCD3-H101I-FEAL | nd | | | | | | | | | | | | | | 0 |
| IgG1-huCD3-H101F-FEAL | nd | | | | | | | | | | | | | | 0 |

T Cell Binding Affinity Determination of IgG1-huCD3-H1L1-FEAL Affinity Mutants

T cells from donor buffy coats (Sanquin, Amsterdam, The Netherlands) were isolated by using RosetteSep human T cell enrichment cocktail (Cat: 15021C.1, Stemcell Technologies, France) according to manufacturer's instructions. Briefly, 50 µL of T cell isolation cocktail was added to 1 mL of buffy coat and incubate at RT for 20 min. Next, the buffy coat was diluted (1:3, v/v) with PBS (cat: 3623140, B.Braun, Germany) and gently transferred to 50 mL falcon tubes (cat: 227261, Greiner bio-one, The Netherlands) filled with 15 mL lymphocyte separation medium (cat: 17-829E, Lonza, Switzerland). Tubes were centrifuged for 20 min at RT 1200×g without brakes. Collect the T cells from the density medium and wash with PBS twice.

2×10E6 T cells/mL were resuspended in FACS buffer and transferred to 50 µL into round bottom 96 well plates (cat: 650101, Greiner bio-one, The Netherlands). 50 µL of the antibody solutions in five-fold dilutions was added starting with 5 µg/mL and incubated for 30 min at 4° C. The 96 plates were centrifuged at 300×g for 5 min at 4° C. and the supernatant discarded. Cells were washed twice with ice cold FACS buffer on ice and the 1:200 diluted secondary antibody (anti IgG Fcγ-PE (fab)'2, cat: 109-116-098, Jackson Immuno Research, UK) added to 100 µL/well and incubated for 30 min and washed twice with FACS buffer. Fluorescence intensity was measured on FACS Canto and geometric mean calculated by FlowJo V10 software. Graphs were made by GraphPad (V6.04). See FIG. 5.

Example 9: In Vitro Cytotoxicity Screening of CD3 Affinity Mutants

Cytotoxicity of CD3 Affinity Mutants on Solid Tumor Cell Lines (Alamar Blue Assay)

T cells from donor buffy coats (Sanquin, Amsterdam, The Netherlands) were isolated by using RosetteSep human T cell enrichment cocktail (Cat: 15021C.1, Stemcell Technologies, France) according to manufacturer's instructions. NCI-N87 (25.000 cells/well) (FIG. 6A), SKOV3 (16.000 cells/well) (FIG. 6B) and MDA-MB-231 (16.000 cells/well) (FIG. 6C) cells were seeded into flat bottom 96 well plates (cat: 655180, Greiner-bio-one, The Netherlands) and adhered for 3-5 h at 37° C. T cells were added to tumor cells in the following ratios: NCI-N87 cell: T cells, 1:3; SKOV3 cell:T cell, 1:4; MDA-MB-231 cell: T cell, 1:8. Subsequently antibody solutions were added in ten-fold dilutions and plates were incubated for 2 days at 37° C. Next, supernatants were discarded and adhered cells were washed twice with PBS. 150 µL of 10% alamar blue (cat: DAL1100, Life Technologies, The Netherlands) solution prepared in RPMI-1640 (cat: BE12-115F, Lonza, Switzerland) medium containing 10% donor bovine serum with iron (cat: 10371-029, Life Technologies, The Netherlands) was added to wells and incubated for 3-5 h at 37° C. The absorbance was measured with Envision multilabel plate reader (PerkinElmer, US). Staurosporine (cat: 56942, Sigma-Aldrich, US) treated cells were set as 100% kill and untreated cells were set as 0% kill. Viable cells were calculated by subtracting staurosporine treated cells from all groups and the percentage was plotted against the untreated group. Graphs were made by GraphPad (V6.04). See FIG. 6.

Cytotoxicity of CD3 Affinity Mutants on a Hematological Cell Line (Chromium Release Assay)

Figure 7:
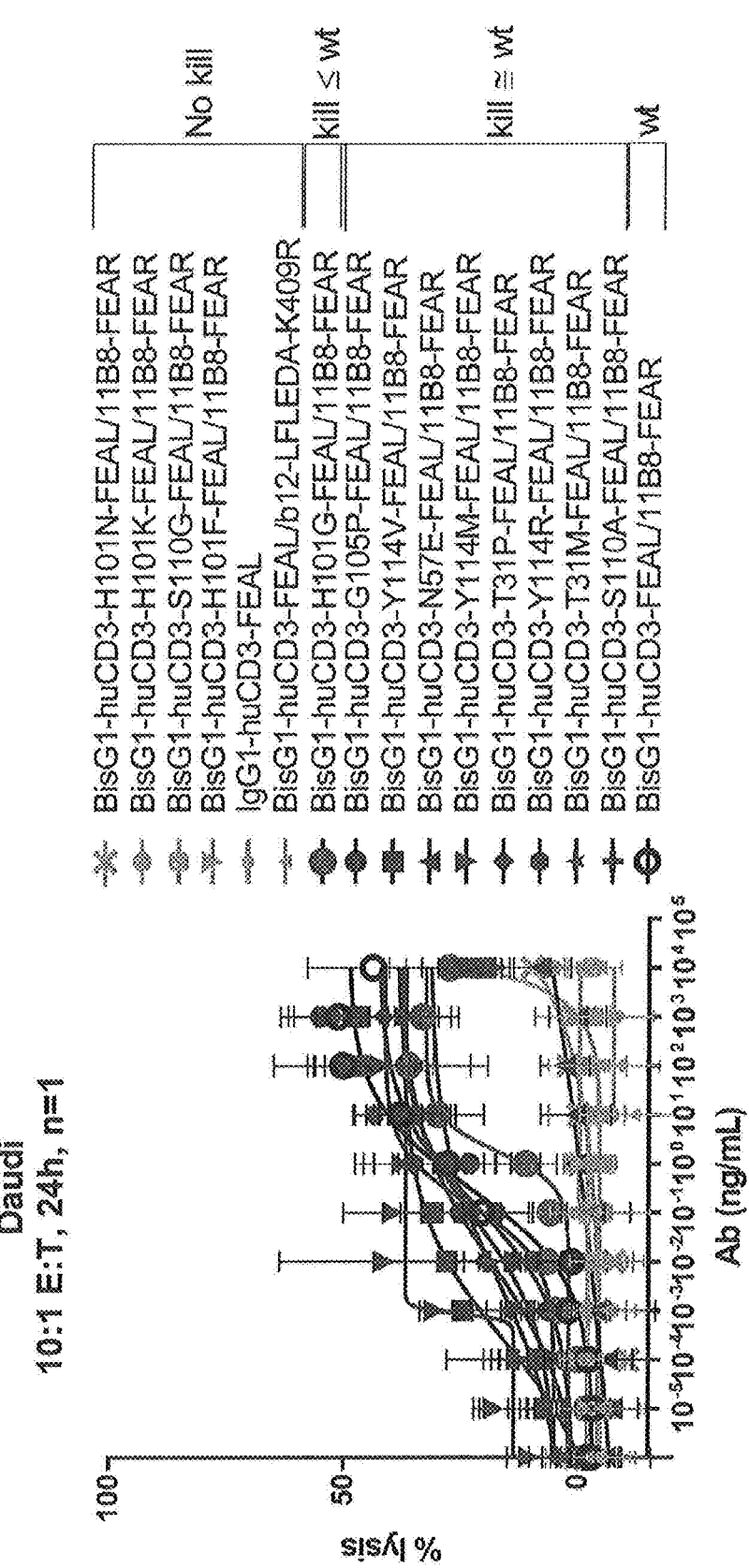
FIG. 7: Cytotoxicity of CD3 affinity variants on a hematological (Daudi) cell line measured by chromium release assay. T cell: Daudi cell ratio=10:1, 24 hours of incubation, 1 donor. The tested affinity variants depicted cover a broad range of cytotoxicity between wild type response and no observed cytotoxicity for the tested tumor cell line.
Figure 8A:
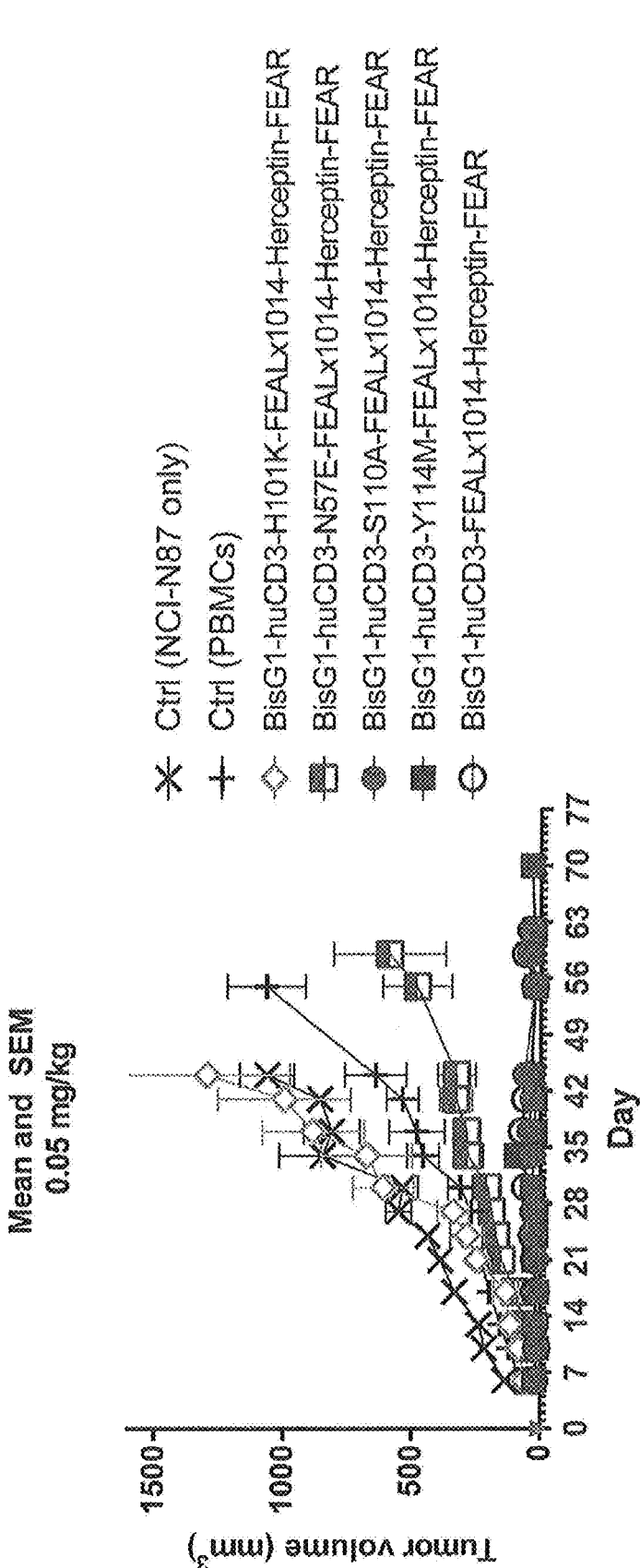
FIGS. 8A-8D: Cytotoxicity of CD3×HER2 bispecific antibodies in a NCI-N87, human PBMC co-engraftment model in NOD-SCID mice. HLA-A-matched human unstimulated PBMCs, as a source of human T cells, were co-inoculated with NCI-N87 tumor cells in NOD-SCID mice at two different dose levels of CD3 affinity antibodies (0.5 and 0.05 mg/kg). Humanized WT CD3 (huCD3) and 4 different CD3 affinity variants (N57E, H101K, S110A, Y114M) were tested.
Figure 8B:
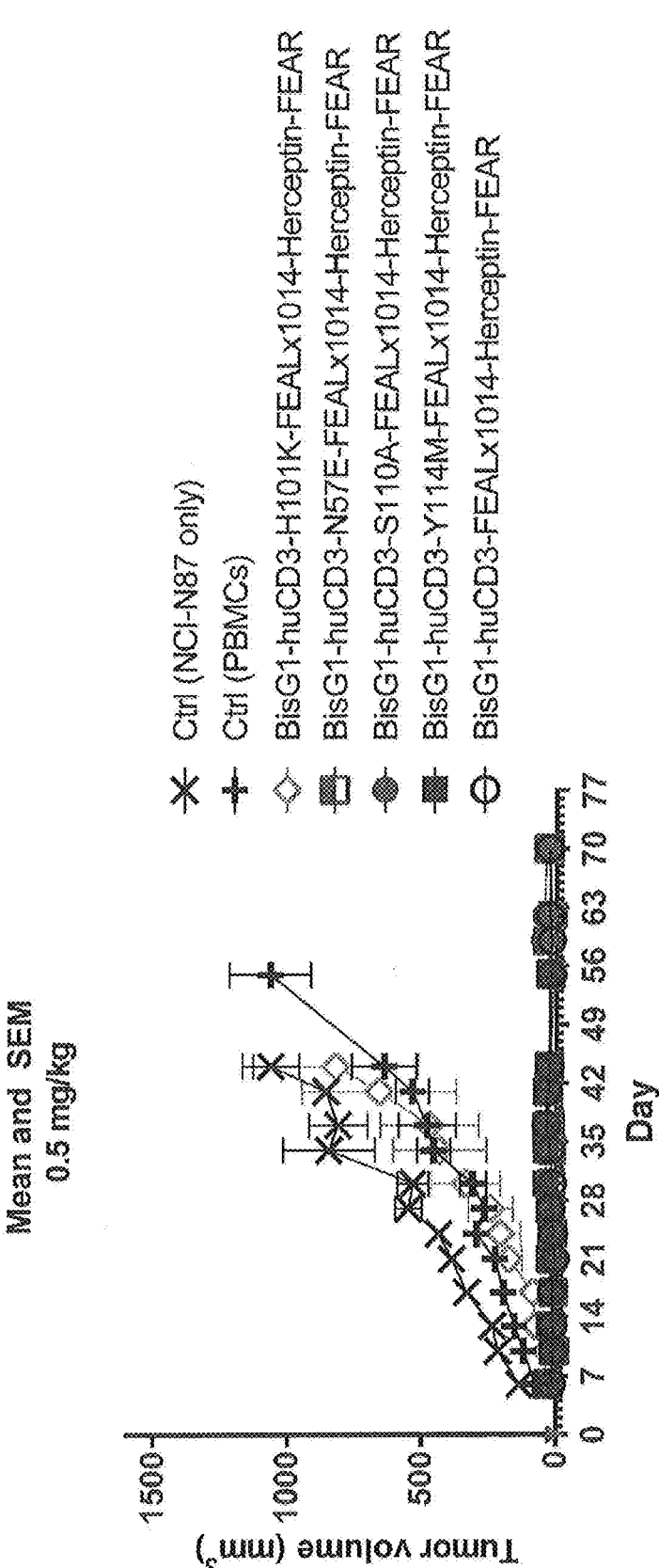
Figure 8C:
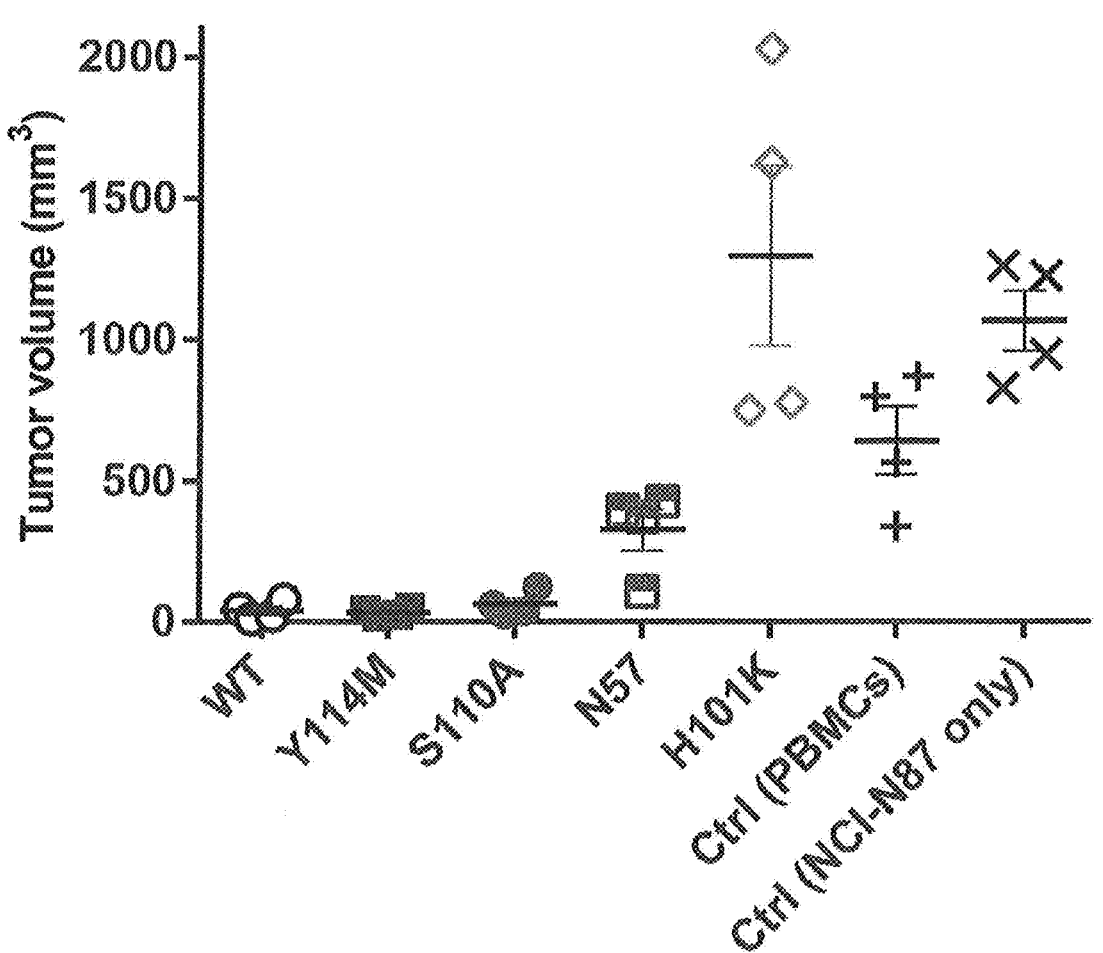
Figure 8D:
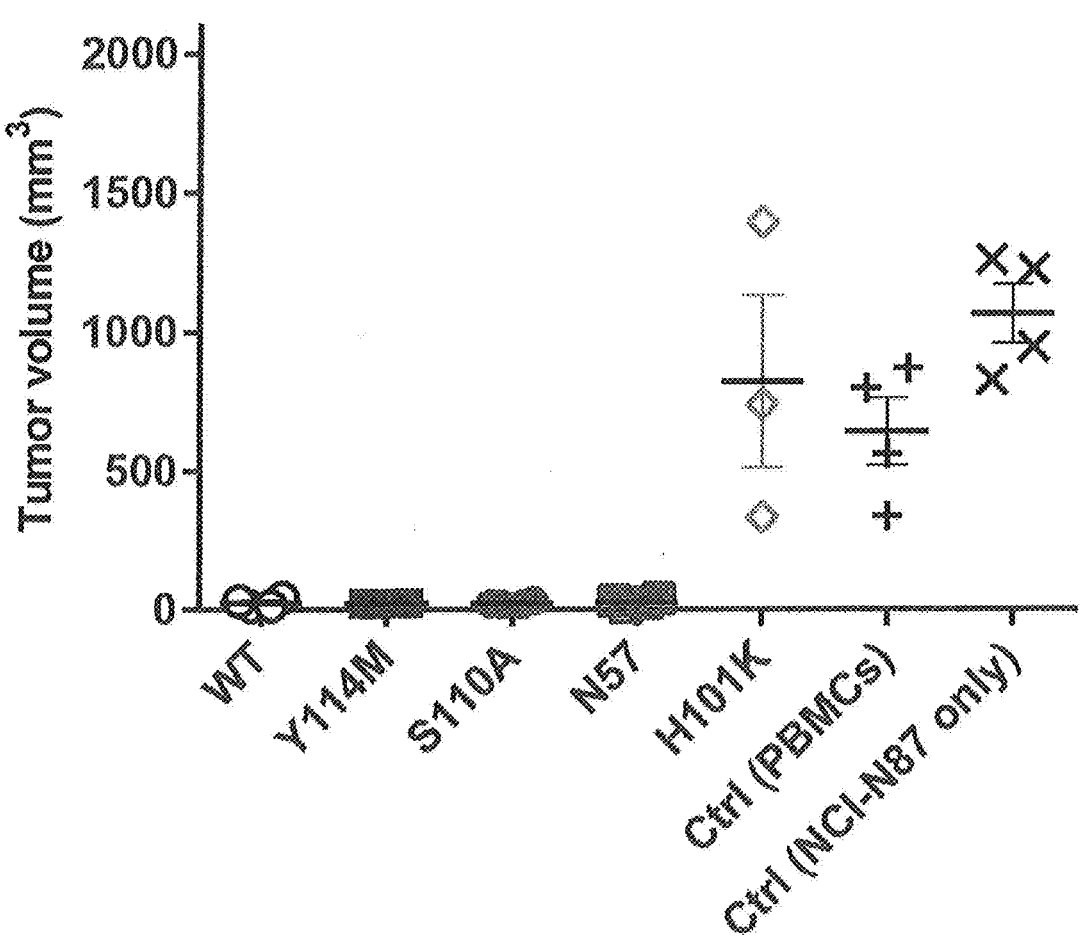

5×10E6 Daudi cells/mL were incubated in complete culture medium with 100 µCi chromium for 1 h under shaking conditions at 37° C. Next, cells were washed twice in PBS and resuspended in 5 mL complete cell culture medium (10% donor bovine serum with iron in RPMI 1640). 5.000 Daudi cells were seeded into round bottom 96 well plates. T cells from donor buffy coats (purchased from Sanquin, Amsterdam, The Netherlands) were isolated by using RosetteSep human T cell enrichment cocktail (Cat: 15021C.1, Stemcell Technologies, France) according to manufacturer's instructions. T cells are added in (tumor cell: T cell) 1:10 ratio to Daudi cells followed by the addition of the antibody solutions in two-fold dilutions. Plates were in incubated 24 h at 37° C. After 24 h, plates were centrifuges at 300×g for 3 min, supernatant was harvested and measured for radioactivity. See FIG. 7.

TABLE 7

| HER2 COPY# | Cells | % of kill | | | |
|---|---|---|---|---|---|
| | | No kill | kill ≤ 50% | kill ≤ wt | kill = wt |
| HER2 ≥ 1,000,000 | NCI-N87 | H101I, H101L, H101K, Y32A | H101F, S110G, H101N | N57E, H101G | S110A, G105P, S110A, T31M, T31P, Y114M, Y114R, Y114V |
| 50,000 ≤ HER2 ≤ 180,000 | SKOV3 | H101I, H101F, H101L, Y32A | H101K | H101G, S110G, H101N, N57E | S110A, G105P, S110A, T31M, T31P, Y114M, Y114R, Y114V |

US 12,673,994 B2

135

TABLE 7-continued

| HER2 COPY# | Cells | % of kill | | | |
|---|---|---|---|---|---|
| | | No kill | kill ≤ 50% | kill ≤ wt | kill = wt |
| HER2 ≤ 30,000 | MDA-MB-231 | H101F, H101I, S110G, Y32A, H101L, H101K, H101N, N57E | H101G | | S110A, G105P, S110A, T31M, T31P, Y114M, Y114R, Y114V |

Example 10: Tumor Efficacy of CD3×HER2 Bispecific Antibodies in a. (Human PBMC+NCI-N87 Cells) Co-Engraftment Model in NOD-SCID Mice The in vivo anti-tumor efficacy of several CD3×HER2 bispecific antibodies was evaluated in a subcutaneous NCI-N87 co-engraftment model (FIG. 8). As a CD3-arm of the bispecific antibody, a humanized WT CD3 (huCD3-FEAL) and 4 different CD3 affinity variants (N57E, H101K, S110A, Y114M) were used. The HER2-targeting arm in all cases was the same (Herceptin-FEAR)

BisG1-huCD3-FEAL×1014-Herceptin-FEAR
BisG1-huCD3-N57E-FEAL×1014-Herceptin-FEAR
BisG1-huCD3-H101K-FEAL×1014-Herceptin-FEAR
BisG1-huCD3-S110A-FEAL×1014-Herceptin-FEAR
BisG1-huCD3-Y114M-FEAL×1014-Herceptin-FEAR In this model, HLA-A-matched human unstimulated PBMCs, as a source of human T cells, were co-inoculated with NCI-N87 tumor cells at two different dose levels (0.5 and 0.05 mg/kg).

Mice were sorted into treatment groups (n=4 per treatment group. At day 0, a mixture containing HLA-A matched hPBMC (5×10E6, Sanquin) and NCI-N87 (5×10E6) cells in 200 µL PBS/0.1% BSA were inoculated subcutaneously (s.c.) in the right flank of each female NOD-SCID mice (NOD.C.B-17-Prkdc$^{scid}$/J), age 6-11 weeks old (Charles-River)). Directly after tumor cell injection, single intravenous dosing (150 L) of five different CD3×HER2 antibodies was performed at two different concentrations (0.5 and 0.05 mg/kg) for all bispecific antibodies. Tumor volumes were determined at least two times per week. Tumor volumes (mm$^3$) were calculated from caliper (PLEXX) measurements as: 0.52×(length)×(width)$^2$.

NCI-N87 cells (ATCC #CRL-5822, gastric carcinoma arising from stomach) were thawed, cultured in RPMI 1640 (Lonza, BE12-115F) supplemented with 10% donor bovine serum with iron (Gibco, cat. no. 10371-029), penicillin/streptomycin and 0.45% glucose (Sigma, G8769), sodium pyruvate (Cambrex, BE13-115E) and 0.075% sodium bicarbonate (Cambrex, BE17-613E). Cells were grown in Cell-STACK culture chambers and harvested in log-phase and counted by trypan blue exclusion.

For each study, hPBMCs were isolated from human HLA-A matched donors for NCI-N87 (HLA-A-01,23) from a buffy coat (Sanquin) by Ficoll density centrifugation. Isolated cells were frozen in nitrogen and thawed before use. All cells were washed in PBS/0.1% BSA, filtered through a cell strainer and resuspended to a concentration of 50×10E6 cells/mL in PBS/0.1% BSA.

Figure 6A:
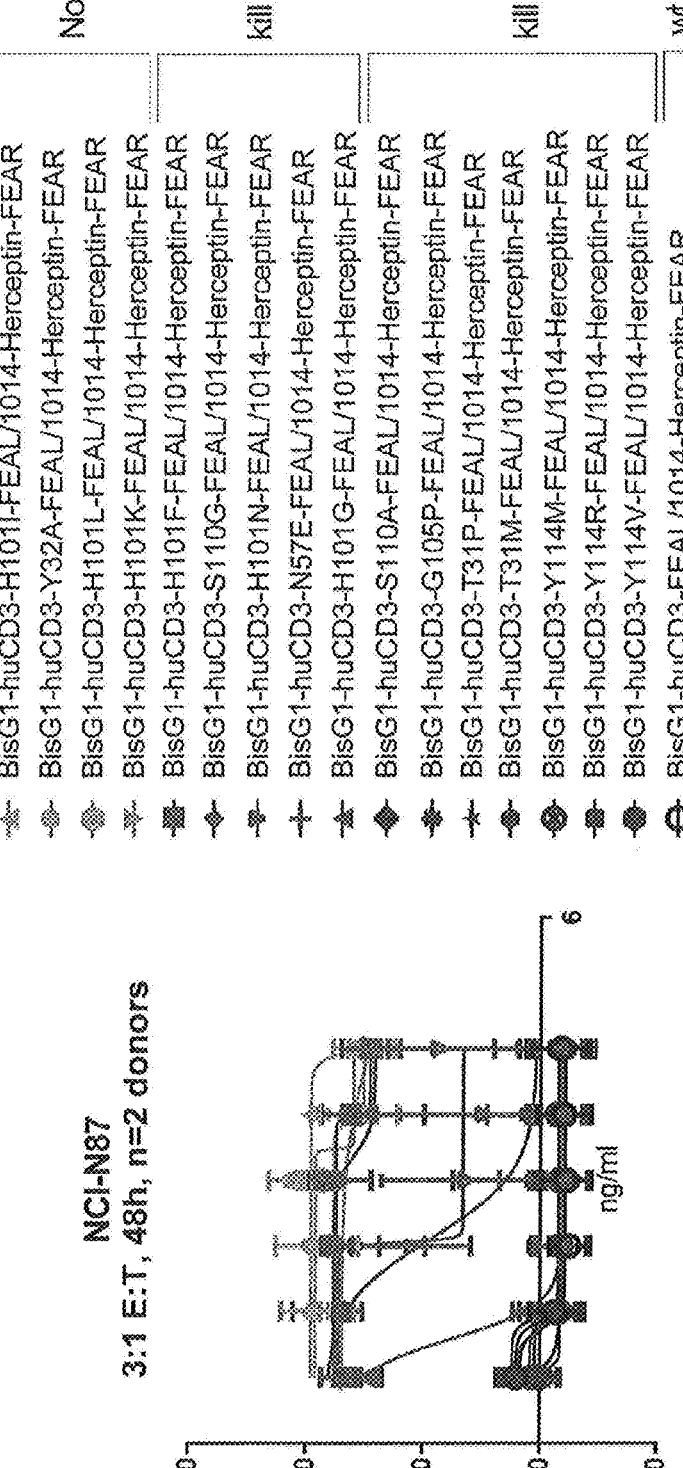
FIGS. 6A-GC: Cytotoxicity of CD3 affinity variants on solid tumor cell lines measured by alamar blue assay.
Figure 6B:
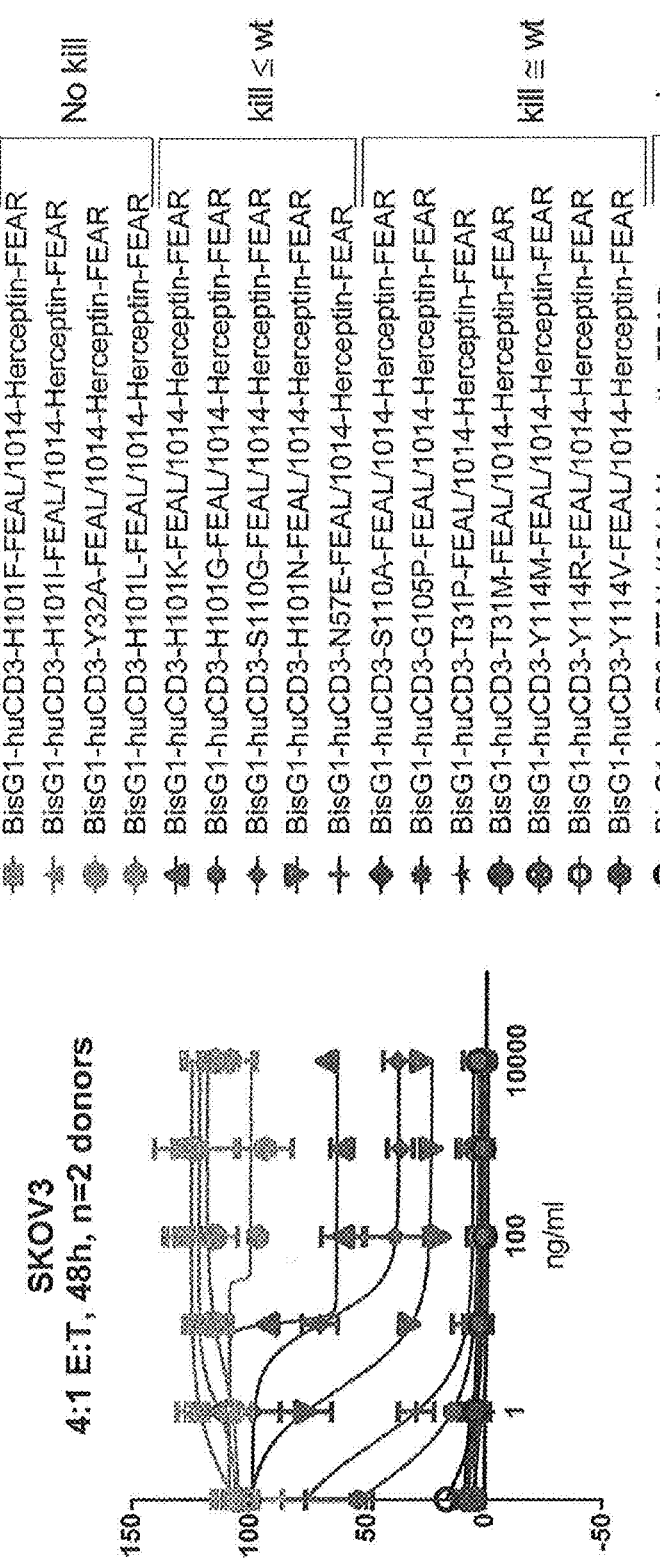
Figure 6C:
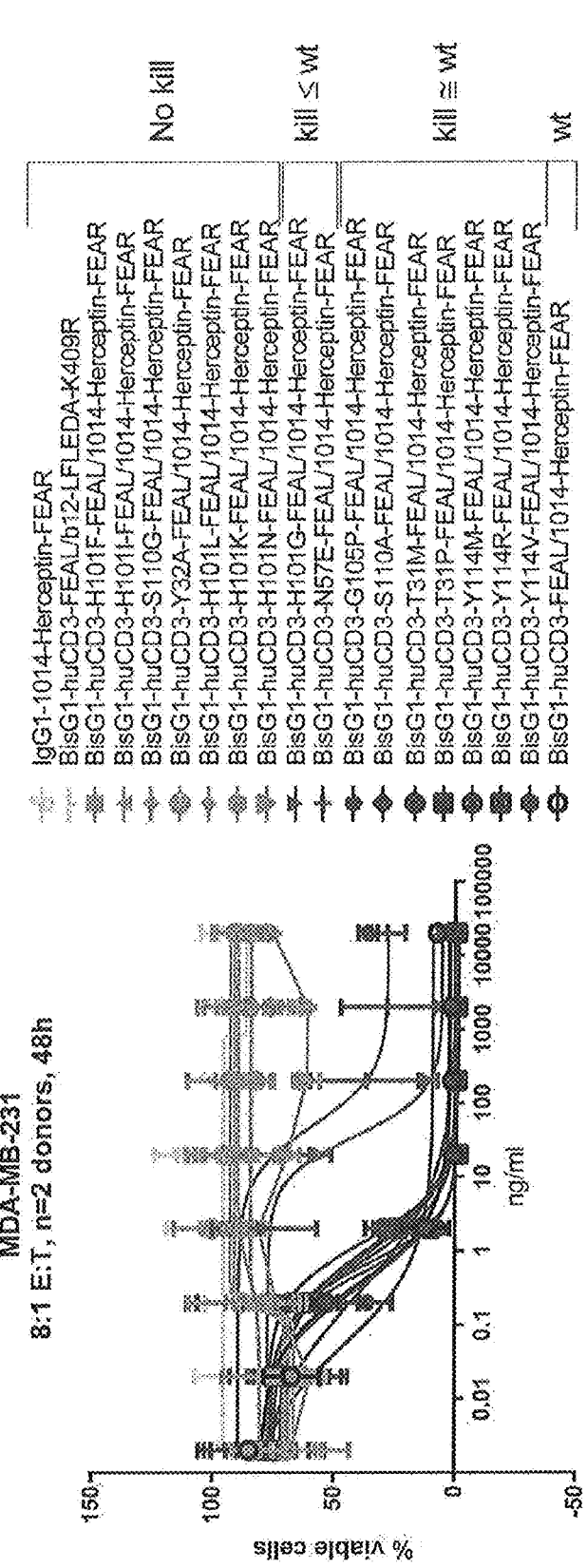

The results are shown in FIG. 8. FIG. 6A-B show average tumor volumes after treatment over time. FIG. 6C-D show dot plot representations of average NCI-N87 tumor volume at day 44. Statistical analysis (Mann-Whitney) on the tumor volumes at day 44, last day that all groups were still intact, revealed at a dose of 0.05 mg/kg a significant tumor growth inhibition (p<0.05) of BisG1-huCD3-FEAL×1014-Herceptin-FEAR, BisG1-huCD3-S110A-FEAL×1014-Herceptin-FEAR and BisG1-huCD3-Y114M-FEAL×1014-Herceptin-FEAR compared to the control (PBMCs) and not of BisG1-huCD3-N57E-FEAL×1014-Herceptin-FEAR and BisG1-huCD3-H101K-FEAL×1014-Herceptin-FEAR. At a dose of 0.5 mg/kg BisG1-huCD3-FEAL×1014-Herceptin-FEAR and all CD3-arm affinity variants, showed significant tumor growth (p<0.05) inhibition compared to the PBS (PBMCs) control group, except BisG1-huCD3-H101K-FEAL×1014-Herceptin-FEAR.

BisG1-huCD3-FEAL×1014-Herceptin-FEAR, BisG1-huCD3-S110A-FEAL×1014-Herceptin-FEAR, and BisG1-huCD3-Y114M-FEAL×1014-Herceptin-FEAR significantly (p<0.05) reduced NCI-N87 tumor volume at dosages of 0.05 and 0.5 mg/kg. BisG1-huCD3-N57E-FEAL×1014-Herceptin-FEAR reduced significantly (p<0.05) NCI-N87 tumor volume only at a dosage of 0.5 mg/kg. BisG1-huCD3-H101K-FEAL×1014-Herceptin-FEAR did not affect NCI-N87 tumor growth at both tested dosages.

LIST OF REFERENCES

[1] Xu et al., 2000, Cell Immunol. 200(1):16-26
[2] Herold et al., 2005, Diabetes, 54(6):1763-9
[3] Staerz, et. al., 1985, Nature 314:628-631
[4] Muller and Kontermann, 2010, BioDrugs 24: 89-98
[5] Lum and Thakur, 2011, BioDrugs 25: 365-379
[6] Linke et al., 2010, MAbs 2: 129-136
[7] Ruf et al., 2010, Br J Clin Pharmacol 69: 617-625
[8] Bokemeyer et al., 2009, J Clin Oncol (Meeting Abstracts), 3036
[9] Helss et al., 2010, Int J Cancer 127: 2209-2221
[10] Jones et al., 2009, Lancet Oncol 10:1179-1187
[11] Klewe et al., 2006, Clin Cancer Res 12:3085-3091
[12] WO 2012/162067
[13] WO 2008/119567
[14] Fundamental Immunology Ch. 7, Paul, W., ed., 2nd ed. Raven Press, N.Y. (1989)
[15] Lefranc M P, et al., 2003, Dev Comp Immunol. January; 27(1):55-77
[16] Brochet, X. et al., 2008, Nucl. Acids Res. 36, W503-508
[17] Gludicelli, V., Brochet, X, Lefranc, M.-P., 2011, Cold Spring Harb Protoc. June 1; 2011 (6)
[18] Sambrook et al., 1989, Molecular Cloning: A laboratory Manual, New York: Cold Spring Harbor Laboratory Press, Ch. 15
[19] WO92/22653
[20] EP 0 629 240
[21] E. Meyers and W. Miller, 1988, Comput. Appl. Biosci 4, 11-17
[22] Needleman and Wunsch, 1970, J. Mol. Biol. 48, 444-453
[23] Clustal W algorithm, Thompson, 1994
[24] T cell Epitope Database from e.g. www.iedb.org/
[25] Perry et al., 2008 Drugs R D 9 (6):385-396
[26] Bryson et al., 2010, Biodrugs 24 (1):1-8
[27] Kabat, E. A. et al., 1991, Sequences of proteins of Immunological Interest. 5th Edition—US Department of Health and Human Services, NIH publication No. 91-3242, pp 662,680,689
[28] Oganesyan et al., 2008, Acta Cryst. (D64):700-4
[29] Canfield et al., 1991, J. Exp. Med. (173):1483-91

US 12,673,994 B2

137                                          138

[30] Duncan et al., 1988, Nature (332):738-40
[31] Shields et al., 2001, J. Biol. Chem. (276):6591-604
[32] Idusogie E E, et al., 2000, J Immunol. 164: 4178-84
[33] Leabman et al., 2013, MAbs; 5(6):896-903
[34] Parren et al., 1992, J. Clin Invest. 90: 1537-1546
[35] Bruhns et al., 2009, Blood 113: 3716-3725
[36] WO 2011/066501
[37] Lightle, S., et al., 2010, Protein Science (19):753-62
[38] Brekke et al., 2006, J Immunol 177:1129-1138
[39] Dall'Acqua W F, et al., 2006, J Immunol 177:1129-1138
[40] Wu et al., 2010, Generation and Characterization of a Dual Variable Domain Immunoglobulin (DVD-Ig™) Molecule, In: Antibody Engineering, Springer Berlin Heidelberg
[41] WO 2011/131746
[42] WO 2002/020039
[43] WO 98/050431
[44] WO 2011/117329
[45] EP 1 870 459
[46] WO 2009/089004
[47] US 2010 00155133
[48] WO 2010/129304
[49] WO 2007/110205
[50] WO 2010/015792
[51] WO 2011/143545
[52] WO 2012/058768
[53] WO 2011/028952
[54] WO 2008/003116
[55] U.S. Pat. No. 7,262,028
[56] U.S. Pat. No. 7,612,181
[57] WO 2010/0226923
[58] U.S. Pat. No. 7,951,918
[59] CN 102250246
[60] WO 2012/025525
[61] WO 2012/025530
[62] WO 2008/157379
[63] WO 2010/080538
[64] Sykes and Johnston, 1997, Nat Biotech 17, 355-59
[65] U.S. Pat. No. 6,077,835
[66] WO 2000/70087
[67] Schakowski et al., 2001, Mol Ther 3, 793-800
[68] WO 2000/46147
[69] Benvenisty and Reshef, 1986, PNAS USA 0.83, 9551-55
[70] Wigler et al., 1978, Cell 14, 725
[71] Coraro and Pearson, 1981, Somatic Cell Genetics 7, 603
[72] U.S. Pat. No. 5,589,466
[73] U.S. Pat. No. 5,973,972
[74] Van Heeke & Schuster, 1989, J Biol Chem 264, 5503-5509
[75] F. Ausubel et al., 1987, ed. Current Protocols in Molecular Biology, Greene Publishing and Wiley Inter-Science New York
[76] Grant et al., 1987, Methods in Enzymol 153, 516-544
[77] Remington: The Science and Practice of Pharmacy, 19th Edition, Gennaro, Ed., Mack Publishing Co., Easton, PA, 1995
[78] Sustained and Controlled Release Drug Delivery Systems, J. R. Robinson, ed., Marcel Dekker, Inc., New York, 1978
[79] Srivastava (ed.), Radiolabeled Monoclonal Antibodies For Imaging And Therapy, Plenum Press 1988
[80] Chase, "Medical Applications of Radioisotopes," in Remington's Pharmaceutical Sciences, 18th Edition, Gennaro et al., (eds.), pp. 624-652, Mack Publishing Co., 1990
[81] Brown, "Clinical Use of Monoclonal Antibodies," in Biotechnology And Pharmacy 227-49, Pezzuto et al., (eds.), Chapman & Hall 1993
[82] U.S. Pat. No. 5,057,313
[83] U.S. Pat. No. 6,331,175
[84] Ritter G, et al.; 2001, Cancer Res., 61:6851-9
[85] Bostrom et al, Science. 2009; 323(5921):1610-4
[86] Bostrom et al, PLosOne. 2011; 6(4)e17887

The invention claimed is:

1. A bispecific antibody comprising a first binding region of an antibody which binds to human CD3, and a second binding region which binds a tumor-associated antigen, wherein the first binding region comprises a heavy chain variable (VH) region and a light chain variable (VL) region, wherein:

(a) the VH region comprises the CDR1, CDR2, and CDR3 sequences set forth in SEQ ID NOs: 54, 2, and 3, respectively, and the VL region comprises the CDR1, CDR2, and CDR3 sequences set forth in SEQ ID NO: 6, the sequence GTN, and SEQ ID NO: 7, respectively;

(b) the VH region comprises the CDR1, CDR2, and CDR3 sequences set forth in SEQ ID NOs: 58, 2, and 3, respectively, and the VL region comprises the CDR1, CDR2, and CDR3 sequences set forth in SEQ ID NO: 6, the sequence GTN, and SEQ ID NO: 7, respectively;

(c) the VH region comprises the CDR1, CDR2, and CDR3 sequences set forth in SEQ ID NOs: 1, 106, and 3, respectively, and the VL region comprises the CDR1, CDR2, and CDR3 sequences set forth in SEQ ID NO: 6, the sequence GTN, and SEQ ID NO: 7, respectively;

(d) the VH region comprises the CDR1, CDR2, and CDR3 sequences set forth in SEQ ID NOs: 1, 2, and 176, respectively, and the VL region comprises the CDR1, CDR2, and CDR3 sequences set forth in SEQ ID NO: 6, the sequence GTN, and SEQ ID NO: 7, respectively;

(e) the VH region comprises the CDR1, CDR2, and CDR3 sequences set forth in SEQ ID NOs: 1, 2, and 184, respectively, and the VL region comprises the CDR1, CDR2, and CDR3 sequences set forth in SEQ ID NO: 6, the sequence GTN, and SEQ ID NO: 7, respectively;

(f) the VH region comprises the CDR1, CDR2, and CDR3 sequences set forth in SEQ ID NOs: 1, 2, and 220, respectively, and the VL region comprises the CDR1, CDR2, and CDR3 sequences set forth in SEQ ID NO: 6, the sequence GTN, and SEQ ID NO: 7, respectively;

(g) the VH region comprises the CDR1, CDR2, and CDR3 sequences set forth in SEQ ID NOs: 1, 2, and 236, respectively, and the VL region comprises the CDR1, CDR2, and CDR3 sequences set forth in SEQ ID NO: 6, the sequence GTN, and SEQ ID NO: 7, respectively;

(h) the VH region comprises the CDR1, CDR2, and CDR3 sequences set forth in SEQ ID NOs: 1, 2, and 244, respectively, and the VL region comprises the CDR1, CDR2, and CDR3 sequences set forth in SEQ ID NO: 6, the sequence GTN, and SEQ ID NO: 7, respectively;

(i) the VH region comprises the CDR1, CDR2, and CDR3 sequences set forth in SEQ ID NOs: 1, 2, and 284, respectively, and the VL region comprises the CDR1, CDR2, and CDR3 sequences set forth in SEQ ID NO: 6, the sequence GTN, and SEQ ID NO: 7, respectively;

(j) the VH region comprises the CDR1, CDR2, and CDR3 sequences set forth in SEQ ID NOs: 1, 2, and 292, respectively, and the VL region comprises the CDR1, CDR2, and CDR3 sequences set forth in SEQ ID NO: 6, the sequence GTN, and SEQ ID NO: 7, respectively; or (k) the VH region comprises the CDR1, CDR2, and CDR3 sequences set forth in SEQ ID NOs: 1, 2, and 298, respectively, and the VL region comprises the CDR1, CDR2, and CDR3 sequences set forth in SEQ ID NO: 6, the sequence GTN, and SEQ ID NO: 7, respectively.

2. The bispecific antibody according to claim 1, wherein the VH region of the first binding region comprises:

(a) a VH sequence as set forth in SEQ ID NO: 55;
(b) a VH sequence as set forth in SEQ ID NO: 59;
(c) a VH sequence as set forth in SEQ ID NO: 107;
(d) a VH sequence as set forth in SEQ ID NO: 177;
(e) a VH sequence as set forth in SEQ ID NO: 185;
(f) a VH sequence as set forth in SEQ ID NO: 221;
(g) a VH sequence as set forth in SEQ ID NO: 237;
(h) a VH sequence as set forth in SEQ ID NO: 245;
(i) a VH sequence as set forth in SEQ ID NO: 285;
(j) a VH sequence as set forth in SEQ ID NO: 293; or
(k) a VH sequence as set forth in SEQ ID NO: 299; and the VL region comprises a VL sequence as set forth in SEQ ID NO: 8 or SEQ ID NO: 10.

3. The bispecific antibody according to claim 1, which is a full-length antibody.

4. The bispecific antibody according to claim 1, which is chimeric or humanized.

5. The bispecific antibody according to claim 1, which is of an isotype selected from the group consisting of IgG1, IgG2, IgG3, and IgG4.

6. The bispecific antibody according to claim 1, which is monovalent, bivalent or multivalent.

7. The bispecific antibody according to claim 1, which comprises a first heavy chain and a second heavy chain.

8. The bispecific antibody according to claim 7, wherein in at least one of said first and second heavy chains, (a) the amino acid in the position corresponding to position D265 in a human IgG1 heavy chain is not D;

(b) the amino acid in the position corresponding to position N297 in a human IgG1 heavy chain is not N;

(c) the amino acids in the positions corresponding to positions L234 and L235 in a human IgG1 heavy chain are not L and L, respectively;

(d) the amino acids in the positions corresponding to positions L234 and L235 in a human IgG1 heavy chain are F and E; or A and A, respectively;

(e) the amino acids in the positions corresponding to positions L234 and L235 in a human IgG1 heavy chain are F and E, respectively;

(f) the amino acids in the positions corresponding to positions L234 and L235 in a human IgG1 heavy chain are A and A, respectively;

(g) the amino acids in the positions corresponding to positions L234, L235, and D265 in a human IgG1 heavy chain are not L, L, and D, respectively;

(h) the amino acids in the positions corresponding to positions L234, L235, and D265 in a human IgG1 heavy chain are F, E, and A; or A, A, and A, respectively;

(i) the amino acids in the positions corresponding to positions L234, L235, and D265 in a human IgG1 heavy chain are F, E, and A, respectively; or (j) the amino acids in the positions corresponding to positions L234, L235, and D265 in a human IgG1 heavy chain, are A, A, and A, respectively.

9. The bispecific antibody according to claim 7, wherein in at least one of said first and second heavy chains, the amino acids in the positions corresponding to positions L234, L235, D265, N297, and P331 in a human IgG1 heavy chain are F, E, A, Q, and S, respectively.

10. The bispecific antibody according to claim 7, wherein each of said first and second heavy chain comprises at least a hinge region, a CH2 region, and a CH3 region, wherein in said first heavy chain, at least one of the amino acids in the positions corresponding to a position selected from the group consisting of T366, L368, K370, D399, F405, Y407, and K409 in a human IgG1 heavy chain has been substituted, and in said second heavy chain, at least one of the amino acids in the positions corresponding to a position selected from the group consisting of T366, L368, K370, D399, F405, Y407, and K409 in a human IgG1 heavy chain has been substituted, and wherein said first and said second heavy chains are not substituted in the same positions.

11. The bispecific antibody according to claim 1, which comprises a first heavy chain and a second heavy chain, wherein in at least one of said first and second heavy chains, one or more amino acids in the positions corresponding to positions L234, L235, D265, N297, and P331 in a human IgG1 heavy chain according to EU numbering, are not L, L, D, N, and P, respectively.

12. The bispecific antibody according to claim 10, wherein (a) the amino acid in the position corresponding to F405 in a human IgG1 heavy chain is L in said first heavy chain, and the amino acid in the position corresponding to K409 in a human IgG1 heavy chain is R in said second heavy chain, or (b) the amino acid in the position corresponding to F405 in a human IgG1 heavy chain is L in said second heavy chain, and the amino acid in the position corresponding to K409 in a human IgG1 heavy chain is R in said first heavy chain.

13. A composition comprising a bispecific antibody according to claim 1 and a carrier.

14. A pharmaceutical composition comprising a bispecific antibody according to claim 1 and a pharmaceutically acceptable carrier.

15. A bispecific antibody comprising a first binding region of an antibody which binds to human CD3, and a second binding region which binds a different target than said first binding region, wherein the first binding region comprises a heavy chain variable (VH) region comprising CDR1, CDR2 and CDR3 sequences set forth in SEQ ID NOs: 1, 2, and 176, and a light chain variable (VL) sequence comprising CDR1, CDR2 and CDR3 sequences set forth in SEQ ID NO: 6, the sequence GTN, and SEQ ID NO: 7.

16. The bispecific antibody of claim 15, wherein the first binding region comprises a VH region comprising the sequence set forth in SEQ ID NO: 177, and a VL region comprising the sequence set forth in SEQ ID NO: 8.

17. A pharmaceutical composition comprising the bispecific antibody of claim 15.

18. A bispecific antibody comprising a first binding region of an antibody which binds to human CD3, and a second binding region which binds a different target than said first binding region, wherein the first binding region comprises a heavy chain variable (VH) region comprising CDR1, CDR2 and CDR3 sequences set forth in SEQ ID NOs: 1, 2, and 184, and a light chain variable (VL) sequence comprising CDR1, CDR2 and CDR3 sequences set forth in SEQ ID NO: 6, the sequence GTN, and SEQ ID NO: 7.

19. The bispecific antibody of claim 18, wherein the first binding region comprises a VH region comprising the sequence set forth in SEQ ID NO: 185, and a VL region comprising the sequence set forth in SEQ ID NO: 8.

20. A pharmaceutical composition comprising the bispecific antibody of claim 18.

* * * * *

SEQUENCE LISTING

<160> NUMBER OF SEQ ID NOS: 417

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Ile Arg Ser Lys Tyr Asn Asn Tyr Ala Thr
1               5                   10

<210> SEQ ID NO 3
<211> LENGTH: 16

```
<212> TYPE: PRT
<213> ORGANISM: Artificial Sequence
<220> FEATURE:
<223> OTHER INFORMATION: Synthetic

<400> SEQUENCE: 3

Val Arg His Gly Asn Phe Gly Asn Ser Tyr Val Ser Trp Phe Ala Tyr
1               5                   10                  15

<210> SEQ ID NO 4
<211> LENGTH: 125
<212> TYPE: PRT
<213> ORGANISM: Artificial Sequence
<220> FEATURE:
<223> OTHER INFORMATION: Synthetic

<400> SEQUENCE: 4

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 5
<211> LENGTH: 375
<212> TYPE: PRT
<213> ORGANISM: Artificial Sequence
<220> FEATURE:
<223> OTHER INFORMATION: Synthetic

<400> SEQUENCE: 5

Gly Ala Ala Gly Thr Gly Ala Ala Gly Cys Thr Gly Gly Thr Gly Gly
1               5                   10                  15

Ala Ala Thr Cys Thr Gly Gly Cys Gly Gly Cys Gly Gly Ala Cys Thr
                20                  25                  30

Gly Gly Thr Gly Cys Ala Gly Cys Cys Thr Gly Gly Cys Gly Gly Ala
            35                  40                  45

Thr Cys Thr Cys Thr Gly Ala Gly Ala Cys Thr Gly Ala Gly Cys Thr
        50                  55                  60

Gly Thr Gly Cys Cys Gly Cys Cys Ala Gly Cys Gly Gly Cys Thr Thr
65                  70                  75                  80

Cys Ala Cys Cys Thr Thr Cys Ala Ala Cys Ala Cys Cys Thr Ala Cys
                85                  90                  95

Gly Cys Cys Ala Thr Gly Ala Ala Cys Thr Gly Gly Gly Thr Gly Cys
                100                 105                 110

Gly Cys Cys Ala Gly Gly Cys Cys Cys Cys Thr Gly Gly Cys Ala Ala
            115                 120                 125

Ala Gly Gly Cys Cys Thr Gly Gly Ala Ala Thr Gly Gly Gly Thr Gly
```

```
      130               135               140

Gly Cys Cys Cys Gly Gly Ala Thr Cys Ala Gly Ala Ala Gly Cys Ala
145               150               155               160

Ala Gly Thr Ala Cys Ala Ala Cys Ala Ala Thr Thr Ala Cys Gly Cys
                165               170               175

Cys Ala Cys Cys Thr Ala Cys Thr Ala Cys Gly Cys Cys Gly Ala Cys
                180               185               190

Ala Gly Cys Gly Thr Gly Ala Ala Gly Gly Ala Cys Cys Gly Gly Thr
        195               200               205

Thr Cys Ala Cys Cys Ala Thr Cys Ala Gly Cys Cys Gly Gly Gly Ala
        210               215               220

Cys Gly Ala Cys Ala Gly Cys Ala Ala Gly Ala Gly Cys Ala Gly Cys
225               230               235               240

Cys Thr Gly Thr Ala Cys Cys Thr Gly Cys Ala Gly Ala Thr Gly Ala
                245               250               255

Ala Cys Ala Ala Cys Cys Thr Gly Ala Ala Ala Cys Cys Gly Ala
                260               265               270

Gly Gly Ala Cys Ala Cys Cys Gly Cys Cys Ala Thr Gly Thr Ala Cys
        275               280               285

Thr Ala Cys Thr Gly Cys Gly Thr Gly Cys Gly Gly Cys Ala Cys Gly
        290               295               300

Gly Cys Ala Ala Cys Thr Thr Cys Gly Gly Cys Ala Ala Cys Ala Gly
305               310               315               320

Cys Thr Ala Thr Gly Thr Gly Thr Cys Thr Thr Gly Gly Thr Thr Thr
                325               330               335

Gly Cys Cys Thr Ala Cys Thr Gly Gly Gly Gly Cys Cys Ala Gly Gly
                340               345               350

Gly Cys Ala Cys Cys Cys Thr Cys Gly Thr Gly Ala Cys Ala Gly Thr
        355               360               365

Gly Thr Cys Thr Ala Gly Cys
    370               375
```

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

```
Thr Gly Ala Val Thr Thr Ser Asn Tyr
1               5
```

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

```
Ala Leu Trp Tyr Ser Asn Leu Trp Val
1               5
```

<210> SEQ ID NO 8
<211> LENGTH: 109
<212> TYPE: PRT
<213> ORGANISM: Artificial Sequence
<220> FEATURE:

<223> OTHER INFORMATION: Synthetic

<400> SEQUENCE: 8

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
                100                 105
```

<210> SEQ ID NO 9
<211> LENGTH: 327
<212> TYPE: PRT
<213> ORGANISM: Artificial Sequence
<220> FEATURE:
<223> OTHER INFORMATION: Synthetic

<400> SEQUENCE: 9

```
Cys Ala Gly Gly Cys Cys Gly Thr Cys Gly Thr Gly Ala Cys Cys Cys
1               5                   10                  15

Ala Gly Gly Ala Ala Cys Cys Cys Ala Gly Cys Thr Thr Thr Thr Cys
            20                  25                  30

Cys Gly Thr Gly Thr Cys Thr Cys Cys Thr Gly Gly Cys Gly Gly Cys
        35                  40                  45

Ala Cys Cys Gly Thr Gly Ala Cys Cys Cys Thr Gly Ala Cys Cys Thr
    50                  55                  60

Gly Cys Ala Gly Ala Thr Cys Thr Thr Cys Thr Ala Cys Ala Gly Gly
65                  70                  75                  80

Cys Gly Cys Cys Gly Thr Gly Ala Cys Cys Ala Cys Cys Ala Gly Cys
                85                  90                  95

Ala Ala Cys Thr Ala Cys Gly Cys Ala Ala Cys Thr Gly Gly Gly
                100                 105                 110

Thr Gly Cys Ala Gly Cys Ala Gly Ala Cys Ala Cys Cys Cys Gly Gly
            115                 120                 125

Cys Cys Ala Gly Gly Cys Cys Thr Thr Thr Ala Gly Ala Gly Gly Ala
    130                 135                 140

Cys Thr Gly Ala Thr Cys Gly Gly Cys Gly Gly Cys Ala Cys Cys Ala
145                 150                 155                 160

Ala Cys Ala Ala Gly Ala Gly Gly Gly Cys Ala Cys Cys Thr Gly Gly
                165                 170                 175

Cys Gly Thr Gly Cys Cys Ala Gly Cys Cys Ala Gly Ala Thr Thr Cys
            180                 185                 190

Ala Gly Cys Gly Gly Cys Ala Gly Cys Cys Thr Gly Ala Thr Cys Gly
        195                 200                 205

Gly Ala Gly Ala Thr Ala Ala Gly Gly Cys Cys Gly Cys Cys Cys Thr
    210                 215                 220

Gly Ala Cys Ala Ala Thr Cys Ala Cys Thr Gly Gly Cys Gly Cys Cys
225                 230                 235                 240
```

-continued

```
Cys Ala Gly Gly Cys Thr Gly Ala Cys Gly Ala Cys Gly Ala Gly Ala
            245                 250                 255

Gly Cys Ala Thr Cys Thr Ala Cys Thr Thr Thr Gly Cys Gly Cys
            260                 265                 270

Cys Cys Thr Gly Thr Gly Gly Thr Ala Cys Ala Gly Cys Ala Ala Cys
        275                 280                 285

Cys Thr Gly Thr Gly Gly Gly Thr Gly Thr Cys Gly Gly Cys Gly
        290                 295                 300

Gly Ala Gly Gly Cys Ala Cys Cys Ala Ala Gly Cys Thr Gly Ala Cys
305                 310                 315                 320

Ala Gly Thr Gly Cys Thr Gly
                325

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 11
<211> LENGTH: 327
<212> TYPE: PRT
<213> ORGANISM: Artificial Sequence
<220> FEATURE:
<223> OTHER INFORMATION: Synthetic

<400> SEQUENCE: 11

Cys Ala Gly Gly Cys Cys Gly Thr Cys Gly Thr Gly Ala Cys Cys Cys
1               5                   10                  15

Ala Gly Gly Ala Ala Cys Cys Cys Ala Gly Cys Thr Thr Thr Cys
            20                  25                  30

Cys Gly Thr Gly Thr Cys Thr Cys Thr Gly Gly Cys Gly Gly Cys
        35                  40                  45

Ala Cys Cys Gly Thr Gly Ala Cys Cys Thr Gly Ala Cys Cys Thr
    50                  55                  60

Gly Cys Ala Gly Ala Thr Cys Thr Thr Cys Thr Ala Cys Ala Gly Gly
65                  70                  75                  80

Cys Gly Cys Cys Gly Thr Gly Ala Cys Cys Ala Cys Cys Ala Gly Cys
                85                  90                  95

Ala Ala Cys Thr Ala Cys Gly Cys Cys Ala Ala Cys Thr Gly Gly Gly
```

-continued

```
                100               105               110

Thr Gly Cys Ala Gly Cys Ala Gly Ala Ala Gly Cys Cys Cys Gly Gly
        115               120               125

Cys Cys Ala Gly Gly Cys Cys Thr Thr Thr Ala Gly Ala Gly Gly Ala
    130               135               140

Cys Thr Gly Ala Thr Cys Gly Gly Cys Gly Gly Cys Ala Cys Cys Ala
145               150               155               160

Ala Cys Ala Ala Gly Ala Gly Gly Gly Cys Ala Cys Cys Thr Gly Gly
                165               170               175

Cys Gly Thr Gly Cys Cys Ala Gly Cys Cys Ala Gly Ala Thr Thr Cys
            180               185               190

Ala Gly Cys Gly Gly Cys Ala Gly Cys Cys Thr Gly Ala Thr Cys Gly
            195               200               205

Gly Ala Gly Ala Thr Ala Ala Gly Gly Cys Cys Gly Cys Cys Cys Thr
        210               215               220

Gly Ala Cys Ala Ala Thr Cys Ala Cys Thr Gly Gly Cys Gly Cys Cys
225               230               235               240

Cys Ala Gly Gly Cys Thr Gly Ala Cys Gly Ala Cys Gly Ala Gly Ala
            245               250               255

Gly Cys Ala Thr Cys Thr Ala Cys Thr Thr Thr Thr Gly Cys Gly Cys
            260               265               270

Cys Cys Thr Gly Thr Gly Gly Thr Ala Cys Ala Gly Cys Ala Ala Cys
        275               280               285

Cys Thr Gly Thr Gly Gly Gly Thr Gly Thr Thr Cys Gly Gly Cys Gly
    290               295               300

Gly Ala Gly Gly Cys Ala Cys Cys Ala Ala Gly Cys Thr Gly Ala Cys
305               310               315               320

Cys Gly Thr Cys Cys Thr Ala
                325
```

```
<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12
```

```
Gly Phe Thr Phe Ala Thr Tyr Ala
1               5
```

```
<210> SEQ ID NO 13
<211> LENGTH: 125
<212> TYPE: PRT
<213> ORGANISM: Artificial Sequence
<220> FEATURE:
<223> OTHER INFORMATION: Synthetic

<400> SEQUENCE: 13
```

```
Glu Val Lys Leu Val Glu Ser Gly Gly Gly Leu Val Gln Pro Gly Gly
1               5               10               15

Ser Leu Arg Leu Ser Cys Ala Ala Ser Gly Phe Thr Phe Ala Thr Tyr
            20               25               30

Ala Met Asn Trp Val Arg Gln Ala Pro Gly Lys Gly Leu Glu Trp Val
        35               40               45

Ala Arg Ile Arg Ser Lys Tyr Asn Asn Tyr Ala Thr Tyr Tyr Ala Asp
    50               55               60
```

```
Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
            100             105             110

Ala Tyr Trp Gly Gln Gly Thr Leu Val Thr Val Ser Ser
        115             120             125

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Gly Phe Thr Phe Cys Thr Tyr Ala
1               5

<210> SEQ ID NO 15
<211> LENGTH: 125
<212> TYPE: PRT
<213> ORGANISM: Artificial Sequence
<220> FEATURE:
<223> OTHER INFORMATION: Synthetic

<400> SEQUENCE: 15

Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Cys Thr Tyr
                20              25              30

Ala Met Asn Trp Val Arg Gln Ala Pro Gly Lys Gly Leu Glu Trp Val
            35              40              45

Ala Arg Ile Arg Ser Lys Tyr Asn Asn Tyr Ala Thr Tyr Tyr Ala Asp
        50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
            100             105             110

Ala Tyr Trp Gly Gln Gly Thr Leu Val Thr Val Ser Ser
        115             120             125

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gly Phe Thr Phe Asp Thr Tyr Ala
1               5

<210> SEQ ID NO 17
<211> LENGTH: 125
<212> TYPE: PRT
<213> ORGANISM: Artificial Sequence
<220> FEATURE:
<223> OTHER INFORMATION: Synthetic
```

-continued

<400> SEQUENCE: 17

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

```
Gly Phe Thr Phe Phe Thr Tyr Ala
1               5
```

<210> SEQ ID NO 19
<211> LENGTH: 125
<212> TYPE: PRT
<213> ORGANISM: Artificial Sequence
<220> FEATURE:
<223> OTHER INFORMATION: Synthetic

<400> SEQUENCE: 19

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Phe Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Gly Thr Tyr Ala
1               5

<210> SEQ ID NO 21
<211> LENGTH: 125
<212> TYPE: PRT
<213> ORGANISM: Artificial Sequence
<220> FEATURE:
<223> OTHER INFORMATION: Synthetic

<400> SEQUENCE: 21

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Phe Thr Phe His Thr Tyr Ala
1               5

<210> SEQ ID NO 23
<211> LENGTH: 125
<212> TYPE: PRT
<213> ORGANISM: Artificial Sequence
<220> FEATURE:
<223> OTHER INFORMATION: Synthetic

<400> SEQUENCE: 23

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe His Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

```
Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Gly Phe Thr Phe Lys Thr Tyr Ala
1               5

<210> SEQ ID NO 25
<211> LENGTH: 125
<212> TYPE: PRT
<213> ORGANISM: Artificial Sequence
<220> FEATURE:
<223> OTHER INFORMATION: Synthetic

<400> SEQUENCE: 25

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Gly Phe Thr Phe Leu Thr Tyr Ala
1               5

<210> SEQ ID NO 27
<211> LENGTH: 125
<212> TYPE: PRT
<213> ORGANISM: Artificial Sequence
<220> FEATURE:
<223> OTHER INFORMATION: Synthetic

<400> SEQUENCE: 27
```

-continued

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

```
Gly Phe Thr Phe Pro Thr Tyr Ala
1               5
```

<210> SEQ ID NO 29
<211> LENGTH: 125
<212> TYPE: PRT
<213> ORGANISM: Artificial Sequence
<220> FEATURE:
<223> OTHER INFORMATION: Synthetic

<400> SEQUENCE: 29

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Gly Phe Thr Phe Gln Thr Tyr Ala
1               5

<210> SEQ ID NO 31
<211> LENGTH: 125
<212> TYPE: PRT
<213> ORGANISM: Artificial Sequence
<220> FEATURE:
<223> OTHER INFORMATION: Synthetic

<400> SEQUENCE: 31

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Gln Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Gly Phe Thr Phe Arg Thr Tyr Ala
1               5

<210> SEQ ID NO 33
<211> LENGTH: 125
<212> TYPE: PRT
<213> ORGANISM: Artificial Sequence
<220> FEATURE:
<223> OTHER INFORMATION: Synthetic

<400> SEQUENCE: 33

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr

-continued

```
                    85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Gly Phe Thr Phe Thr Thr Tyr Ala
1               5

<210> SEQ ID NO 35
<211> LENGTH: 125
<212> TYPE: PRT
<213> ORGANISM: Artificial Sequence
<220> FEATURE:
<223> OTHER INFORMATION: Synthetic

<400> SEQUENCE: 35

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Val Thr Tyr Ala
1               5

<210> SEQ ID NO 37
<211> LENGTH: 125
<212> TYPE: PRT
<213> ORGANISM: Artificial Sequence
<220> FEATURE:
<223> OTHER INFORMATION: Synthetic

<400> SEQUENCE: 37

Glu Val Lys Leu Val Glu Ser Gly Gly Gly Leu Val Gln Pro Gly Gly
```

-continued

```
1               5                   10                  15

Ser Leu Arg Leu Ser Cys Ala Ala Ser Gly Phe Thr Phe Val Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

```
Gly Phe Thr Phe Trp Thr Tyr Ala
1               5
```

<210> SEQ ID NO 39
<211> LENGTH: 125
<212> TYPE: PRT
<213> ORGANISM: Artificial Sequence
<220> FEATURE:
<223> OTHER INFORMATION: Synthetic

<400> SEQUENCE: 39

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Trp Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

-continued

```
Gly Phe Thr Phe Asn Ala Tyr Ala
1               5

<210> SEQ ID NO 41
<211> LENGTH: 125
<212> TYPE: PRT
<213> ORGANISM: Artificial Sequence
<220> FEATURE:
<223> OTHER INFORMATION: Synthetic

<400> SEQUENCE: 41

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ala Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Gly Phe Thr Phe Asn Cys Tyr Ala
1               5

<210> SEQ ID NO 43
<211> LENGTH: 125
<212> TYPE: PRT
<213> ORGANISM: Artificial Sequence
<220> FEATURE:
<223> OTHER INFORMATION: Synthetic

<400> SEQUENCE: 43

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Cys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95
```

-continued

```
Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Gly Phe Thr Phe Asn Asp Tyr Ala
1               5

<210> SEQ ID NO 45
<211> LENGTH: 125
<212> TYPE: PRT
<213> ORGANISM: Artificial Sequence
<220> FEATURE:
<223> OTHER INFORMATION: Synthetic

<400> SEQUENCE: 45

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Gly Phe Thr Phe Asn Glu Tyr Ala
1               5

<210> SEQ ID NO 47
<211> LENGTH: 125
<212> TYPE: PRT
<213> ORGANISM: Artificial Sequence
<220> FEATURE:
<223> OTHER INFORMATION: Synthetic

<400> SEQUENCE: 47

Glu Val Lys Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Asn Glu Tyr
        20                      25                      30

Ala Met Asn Trp Val Arg Gln Ala Pro Gly Lys Gly Leu Glu Trp Val
        35                      40                      45

Ala Arg Ile Arg Ser Lys Tyr Asn Asn Tyr Ala Thr Tyr Tyr Ala Asp
    50                      55                      60

Ser Val Lys Asp Arg Phe Thr Ile Ser Arg Asp Asp Ser Lys Ser Ser
65                      70                      75                      80

Leu Tyr Leu Gln Met Asn Asn Leu Lys Thr Glu Asp Thr Ala Met Tyr
                85                      90                      95

Tyr Cys Val Arg His Gly Asn Phe Gly Asn Ser Tyr Val Ser Trp Phe
                100                     105                     110

Ala Tyr Trp Gly Gln Gly Thr Leu Val Thr Val Ser Ser
        115                     120                     125

<210> SEQ ID NO 48
<211> LENGTH: 8
<212> TYPE: PRT
<213> ORGANISM: Artificial Sequence
<220> FEATURE:
<223> OTHER INFORMATION: Synthetic

<400> SEQUENCE: 48

Gly Phe Thr Phe Asn Phe Tyr Ala
1               5

<210> SEQ ID NO 49
<211> LENGTH: 125
<212> TYPE: PRT
<213> ORGANISM: Artificial Sequence
<220> FEATURE:
<223> OTHER INFORMATION: Synthetic

<400> SEQUENCE: 49

Glu Val Lys Leu Val Glu Ser Gly Gly Gly Leu Val Gln Pro Gly Gly
1               5                       10                      15

Ser Leu Arg Leu Ser Cys Ala Ala Ser Gly Phe Thr Phe Asn Phe Tyr
        20                      25                      30

Ala Met Asn Trp Val Arg Gln Ala Pro Gly Lys Gly Leu Glu Trp Val
        35                      40                      45

Ala Arg Ile Arg Ser Lys Tyr Asn Asn Tyr Ala Thr Tyr Tyr Ala Asp
    50                      55                      60

Ser Val Lys Asp Arg Phe Thr Ile Ser Arg Asp Asp Ser Lys Ser Ser
65                      70                      75                      80

Leu Tyr Leu Gln Met Asn Asn Leu Lys Thr Glu Asp Thr Ala Met Tyr
                85                      90                      95

Tyr Cys Val Arg His Gly Asn Phe Gly Asn Ser Tyr Val Ser Trp Phe
                100                     105                     110

Ala Tyr Trp Gly Gln Gly Thr Leu Val Thr Val Ser Ser
        115                     120                     125

<210> SEQ ID NO 50
<211> LENGTH: 8
<212> TYPE: PRT
<213> ORGANISM: Artificial Sequence
<220> FEATURE:
<223> OTHER INFORMATION: Synthetic

<400> SEQUENCE: 50

Gly Phe Thr Phe Asn His Tyr Ala 1                 5

<210> SEQ ID NO 51
<211> LENGTH: 125
<212> TYPE: PRT
<213> ORGANISM: Artificial Sequence
<220> FEATURE:
<223> OTHER INFORMATION: Synthetic

<400> SEQUENCE: 51

Glu Val Lys Leu Val Glu Ser Gly Gly Gly Leu Val Gln Pro Gly Gly
1                 5                   10                  15

Ser Leu Arg Leu Ser Cys Ala Ala Ser Gly Phe Thr Phe Asn His Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Asn Leu Tyr Ala
1                 5

<210> SEQ ID NO 53
<211> LENGTH: 125
<212> TYPE: PRT
<213> ORGANISM: Artificial Sequence
<220> FEATURE:
<223> OTHER INFORMATION: Synthetic

<400> SEQUENCE: 53

Glu Val Lys Leu Val Glu Ser Gly Gly Gly Leu Val Gln Pro Gly Gly
1                 5                   10                  15

Ser Leu Arg Leu Ser Cys Ala Ala Ser Gly Phe Thr Phe Asn Leu Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

```
Ala Tyr Trp Gly Gln Gly Thr Leu Val Thr Val Ser Ser
        115                 120                 125

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Gly Phe Thr Phe Asn Met Tyr Ala
1               5

<210> SEQ ID NO 55
<211> LENGTH: 125
<212> TYPE: PRT
<213> ORGANISM: Artificial Sequence
<220> FEATURE:
<223> OTHER INFORMATION: Synthetic

<400> SEQUENCE: 55

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Met Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 56
<211> LENGTH: 8
<212> TYPE: PRT
<213> ORGANISM: Artificial Sequence
<220> FEATURE:
<223> OTHER INFORMATION: Synthetic

<400> SEQUENCE: 56

Gly Phe Thr Phe Asn Asn Tyr Ala
1               5

<210> SEQ ID NO 57
<211> LENGTH: 125
<212> TYPE: PRT
<213> ORGANISM: Artificial Sequence
<220> FEATURE:
<223> OTHER INFORMATION: Synthetic

<400> SEQUENCE: 57

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30
```

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 58
<211> LENGTH: 8
<212> TYPE: PRT
<213> ORGANISM: Artificial Sequence
<220> FEATURE:
<223> OTHER INFORMATION: Synthetic

<400> SEQUENCE: 58

Gly Phe Thr Phe Asn Pro Tyr Ala
1               5

<210> SEQ ID NO 59
<211> LENGTH: 125
<212> TYPE: PRT
<213> ORGANISM: Artificial Sequence
<220> FEATURE:
<223> OTHER INFORMATION: Synthetic

<400> SEQUENCE: 59

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Pro Tyr
        20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Gly Phe Thr Phe Asn Gln Tyr Ala
1               5
```

<210> SEQ ID NO 61
<211> LENGTH: 125
<212> TYPE: PRT
<213> ORGANISM: Artificial Sequence
<220> FEATURE:
<223> OTHER INFORMATION: Synthetic

<400> SEQUENCE: 61

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Gln Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62

Gly Phe Thr Phe Asn Trp Tyr Ala
1               5

<210> SEQ ID NO 63
<211> LENGTH: 125
<212> TYPE: PRT
<213> ORGANISM: Artificial Sequence
<220> FEATURE:
<223> OTHER INFORMATION: Synthetic

<400> SEQUENCE: 63

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Trp Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser

-continued

```
              115                 120                 125
```

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

```
Gly Phe Thr Phe Asn Tyr Tyr Ala
1               5
```

<210> SEQ ID NO 65
<211> LENGTH: 125
<212> TYPE: PRT
<213> ORGANISM: Artificial Sequence
<220> FEATURE:
<223> OTHER INFORMATION: Synthetic

<400> SEQUENCE: 65

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Tyr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

```
Gly Phe Thr Phe Asn Thr Ala Ala
1               5
```

<210> SEQ ID NO 67
<211> LENGTH: 125
<212> TYPE: PRT
<213> ORGANISM: Artificial Sequence
<220> FEATURE:
<223> OTHER INFORMATION: Synthetic

<400> SEQUENCE: 67

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Ala
            20                  25                  30

Ala Met Asn Trp Val Arg Gln Ala Pro Gly Lys Gly Leu Glu Trp Val
```

```
                35                    40                    45

Ala Arg Ile Arg Ser Lys Tyr Asn Asn Tyr Ala Thr Tyr Tyr Ala Asp
        50                    55                    60

Ser Val Lys Asp Arg Phe Thr Ile Ser Arg Asp Asp Ser Lys Ser Ser
65                    70                    75                    80

Leu Tyr Leu Gln Met Asn Asn Leu Lys Thr Glu Asp Thr Ala Met Tyr
                85                    90                    95

Tyr Cys Val Arg His Gly Asn Phe Gly Asn Ser Tyr Val Ser Trp Phe
                100                   105                   110

Ala Tyr Trp Gly Gln Gly Thr Leu Val Thr Val Ser Ser
        115                   120                   125

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Asn Thr Cys Ala
1               5

<210> SEQ ID NO 69
<211> LENGTH: 125
<212> TYPE: PRT
<213> ORGANISM: Artificial Sequence
<220> FEATURE:
<223> OTHER INFORMATION: Synthetic

<400> SEQUENCE: 69

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Cys
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Gly Phe Thr Phe Asn Thr Phe Ala
1               5

<210> SEQ ID NO 71
```

<211> LENGTH: 125
<212> TYPE: PRT
<213> ORGANISM: Artificial Sequence
<220> FEATURE:
<223> OTHER INFORMATION: Synthetic

<400> SEQUENCE: 71

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Phe
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

```
Gly Phe Thr Phe Asn Thr Gly Ala
1               5
```

<210> SEQ ID NO 73
<211> LENGTH: 125
<212> TYPE: PRT
<213> ORGANISM: Artificial Sequence
<220> FEATURE:
<223> OTHER INFORMATION: Synthetic

<400> SEQUENCE: 73

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Gly
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

Gly Phe Thr Phe Asn Thr His Ala
1               5

<210> SEQ ID NO 75
<211> LENGTH: 125
<212> TYPE: PRT
<213> ORGANISM: Artificial Sequence
<220> FEATURE:
<223> OTHER INFORMATION: Synthetic

<400> SEQUENCE: 75

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Phe Thr Phe Asn Thr Ile Ala
1               5

<210> SEQ ID NO 77
<211> LENGTH: 125
<212> TYPE: PRT
<213> ORGANISM: Artificial Sequence
<220> FEATURE:
<223> OTHER INFORMATION: Synthetic

<400> SEQUENCE: 77

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Ile
            20                  25                  30

Ala Met Asn Trp Val Arg Gln Ala Pro Gly Lys Gly Leu Glu Trp Val
        35                  40                  45

-continued

```
Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Gly Phe Thr Phe Asn Thr Lys Ala
1               5

<210> SEQ ID NO 79
<211> LENGTH: 125
<212> TYPE: PRT
<213> ORGANISM: Artificial Sequence
<220> FEATURE:
<223> OTHER INFORMATION: Synthetic

<400> SEQUENCE: 79

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Lys
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 80
<211> LENGTH: 8
<212> TYPE: PRT
<213> ORGANISM: Artificial Sequence
<220> FEATURE:
<223> OTHER INFORMATION: Synthetic

<400> SEQUENCE: 80

Gly Phe Thr Phe Asn Thr Leu Ala
1               5

<210> SEQ ID NO 81
<211> LENGTH: 125
<212> TYPE: PRT
```

<213> ORGANISM: Artificial Sequence
<220> FEATURE:
<223> OTHER INFORMATION: Synthetic

<400> SEQUENCE: 81

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Leu
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

```
Gly Phe Thr Phe Asn Thr Met Ala
1               5
```

<210> SEQ ID NO 83
<211> LENGTH: 125
<212> TYPE: PRT
<213> ORGANISM: Artificial Sequence
<220> FEATURE:
<223> OTHER INFORMATION: Synthetic

<400> SEQUENCE: 83

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Met
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 84

```
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Asn Thr Asn Ala
1               5

<210> SEQ ID NO 85
<211> LENGTH: 125
<212> TYPE: PRT
<213> ORGANISM: Artificial Sequence
<220> FEATURE:
<223> OTHER INFORMATION: Synthetic

<400> SEQUENCE: 85

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Gly Phe Thr Phe Asn Thr Pro Ala
1               5

<210> SEQ ID NO 87
<211> LENGTH: 125
<212> TYPE: PRT
<213> ORGANISM: Artificial Sequence
<220> FEATURE:
<223> OTHER INFORMATION: Synthetic

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Pro
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

```
Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Gly Phe Thr Phe Asn Thr Gln Ala
1               5

<210> SEQ ID NO 89
<211> LENGTH: 125
<212> TYPE: PRT
<213> ORGANISM: Artificial Sequence
<220> FEATURE:
<223> OTHER INFORMATION: Synthetic

<400> SEQUENCE: 89

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Gln
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 90
<211> LENGTH: 8
<212> TYPE: PRT
<213> ORGANISM: Artificial Sequence
<220> FEATURE:
<223> OTHER INFORMATION: Synthetic

<400> SEQUENCE: 90

Gly Phe Thr Phe Asn Thr Arg Ala
1               5

<210> SEQ ID NO 91
<211> LENGTH: 125
<212> TYPE: PRT
<213> ORGANISM: Artificial Sequence
<220> FEATURE:
```

<223> OTHER INFORMATION: Synthetic

<400> SEQUENCE: 91

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Arg
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

```
Gly Phe Thr Phe Asn Thr Ser Ala
1               5
```

<210> SEQ ID NO 93
<211> LENGTH: 125
<212> TYPE: PRT
<213> ORGANISM: Artificial Sequence
<220> FEATURE:
<223> OTHER INFORMATION: Synthetic

<400> SEQUENCE: 93

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Ser
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 94
<211> LENGTH: 8
<212> TYPE: PRT

<213> ORGANISM: Artificial Sequence
<220> FEATURE:
<223> OTHER INFORMATION: Synthetic

<400> SEQUENCE: 94

Gly Phe Thr Phe Asn Thr Thr Ala
1               5

<210> SEQ ID NO 95
<211> LENGTH: 125
<212> TYPE: PRT
<213> ORGANISM: Artificial Sequence
<220> FEATURE:
<223> OTHER INFORMATION: Synthetic

<400> SEQUENCE: 95

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Thr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Gly Phe Thr Phe Asn Thr Val Ala
1               5

<210> SEQ ID NO 97
<211> LENGTH: 125
<212> TYPE: PRT
<213> ORGANISM: Artificial Sequence
<220> FEATURE:
<223> OTHER INFORMATION: Synthetic

<400> SEQUENCE: 97

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Val
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser

-continued

```
65                    70                    75                    80

Leu Tyr Leu Gln Met Asn Asn Leu Lys Thr Glu Asp Thr Ala Met Tyr
                85                    90                    95

Tyr Cys Val Arg His Gly Asn Phe Gly Asn Ser Tyr Val Ser Trp Phe
                100                   105                   110

Ala Tyr Trp Gly Gln Gly Thr Leu Val Thr Val Ser Ser
        115                   120                   125

<210> SEQ ID NO 98
<211> LENGTH: 8
<212> TYPE: PRT
<213> ORGANISM: Artificial Sequence
<220> FEATURE:
<223> OTHER INFORMATION: Synthetic

<400> SEQUENCE: 98

Gly Phe Thr Phe Asn Thr Trp Ala
1               5

<210> SEQ ID NO 99
<211> LENGTH: 125
<212> TYPE: PRT
<213> ORGANISM: Artificial Sequence
<220> FEATURE:
<223> OTHER INFORMATION: Synthetic

<400> SEQUENCE: 99

Glu Val Lys Leu Val Glu Ser Gly Gly Gly Leu Val Gln Pro Gly Gly
1               5                    10                   15

Ser Leu Arg Leu Ser Cys Ala Ala Ser Gly Phe Thr Phe Asn Thr Trp
                20                   25                   30

Ala Met Asn Trp Val Arg Gln Ala Pro Gly Lys Gly Leu Glu Trp Val
        35                   40                   45

Ala Arg Ile Arg Ser Lys Tyr Asn Asn Tyr Ala Thr Tyr Tyr Ala Asp
    50                   55                   60

Ser Val Lys Asp Arg Phe Thr Ile Ser Arg Asp Asp Ser Lys Ser Ser
65                   70                   75                   80

Leu Tyr Leu Gln Met Asn Asn Leu Lys Thr Glu Asp Thr Ala Met Tyr
                85                    90                   95

Tyr Cys Val Arg His Gly Asn Phe Gly Asn Ser Tyr Val Ser Trp Phe
                100                   105                   110

Ala Tyr Trp Gly Gln Gly Thr Leu Val Thr Val Ser Ser
        115                   120                   125

<210> SEQ ID NO 100
<211> LENGTH: 10
<212> TYPE: PRT
<213> ORGANISM: Artificial Sequence
<220> FEATURE:
<223> OTHER INFORMATION: Synthetic

<400> SEQUENCE: 100

Ile Arg Ser Lys Tyr Asn Ala Tyr Ala Thr
1               5                   10

<210> SEQ ID NO 101
<211> LENGTH: 125
<212> TYPE: PRT
<213> ORGANISM: Artificial Sequence
<220> FEATURE:
<223> OTHER INFORMATION: Synthetic
```

<400> SEQUENCE: 101

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Ala Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Ile Arg Ser Lys Tyr Asn Cys Tyr Ala Thr
1               5                   10

<210> SEQ ID NO 103
<211> LENGTH: 125
<212> TYPE: PRT
<213> ORGANISM: Artificial Sequence
<220> FEATURE:
<223> OTHER INFORMATION: Synthetic

<400> SEQUENCE: 103

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Cys Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 104
<211> LENGTH: 10
<212> TYPE: PRT
<213> ORGANISM: Artificial Sequence
<220> FEATURE:

<223> OTHER INFORMATION: Synthetic

<400> SEQUENCE: 104

Ile Arg Ser Lys Tyr Asn Asp Tyr Ala Thr
1               5                   10

<210> SEQ ID NO 105
<211> LENGTH: 125
<212> TYPE: PRT
<213> ORGANISM: Artificial Sequence
<220> FEATURE:
<223> OTHER INFORMATION: Synthetic

<400> SEQUENCE: 105

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asp Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 106
<211> LENGTH: 10
<212> TYPE: PRT
<213> ORGANISM: Artificial Sequence
<220> FEATURE:
<223> OTHER INFORMATION: Synthetic

<400> SEQUENCE: 106

Ile Arg Ser Lys Tyr Asn Glu Tyr Ala Thr
1               5                   10

<210> SEQ ID NO 107
<211> LENGTH: 125
<212> TYPE: PRT
<213> ORGANISM: Artificial Sequence
<220> FEATURE:
<223> OTHER INFORMATION: Synthetic

<400> SEQUENCE: 107

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Glu Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

```
Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
        100             105             110

Ala Tyr Trp Gly Gln Gly Thr Leu Val Thr Val Ser Ser
        115             120             125
```

<210> SEQ ID NO 108
<211> LENGTH: 10
<212> TYPE: PRT
<213> ORGANISM: Artificial Sequence
<220> FEATURE:
<223> OTHER INFORMATION: Synthetic

<400> SEQUENCE: 108

```
Ile Arg Ser Lys Tyr Asn Phe Tyr Ala Thr
1               5               10
```

<210> SEQ ID NO 109
<211> LENGTH: 125
<212> TYPE: PRT
<213> ORGANISM: Artificial Sequence
<220> FEATURE:
<223> OTHER INFORMATION: Synthetic

<400> SEQUENCE: 109

```
Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
        35              40              45

Ala Arg Ile Arg Ser Lys Tyr Asn Phe Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
        100             105             110

Ala Tyr Trp Gly Gln Gly Thr Leu Val Thr Val Ser Ser
        115             120             125
```

<210> SEQ ID NO 110
<211> LENGTH: 10
<212> TYPE: PRT
<213> ORGANISM: Artificial Sequence
<220> FEATURE:
<223> OTHER INFORMATION: Synthetic

<400> SEQUENCE: 110

```
Ile Arg Ser Lys Tyr Asn Gly Tyr Ala Thr
1               5               10
```

<210> SEQ ID NO 111
<211> LENGTH: 125
<212> TYPE: PRT
<213> ORGANISM: Artificial Sequence
<220> FEATURE:
<223> OTHER INFORMATION: Synthetic

<400> SEQUENCE: 111

-continued

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Gly Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

```
<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Ile Arg Ser Lys Tyr Asn Ile Tyr Ala Thr
1               5                   10
```

```
<210> SEQ ID NO 113
<211> LENGTH: 125
<212> TYPE: PRT
<213> ORGANISM: Artificial Sequence
<220> FEATURE:
<223> OTHER INFORMATION: Synthetic

<400> SEQUENCE: 113

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Ile Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

```
<210> SEQ ID NO 114
<211> LENGTH: 10
<212> TYPE: PRT
<213> ORGANISM: Artificial Sequence
<220> FEATURE:
<223> OTHER INFORMATION: Synthetic
```

-continued

```
<400> SEQUENCE: 114

Ile Arg Ser Lys Tyr Asn Lys Tyr Ala Thr
1               5                   10

<210> SEQ ID NO 115
<211> LENGTH: 125
<212> TYPE: PRT
<213> ORGANISM: Artificial Sequence
<220> FEATURE:
<223> OTHER INFORMATION: Synthetic

<400> SEQUENCE: 115

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Lys Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 116
<211> LENGTH: 10
<212> TYPE: PRT
<213> ORGANISM: Artificial Sequence
<220> FEATURE:
<223> OTHER INFORMATION: Synthetic

<400> SEQUENCE: 116

Ile Arg Ser Lys Tyr Asn Leu Tyr Ala Thr
1               5                   10

<210> SEQ ID NO 117
<211> LENGTH: 125
<212> TYPE: PRT
<213> ORGANISM: Artificial Sequence
<220> FEATURE:
<223> OTHER INFORMATION: Synthetic

<400> SEQUENCE: 117

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Leu Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95
```

-continued

```
Tyr Cys Val Arg His Gly Asn Phe Gly Asn Ser Tyr Val Ser Trp Phe
        100                 105                 110

Ala Tyr Trp Gly Gln Gly Thr Leu Val Thr Val Ser Ser
        115                 120                 125

<210> SEQ ID NO 118
<211> LENGTH: 10
<212> TYPE: PRT
<213> ORGANISM: Artificial Sequence
<220> FEATURE:
<223> OTHER INFORMATION: Synthetic

<400> SEQUENCE: 118

Ile Arg Ser Lys Tyr Asn Met Tyr Ala Thr
1               5               10

<210> SEQ ID NO 119
<211> LENGTH: 125
<212> TYPE: PRT
<213> ORGANISM: Artificial Sequence
<220> FEATURE:
<223> OTHER INFORMATION: Synthetic

<400> SEQUENCE: 119

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Met Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
        100                 105                 110

Ala Tyr Trp Gly Gln Gly Thr Leu Val Thr Val Ser Ser
        115                 120                 125

<210> SEQ ID NO 120
<211> LENGTH: 10
<212> TYPE: PRT
<213> ORGANISM: Artificial Sequence
<220> FEATURE:
<223> OTHER INFORMATION: Synthetic

<400> SEQUENCE: 120

Ile Arg Ser Lys Tyr Asn Pro Tyr Ala Thr
1               5               10

<210> SEQ ID NO 121
<211> LENGTH: 125
<212> TYPE: PRT
<213> ORGANISM: Artificial Sequence
<220> FEATURE:
<223> OTHER INFORMATION: Synthetic

<400> SEQUENCE: 121

Glu Val Lys Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Pro Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 122
<211> LENGTH: 10
<212> TYPE: PRT
<213> ORGANISM: Artificial Sequence
<220> FEATURE:
<223> OTHER INFORMATION: Synthetic

<400> SEQUENCE: 122

Ile Arg Ser Lys Tyr Asn Gln Tyr Ala Thr
1               5                   10

<210> SEQ ID NO 123
<211> LENGTH: 125
<212> TYPE: PRT
<213> ORGANISM: Artificial Sequence
<220> FEATURE:
<223> OTHER INFORMATION: Synthetic

<400> SEQUENCE: 123

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Gln Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 124
<211> LENGTH: 10
<212> TYPE: PRT
<213> ORGANISM: Artificial Sequence
<220> FEATURE:
<223> OTHER INFORMATION: Synthetic

<400> SEQUENCE: 124
```

```
Ile Arg Ser Lys Tyr Asn Arg Tyr Ala Thr
1               5                   10

<210> SEQ ID NO 125
<211> LENGTH: 125
<212> TYPE: PRT
<213> ORGANISM: Artificial Sequence
<220> FEATURE:
<223> OTHER INFORMATION: Synthetic

<400> SEQUENCE: 125

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Arg Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 126
<211> LENGTH: 10
<212> TYPE: PRT
<213> ORGANISM: Artificial Sequence
<220> FEATURE:
<223> OTHER INFORMATION: Synthetic

<400> SEQUENCE: 126

Ile Arg Ser Lys Tyr Asn Thr Tyr Ala Thr
1               5                   10

<210> SEQ ID NO 127
<211> LENGTH: 125
<212> TYPE: PRT
<213> ORGANISM: Artificial Sequence
<220> FEATURE:
<223> OTHER INFORMATION: Synthetic

<400> SEQUENCE: 127

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Thr Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
```

-continued

```
                    100              105              110

Ala Tyr Trp Gly Gln Gly Thr Leu Val Thr Val Ser Ser
        115              120              125

<210> SEQ ID NO 128
<211> LENGTH: 10
<212> TYPE: PRT
<213> ORGANISM: Artificial Sequence
<220> FEATURE:
<223> OTHER INFORMATION: Synthetic

<400> SEQUENCE: 128

Ile Arg Ser Lys Tyr Asn Val Tyr Ala Thr
1               5               10

<210> SEQ ID NO 129
<211> LENGTH: 125
<212> TYPE: PRT
<213> ORGANISM: Artificial Sequence
<220> FEATURE:
<223> OTHER INFORMATION: Synthetic

<400> SEQUENCE: 129

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Val Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 130
<211> LENGTH: 10
<212> TYPE: PRT
<213> ORGANISM: Artificial Sequence
<220> FEATURE:
<223> OTHER INFORMATION: Synthetic

<400> SEQUENCE: 130

Ile Arg Ser Lys Tyr Asn Trp Tyr Ala Thr
1               5                   10

<210> SEQ ID NO 131
<211> LENGTH: 125
<212> TYPE: PRT
<213> ORGANISM: Artificial Sequence
<220> FEATURE:
<223> OTHER INFORMATION: Synthetic

<400> SEQUENCE: 131

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
```

-continued

```
                20                25                30

Ala Met Asn Trp Val Arg Gln Ala Pro Gly Lys Gly Leu Glu Trp Val
        35                40                45

Ala Arg Ile Arg Ser Lys Tyr Asn Trp Tyr Ala Thr Tyr Tyr Ala Asp
    50                55                60

Ser Val Lys Asp Arg Phe Thr Ile Ser Arg Asp Asp Ser Lys Ser Ser
65                70                75                80

Leu Tyr Leu Gln Met Asn Asn Leu Lys Thr Glu Asp Thr Ala Met Tyr
                85                90                95

Tyr Cys Val Arg His Gly Asn Phe Gly Asn Ser Tyr Val Ser Trp Phe
                100                105                110

Ala Tyr Trp Gly Gln Gly Thr Leu Val Thr Val Ser Ser
        115                120                125

<210> SEQ ID NO 132
<211> LENGTH: 10
<212> TYPE: PRT
<213> ORGANISM: Artificial Sequence
<220> FEATURE:
<223> OTHER INFORMATION: Synthetic

<400> SEQUENCE: 132

Ile Arg Ser Lys Tyr Asn Tyr Tyr Ala Thr
1                5                10

<210> SEQ ID NO 133
<211> LENGTH: 125
<212> TYPE: PRT
<213> ORGANISM: Artificial Sequence
<220> FEATURE:
<223> OTHER INFORMATION: Synthetic

<400> SEQUENCE: 133

Glu Val Lys Leu Val Glu Ser Gly Gly Gly Leu Val Gln Pro Gly Gly
1                5                10                15

Ser Leu Arg Leu Ser Cys Ala Ala Ser Gly Phe Thr Phe Asn Thr Tyr
                20                25                30

Ala Met Asn Trp Val Arg Gln Ala Pro Gly Lys Gly Leu Glu Trp Val
        35                40                45

Ala Arg Ile Arg Ser Lys Tyr Asn Tyr Tyr Ala Thr Tyr Tyr Ala Asp
    50                55                60

Ser Val Lys Asp Arg Phe Thr Ile Ser Arg Asp Asp Ser Lys Ser Ser
65                70                75                80

Leu Tyr Leu Gln Met Asn Asn Leu Lys Thr Glu Asp Thr Ala Met Tyr
                85                90                95

Tyr Cys Val Arg His Gly Asn Phe Gly Asn Ser Tyr Val Ser Trp Phe
                100                105                110

Ala Tyr Trp Gly Gln Gly Thr Leu Val Thr Val Ser Ser
        115                120                125

<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

Ile Arg Ser Lys Tyr Asn Asn Tyr Cys Thr
1                5                10
```

```
<210> SEQ ID NO 135
<211> LENGTH: 125
<212> TYPE: PRT
<213> ORGANISM: Artificial Sequence
<220> FEATURE:
<223> OTHER INFORMATION: Synthetic

<400> SEQUENCE: 135

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Cys Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 136
<211> LENGTH: 10
<212> TYPE: PRT
<213> ORGANISM: Artificial Sequence
<220> FEATURE:
<223> OTHER INFORMATION: Synthetic

<400> SEQUENCE: 136

Ile Arg Ser Lys Tyr Asn Asn Tyr Asp Thr
1               5                   10

<210> SEQ ID NO 137
<211> LENGTH: 125
<212> TYPE: PRT
<213> ORGANISM: Artificial Sequence
<220> FEATURE:
<223> OTHER INFORMATION: Synthetic

<400> SEQUENCE: 137

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Asp Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110
```

-continued

```
Ala Tyr Trp Gly Gln Gly Thr Leu Val Thr Val Ser Ser
        115                 120                 125

<210> SEQ ID NO 138
<211> LENGTH: 10
<212> TYPE: PRT
<213> ORGANISM: Artificial Sequence
<220> FEATURE:
<223> OTHER INFORMATION: Synthetic

<400> SEQUENCE: 138

Ile Arg Ser Lys Tyr Asn Asn Tyr Glu Thr
1               5                   10

<210> SEQ ID NO 139
<211> LENGTH: 125
<212> TYPE: PRT
<213> ORGANISM: Artificial Sequence
<220> FEATURE:
<223> OTHER INFORMATION: Synthetic

<400> SEQUENCE: 139

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Glu Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 140
<211> LENGTH: 10
<212> TYPE: PRT
<213> ORGANISM: Artificial Sequence
<220> FEATURE:
<223> OTHER INFORMATION: Synthetic

<400> SEQUENCE: 140

Ile Arg Ser Lys Tyr Asn Asn Tyr Phe Thr
1               5                   10

<210> SEQ ID NO 141
<211> LENGTH: 125
<212> TYPE: PRT
<213> ORGANISM: Artificial Sequence
<220> FEATURE:
<223> OTHER INFORMATION: Synthetic

<400> SEQUENCE: 141

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30
```

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Phe Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125
```

```
<210> SEQ ID NO 142
<211> LENGTH: 10
<212> TYPE: PRT
<213> ORGANISM: Artificial Sequence
<220> FEATURE:
<223> OTHER INFORMATION: Synthetic

<400> SEQUENCE: 142

Ile Arg Ser Lys Tyr Asn Asn Tyr Gly Thr
1               5                   10
```

```
<210> SEQ ID NO 143
<211> LENGTH: 125
<212> TYPE: PRT
<213> ORGANISM: Artificial Sequence
<220> FEATURE:
<223> OTHER INFORMATION: Synthetic

<400> SEQUENCE: 143

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Gly Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125
```

```
<210> SEQ ID NO 144
<211> LENGTH: 10
<212> TYPE: PRT
<213> ORGANISM: Artificial Sequence
<220> FEATURE:
<223> OTHER INFORMATION: Synthetic

<400> SEQUENCE: 144

Ile Arg Ser Lys Tyr Asn Asn Tyr His Thr
1               5                   10
```

<210> SEQ ID NO 145
<211> LENGTH: 125
<212> TYPE: PRT
<213> ORGANISM: Artificial Sequence
<220> FEATURE:
<223> OTHER INFORMATION: Synthetic

<400> SEQUENCE: 145

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr His Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 146
<211> LENGTH: 10
<212> TYPE: PRT
<213> ORGANISM: Artificial Sequence
<220> FEATURE:
<223> OTHER INFORMATION: Synthetic

<400> SEQUENCE: 146

Ile Arg Ser Lys Tyr Asn Asn Tyr Ile Thr
1               5                   10

<210> SEQ ID NO 147
<211> LENGTH: 125
<212> TYPE: PRT
<213> ORGANISM: Artificial Sequence
<220> FEATURE:
<223> OTHER INFORMATION: Synthetic

<400> SEQUENCE: 147

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ile Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 148
<211> LENGTH: 10
<212> TYPE: PRT
<213> ORGANISM: Artificial Sequence
<220> FEATURE:
<223> OTHER INFORMATION: Synthetic

<400> SEQUENCE: 148

Ile Arg Ser Lys Tyr Asn Asn Tyr Lys Thr
1               5                   10

<210> SEQ ID NO 149
<211> LENGTH: 125
<212> TYPE: PRT
<213> ORGANISM: Artificial Sequence
<220> FEATURE:
<223> OTHER INFORMATION: Synthetic

<400> SEQUENCE: 149

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Lys Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 150
<211> LENGTH: 10
<212> TYPE: PRT
<213> ORGANISM: Artificial Sequence
<220> FEATURE:
<223> OTHER INFORMATION: Synthetic

<400> SEQUENCE: 150

Ile Arg Ser Lys Tyr Asn Asn Tyr Leu Thr
1               5                   10

<210> SEQ ID NO 151
<211> LENGTH: 125
<212> TYPE: PRT
<213> ORGANISM: Artificial Sequence
<220> FEATURE:
<223> OTHER INFORMATION: Synthetic

<400> SEQUENCE: 151

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

-continued

```
Ala Arg Ile Arg Ser Lys Tyr Asn Asn Tyr Leu Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 152
<211> LENGTH: 10
<212> TYPE: PRT
<213> ORGANISM: Artificial Sequence
<220> FEATURE:
<223> OTHER INFORMATION: Synthetic

<400> SEQUENCE: 152

Ile Arg Ser Lys Tyr Asn Asn Tyr Met Thr
1               5                   10

<210> SEQ ID NO 153
<211> LENGTH: 125
<212> TYPE: PRT
<213> ORGANISM: Artificial Sequence
<220> FEATURE:
<223> OTHER INFORMATION: Synthetic

<400> SEQUENCE: 153

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Met Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 154
<211> LENGTH: 10
<212> TYPE: PRT
<213> ORGANISM: Artificial Sequence
<220> FEATURE:
<223> OTHER INFORMATION: Synthetic

<400> SEQUENCE: 154

Ile Arg Ser Lys Tyr Asn Asn Tyr Asn Thr
1               5                   10

<210> SEQ ID NO 155
<211> LENGTH: 125
```

<212> TYPE: PRT
<213> ORGANISM: Artificial Sequence
<220> FEATURE:
<223> OTHER INFORMATION: Synthetic

<400> SEQUENCE: 155

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Asn Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 156
<211> LENGTH: 10
<212> TYPE: PRT
<213> ORGANISM: Artificial Sequence
<220> FEATURE:
<223> OTHER INFORMATION: Synthetic

<400> SEQUENCE: 156

Ile Arg Ser Lys Tyr Asn Asn Tyr Pro Thr
1               5                   10

<210> SEQ ID NO 157
<211> LENGTH: 125
<212> TYPE: PRT
<213> ORGANISM: Artificial Sequence
<220> FEATURE:
<223> OTHER INFORMATION: Synthetic

<400> SEQUENCE: 157

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Pro Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

```
<210> SEQ ID NO 158
<211> LENGTH: 10
<212> TYPE: PRT
<213> ORGANISM: Artificial Sequence
<220> FEATURE:
<223> OTHER INFORMATION: Synthetic

<400> SEQUENCE: 158

Ile Arg Ser Lys Tyr Asn Asn Tyr Gln Thr
1               5                   10

<210> SEQ ID NO 159
<211> LENGTH: 125
<212> TYPE: PRT
<213> ORGANISM: Artificial Sequence
<220> FEATURE:
<223> OTHER INFORMATION: Synthetic

<400> SEQUENCE: 159

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Gln Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 160
<211> LENGTH: 10
<212> TYPE: PRT
<213> ORGANISM: Artificial Sequence
<220> FEATURE:
<223> OTHER INFORMATION: Synthetic

<400> SEQUENCE: 160

Ile Arg Ser Lys Tyr Asn Asn Tyr Arg Thr
1               5                   10

<210> SEQ ID NO 161
<211> LENGTH: 125
<212> TYPE: PRT
<213> ORGANISM: Artificial Sequence
<220> FEATURE:
<223> OTHER INFORMATION: Synthetic

<400> SEQUENCE: 161

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Arg Thr Tyr Tyr Ala Asp
```

-continued

```
        50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
            100             105             110

Ala Tyr Trp Gly Gln Gly Thr Leu Val Thr Val Ser Ser
        115             120             125

<210> SEQ ID NO 162
<211> LENGTH: 10
<212> TYPE: PRT
<213> ORGANISM: Artificial Sequence
<220> FEATURE:
<223> OTHER INFORMATION: Synthetic

<400> SEQUENCE: 162

Ile Arg Ser Lys Tyr Asn Asn Tyr Ser Thr
1               5               10

<210> SEQ ID NO 163
<211> LENGTH: 125
<212> TYPE: PRT
<213> ORGANISM: Artificial Sequence
<220> FEATURE:
<223> OTHER INFORMATION: Synthetic

<400> SEQUENCE: 163

Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
        35              40              45

Ala Arg Ile Arg Ser Lys Tyr Asn Asn Tyr Ser Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
            100             105             110

Ala Tyr Trp Gly Gln Gly Thr Leu Val Thr Val Ser Ser
        115             120             125

<210> SEQ ID NO 164
<211> LENGTH: 10
<212> TYPE: PRT
<213> ORGANISM: Artificial Sequence
<220> FEATURE:
<223> OTHER INFORMATION: Synthetic

<400> SEQUENCE: 164

Ile Arg Ser Lys Tyr Asn Asn Tyr Val Thr
1               5               10

<210> SEQ ID NO 165
<211> LENGTH: 125
<212> TYPE: PRT
<213> ORGANISM: Artificial Sequence
```

-continued

<220> FEATURE:
<223> OTHER INFORMATION: Synthetic

<400> SEQUENCE: 165

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Val Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 166
<211> LENGTH: 10
<212> TYPE: PRT
<213> ORGANISM: Artificial Sequence
<220> FEATURE:
<223> OTHER INFORMATION: Synthetic

<400> SEQUENCE: 166

Ile Arg Ser Lys Tyr Asn Asn Tyr Trp Thr
1               5                   10

<210> SEQ ID NO 167
<211> LENGTH: 125
<212> TYPE: PRT
<213> ORGANISM: Artificial Sequence
<220> FEATURE:
<223> OTHER INFORMATION: Synthetic

<400> SEQUENCE: 167

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Trp Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 168
<211> LENGTH: 10

<212> TYPE: PRT
<213> ORGANISM: Artificial Sequence
<220> FEATURE:
<223> OTHER INFORMATION: Synthetic

<400> SEQUENCE: 168

```
Ile Arg Ser Lys Tyr Asn Asn Tyr Tyr Thr
1               5                   10
```

<210> SEQ ID NO 169
<211> LENGTH: 125
<212> TYPE: PRT
<213> ORGANISM: Artificial Sequence
<220> FEATURE:
<223> OTHER INFORMATION: Synthetic

<400> SEQUENCE: 169

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Tyr Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 170
<211> LENGTH: 16
<212> TYPE: PRT
<213> ORGANISM: Artificial Sequence
<220> FEATURE:
<223> OTHER INFORMATION: Synthetic

<400> SEQUENCE: 170

```
Val Arg Ala Gly Asn Phe Gly Asn Ser Tyr Val Ser Trp Phe Ala Tyr
1               5                   10                  15
```

<210> SEQ ID NO 171
<211> LENGTH: 125
<212> TYPE: PRT
<213> ORGANISM: Artificial Sequence
<220> FEATURE:
<223> OTHER INFORMATION: Synthetic

<400> SEQUENCE: 171

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

-continued

```
Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Ala Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 172
<211> LENGTH: 16
<212> TYPE: PRT
<213> ORGANISM: Artificial Sequence
<220> FEATURE:
<223> OTHER INFORMATION: Synthetic

<400> SEQUENCE: 172

Val Arg Cys Gly Asn Phe Gly Asn Ser Tyr Val Ser Trp Phe Ala Tyr
1                   5                   10                  15

<210> SEQ ID NO 173
<211> LENGTH: 125
<212> TYPE: PRT
<213> ORGANISM: Artificial Sequence
<220> FEATURE:
<223> OTHER INFORMATION: Synthetic

<400> SEQUENCE: 173

Glu Val Lys Leu Val Glu Ser Gly Gly Gly Leu Val Gln Pro Gly Gly
1                   5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Cys Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 174
<211> LENGTH: 16
<212> TYPE: PRT
<213> ORGANISM: Artificial Sequence
<220> FEATURE:
<223> OTHER INFORMATION: Synthetic

<400> SEQUENCE: 174

Val Arg Phe Gly Asn Phe Gly Asn Ser Tyr Val Ser Trp Phe Ala Tyr
1                   5                   10                  15

<210> SEQ ID NO 175
<211> LENGTH: 125
<212> TYPE: PRT
<213> ORGANISM: Artificial Sequence
<220> FEATURE:
<223> OTHER INFORMATION: Synthetic
```

<400> SEQUENCE: 175

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Phe Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 176
<211> LENGTH: 16
<212> TYPE: PRT
<213> ORGANISM: Artificial Sequence
<220> FEATURE:
<223> OTHER INFORMATION: Synthetic

<400> SEQUENCE: 176

Val Arg Gly Gly Asn Phe Gly Asn Ser Tyr Val Ser Trp Phe Ala Tyr
1               5                   10                  15

<210> SEQ ID NO 177
<211> LENGTH: 125
<212> TYPE: PRT
<213> ORGANISM: Artificial Sequence
<220> FEATURE:
<223> OTHER INFORMATION: Synthetic

<400> SEQUENCE: 177

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Gly Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 178
<211> LENGTH: 16
<212> TYPE: PRT
<213> ORGANISM: Artificial Sequence
<220> FEATURE:
<223> OTHER INFORMATION: Synthetic

<400> SEQUENCE: 178

Val Arg Ile Gly Asn Phe Gly Asn Ser Tyr Val Ser Trp Phe Ala Tyr
1               5                   10                  15

<210> SEQ ID NO 179
<211> LENGTH: 125
<212> TYPE: PRT
<213> ORGANISM: Artificial Sequence
<220> FEATURE:
<223> OTHER INFORMATION: Synthetic

<400> SEQUENCE: 179

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Ile Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 180
<211> LENGTH: 16
<212> TYPE: PRT
<213> ORGANISM: Artificial Sequence
<220> FEATURE:
<223> OTHER INFORMATION: Synthetic

<400> SEQUENCE: 180

Val Arg Lys Gly Asn Phe Gly Asn Ser Tyr Val Ser Trp Phe Ala Tyr
1               5                   10                  15

<210> SEQ ID NO 181
<211> LENGTH: 125
<212> TYPE: PRT
<213> ORGANISM: Artificial Sequence
<220> FEATURE:
<223> OTHER INFORMATION: Synthetic

<400> SEQUENCE: 181

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

```
Leu Tyr Leu Gln Met Asn Asn Leu Lys Thr Glu Asp Thr Ala Met Tyr
                85                  90                  95

Tyr Cys Val Arg Lys Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 182
<211> LENGTH: 16
<212> TYPE: PRT
<213> ORGANISM: Artificial Sequence
<220> FEATURE:
<223> OTHER INFORMATION: Synthetic

<400> SEQUENCE: 182

```
Val Arg Leu Gly Asn Phe Gly Asn Ser Tyr Val Ser Trp Phe Ala Tyr
1               5                   10                  15
```

<210> SEQ ID NO 183
<211> LENGTH: 125
<212> TYPE: PRT
<213> ORGANISM: Artificial Sequence
<220> FEATURE:
<223> OTHER INFORMATION: Synthetic

<400> SEQUENCE: 183

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Leu Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 184
<211> LENGTH: 16
<212> TYPE: PRT
<213> ORGANISM: Artificial Sequence
<220> FEATURE:
<223> OTHER INFORMATION: Synthetic

<400> SEQUENCE: 184

```
Val Arg Asn Gly Asn Phe Gly Asn Ser Tyr Val Ser Trp Phe Ala Tyr
1               5                   10                  15
```

<210> SEQ ID NO 185
<211> LENGTH: 125
<212> TYPE: PRT
<213> ORGANISM: Artificial Sequence
<220> FEATURE:
<223> OTHER INFORMATION: Synthetic

<400> SEQUENCE: 185

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Asn Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 186
<211> LENGTH: 16
<212> TYPE: PRT
<213> ORGANISM: Artificial Sequence
<220> FEATURE:
<223> OTHER INFORMATION: Synthetic

<400> SEQUENCE: 186

Val Arg Pro Gly Asn Phe Gly Asn Ser Tyr Val Ser Trp Phe Ala Tyr
1               5                   10                  15

<210> SEQ ID NO 187
<211> LENGTH: 125
<212> TYPE: PRT
<213> ORGANISM: Artificial Sequence
<220> FEATURE:
<223> OTHER INFORMATION: Synthetic

<400> SEQUENCE: 187

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Pro Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 188
<211> LENGTH: 16
<212> TYPE: PRT
<213> ORGANISM: Artificial Sequence
<220> FEATURE:
<223> OTHER INFORMATION: Synthetic
```

-continued

<400> SEQUENCE: 188

Val Arg Gln Gly Asn Phe Gly Asn Ser Tyr Val Ser Trp Phe Ala Tyr
1               5                   10                  15

<210> SEQ ID NO 189
<211> LENGTH: 125
<212> TYPE: PRT
<213> ORGANISM: Artificial Sequence
<220> FEATURE:
<223> OTHER INFORMATION: Synthetic

<400> SEQUENCE: 189

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
            85                  90                  95

Tyr Cys Val Arg Gln Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 190
<211> LENGTH: 16
<212> TYPE: PRT
<213> ORGANISM: Artificial Sequence
<220> FEATURE:
<223> OTHER INFORMATION: Synthetic

<400> SEQUENCE: 190

Val Arg Arg Gly Asn Phe Gly Asn Ser Tyr Val Ser Trp Phe Ala Tyr
1               5                   10                  15

<210> SEQ ID NO 191
<211> LENGTH: 125
<212> TYPE: PRT
<213> ORGANISM: Artificial Sequence
<220> FEATURE:
<223> OTHER INFORMATION: Synthetic

<400> SEQUENCE: 191

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr

```
                  85                    90                    95

Tyr Cys Val Arg Arg Gly Asn Phe Gly Asn Ser Tyr Val Ser Trp Phe
              100                   105                   110

Ala Tyr Trp Gly Gln Gly Thr Leu Val Thr Val Ser Ser
          115                   120                   125

<210> SEQ ID NO 192
<211> LENGTH: 16
<212> TYPE: PRT
<213> ORGANISM: Artificial Sequence
<220> FEATURE:
<223> OTHER INFORMATION: Synthetic

<400> SEQUENCE: 192

Val Arg Ser Gly Asn Phe Gly Asn Ser Tyr Val Ser Trp Phe Ala Tyr
1               5                   10                  15

<210> SEQ ID NO 193
<211> LENGTH: 125
<212> TYPE: PRT
<213> ORGANISM: Artificial Sequence
<220> FEATURE:
<223> OTHER INFORMATION: Synthetic

<400> SEQUENCE: 193

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
              20                    25                    30

Ala Met Asn Trp Val Arg Gln Ala Pro Gly Lys Gly Leu Glu Trp Val
          35                    40                    45

Ala Arg Ile Arg Ser Lys Tyr Asn Asn Tyr Ala Thr Tyr Tyr Ala Asp
      50                    55                    60

Ser Val Lys Asp Arg Phe Thr Ile Ser Arg Asp Asp Ser Lys Ser Ser
65                    70                    75                    80

Leu Tyr Leu Gln Met Asn Asn Leu Lys Thr Glu Asp Thr Ala Met Tyr
              85                    90                    95

Tyr Cys Val Arg Ser Gly Asn Phe Gly Asn Ser Tyr Val Ser Trp Phe
              100                   105                   110

Ala Tyr Trp Gly Gln Gly Thr Leu Val Thr Val Ser Ser
          115                   120                   125

<210> SEQ ID NO 194
<211> LENGTH: 16
<212> TYPE: PRT
<213> ORGANISM: Artificial Sequence
<220> FEATURE:
<223> OTHER INFORMATION: Synthetic

<400> SEQUENCE: 194

Val Arg Thr Gly Asn Phe Gly Asn Ser Tyr Val Ser Trp Phe Ala Tyr
1               5                   10                  15

<210> SEQ ID NO 195
<211> LENGTH: 125
<212> TYPE: PRT
<213> ORGANISM: Artificial Sequence
<220> FEATURE:
<223> OTHER INFORMATION: Synthetic

<400> SEQUENCE: 195

Glu Val Lys Leu Val Glu Ser Gly Gly Gly Leu Val Gln Pro Gly Gly
```

```
1               5                    10                   15

Ser Leu Arg Leu Ser Cys Ala Ala Ser Gly Phe Thr Phe Asn Thr Tyr
            20                   25                   30

Ala Met Asn Trp Val Arg Gln Ala Pro Gly Lys Gly Leu Glu Trp Val
            35                   40                   45

Ala Arg Ile Arg Ser Lys Tyr Asn Asn Tyr Ala Thr Tyr Tyr Ala Asp
    50                   55                   60

Ser Val Lys Asp Arg Phe Thr Ile Ser Arg Asp Asp Ser Lys Ser Ser
65                   70                   75                   80

Leu Tyr Leu Gln Met Asn Asn Leu Lys Thr Glu Asp Thr Ala Met Tyr
                85                   90                   95

Tyr Cys Val Arg Thr Gly Asn Phe Gly Asn Ser Tyr Val Ser Trp Phe
            100                  105                  110

Ala Tyr Trp Gly Gln Gly Thr Leu Val Thr Val Ser Ser
        115                  120                  125
```

<210> SEQ ID NO 196
<211> LENGTH: 16
<212> TYPE: PRT
<213> ORGANISM: Artificial Sequence
<220> FEATURE:
<223> OTHER INFORMATION: Synthetic

<400> SEQUENCE: 196

```
Val Arg Val Gly Asn Phe Gly Asn Ser Tyr Val Ser Trp Phe Ala Tyr
1               5                    10                   15
```

<210> SEQ ID NO 197
<211> LENGTH: 125
<212> TYPE: PRT
<213> ORGANISM: Artificial Sequence
<220> FEATURE:
<223> OTHER INFORMATION: Synthetic

<400> SEQUENCE: 197

```
Glu Val Lys Leu Val Glu Ser Gly Gly Gly Leu Val Gln Pro Gly Gly
1               5                    10                   15

Ser Leu Arg Leu Ser Cys Ala Ala Ser Gly Phe Thr Phe Asn Thr Tyr
            20                   25                   30

Ala Met Asn Trp Val Arg Gln Ala Pro Gly Lys Gly Leu Glu Trp Val
            35                   40                   45

Ala Arg Ile Arg Ser Lys Tyr Asn Asn Tyr Ala Thr Tyr Tyr Ala Asp
    50                   55                   60

Ser Val Lys Asp Arg Phe Thr Ile Ser Arg Asp Asp Ser Lys Ser Ser
65                   70                   75                   80

Leu Tyr Leu Gln Met Asn Asn Leu Lys Thr Glu Asp Thr Ala Met Tyr
                85                   90                   95

Tyr Cys Val Arg Val Gly Asn Phe Gly Asn Ser Tyr Val Ser Trp Phe
            100                  105                  110

Ala Tyr Trp Gly Gln Gly Thr Leu Val Thr Val Ser Ser
        115                  120                  125
```

<210> SEQ ID NO 198
<211> LENGTH: 16
<212> TYPE: PRT
<213> ORGANISM: Artificial Sequence
<220> FEATURE:
<223> OTHER INFORMATION: Synthetic

<400> SEQUENCE: 198

```
Val Arg Trp Gly Asn Phe Gly Asn Ser Tyr Val Ser Trp Phe Ala Tyr
1               5                   10                  15
```

<210> SEQ ID NO 199
<211> LENGTH: 125
<212> TYPE: PRT
<213> ORGANISM: Artificial Sequence
<220> FEATURE:
<223> OTHER INFORMATION: Synthetic

<400> SEQUENCE: 199

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Trp Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 200
<211> LENGTH: 16
<212> TYPE: PRT
<213> ORGANISM: Artificial Sequence
<220> FEATURE:
<223> OTHER INFORMATION: Synthetic

<400> SEQUENCE: 200

```
Val Arg Tyr Gly Asn Phe Gly Asn Ser Tyr Val Ser Trp Phe Ala Tyr
1               5                   10                  15
```

<210> SEQ ID NO 201
<211> LENGTH: 125
<212> TYPE: PRT
<213> ORGANISM: Artificial Sequence
<220> FEATURE:
<223> OTHER INFORMATION: Synthetic

<400> SEQUENCE: 201

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95
```

```
Tyr Cys Val Arg Tyr Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 202
<211> LENGTH: 16
<212> TYPE: PRT
<213> ORGANISM: Artificial Sequence
<220> FEATURE:
<223> OTHER INFORMATION: Synthetic

<400> SEQUENCE: 202

Val Arg His Gly Asn Phe Ala Asn Ser Tyr Val Ser Trp Phe Ala Tyr
1               5                   10                  15

<210> SEQ ID NO 203
<211> LENGTH: 125
<212> TYPE: PRT
<213> ORGANISM: Artificial Sequence
<220> FEATURE:
<223> OTHER INFORMATION: Synthetic

<400> SEQUENCE: 203

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Ala Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 204
<211> LENGTH: 16
<212> TYPE: PRT
<213> ORGANISM: Artificial Sequence
<220> FEATURE:
<223> OTHER INFORMATION: Synthetic

<400> SEQUENCE: 204

Val Arg His Gly Asn Phe Cys Asn Ser Tyr Val Ser Trp Phe Ala Tyr
1               5                   10                  15

<210> SEQ ID NO 205
<211> LENGTH: 125
<212> TYPE: PRT
<213> ORGANISM: Artificial Sequence
<220> FEATURE:
<223> OTHER INFORMATION: Synthetic

<400> SEQUENCE: 205

Glu Val Lys Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Asn Thr Tyr
        20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Cys Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 206
<211> LENGTH: 16
<212> TYPE: PRT
<213> ORGANISM: Artificial Sequence
<220> FEATURE:
<223> OTHER INFORMATION: Synthetic

<400> SEQUENCE: 206

```
Val Arg His Gly Asn Phe Glu Asn Ser Tyr Val Ser Trp Phe Ala Tyr
1               5                   10                  15
```

<210> SEQ ID NO 207
<211> LENGTH: 125
<212> TYPE: PRT
<213> ORGANISM: Artificial Sequence
<220> FEATURE:
<223> OTHER INFORMATION: Synthetic

<400> SEQUENCE: 207

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
        20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Glu Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 208
<211> LENGTH: 16
<212> TYPE: PRT
<213> ORGANISM: Artificial Sequence
<220> FEATURE:
<223> OTHER INFORMATION: Synthetic

<400> SEQUENCE: 208

```
Val Arg His Gly Asn Phe Phe Asn Ser Tyr Val Ser Trp Phe Ala Tyr
```

-continued

```
1               5               10              15
```

<210> SEQ ID NO 209
<211> LENGTH: 125
<212> TYPE: PRT
<213> ORGANISM: Artificial Sequence
<220> FEATURE:
<223> OTHER INFORMATION: Synthetic

<400> SEQUENCE: 209

```
Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
        35              40              45

Ala Arg Ile Arg Ser Lys Tyr Asn Asn Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
            85              90              95

Tyr Cys Val Arg His Gly Asn Phe Phe Asn Ser Tyr Val Ser Trp Phe
            100             105             110

Ala Tyr Trp Gly Gln Gly Thr Leu Val Thr Val Ser Ser
        115             120             125
```

<210> SEQ ID NO 210
<211> LENGTH: 16
<212> TYPE: PRT
<213> ORGANISM: Artificial Sequence
<220> FEATURE:
<223> OTHER INFORMATION: Synthetic

<400> SEQUENCE: 210

```
Val Arg His Gly Asn Phe His Asn Ser Tyr Val Ser Trp Phe Ala Tyr
1               5               10              15
```

<210> SEQ ID NO 211
<211> LENGTH: 125
<212> TYPE: PRT
<213> ORGANISM: Artificial Sequence
<220> FEATURE:
<223> OTHER INFORMATION: Synthetic

<400> SEQUENCE: 211

```
Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
        35              40              45

Ala Arg Ile Arg Ser Lys Tyr Asn Asn Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
            85              90              95

Tyr Cys Val Arg His Gly Asn Phe His Asn Ser Tyr Val Ser Trp Phe
            100             105             110
```

Ala Tyr Trp Gly Gln Gly Thr Leu Val Thr Val Ser Ser
        115                 120                 125

<210> SEQ ID NO 212
<211> LENGTH: 16
<212> TYPE: PRT
<213> ORGANISM: Artificial Sequence
<220> FEATURE:
<223> OTHER INFORMATION: Synthetic

<400> SEQUENCE: 212

Val Arg His Gly Asn Phe Ile Asn Ser Tyr Val Ser Trp Phe Ala Tyr
1               5                   10                  15

<210> SEQ ID NO 213
<211> LENGTH: 125
<212> TYPE: PRT
<213> ORGANISM: Artificial Sequence
<220> FEATURE:
<223> OTHER INFORMATION: Synthetic

<400> SEQUENCE: 213

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Ile Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 214
<211> LENGTH: 16
<212> TYPE: PRT
<213> ORGANISM: Artificial Sequence
<220> FEATURE:
<223> OTHER INFORMATION: Synthetic

<400> SEQUENCE: 214

Val Arg His Gly Asn Phe Leu Asn Ser Tyr Val Ser Trp Phe Ala Tyr
1               5                   10                  15

<210> SEQ ID NO 215
<211> LENGTH: 125
<212> TYPE: PRT
<213> ORGANISM: Artificial Sequence
<220> FEATURE:
<223> OTHER INFORMATION: Synthetic

<400> SEQUENCE: 215

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Leu Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 216
<211> LENGTH: 16
<212> TYPE: PRT
<213> ORGANISM: Artificial Sequence
<220> FEATURE:
<223> OTHER INFORMATION: Synthetic

<400> SEQUENCE: 216

Val Arg His Gly Asn Phe Met Asn Ser Tyr Val Ser Trp Phe Ala Tyr
1               5                   10                  15

<210> SEQ ID NO 217
<211> LENGTH: 125
<212> TYPE: PRT
<213> ORGANISM: Artificial Sequence
<220> FEATURE:
<223> OTHER INFORMATION: Synthetic

<400> SEQUENCE: 217

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
        20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Met Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 218
<211> LENGTH: 16
<212> TYPE: PRT
<213> ORGANISM: Artificial Sequence
<220> FEATURE:
<223> OTHER INFORMATION: Synthetic

<400> SEQUENCE: 218

Val Arg His Gly Asn Phe Asn Asn Ser Tyr Val Ser Trp Phe Ala Tyr
1               5                   10                  15
```

<210> SEQ ID NO 219
<211> LENGTH: 125
<212> TYPE: PRT
<213> ORGANISM: Artificial Sequence
<220> FEATURE:
<223> OTHER INFORMATION: Synthetic

<400> SEQUENCE: 219

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Asn Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 220
<211> LENGTH: 16
<212> TYPE: PRT
<213> ORGANISM: Artificial Sequence
<220> FEATURE:
<223> OTHER INFORMATION: Synthetic

<400> SEQUENCE: 220

Val Arg His Gly Asn Phe Pro Asn Ser Tyr Val Ser Trp Phe Ala Tyr
1               5                   10                  15

<210> SEQ ID NO 221
<211> LENGTH: 125
<212> TYPE: PRT
<213> ORGANISM: Artificial Sequence
<220> FEATURE:
<223> OTHER INFORMATION: Synthetic

<400> SEQUENCE: 221

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Pro Asn Ser Tyr Val Ser Trp Phe
            100                 105                 110

Ala Tyr Trp Gly Gln Gly Thr Leu Val Thr Val Ser Ser

```
                115                120                125

<210> SEQ ID NO 222
<211> LENGTH: 16
<212> TYPE: PRT
<213> ORGANISM: Artificial Sequence
<220> FEATURE:
<223> OTHER INFORMATION: Synthetic

<400> SEQUENCE: 222

Val Arg His Gly Asn Phe Gln Asn Ser Tyr Val Ser Trp Phe Ala Tyr
1               5                   10                  15

<210> SEQ ID NO 223
<211> LENGTH: 125
<212> TYPE: PRT
<213> ORGANISM: Artificial Sequence
<220> FEATURE:
<223> OTHER INFORMATION: Synthetic

<400> SEQUENCE: 223

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gln Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 224
<211> LENGTH: 16
<212> TYPE: PRT
<213> ORGANISM: Artificial Sequence
<220> FEATURE:
<223> OTHER INFORMATION: Synthetic

<400> SEQUENCE: 224

Val Arg His Gly Asn Phe Arg Asn Ser Tyr Val Ser Trp Phe Ala Tyr
1               5                   10                  15

<210> SEQ ID NO 225
<211> LENGTH: 125
<212> TYPE: PRT
<213> ORGANISM: Artificial Sequence
<220> FEATURE:
<223> OTHER INFORMATION: Synthetic

<400> SEQUENCE: 225

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
```

-continued

```
              35              40              45

Ala Arg Ile Arg Ser Lys Tyr Asn Asn Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Arg Asn Ser Tyr Val Ser Trp Phe
            100             105             110

Ala Tyr Trp Gly Gln Gly Thr Leu Val Thr Val Ser Ser
        115             120             125

<210> SEQ ID NO 226
<211> LENGTH: 16
<212> TYPE: PRT
<213> ORGANISM: Artificial Sequence
<220> FEATURE:
<223> OTHER INFORMATION: Synthetic

<400> SEQUENCE: 226

Val Arg His Gly Asn Phe Ser Asn Ser Tyr Val Ser Trp Phe Ala Tyr
1               5               10              15

<210> SEQ ID NO 227
<211> LENGTH: 125
<212> TYPE: PRT
<213> ORGANISM: Artificial Sequence
<220> FEATURE:
<223> OTHER INFORMATION: Synthetic

<400> SEQUENCE: 227

Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
                20              25              30

Ala Met Asn Trp Val Arg Gln Ala Pro Gly Lys Gly Leu Glu Trp Val
                35              40              45

Ala Arg Ile Arg Ser Lys Tyr Asn Asn Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Ser Asn Ser Tyr Val Ser Trp Phe
            100             105             110

Ala Tyr Trp Gly Gln Gly Thr Leu Val Thr Val Ser Ser
        115             120             125

<210> SEQ ID NO 228
<211> LENGTH: 16
<212> TYPE: PRT
<213> ORGANISM: Artificial Sequence
<220> FEATURE:
<223> OTHER INFORMATION: Synthetic

<400> SEQUENCE: 228

Val Arg His Gly Asn Phe Thr Asn Ser Tyr Val Ser Trp Phe Ala Tyr
1               5               10              15

<210> SEQ ID NO 229
```

<211> LENGTH: 125
<212> TYPE: PRT
<213> ORGANISM: Artificial Sequence
<220> FEATURE:
<223> OTHER INFORMATION: Synthetic

<400> SEQUENCE: 229

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Thr Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 230
<211> LENGTH: 16
<212> TYPE: PRT
<213> ORGANISM: Artificial Sequence
<220> FEATURE:
<223> OTHER INFORMATION: Synthetic

<400> SEQUENCE: 230

```
Val Arg His Gly Asn Phe Val Asn Ser Tyr Val Ser Trp Phe Ala Tyr
1               5                   10                  15
```

<210> SEQ ID NO 231
<211> LENGTH: 125
<212> TYPE: PRT
<213> ORGANISM: Artificial Sequence
<220> FEATURE:
<223> OTHER INFORMATION: Synthetic

<400> SEQUENCE: 231

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Val Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 232
<211> LENGTH: 16
<212> TYPE: PRT
<213> ORGANISM: Artificial Sequence
<220> FEATURE:
<223> OTHER INFORMATION: Synthetic

<400> SEQUENCE: 232

Val Arg His Gly Asn Phe Trp Asn Ser Tyr Val Ser Trp Phe Ala Tyr
1               5                   10                  15

<210> SEQ ID NO 233
<211> LENGTH: 125
<212> TYPE: PRT
<213> ORGANISM: Artificial Sequence
<220> FEATURE:
<223> OTHER INFORMATION: Synthetic

<400> SEQUENCE: 233

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Trp Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 234
<211> LENGTH: 16
<212> TYPE: PRT
<213> ORGANISM: Artificial Sequence
<220> FEATURE:
<223> OTHER INFORMATION: Synthetic

<400> SEQUENCE: 234

Val Arg His Gly Asn Phe Tyr Asn Ser Tyr Val Ser Trp Phe Ala Tyr
1               5                   10                  15

<210> SEQ ID NO 235
<211> LENGTH: 125
<212> TYPE: PRT
<213> ORGANISM: Artificial Sequence
<220> FEATURE:
<223> OTHER INFORMATION: Synthetic

<400> SEQUENCE: 235

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

-continued

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Tyr Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 236
<211> LENGTH: 16
<212> TYPE: PRT
<213> ORGANISM: Artificial Sequence
<220> FEATURE:
<223> OTHER INFORMATION: Synthetic

<400> SEQUENCE: 236

Val Arg His Gly Asn Phe Gly Asn Ser Tyr Val Ala Trp Phe Ala Tyr
1               5                   10                  15

<210> SEQ ID NO 237
<211> LENGTH: 125
<212> TYPE: PRT
<213> ORGANISM: Artificial Sequence
<220> FEATURE:
<223> OTHER INFORMATION: Synthetic

<400> SEQUENCE: 237

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ala Trp Phe
            100                 105                 110

Ala Tyr Trp Gly Gln Gly Thr Leu Val Thr Val Ser Ser
        115                 120                 125

<210> SEQ ID NO 238
<211> LENGTH: 16
<212> TYPE: PRT
<213> ORGANISM: Artificial Sequence
<220> FEATURE:
<223> OTHER INFORMATION: Synthetic

<400> SEQUENCE: 238

Val Arg His Gly Asn Phe Gly Asn Ser Tyr Val Cys Trp Phe Ala Tyr
1               5                   10                  15

<210> SEQ ID NO 239
<211> LENGTH: 125
<212> TYPE: PRT

-continued

<213> ORGANISM: Artificial Sequence
<220> FEATURE:
<223> OTHER INFORMATION: Synthetic

<400> SEQUENCE: 239

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Cys Trp Phe
            100                 105                 110

Ala Tyr Trp Gly Gln Gly Thr Leu Val Thr Val Ser Ser
        115                 120                 125

<210> SEQ ID NO 240
<211> LENGTH: 16
<212> TYPE: PRT
<213> ORGANISM: Artificial Sequence
<220> FEATURE:
<223> OTHER INFORMATION: Synthetic

<400> SEQUENCE: 240

Val Arg His Gly Asn Phe Gly Asn Ser Tyr Val Glu Trp Phe Ala Tyr
1               5                   10                  15

<210> SEQ ID NO 241
<211> LENGTH: 125
<212> TYPE: PRT
<213> ORGANISM: Artificial Sequence
<220> FEATURE:
<223> OTHER INFORMATION: Synthetic

<400> SEQUENCE: 241

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Glu Trp Phe
            100                 105                 110

Ala Tyr Trp Gly Gln Gly Thr Leu Val Thr Val Ser Ser
        115                 120                 125

<210> SEQ ID NO 242

```
<211> LENGTH: 16
<212> TYPE: PRT
<213> ORGANISM: Artificial Sequence
<220> FEATURE:
<223> OTHER INFORMATION: Synthetic

<400> SEQUENCE: 242

Val Arg His Gly Asn Phe Gly Asn Ser Tyr Val Phe Trp Phe Ala Tyr
1               5                   10                  15

<210> SEQ ID NO 243
<211> LENGTH: 125
<212> TYPE: PRT
<213> ORGANISM: Artificial Sequence
<220> FEATURE:
<223> OTHER INFORMATION: Synthetic

<400> SEQUENCE: 243

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Phe Trp Phe
            100                 105                 110

Ala Tyr Trp Gly Gln Gly Thr Leu Val Thr Val Ser Ser
        115                 120                 125

<210> SEQ ID NO 244
<211> LENGTH: 16
<212> TYPE: PRT
<213> ORGANISM: Artificial Sequence
<220> FEATURE:
<223> OTHER INFORMATION: Synthetic

<400> SEQUENCE: 244

Val Arg His Gly Asn Phe Gly Asn Ser Tyr Val Gly Trp Phe Ala Tyr
1               5                   10                  15

<210> SEQ ID NO 245
<211> LENGTH: 125
<212> TYPE: PRT
<213> ORGANISM: Artificial Sequence
<220> FEATURE:
<223> OTHER INFORMATION: Synthetic

<400> SEQUENCE: 245

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

```
Ser Val Lys Asp Arg Phe Thr Ile Ser Arg Asp Asp Ser Lys Ser Ser
65              70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Gly Trp Phe
            100                 105                 110

Ala Tyr Trp Gly Gln Gly Thr Leu Val Thr Val Ser Ser
        115                 120                 125

<210> SEQ ID NO 246
<211> LENGTH: 16
<212> TYPE: PRT
<213> ORGANISM: Artificial Sequence
<220> FEATURE:
<223> OTHER INFORMATION: Synthetic

<400> SEQUENCE: 246

Val Arg His Gly Asn Phe Gly Asn Ser Tyr Val His Trp Phe Ala Tyr
1               5                   10                  15

<210> SEQ ID NO 247
<211> LENGTH: 125
<212> TYPE: PRT
<213> ORGANISM: Artificial Sequence
<220> FEATURE:
<223> OTHER INFORMATION: Synthetic

<400> SEQUENCE: 247

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65              70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val His Trp Phe
            100                 105                 110

Ala Tyr Trp Gly Gln Gly Thr Leu Val Thr Val Ser Ser
        115                 120                 125

<210> SEQ ID NO 248
<211> LENGTH: 16
<212> TYPE: PRT
<213> ORGANISM: Artificial Sequence
<220> FEATURE:
<223> OTHER INFORMATION: Synthetic

<400> SEQUENCE: 248

Val Arg His Gly Asn Phe Gly Asn Ser Tyr Val Lys Trp Phe Ala Tyr
1               5                   10                  15

<210> SEQ ID NO 249
<211> LENGTH: 125
<212> TYPE: PRT
<213> ORGANISM: Artificial Sequence
<220> FEATURE:
```

<223> OTHER INFORMATION: Synthetic

<400> SEQUENCE: 249

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Lys Trp Phe
            100                 105                 110

Ala Tyr Trp Gly Gln Gly Thr Leu Val Thr Val Ser Ser
        115                 120                 125
```

<210> SEQ ID NO 250
<211> LENGTH: 16
<212> TYPE: PRT
<213> ORGANISM: Artificial Sequence
<220> FEATURE:
<223> OTHER INFORMATION: Synthetic

<400> SEQUENCE: 250

```
Val Arg His Gly Asn Phe Gly Asn Ser Tyr Val Leu Trp Phe Ala Tyr
1               5                   10                  15
```

<210> SEQ ID NO 251
<211> LENGTH: 125
<212> TYPE: PRT
<213> ORGANISM: Artificial Sequence
<220> FEATURE:
<223> OTHER INFORMATION: Synthetic

<400> SEQUENCE: 251

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Leu Trp Phe
            100                 105                 110

Ala Tyr Trp Gly Gln Gly Thr Leu Val Thr Val Ser Ser
        115                 120                 125
```

<210> SEQ ID NO 252
<211> LENGTH: 16
<212> TYPE: PRT

-continued

```
<213> ORGANISM: Artificial Sequence
<220> FEATURE:
<223> OTHER INFORMATION: Synthetic

<400> SEQUENCE: 252

Val Arg His Gly Asn Phe Gly Asn Ser Tyr Val Asn Trp Phe Ala Tyr
1               5                   10                  15

<210> SEQ ID NO 253
<211> LENGTH: 125
<212> TYPE: PRT
<213> ORGANISM: Artificial Sequence
<220> FEATURE:
<223> OTHER INFORMATION: Synthetic

<400> SEQUENCE: 253

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Asn Trp Phe
            100                 105                 110

Ala Tyr Trp Gly Gln Gly Thr Leu Val Thr Val Ser Ser
        115                 120                 125

<210> SEQ ID NO 254
<211> LENGTH: 16
<212> TYPE: PRT
<213> ORGANISM: Artificial Sequence
<220> FEATURE:
<223> OTHER INFORMATION: Synthetic

<400> SEQUENCE: 254

Val Arg His Gly Asn Phe Gly Asn Ser Tyr Val Pro Trp Phe Ala Tyr
1               5                   10                  15

<210> SEQ ID NO 255
<211> LENGTH: 125
<212> TYPE: PRT
<213> ORGANISM: Artificial Sequence
<220> FEATURE:
<223> OTHER INFORMATION: Synthetic

<400> SEQUENCE: 255

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
```

-continued

```
65                    70                    75                    80

Leu Tyr Leu Gln Met Asn Asn Leu Lys Thr Glu Asp Thr Ala Met Tyr
                85                    90                    95

Tyr Cys Val Arg His Gly Asn Phe Gly Asn Ser Tyr Val Pro Trp Phe
                100                   105                   110

Ala Tyr Trp Gly Gln Gly Thr Leu Val Thr Val Ser Ser
        115                   120                   125

<210> SEQ ID NO 256
<211> LENGTH: 16
<212> TYPE: PRT
<213> ORGANISM: Artificial Sequence
<220> FEATURE:
<223> OTHER INFORMATION: Synthetic

<400> SEQUENCE: 256

Val Arg His Gly Asn Phe Gly Asn Ser Tyr Val Gln Trp Phe Ala Tyr
1                   5                   10                   15

<210> SEQ ID NO 257
<211> LENGTH: 125
<212> TYPE: PRT
<213> ORGANISM: Artificial Sequence
<220> FEATURE:
<223> OTHER INFORMATION: Synthetic

<400> SEQUENCE: 257

Glu Val Lys Leu Val Glu Ser Gly Gly Gly Leu Val Gln Pro Gly Gly
1                   5                   10                   15

Ser Leu Arg Leu Ser Cys Ala Ala Ser Gly Phe Thr Phe Asn Thr Tyr
                20                    25                    30

Ala Met Asn Trp Val Arg Gln Ala Pro Gly Lys Gly Leu Glu Trp Val
        35                    40                    45

Ala Arg Ile Arg Ser Lys Tyr Asn Asn Tyr Ala Thr Tyr Tyr Ala Asp
    50                    55                    60

Ser Val Lys Asp Arg Phe Thr Ile Ser Arg Asp Asp Ser Lys Ser Ser
65                    70                    75                    80

Leu Tyr Leu Gln Met Asn Asn Leu Lys Thr Glu Asp Thr Ala Met Tyr
                85                    90                    95

Tyr Cys Val Arg His Gly Asn Phe Gly Asn Ser Tyr Val Gln Trp Phe
                100                   105                   110

Ala Tyr Trp Gly Gln Gly Thr Leu Val Thr Val Ser Ser
        115                   120                   125

<210> SEQ ID NO 258
<211> LENGTH: 16
<212> TYPE: PRT
<213> ORGANISM: Artificial Sequence
<220> FEATURE:
<223> OTHER INFORMATION: Synthetic

<400> SEQUENCE: 258

Val Arg His Gly Asn Phe Gly Asn Ser Tyr Val Arg Trp Phe Ala Tyr
1                   5                   10                   15

<210> SEQ ID NO 259
<211> LENGTH: 125
<212> TYPE: PRT
<213> ORGANISM: Artificial Sequence
<220> FEATURE:
<223> OTHER INFORMATION: Synthetic
```

```
<400> SEQUENCE: 259

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Arg Trp Phe
            100                 105                 110

Ala Tyr Trp Gly Gln Gly Thr Leu Val Thr Val Ser Ser
        115                 120                 125

<210> SEQ ID NO 260
<211> LENGTH: 16
<212> TYPE: PRT
<213> ORGANISM: Artificial Sequence
<220> FEATURE:
<223> OTHER INFORMATION: Synthetic

<400> SEQUENCE: 260

Val Arg His Gly Asn Phe Gly Asn Ser Tyr Val Thr Trp Phe Ala Tyr
1               5                   10                  15

<210> SEQ ID NO 261
<211> LENGTH: 125
<212> TYPE: PRT
<213> ORGANISM: Artificial Sequence
<220> FEATURE:
<223> OTHER INFORMATION: Synthetic

<400> SEQUENCE: 261

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Thr Trp Phe
            100                 105                 110

Ala Tyr Trp Gly Gln Gly Thr Leu Val Thr Val Ser Ser
        115                 120                 125

<210> SEQ ID NO 262
<211> LENGTH: 16
<212> TYPE: PRT
<213> ORGANISM: Artificial Sequence
<220> FEATURE:
```

<223> OTHER INFORMATION: Synthetic

<400> SEQUENCE: 262

Val Arg His Gly Asn Phe Gly Asn Ser Tyr Val Trp Trp Phe Ala Tyr
1               5                   10                  15

<210> SEQ ID NO 263
<211> LENGTH: 125
<212> TYPE: PRT
<213> ORGANISM: Artificial Sequence
<220> FEATURE:
<223> OTHER INFORMATION: Synthetic

<400> SEQUENCE: 263

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Trp Trp Phe
            100                 105                 110

Ala Tyr Trp Gly Gln Gly Thr Leu Val Thr Val Ser Ser
        115                 120                 125

<210> SEQ ID NO 264
<211> LENGTH: 16
<212> TYPE: PRT
<213> ORGANISM: Artificial Sequence
<220> FEATURE:
<223> OTHER INFORMATION: Synthetic

<400> SEQUENCE: 264

Val Arg His Gly Asn Phe Gly Asn Ser Tyr Val Tyr Trp Phe Ala Tyr
1               5                   10                  15

<210> SEQ ID NO 265
<211> LENGTH: 125
<212> TYPE: PRT
<213> ORGANISM: Artificial Sequence
<220> FEATURE:
<223> OTHER INFORMATION: Synthetic

<400> SEQUENCE: 265

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

-continued

```
Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Tyr Trp Phe
            100             105             110

Ala Tyr Trp Gly Gln Gly Thr Leu Val Thr Val Ser Ser
        115             120             125

<210> SEQ ID NO 266
<211> LENGTH: 16
<212> TYPE: PRT
<213> ORGANISM: Artificial Sequence
<220> FEATURE:
<223> OTHER INFORMATION: Synthetic

<400> SEQUENCE: 266

Val Arg His Gly Asn Phe Gly Asn Ser Tyr Val Ser Trp Phe Ala Ala
1               5               10              15

<210> SEQ ID NO 267
<211> LENGTH: 125
<212> TYPE: PRT
<213> ORGANISM: Artificial Sequence
<220> FEATURE:
<223> OTHER INFORMATION: Synthetic

<400> SEQUENCE: 267

Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
        35              40              45

Ala Arg Ile Arg Ser Lys Tyr Asn Asn Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
            100             105             110

Ala Ala Trp Gly Gln Gly Thr Leu Val Thr Val Ser Ser
        115             120             125

<210> SEQ ID NO 268
<211> LENGTH: 16
<212> TYPE: PRT
<213> ORGANISM: Artificial Sequence
<220> FEATURE:
<223> OTHER INFORMATION: Synthetic

<400> SEQUENCE: 268

Val Arg His Gly Asn Phe Gly Asn Ser Tyr Val Ser Trp Phe Ala Cys
1               5               10              15

<210> SEQ ID NO 269
<211> LENGTH: 125
<212> TYPE: PRT
<213> ORGANISM: Artificial Sequence
<220> FEATURE:
<223> OTHER INFORMATION: Synthetic

<400> SEQUENCE: 269
```

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Cys Trp Gly Gln Gly Thr Leu Val Thr Val Ser Ser
            115                 120                 125

<210> SEQ ID NO 270
<211> LENGTH: 16
<212> TYPE: PRT
<213> ORGANISM: Artificial Sequence
<220> FEATURE:
<223> OTHER INFORMATION: Synthetic

<400> SEQUENCE: 270

Val Arg His Gly Asn Phe Gly Asn Ser Tyr Val Ser Trp Phe Ala Glu
1               5                   10                  15

<210> SEQ ID NO 271
<211> LENGTH: 125
<212> TYPE: PRT
<213> ORGANISM: Artificial Sequence
<220> FEATURE:
<223> OTHER INFORMATION: Synthetic

<400> SEQUENCE: 271

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Glu Trp Gly Gln Gly Thr Leu Val Thr Val Ser Ser
            115                 120                 125

<210> SEQ ID NO 272
<211> LENGTH: 16
<212> TYPE: PRT
<213> ORGANISM: Artificial Sequence
<220> FEATURE:
<223> OTHER INFORMATION: Synthetic
```

-continued

```
<400> SEQUENCE: 272

Val Arg His Gly Asn Phe Gly Asn Ser Tyr Val Ser Trp Phe Ala Phe
1               5                   10                  15

<210> SEQ ID NO 273
<211> LENGTH: 125
<212> TYPE: PRT
<213> ORGANISM: Artificial Sequence
<220> FEATURE:
<223> OTHER INFORMATION: Synthetic

<400> SEQUENCE: 273

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Phe Trp Gly Gln Gly Thr Leu Val Thr Val Ser Ser
        115                 120                 125

<210> SEQ ID NO 274
<211> LENGTH: 16
<212> TYPE: PRT
<213> ORGANISM: Artificial Sequence
<220> FEATURE:
<223> OTHER INFORMATION: Synthetic

<400> SEQUENCE: 274

Val Arg His Gly Asn Phe Gly Asn Ser Tyr Val Ser Trp Phe Ala Gly
1               5                   10                  15

<210> SEQ ID NO 275
<211> LENGTH: 125
<212> TYPE: PRT
<213> ORGANISM: Artificial Sequence
<220> FEATURE:
<223> OTHER INFORMATION: Synthetic

<400> SEQUENCE: 275

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95
```

-continued

```
Tyr Cys Val Arg His Gly Asn Phe Gly Asn Ser Tyr Val Ser Trp Phe
            100                 105                 110

Ala Gly Trp Gly Gln Gly Thr Leu Val Thr Val Ser Ser
        115                 120                 125

<210> SEQ ID NO 276
<211> LENGTH: 16
<212> TYPE: PRT
<213> ORGANISM: Artificial Sequence
<220> FEATURE:
<223> OTHER INFORMATION: Synthetic

<400> SEQUENCE: 276

Val Arg His Gly Asn Phe Gly Asn Ser Tyr Val Ser Trp Phe Ala His
1               5                   10                  15

<210> SEQ ID NO 277
<211> LENGTH: 125
<212> TYPE: PRT
<213> ORGANISM: Artificial Sequence
<220> FEATURE:
<223> OTHER INFORMATION: Synthetic

<400> SEQUENCE: 277

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala His Trp Gly Gln Gly Thr Leu Val Thr Val Ser Ser
        115                 120                 125

<210> SEQ ID NO 278
<211> LENGTH: 16
<212> TYPE: PRT
<213> ORGANISM: Artificial Sequence
<220> FEATURE:
<223> OTHER INFORMATION: Synthetic

<400> SEQUENCE: 278

Val Arg His Gly Asn Phe Gly Asn Ser Tyr Val Ser Trp Phe Ala Ile
1               5                   10                  15

<210> SEQ ID NO 279
<211> LENGTH: 125
<212> TYPE: PRT
<213> ORGANISM: Artificial Sequence
<220> FEATURE:
<223> OTHER INFORMATION: Synthetic

<400> SEQUENCE: 279

Glu Val Lys Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Thr Tyr
         20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
             85                  90                  95

Tyr Cys Val Arg His Gly Asn Phe Gly Asn Ser Tyr Val Ser Trp Phe
            100                 105                 110

Ala Ile Trp Gly Gln Gly Thr Leu Val Thr Val Ser Ser
        115                 120                 125
```

```
<210> SEQ ID NO 280
<211> LENGTH: 16
<212> TYPE: PRT
<213> ORGANISM: Artificial Sequence
<220> FEATURE:
<223> OTHER INFORMATION: Synthetic

<400> SEQUENCE: 280

Val Arg His Gly Asn Phe Gly Asn Ser Tyr Val Ser Trp Phe Ala Lys
1               5                   10                  15
```

```
<210> SEQ ID NO 281
<211> LENGTH: 125
<212> TYPE: PRT
<213> ORGANISM: Artificial Sequence
<220> FEATURE:
<223> OTHER INFORMATION: Synthetic

<400> SEQUENCE: 281

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
         20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
             85                  90                  95

Tyr Cys Val Arg His Gly Asn Phe Gly Asn Ser Tyr Val Ser Trp Phe
            100                 105                 110

Ala Lys Trp Gly Gln Gly Thr Leu Val Thr Val Ser Ser
        115                 120                 125
```

```
<210> SEQ ID NO 282
<211> LENGTH: 16
<212> TYPE: PRT
<213> ORGANISM: Artificial Sequence
<220> FEATURE:
<223> OTHER INFORMATION: Synthetic

<400> SEQUENCE: 282
```

-continued

```
Val Arg His Gly Asn Phe Gly Asn Ser Tyr Val Ser Trp Phe Ala Leu
1               5                   10                  15

<210> SEQ ID NO 283
<211> LENGTH: 125
<212> TYPE: PRT
<213> ORGANISM: Artificial Sequence
<220> FEATURE:
<223> OTHER INFORMATION: Synthetic

<400> SEQUENCE: 283

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Leu Trp Gly Gln Gly Thr Leu Val Thr Val Ser Ser
        115                 120                 125

<210> SEQ ID NO 284
<211> LENGTH: 16
<212> TYPE: PRT
<213> ORGANISM: Artificial Sequence
<220> FEATURE:
<223> OTHER INFORMATION: Synthetic

<400> SEQUENCE: 284

Val Arg His Gly Asn Phe Gly Asn Ser Tyr Val Ser Trp Phe Ala Met
1               5                   10                  15

<210> SEQ ID NO 285
<211> LENGTH: 125
<212> TYPE: PRT
<213> ORGANISM: Artificial Sequence
<220> FEATURE:
<223> OTHER INFORMATION: Synthetic

<400> SEQUENCE: 285

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
```

-continued

```
             100              105              110

Ala Met Trp Gly Gln Gly Thr Leu Val Thr Val Ser Ser
        115              120              125

<210> SEQ ID NO 286
<211> LENGTH: 16
<212> TYPE: PRT
<213> ORGANISM: Artificial Sequence
<220> FEATURE:
<223> OTHER INFORMATION: Synthetic

<400> SEQUENCE: 286

Val Arg His Gly Asn Phe Gly Asn Ser Tyr Val Ser Trp Phe Ala Asn
1               5                   10                  15

<210> SEQ ID NO 287
<211> LENGTH: 125
<212> TYPE: PRT
<213> ORGANISM: Artificial Sequence
<220> FEATURE:
<223> OTHER INFORMATION: Synthetic

<400> SEQUENCE: 287

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100              105              110

Ala Asn Trp Gly Gln Gly Thr Leu Val Thr Val Ser Ser
        115              120              125

<210> SEQ ID NO 288
<211> LENGTH: 16
<212> TYPE: PRT
<213> ORGANISM: Artificial Sequence
<220> FEATURE:
<223> OTHER INFORMATION: Synthetic

<400> SEQUENCE: 288

Val Arg His Gly Asn Phe Gly Asn Ser Tyr Val Ser Trp Phe Ala Pro
1               5                   10                  15

<210> SEQ ID NO 289
<211> LENGTH: 125
<212> TYPE: PRT
<213> ORGANISM: Artificial Sequence
<220> FEATURE:
<223> OTHER INFORMATION: Synthetic

<400> SEQUENCE: 289

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
```

-continued

```
             20              25              30

Ala Met Asn Trp Val Arg Gln Ala Pro Gly Lys Gly Leu Glu Trp Val
        35              40              45

Ala Arg Ile Arg Ser Lys Tyr Asn Asn Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
            100             105             110

Ala Pro Trp Gly Gln Gly Thr Leu Val Thr Val Ser Ser
        115             120             125
```

<210> SEQ ID NO 290
<211> LENGTH: 16
<212> TYPE: PRT
<213> ORGANISM: Artificial Sequence
<220> FEATURE:
<223> OTHER INFORMATION: Synthetic

<400> SEQUENCE: 290

```
Val Arg His Gly Asn Phe Gly Asn Ser Tyr Val Ser Trp Phe Ala Gln
1               5               10              15
```

<210> SEQ ID NO 291
<211> LENGTH: 125
<212> TYPE: PRT
<213> ORGANISM: Artificial Sequence
<220> FEATURE:
<223> OTHER INFORMATION: Synthetic

<400> SEQUENCE: 291

```
Glu Val Lys Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
        35              40              45

Ala Arg Ile Arg Ser Lys Tyr Asn Asn Tyr Ala Thr Tyr Tyr Ala Asp
    50              55              60

Ser Val Lys Asp Arg Phe Thr Ile Ser Arg Asp Asp Ser Lys Ser Ser
65              70              75              80

Leu Tyr Leu Gln Met Asn Asn Leu Lys Thr Glu Asp Thr Ala Met Tyr
                85              90              95

Tyr Cys Val Arg His Gly Asn Phe Gly Asn Ser Tyr Val Ser Trp Phe
            100             105             110

Ala Gln Trp Gly Gln Gly Thr Leu Val Thr Val Ser Ser
        115             120             125
```

<210> SEQ ID NO 292
<211> LENGTH: 16
<212> TYPE: PRT
<213> ORGANISM: Artificial Sequence
<220> FEATURE:
<223> OTHER INFORMATION: Synthetic

<400> SEQUENCE: 292

```
Val Arg His Gly Asn Phe Gly Asn Ser Tyr Val Ser Trp Phe Ala Arg
1               5               10              15
```

<210> SEQ ID NO 293
<211> LENGTH: 125
<212> TYPE: PRT
<213> ORGANISM: Artificial Sequence
<220> FEATURE:
<223> OTHER INFORMATION: Synthetic

<400> SEQUENCE: 293

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Arg Trp Gly Gln Gly Thr Leu Val Thr Val Ser Ser
        115                 120                 125

<210> SEQ ID NO 294
<211> LENGTH: 16
<212> TYPE: PRT
<213> ORGANISM: Artificial Sequence
<220> FEATURE:
<223> OTHER INFORMATION: Synthetic

<400> SEQUENCE: 294

Val Arg His Gly Asn Phe Gly Asn Ser Tyr Val Ser Trp Phe Ala Ser
1               5                   10                  15

<210> SEQ ID NO 295
<211> LENGTH: 125
<212> TYPE: PRT
<213> ORGANISM: Artificial Sequence
<220> FEATURE:
<223> OTHER INFORMATION: Synthetic

<400> SEQUENCE: 295

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

```
Ala Ser Trp Gly Gln Gly Thr Leu Val Thr Val Ser Ser
        115                 120                 125

<210> SEQ ID NO 296
<211> LENGTH: 16
<212> TYPE: PRT
<213> ORGANISM: Artificial Sequence
<220> FEATURE:
<223> OTHER INFORMATION: Synthetic

<400> SEQUENCE: 296

Val Arg His Gly Asn Phe Gly Asn Ser Tyr Val Ser Trp Phe Ala Thr
1               5                   10                  15

<210> SEQ ID NO 297
<211> LENGTH: 125
<212> TYPE: PRT
<213> ORGANISM: Artificial Sequence
<220> FEATURE:
<223> OTHER INFORMATION: Synthetic

<400> SEQUENCE: 297

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
        20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Thr Trp Gly Gln Gly Thr Leu Val Thr Val Ser Ser
        115                 120                 125

<210> SEQ ID NO 298
<211> LENGTH: 16
<212> TYPE: PRT
<213> ORGANISM: Artificial Sequence
<220> FEATURE:
<223> OTHER INFORMATION: Synthetic

<400> SEQUENCE: 298

Val Arg His Gly Asn Phe Gly Asn Ser Tyr Val Ser Trp Phe Ala Val
1               5                   10                  15

<210> SEQ ID NO 299
<211> LENGTH: 125
<212> TYPE: PRT
<213> ORGANISM: Artificial Sequence
<220> FEATURE:
<223> OTHER INFORMATION: Synthetic

<400> SEQUENCE: 299

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
        20                  25                  30
```

-continued

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Val Trp Gly Gln Gly Thr Leu Val Thr Val Ser Ser
        115                 120                 125
```

```
<210> SEQ ID NO 300
<211> LENGTH: 16
<212> TYPE: PRT
<213> ORGANISM: Artificial Sequence
<220> FEATURE:
<223> OTHER INFORMATION: Synthetic

<400> SEQUENCE: 300

Val Arg His Gly Asn Phe Gly Asn Ser Tyr Val Ser Trp Phe Ala Trp
1               5                   10                  15
```

```
<210> SEQ ID NO 301
<211> LENGTH: 125
<212> TYPE: PRT
<213> ORGANISM: Artificial Sequence
<220> FEATURE:
<223> OTHER INFORMATION: Synthetic

<400> SEQUENCE: 301

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
        20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Trp Trp Gly Gln Gly Thr Leu Val Thr Val Ser Ser
        115                 120                 125
```

```
<210> SEQ ID NO 302
<211> LENGTH: 9
<212> TYPE: PRT
<213> ORGANISM: Artificial Sequence
<220> FEATURE:
<223> OTHER INFORMATION: Synthetic

<400> SEQUENCE: 302

Thr Gly Ala Val Thr Ala Ser Asn Tyr
1               5
```

-continued

```
<210> SEQ ID NO 303
<211> LENGTH: 109
<212> TYPE: PRT
<213> ORGANISM: Artificial Sequence
<220> FEATURE:
<223> OTHER INFORMATION: Synthetic

<400> SEQUENCE: 303

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Ala Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Thr Gly Ala Val Thr Asp Ser Asn Tyr
1               5

<210> SEQ ID NO 305
<211> LENGTH: 109
<212> TYPE: PRT
<213> ORGANISM: Artificial Sequence
<220> FEATURE:
<223> OTHER INFORMATION: Synthetic

<400> SEQUENCE: 305

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Asp Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 306
<211> LENGTH: 9
<212> TYPE: PRT
<213> ORGANISM: Artificial Sequence
```

-continued

```
<220> FEATURE:
<223> OTHER INFORMATION: Synthetic

<400> SEQUENCE: 306

Thr Gly Ala Val Thr Glu Ser Asn Tyr
1               5

<210> SEQ ID NO 307
<211> LENGTH: 109
<212> TYPE: PRT
<213> ORGANISM: Artificial Sequence
<220> FEATURE:
<223> OTHER INFORMATION: Synthetic

<400> SEQUENCE: 307

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Glu Ser
                20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 308
<211> LENGTH: 9
<212> TYPE: PRT
<213> ORGANISM: Artificial Sequence
<220> FEATURE:
<223> OTHER INFORMATION: Synthetic

<400> SEQUENCE: 308

Thr Gly Ala Val Thr Phe Ser Asn Tyr
1               5

<210> SEQ ID NO 309
<211> LENGTH: 109
<212> TYPE: PRT
<213> ORGANISM: Artificial Sequence
<220> FEATURE:
<223> OTHER INFORMATION: Synthetic

<400> SEQUENCE: 309

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Phe Ser
                20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95
```

```
Leu Trp Val Phe Gly Gly Gly Thr Lys Leu Thr Val Leu
            100                 105

<210> SEQ ID NO 310
<211> LENGTH: 9
<212> TYPE: PRT
<213> ORGANISM: Artificial Sequence
<220> FEATURE:
<223> OTHER INFORMATION: Synthetic

<400> SEQUENCE: 310

Thr Gly Ala Val Thr Gly Ser Asn Tyr
1               5

<210> SEQ ID NO 311
<211> LENGTH: 109
<212> TYPE: PRT
<213> ORGANISM: Artificial Sequence
<220> FEATURE:
<223> OTHER INFORMATION: Synthetic

<400> SEQUENCE: 311

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Gly Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 312
<211> LENGTH: 9
<212> TYPE: PRT
<213> ORGANISM: Artificial Sequence
<220> FEATURE:
<223> OTHER INFORMATION: Synthetic

<400> SEQUENCE: 312

Thr Gly Ala Val Thr His Ser Asn Tyr
1               5

<210> SEQ ID NO 313
<211> LENGTH: 109
<212> TYPE: PRT
<213> ORGANISM: Artificial Sequence
<220> FEATURE:
<223> OTHER INFORMATION: Synthetic

<400> SEQUENCE: 313

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr His Ser
            20                  25                  30

Asn Tyr Ala Asn Trp Val Gln Gln Lys Pro Gly Gln Ala Phe Arg Gly
        35                  40                  45
```

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 314
<211> LENGTH: 9
<212> TYPE: PRT
<213> ORGANISM: Artificial Sequence
<220> FEATURE:
<223> OTHER INFORMATION: Synthetic

<400> SEQUENCE: 314

Thr Gly Ala Val Thr Lys Ser Asn Tyr
1               5

<210> SEQ ID NO 315
<211> LENGTH: 109
<212> TYPE: PRT
<213> ORGANISM: Artificial Sequence
<220> FEATURE:
<223> OTHER INFORMATION: Synthetic

<400> SEQUENCE: 315

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Lys Ser
                20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 316
<211> LENGTH: 9
<212> TYPE: PRT
<213> ORGANISM: Artificial Sequence
<220> FEATURE:
<223> OTHER INFORMATION: Synthetic

<400> SEQUENCE: 316

Thr Gly Ala Val Thr Leu Ser Asn Tyr
1               5

<210> SEQ ID NO 317
<211> LENGTH: 109
<212> TYPE: PRT
<213> ORGANISM: Artificial Sequence
<220> FEATURE:
<223> OTHER INFORMATION: Synthetic

<400> SEQUENCE: 317

-continued

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Leu Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
                100                 105
```

```
<210> SEQ ID NO 318
<211> LENGTH: 9
<212> TYPE: PRT
<213> ORGANISM: Artificial Sequence
<220> FEATURE:
<223> OTHER INFORMATION: Synthetic

<400> SEQUENCE: 318

Thr Gly Ala Val Thr Met Ser Asn Tyr
1               5
```

```
<210> SEQ ID NO 319
<211> LENGTH: 109
<212> TYPE: PRT
<213> ORGANISM: Artificial Sequence
<220> FEATURE:
<223> OTHER INFORMATION: Synthetic

<400> SEQUENCE: 319

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Met Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
                100                 105
```

```
<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Thr Gly Ala Val Thr Asn Ser Asn Tyr
1               5
```

-continued

<210> SEQ ID NO 321
<211> LENGTH: 109
<212> TYPE: PRT
<213> ORGANISM: Artificial Sequence
<220> FEATURE:
<223> OTHER INFORMATION: Synthetic

<400> SEQUENCE: 321

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Asn Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 322
<211> LENGTH: 9
<212> TYPE: PRT
<213> ORGANISM: Artificial Sequence
<220> FEATURE:
<223> OTHER INFORMATION: Synthetic

<400> SEQUENCE: 322

Thr Gly Ala Val Thr Pro Ser Asn Tyr
1               5

<210> SEQ ID NO 323
<211> LENGTH: 109
<212> TYPE: PRT
<213> ORGANISM: Artificial Sequence
<220> FEATURE:
<223> OTHER INFORMATION: Synthetic

<400> SEQUENCE: 323

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Pro Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 324
<211> LENGTH: 9
<212> TYPE: PRT

-continued

```
<213> ORGANISM: Artificial Sequence
<220> FEATURE:
<223> OTHER INFORMATION: Synthetic

<400> SEQUENCE: 324

Thr Gly Ala Val Thr Gln Ser Asn Tyr
1               5

<210> SEQ ID NO 325
<211> LENGTH: 109
<212> TYPE: PRT
<213> ORGANISM: Artificial Sequence
<220> FEATURE:
<223> OTHER INFORMATION: Synthetic

<400> SEQUENCE: 325

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Gln Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 326
<211> LENGTH: 9
<212> TYPE: PRT
<213> ORGANISM: Artificial Sequence
<220> FEATURE:
<223> OTHER INFORMATION: Synthetic

<400> SEQUENCE: 326

Thr Gly Ala Val Thr Arg Ser Asn Tyr
1               5

<210> SEQ ID NO 327
<211> LENGTH: 109
<212> TYPE: PRT
<213> ORGANISM: Artificial Sequence
<220> FEATURE:
<223> OTHER INFORMATION: Synthetic

<400> SEQUENCE: 327

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Arg Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
```

-continued

```
                    85              90              95

Leu Trp Val Phe Gly Gly Gly Thr Lys Leu Thr Val Leu
              100             105

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Thr Gly Ala Val Thr Val Ser Asn Tyr
1               5

<210> SEQ ID NO 329
<211> LENGTH: 109
<212> TYPE: PRT
<213> ORGANISM: Artificial Sequence
<220> FEATURE:
<223> OTHER INFORMATION: Synthetic

<400> SEQUENCE: 329

Gln Ala Val Val Thr Gln Glu Pro Ser Phe Ser Val Ser Pro Gly Gly
1               5               10              15

Thr Val Thr Leu Thr Cys Arg Ser Ser Thr Gly Ala Val Thr Val Ser
              20              25              30

Asn Tyr Ala Asn Trp Val Gln Gln Lys Pro Gly Gln Ala Phe Arg Gly
        35              40              45

Leu Ile Gly Gly Thr Asn Lys Arg Ala Pro Gly Val Pro Ala Arg Phe
    50              55              60

Ser Gly Ser Leu Ile Gly Asp Lys Ala Ala Leu Thr Ile Thr Gly Ala
65              70              75              80

Gln Ala Asp Asp Glu Ser Ile Tyr Phe Cys Ala Leu Trp Tyr Ser Asn
              85              90              95

Leu Trp Val Phe Gly Gly Gly Thr Lys Leu Thr Val Leu
              100             105

<210> SEQ ID NO 330
<211> LENGTH: 9
<212> TYPE: PRT
<213> ORGANISM: Artificial Sequence
<220> FEATURE:
<223> OTHER INFORMATION: Synthetic

<400> SEQUENCE: 330

Thr Gly Ala Val Thr Tyr Ser Asn Tyr
1               5

<210> SEQ ID NO 331
<211> LENGTH: 109
<212> TYPE: PRT
<213> ORGANISM: Artificial Sequence
<220> FEATURE:
<223> OTHER INFORMATION: Synthetic

<400> SEQUENCE: 331

Gln Ala Val Val Thr Gln Glu Pro Ser Phe Ser Val Ser Pro Gly Gly
1               5               10              15

Thr Val Thr Leu Thr Cys Arg Ser Ser Thr Gly Ala Val Thr Tyr Ser
              20              25              30

Asn Tyr Ala Asn Trp Val Gln Gln Lys Pro Gly Gln Ala Phe Arg Gly
```

```
            35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 332
<211> LENGTH: 9
<212> TYPE: PRT
<213> ORGANISM: Artificial Sequence
<220> FEATURE:
<223> OTHER INFORMATION: Synthetic

<400> SEQUENCE: 332

Ala Ala Trp Tyr Ser Asn Leu Trp Val
1               5

<210> SEQ ID NO 333
<211> LENGTH: 109
<212> TYPE: PRT
<213> ORGANISM: Artificial Sequence
<220> FEATURE:
<223> OTHER INFORMATION: Synthetic

<400> SEQUENCE: 333

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Ala Trp Tyr Ser Asn
                85                  90                  95

Leu Trp Val Phe Gly Gly Gly Thr Lys Leu Thr Val Leu
            100                 105

<210> SEQ ID NO 334
<211> LENGTH: 9
<212> TYPE: PRT
<213> ORGANISM: Artificial Sequence
<220> FEATURE:
<223> OTHER INFORMATION: Synthetic

<400> SEQUENCE: 334

Ala Cys Trp Tyr Ser Asn Leu Trp Val
1               5

<210> SEQ ID NO 335
<211> LENGTH: 109
<212> TYPE: PRT
<213> ORGANISM: Artificial Sequence
<220> FEATURE:
<223> OTHER INFORMATION: Synthetic
```

-continued

```
<400> SEQUENCE: 335

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Cys Trp Tyr Ser Asn
                85                  90                  95

Leu Trp Val Phe Gly Gly Gly Thr Lys Leu Thr Val Leu
            100                 105

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Ala Asp Trp Tyr Ser Asn Leu Trp Val
1               5

<210> SEQ ID NO 337
<211> LENGTH: 109
<212> TYPE: PRT
<213> ORGANISM: Artificial Sequence
<220> FEATURE:
<223> OTHER INFORMATION: Synthetic

<400> SEQUENCE: 337

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Asp Trp Tyr Ser Asn
                85                  90                  95

Leu Trp Val Phe Gly Gly Gly Thr Lys Leu Thr Val Leu
            100                 105

<210> SEQ ID NO 338
<211> LENGTH: 9
<212> TYPE: PRT
<213> ORGANISM: Artificial Sequence
<220> FEATURE:
<223> OTHER INFORMATION: Synthetic

<400> SEQUENCE: 338

Ala Glu Trp Tyr Ser Asn Leu Trp Val
1               5
```

-continued

<210> SEQ ID NO 339
<211> LENGTH: 109
<212> TYPE: PRT
<213> ORGANISM: Artificial Sequence
<220> FEATURE:
<223> OTHER INFORMATION: Synthetic

<400> SEQUENCE: 339

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Glu Trp Tyr Ser Asn
                85                  90                  95

Leu Trp Val Phe Gly Gly Gly Thr Lys Leu Thr Val Leu
            100                 105

<210> SEQ ID NO 340
<211> LENGTH: 9
<212> TYPE: PRT
<213> ORGANISM: Artificial Sequence
<220> FEATURE:
<223> OTHER INFORMATION: Synthetic

<400> SEQUENCE: 340

Ala Phe Trp Tyr Ser Asn Leu Trp Val
1               5

<210> SEQ ID NO 341
<211> LENGTH: 109
<212> TYPE: PRT
<213> ORGANISM: Artificial Sequence
<220> FEATURE:
<223> OTHER INFORMATION: Synthetic

<400> SEQUENCE: 341

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Phe Trp Tyr Ser Asn
                85                  90                  95

Leu Trp Val Phe Gly Gly Gly Thr Lys Leu Thr Val Leu
            100                 105

<210> SEQ ID NO 342
<211> LENGTH: 9

<212> TYPE: PRT
<213> ORGANISM: Artificial Sequence
<220> FEATURE:
<223> OTHER INFORMATION: Synthetic

<400> SEQUENCE: 342

Ala Gly Trp Tyr Ser Asn Leu Trp Val
1               5

<210> SEQ ID NO 343
<211> LENGTH: 109
<212> TYPE: PRT
<213> ORGANISM: Artificial Sequence
<220> FEATURE:
<223> OTHER INFORMATION: Synthetic

<400> SEQUENCE: 343

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Gly Trp Tyr Ser Asn
            85                  90                  95

Leu Trp Val Phe Gly Gly Gly Thr Lys Leu Thr Val Leu
            100                 105

<210> SEQ ID NO 344
<211> LENGTH: 9
<212> TYPE: PRT
<213> ORGANISM: Artificial Sequence
<220> FEATURE:
<223> OTHER INFORMATION: Synthetic

<400> SEQUENCE: 344

Ala Ile Trp Tyr Ser Asn Leu Trp Val
1               5

<210> SEQ ID NO 345
<211> LENGTH: 109
<212> TYPE: PRT
<213> ORGANISM: Artificial Sequence
<220> FEATURE:
<223> OTHER INFORMATION: Synthetic

<400> SEQUENCE: 345

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

-continued

```
Gln Ala Asp Asp Glu Ser Ile Tyr Phe Cys Ala Ile Trp Tyr Ser Asn
                    85                  90                  95

Leu Trp Val Phe Gly Gly Gly Thr Lys Leu Thr Val Leu
            100                 105

<210> SEQ ID NO 346
<211> LENGTH: 9
<212> TYPE: PRT
<213> ORGANISM: Artificial Sequence
<220> FEATURE:
<223> OTHER INFORMATION: Synthetic

<400> SEQUENCE: 346

Ala Lys Trp Tyr Ser Asn Leu Trp Val
1               5

<210> SEQ ID NO 347
<211> LENGTH: 109
<212> TYPE: PRT
<213> ORGANISM: Artificial Sequence
<220> FEATURE:
<223> OTHER INFORMATION: Synthetic

<400> SEQUENCE: 347

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Lys Trp Tyr Ser Asn
                    85                  90                  95

Leu Trp Val Phe Gly Gly Gly Thr Lys Leu Thr Val Leu
            100                 105

<210> SEQ ID NO 348
<211> LENGTH: 9
<212> TYPE: PRT
<213> ORGANISM: Artificial Sequence
<220> FEATURE:
<223> OTHER INFORMATION: Synthetic

<400> SEQUENCE: 348

Ala Met Trp Tyr Ser Asn Leu Trp Val
1               5

<210> SEQ ID NO 349
<211> LENGTH: 109
<212> TYPE: PRT
<213> ORGANISM: Artificial Sequence
<220> FEATURE:
<223> OTHER INFORMATION: Synthetic

<400> SEQUENCE: 349

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30
```

-continued

```
Asn Tyr Ala Asn Trp Val Gln Gln Lys Pro Gly Gln Ala Phe Arg Gly
        35              40              45
Leu Ile Gly Gly Thr Asn Lys Arg Ala Pro Gly Val Pro Ala Arg Phe
    50              55              60
Ser Gly Ser Leu Ile Gly Asp Lys Ala Ala Leu Thr Ile Thr Gly Ala
65              70              75              80
Gln Ala Asp Asp Glu Ser Ile Tyr Phe Cys Ala Met Trp Tyr Ser Asn
                85              90              95
Leu Trp Val Phe Gly Gly Gly Thr Lys Leu Thr Val Leu
            100             105
```

```
<210> SEQ ID NO 350
<211> LENGTH: 9
<212> TYPE: PRT
<213> ORGANISM: Artificial Sequence
<220> FEATURE:
<223> OTHER INFORMATION: Synthetic

<400> SEQUENCE: 350

Ala Asn Trp Tyr Ser Asn Leu Trp Val
1               5
```

```
<210> SEQ ID NO 351
<211> LENGTH: 109
<212> TYPE: PRT
<213> ORGANISM: Artificial Sequence
<220> FEATURE:
<223> OTHER INFORMATION: Synthetic

<400> SEQUENCE: 351

Gln Ala Val Val Thr Gln Glu Pro Ser Phe Ser Val Ser Pro Gly Gly
1               5               10              15
Thr Val Thr Leu Thr Cys Arg Ser Ser Thr Gly Ala Val Thr Thr Ser
            20              25              30
Asn Tyr Ala Asn Trp Val Gln Gln Lys Pro Gly Gln Ala Phe Arg Gly
        35              40              45
Leu Ile Gly Gly Thr Asn Lys Arg Ala Pro Gly Val Pro Ala Arg Phe
    50              55              60
Ser Gly Ser Leu Ile Gly Asp Lys Ala Ala Leu Thr Ile Thr Gly Ala
65              70              75              80
Gln Ala Asp Asp Glu Ser Ile Tyr Phe Cys Ala Asn Trp Tyr Ser Asn
                85              90              95
Leu Trp Val Phe Gly Gly Gly Thr Lys Leu Thr Val Leu
            100             105
```

```
<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Ala Pro Trp Tyr Ser Asn Leu Trp Val
1               5
```

```
<210> SEQ ID NO 353
<211> LENGTH: 109
<212> TYPE: PRT
<213> ORGANISM: Artificial Sequence
<220> FEATURE:
<223> OTHER INFORMATION: Synthetic
```

-continued

<400> SEQUENCE: 353

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Pro Trp Tyr Ser Asn
                85                  90                  95

Leu Trp Val Phe Gly Gly Gly Thr Lys Leu Thr Val Leu
            100                 105

<210> SEQ ID NO 354
<211> LENGTH: 9
<212> TYPE: PRT
<213> ORGANISM: Artificial Sequence
<220> FEATURE:
<223> OTHER INFORMATION: Synthetic

<400> SEQUENCE: 354

Ala Arg Trp Tyr Ser Asn Leu Trp Val
1               5

<210> SEQ ID NO 355
<211> LENGTH: 109
<212> TYPE: PRT
<213> ORGANISM: Artificial Sequence
<220> FEATURE:
<223> OTHER INFORMATION: Synthetic

<400> SEQUENCE: 355

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Arg Trp Tyr Ser Asn
                85                  90                  95

Leu Trp Val Phe Gly Gly Gly Thr Lys Leu Thr Val Leu
            100                 105

<210> SEQ ID NO 356
<211> LENGTH: 9
<212> TYPE: PRT
<213> ORGANISM: Artificial Sequence
<220> FEATURE:
<223> OTHER INFORMATION: Synthetic

<400> SEQUENCE: 356

Ala Ser Trp Tyr Ser Asn Leu Trp Val 1               5

<210> SEQ ID NO 357
<211> LENGTH: 109
<212> TYPE: PRT
<213> ORGANISM: Artificial Sequence
<220> FEATURE:
<223> OTHER INFORMATION: Synthetic

<400> SEQUENCE: 357

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Ser Trp Tyr Ser Asn
                85                  90                  95

Leu Trp Val Phe Gly Gly Gly Thr Lys Leu Thr Val Leu
            100                 105

<210> SEQ ID NO 358
<211> LENGTH: 9
<212> TYPE: PRT
<213> ORGANISM: Artificial Sequence
<220> FEATURE:
<223> OTHER INFORMATION: Synthetic

<400> SEQUENCE: 358

Ala Thr Trp Tyr Ser Asn Leu Trp Val
1               5

<210> SEQ ID NO 359
<211> LENGTH: 109
<212> TYPE: PRT
<213> ORGANISM: Artificial Sequence
<220> FEATURE:
<223> OTHER INFORMATION: Synthetic

<400> SEQUENCE: 359

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Thr Trp Tyr Ser Asn
                85                  90                  95

Leu Trp Val Phe Gly Gly Gly Thr Lys Leu Thr Val Leu
            100                 105

<210> SEQ ID NO 360

-continued

```
<211> LENGTH: 9
<212> TYPE: PRT
<213> ORGANISM: Artificial Sequence
<220> FEATURE:
<223> OTHER INFORMATION: Synthetic

<400> SEQUENCE: 360

Ala Val Trp Tyr Ser Asn Leu Trp Val
1               5

<210> SEQ ID NO 361
<211> LENGTH: 109
<212> TYPE: PRT
<213> ORGANISM: Artificial Sequence
<220> FEATURE:
<223> OTHER INFORMATION: Synthetic

<400> SEQUENCE: 361

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Val Trp Tyr Ser Asn
                85                  90                  95

Leu Trp Val Phe Gly Gly Gly Thr Lys Leu Thr Val Leu
            100                 105

<210> SEQ ID NO 362
<211> LENGTH: 9
<212> TYPE: PRT
<213> ORGANISM: Artificial Sequence
<220> FEATURE:
<223> OTHER INFORMATION: Synthetic

<400> SEQUENCE: 362

Ala Trp Trp Tyr Ser Asn Leu Trp Val
1               5

<210> SEQ ID NO 363
<211> LENGTH: 109
<212> TYPE: PRT
<213> ORGANISM: Artificial Sequence
<220> FEATURE:
<223> OTHER INFORMATION: Synthetic

<400> SEQUENCE: 363

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80
```

-continued

```
Gln Ala Asp Asp Glu Ser Ile Tyr Phe Cys Ala Trp Trp Tyr Ser Asn
                85                  90                  95

Leu Trp Val Phe Gly Gly Gly Thr Lys Leu Thr Val Leu
            100                 105

<210> SEQ ID NO 364
<211> LENGTH: 9
<212> TYPE: PRT
<213> ORGANISM: Artificial Sequence
<220> FEATURE:
<223> OTHER INFORMATION: Synthetic

<400> SEQUENCE: 364

Ala Tyr Trp Tyr Ser Asn Leu Trp Val
1               5

<210> SEQ ID NO 365
<211> LENGTH: 109
<212> TYPE: PRT
<213> ORGANISM: Artificial Sequence
<220> FEATURE:
<223> OTHER INFORMATION: Synthetic

<400> SEQUENCE: 365

Gln Ala Val Val Thr Gln Glu Pro Ser Phe Ser Val Ser Pro Gly Gly
1               5                  10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Tyr Trp Tyr Ser Asn
                85                  90                  95

Leu Trp Val Phe Gly Gly Gly Thr Lys Leu Thr Val Leu
            100                 105

<210> SEQ ID NO 366
<211> LENGTH: 9
<212> TYPE: PRT
<213> ORGANISM: Artificial Sequence
<220> FEATURE:
<223> OTHER INFORMATION: Synthetic

<400> SEQUENCE: 366

Ala Leu Trp Tyr Ser Asn Asp Trp Val
1               5

<210> SEQ ID NO 367
<211> LENGTH: 109
<212> TYPE: PRT
<213> ORGANISM: Artificial Sequence
<220> FEATURE:
<223> OTHER INFORMATION: Synthetic

<400> SEQUENCE: 367

Gln Ala Val Val Thr Gln Glu Pro Ser Phe Ser Val Ser Pro Gly Gly
1               5                  10                  15

Thr Val Thr Leu Thr Cys Arg Ser Ser Thr Gly Ala Val Thr Thr Ser
            20                  25                  30
```

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Asp Trp Val Phe Gly Gly Gly Thr Lys Leu Thr Val Leu
            100                 105

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Ala Leu Trp Tyr Ser Asn Glu Trp Val
1               5

<210> SEQ ID NO 369
<211> LENGTH: 109
<212> TYPE: PRT
<213> ORGANISM: Artificial Sequence
<220> FEATURE:
<223> OTHER INFORMATION: Synthetic

<400> SEQUENCE: 369

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Glu Trp Val Phe Gly Gly Gly Thr Lys Leu Thr Val Leu
            100                 105

<210> SEQ ID NO 370
<211> LENGTH: 9
<212> TYPE: PRT
<213> ORGANISM: Artificial Sequence
<220> FEATURE:
<223> OTHER INFORMATION: Synthetic

<400> SEQUENCE: 370

Ala Leu Trp Tyr Ser Asn Phe Trp Val
1               5

<210> SEQ ID NO 371
<211> LENGTH: 109
<212> TYPE: PRT
<213> ORGANISM: Artificial Sequence
<220> FEATURE:

<223> OTHER INFORMATION: Synthetic

<400> SEQUENCE: 371

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Phe Trp Val Phe Gly Gly Gly Thr Lys Leu Thr Val Leu
            100                 105
```

<210> SEQ ID NO 372
<211> LENGTH: 9
<212> TYPE: PRT
<213> ORGANISM: Artificial Sequence
<220> FEATURE:
<223> OTHER INFORMATION: Synthetic

<400> SEQUENCE: 372

```
Ala Leu Trp Tyr Ser Asn Gly Trp Val
1               5
```

<210> SEQ ID NO 373
<211> LENGTH: 109
<212> TYPE: PRT
<213> ORGANISM: Artificial Sequence
<220> FEATURE:
<223> OTHER INFORMATION: Synthetic

<400> SEQUENCE: 373

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Gly Trp Val Phe Gly Gly Gly Thr Lys Leu Thr Val Leu
            100                 105
```

<210> SEQ ID NO 374
<211> LENGTH: 9
<212> TYPE: PRT
<213> ORGANISM: Artificial Sequence
<220> FEATURE:
<223> OTHER INFORMATION: Synthetic

<400> SEQUENCE: 374

```
Ala Leu Trp Tyr Ser Asn His Trp Val
1               5
```

<210> SEQ ID NO 375
<211> LENGTH: 109
<212> TYPE: PRT
<213> ORGANISM: Artificial Sequence
<220> FEATURE:
<223> OTHER INFORMATION: Synthetic

<400> SEQUENCE: 375

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 376
<211> LENGTH: 9
<212> TYPE: PRT
<213> ORGANISM: Artificial Sequence
<220> FEATURE:
<223> OTHER INFORMATION: Synthetic

<400> SEQUENCE: 376

```
Ala Leu Trp Tyr Ser Asn Lys Trp Val
1               5
```

<210> SEQ ID NO 377
<211> LENGTH: 109
<212> TYPE: PRT
<213> ORGANISM: Artificial Sequence
<220> FEATURE:
<223> OTHER INFORMATION: Synthetic

<400> SEQUENCE: 377

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Lys Trp Val Phe Gly Gly Gly Thr Lys Leu Thr Val Leu
            100                 105
```

```
<210> SEQ ID NO 378
<211> LENGTH: 9
<212> TYPE: PRT
<213> ORGANISM: Artificial Sequence
<220> FEATURE:
<223> OTHER INFORMATION: Synthetic

<400> SEQUENCE: 378

Ala Leu Trp Tyr Ser Asn Met Trp Val
1               5

<210> SEQ ID NO 379
<211> LENGTH: 109
<212> TYPE: PRT
<213> ORGANISM: Artificial Sequence
<220> FEATURE:
<223> OTHER INFORMATION: Synthetic

<400> SEQUENCE: 379

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Met Trp Val Phe Gly Gly Gly Thr Lys Leu Thr Val Leu
            100                 105

<210> SEQ ID NO 380
<211> LENGTH: 9
<212> TYPE: PRT
<213> ORGANISM: Artificial Sequence
<220> FEATURE:
<223> OTHER INFORMATION: Synthetic

<400> SEQUENCE: 380

Ala Leu Trp Tyr Ser Asn Asn Trp Val
1               5

<210> SEQ ID NO 381
<211> LENGTH: 109
<212> TYPE: PRT
<213> ORGANISM: Artificial Sequence
<220> FEATURE:
<223> OTHER INFORMATION: Synthetic

<400> SEQUENCE: 381

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
```

```
65               70                75                80

Gln Ala Asp Asp Glu Ser Ile Tyr Phe Cys Ala Leu Trp Tyr Ser Asn
                85                90                95

Asn Trp Val Phe Gly Gly Gly Thr Lys Leu Thr Val Leu
            100              105

<210> SEQ ID NO 382
<211> LENGTH: 9
<212> TYPE: PRT
<213> ORGANISM: Artificial Sequence
<220> FEATURE:
<223> OTHER INFORMATION: Synthetic

<400> SEQUENCE: 382

Ala Leu Trp Tyr Ser Asn Pro Trp Val
1               5

<210> SEQ ID NO 383
<211> LENGTH: 109
<212> TYPE: PRT
<213> ORGANISM: Artificial Sequence
<220> FEATURE:
<223> OTHER INFORMATION: Synthetic

<400> SEQUENCE: 383

Gln Ala Val Val Thr Gln Glu Pro Ser Phe Ser Val Ser Pro Gly Gly
1               5                10                15

Thr Val Thr Leu Thr Cys Arg Ser Ser Thr Gly Ala Val Thr Thr Ser
            20                25                30

Asn Tyr Ala Asn Trp Val Gln Gln Lys Pro Gly Gln Ala Phe Arg Gly
        35                40                45

Leu Ile Gly Gly Thr Asn Lys Arg Ala Pro Gly Val Pro Ala Arg Phe
    50                55                60

Ser Gly Ser Leu Ile Gly Asp Lys Ala Ala Leu Thr Ile Thr Gly Ala
65               70                75                80

Gln Ala Asp Asp Glu Ser Ile Tyr Phe Cys Ala Leu Trp Tyr Ser Asn
                85                90                95

Pro Trp Val Phe Gly Gly Gly Thr Lys Leu Thr Val Leu
            100              105

<210> SEQ ID NO 384
<211> LENGTH: 9
<212> TYPE: PRT
<213> ORGANISM: Artificial Sequence
<220> FEATURE:
<223> OTHER INFORMATION: Synthetic

<400> SEQUENCE: 384

Ala Leu Trp Tyr Ser Asn Gln Trp Val
1               5

<210> SEQ ID NO 385
<211> LENGTH: 109
<212> TYPE: PRT
<213> ORGANISM: Artificial Sequence
<220> FEATURE:
<223> OTHER INFORMATION: Synthetic

<400> SEQUENCE: 385

Gln Ala Val Val Thr Gln Glu Pro Ser Phe Ser Val Ser Pro Gly Gly
1               5                10                15

Thr Val Thr Leu Thr Cys Arg Ser Ser Thr Gly Ala Val Thr Thr Ser
```

-continued

```
                20              25              30

Asn Tyr Ala Asn Trp Val Gln Gln Lys Pro Gly Gln Ala Phe Arg Gly
        35              40              45

Leu Ile Gly Gly Thr Asn Lys Arg Ala Pro Gly Val Pro Ala Arg Phe
    50              55              60

Ser Gly Ser Leu Ile Gly Asp Lys Ala Ala Leu Thr Ile Thr Gly Ala
65              70              75              80

Gln Ala Asp Asp Glu Ser Ile Tyr Phe Cys Ala Leu Trp Tyr Ser Asn
                85              90              95

Gln Trp Val Phe Gly Gly Gly Thr Lys Leu Thr Val Leu
            100             105

<210> SEQ ID NO 386
<211> LENGTH: 9
<212> TYPE: PRT
<213> ORGANISM: Artificial Sequence
<220> FEATURE:
<223> OTHER INFORMATION: Synthetic

<400> SEQUENCE: 386

Ala Leu Trp Tyr Ser Asn Ser Trp Val
1               5

<210> SEQ ID NO 387
<211> LENGTH: 109
<212> TYPE: PRT
<213> ORGANISM: Artificial Sequence
<220> FEATURE:
<223> OTHER INFORMATION: Synthetic

<400> SEQUENCE: 387

Gln Ala Val Val Thr Gln Glu Pro Ser Phe Ser Val Ser Pro Gly Gly
1               5               10              15

Thr Val Thr Leu Thr Cys Arg Ser Ser Thr Gly Ala Val Thr Thr Ser
            20              25              30

Asn Tyr Ala Asn Trp Val Gln Gln Lys Pro Gly Gln Ala Phe Arg Gly
        35              40              45

Leu Ile Gly Gly Thr Asn Lys Arg Ala Pro Gly Val Pro Ala Arg Phe
    50              55              60

Ser Gly Ser Leu Ile Gly Asp Lys Ala Ala Leu Thr Ile Thr Gly Ala
65              70              75              80

Gln Ala Asp Asp Glu Ser Ile Tyr Phe Cys Ala Leu Trp Tyr Ser Asn
                85              90              95

Ser Trp Val Phe Gly Gly Gly Thr Lys Leu Thr Val Leu
            100             105

<210> SEQ ID NO 388
<211> LENGTH: 9
<212> TYPE: PRT
<213> ORGANISM: Artificial Sequence
<220> FEATURE:
<223> OTHER INFORMATION: Synthetic

<400> SEQUENCE: 388

Ala Leu Trp Tyr Ser Asn Thr Trp Val
1               5

<210> SEQ ID NO 389
<211> LENGTH: 109
<212> TYPE: PRT
<213> ORGANISM: Artificial Sequence
```

<220> FEATURE:
<223> OTHER INFORMATION: Synthetic

<400> SEQUENCE: 389

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Thr Trp Val Phe Gly Gly Gly Thr Lys Leu Thr Val Leu
            100                 105
```

<210> SEQ ID NO 390
<211> LENGTH: 9
<212> TYPE: PRT
<213> ORGANISM: Artificial Sequence
<220> FEATURE:
<223> OTHER INFORMATION: Synthetic

<400> SEQUENCE: 390

```
Ala Leu Trp Tyr Ser Asn Val Trp Val
1               5
```

<210> SEQ ID NO 391
<211> LENGTH: 109
<212> TYPE: PRT
<213> ORGANISM: Artificial Sequence
<220> FEATURE:
<223> OTHER INFORMATION: Synthetic

<400> SEQUENCE: 391

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Val Trp Val Phe Gly Gly Gly Thr Lys Leu Thr Val Leu
            100                 105
```

<210> SEQ ID NO 392
<211> LENGTH: 9
<212> TYPE: PRT
<213> ORGANISM: Artificial Sequence
<220> FEATURE:
<223> OTHER INFORMATION: Synthetic

<400> SEQUENCE: 392

-continued

Ala Leu Trp Tyr Ser Asn Trp Trp Val
1               5

<210> SEQ ID NO 393
<211> LENGTH: 109
<212> TYPE: PRT
<213> ORGANISM: Artificial Sequence
<220> FEATURE:
<223> OTHER INFORMATION: Synthetic

<400> SEQUENCE: 393

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Trp Trp Val Phe Gly Gly Gly Thr Lys Leu Thr Val Leu
            100                 105

<210> SEQ ID NO 394
<211> LENGTH: 9
<212> TYPE: PRT
<213> ORGANISM: Artificial Sequence
<220> FEATURE:
<223> OTHER INFORMATION: Synthetic

<400> SEQUENCE: 394

Ala Leu Trp Tyr Ser Asn Tyr Trp Val
1               5

<210> SEQ ID NO 395
<211> LENGTH: 109
<212> TYPE: PRT
<213> ORGANISM: Artificial Sequence
<220> FEATURE:
<223> OTHER INFORMATION: Synthetic

<400> SEQUENCE: 395

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Tyr Trp Val Phe Gly Gly Gly Thr Lys Leu Thr Val Leu
            100                 105

-continued

```
<210> SEQ ID NO 396
<211> LENGTH: 252
<212> TYPE: PRT
<213> ORGANISM: Homo Sapiens

<400> SEQUENCE: 396

Lys Thr Thr Gln Pro Asn Ser Met Glu Ser Asn Glu Glu Glu Pro Val
1               5                   10                  15

His Leu Pro Cys Asn His Ser Thr Ile Ser Gly Thr Asp Tyr Ile His
            20                  25                  30

Trp Tyr Arg Gln Leu Pro Ser Gln Gly Pro Glu Tyr Val Ile His Gly
        35                  40                  45

Leu Thr Ser Asn Val Asn Asn Arg Met Ala Ser Leu Ala Ile Ala Glu
    50                  55                  60

Asp Arg Lys Ser Ser Thr Leu Ile Leu His Arg Ala Thr Leu Arg Asp
65                  70                  75                  80

Ala Ala Val Tyr Tyr Cys Ile Leu Pro Leu Ala Gly Gly Thr Ser Tyr
                85                  90                  95

Gly Lys Leu Thr Phe Gly Gln Gly Thr Ile Leu Thr Val His Pro Asn
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser Cys Asp Val
        195                 200                 205

Lys Leu Val Glu Lys Ser Phe Glu Thr Asp Thr Asn Leu Asn Phe Gln
    210                 215                 220

Asn Leu Ser Val Ile Gly Phe Arg Ile Leu Leu Leu Lys Val Ala Gly
225                 230                 235                 240

Phe Asn Leu Leu Met Thr Leu Arg Leu Trp Ser Ser
                245                 250

<210> SEQ ID NO 397
<211> LENGTH: 288
<212> TYPE: PRT
<213> ORGANISM: Homo Sapiens

<400> SEQUENCE: 397

Gly Val Ser Gln Ser Pro Arg Tyr Lys Val Ala Lys Arg Gly Gln Asp
1               5                   10                  15

Val Ala Leu Arg Cys Asp Pro Ile Ser Gly His Val Ser Leu Phe Trp
            20                  25                  30

Tyr Gln Gln Ala Leu Gly Gln Gly Pro Glu Phe Leu Thr Tyr Phe Gln
            35                  40                  45

Asn Glu Ala Gln Leu Asp Lys Ser Gly Leu Pro Ser Asp Arg Phe Phe
    50                  55                  60

Ala Glu Arg Pro Glu Gly Ser Val Ser Thr Leu Lys Ile Gln Arg Thr
65                  70                  75                  80
```

```
Gln Gln Glu Asp Ser Ala Val Tyr Leu Cys Ala Ser Ser Leu Gly Gln
                85                  90                  95

Ala Tyr Glu Gln Tyr Phe Gly Pro Gly Thr Arg Leu Thr Val Thr Glu
            100                 105                 110

Asp Leu Asn Lys Val Phe Pro Pro Glu Val Ala Val Phe Glu Pro Ser
            115                 120                 125

Glu Ala Glu Ile Ser His Thr Gln Lys Ala Thr Leu Val Cys Leu Ala
        130                 135                 140

Thr Gly Phe Phe Pro Asp His Val Glu Leu Ser Trp Trp Val Asn Gly
145                 150                 155                 160

Lys Glu Val His Ser Gly Val Ser Thr Asp Pro Gln Pro Leu Lys Glu
                165                 170                 175

Gln Pro Ala Leu Asn Asp Ser Arg Tyr Cys Leu Ser Ser Arg Leu Arg
            180                 185                 190

Val Ser Ala Thr Phe Trp Gln Asn Pro Arg Asn His Phe Arg Cys Gln
            195                 200                 205

Val Gln Phe Tyr Gly Leu Ser Glu Asn Asp Glu Trp Thr Gln Asp Arg
        210                 215                 220

Ala Lys Pro Val Thr Gln Ile Val Ser Ala Glu Ala Trp Gly Arg Ala
225                 230                 235                 240

Asp Cys Gly Phe Thr Ser Val Ser Tyr Gln Gln Gly Val Leu Ser Ala
                245                 250                 255

Thr Ile Leu Tyr Glu Ile Leu Leu Gly Lys Ala Thr Leu Tyr Ala Val
                260                 265                 270

Leu Val Ser Ala Leu Val Leu Met Ala Met Val Lys Arg Lys Asp Phe
            275                 280                 285
```

```
<210> SEQ ID NO 398
<211> LENGTH: 150
<212> TYPE: PRT
<213> ORGANISM: Homo Sapiens

<400> SEQUENCE: 398

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
                20                  25                  30

Asp Ile Thr Arg Leu Asp Leu Gly Lys Arg Ile Leu Asp Pro Arg Gly
            35                  40                  45

Ile Tyr Arg Cys Asn Gly Thr Asp Ile Tyr Lys Asp Lys Glu Ser Thr
        50                  55                  60

Val Gln Val His Tyr Arg Met Cys Gln Ser Cys Val Glu Leu Asp Pro
65                  70                  75                  80

Ala Thr Val Ala Gly Ile Ile Val Thr Asp Val Ile Ala Thr Leu Leu
                85                  90                  95

Leu Ala Leu Gly Val Phe Cys Phe Ala Gly His Glu Thr Gly Arg Leu
            100                 105                 110

Ser Gly Ala Ala Asp Thr Gln Ala Leu Leu Arg Asn Asp Gln Val Tyr
            115                 120                 125

Gln Pro Leu Arg Asp Arg Asp Asp Ala Gln Tyr Ser His Leu Gly Gly
        130                 135                 140

Asn Trp Ala Arg Asn Lys
145                 150
```

```
<210> SEQ ID NO 399
```

<211> LENGTH: 186
<212> TYPE: PRT
<213> ORGANISM: Homo Sapiens

<400> SEQUENCE: 399

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
            35                  40                  45

Glu Asp Asp Lys Asn Ile Gly Ser Asp Glu Asp His Leu Ser Leu Lys
        50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
                100                 105                 110

Val Ile Val Asp Ile Cys Ile Thr Gly Gly Leu Leu Leu Leu Val Tyr
            115                 120                 125

Tyr Trp Ser Lys Asn Arg Lys Ala Lys Ala Lys Pro Val Thr Arg Gly
        130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
                180                 185
```

<210> SEQ ID NO 400
<211> LENGTH: 160
<212> TYPE: PRT
<213> ORGANISM: Homo Sapiens

<400> SEQUENCE: 400

```
Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
                20                  25                  30

Trp Phe Lys Asp Gly Lys Met Ile Gly Phe Leu Thr Glu Asp Lys Lys
            35                  40                  45

Lys Trp Asn Leu Gly Ser Asn Ala Lys Asp Pro Arg Gly Met Tyr Gln
        50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Ala Thr Ile Ser Gly Phe
                85                  90                  95

Leu Phe Ala Glu Ile Val Ser Ile Phe Val Leu Ala Val Gly Val Tyr
                100                 105                 110

Phe Ile Ala Gly Gln Asp Gly Val Arg Gln Ser Arg Ala Ser Asp Lys
            115                 120                 125

Gln Thr Leu Leu Pro Asn Asp Gln Leu Tyr Gln Pro Leu Lys Asp Arg
        130                 135                 140

Glu Asp Asp Gln Tyr Ser His Leu Gln Gly Asn Gln Leu Arg Arg Asn
145                 150                 155                 160
```

```
<210> SEQ ID NO 401
<211> LENGTH: 143
<212> TYPE: PRT
<213> ORGANISM: Homo Sapiens

<400> SEQUENCE: 401

Gln Ser Phe Gly Leu Leu Asp Pro Lys Leu Cys Tyr Leu Leu Asp Gly
1               5                   10                  15

Ile Leu Phe Ile Tyr Gly Val Ile Leu Thr Ala Leu Phe Leu Arg Val
            20                  25                  30

Lys Phe Ser Arg Ser Ala Asp Ala Pro Ala Tyr Gln Gln Gly Gln Asn
        35                  40                  45

Gln Leu Tyr Asn Glu Leu Asn Leu Gly Arg Arg Glu Glu Tyr Asp Val
    50                  55                  60

Leu Asp Lys Arg Arg Gly Arg Asp Pro Glu Met Gly Gly Lys Pro Gln
65                  70                  75                  80

Arg Arg Lys Asn Pro Gln Glu Gly Leu Tyr Asn Glu Leu Gln Lys Asp
                85                  90                  95

Lys Met Ala Glu Ala Tyr Ser Glu Ile Gly Met Lys Gly Glu Arg Arg
            100                 105                 110

Arg Gly Lys Gly His Asp Gly Leu Tyr Gln Gly Leu Ser Thr Ala Thr
        115                 120                 125

Lys Asp Thr Tyr Asp Ala Leu His Met Gln Ala Leu Pro Pro Arg
    130                 135                 140

<210> SEQ ID NO 402
<211> LENGTH: 255
<212> TYPE: PRT
<213> ORGANISM: Artificial Sequence
<220> FEATURE:
<223> OTHER INFORMATION: Synthetic

<400> SEQUENCE: 402

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Gly Gly Gly Gly Ser
            20                  25                  30

Gly Gly Gly Gly Ser Gly Gly Gly Gly Ser Glu Ile Val Leu Thr Gln
        35                  40                  45

Ser Pro Ala Thr Leu Ser Leu Ser Pro Gly Glu Arg Ala Thr Leu Ser
    50                  55                  60

Cys Arg Ala Ser Gln Ser Val Ser Ser Tyr Leu Ala Trp Tyr Gln Gln
65                  70                  75                  80

Lys Pro Gly Gln Ala Pro Arg Leu Leu Ile Tyr Asp Ala Ser Asn Arg
                85                  90                  95

Ala Thr Gly Ile Pro Ala Arg Phe Ser Gly Ser Gly Ser Gly Thr Asp
            100                 105                 110

Phe Thr Leu Thr Ile Ser Ser Leu Glu Pro Glu Asp Phe Ala Val Tyr
        115                 120                 125

Tyr Cys Gln Gln Arg Ser Asn Trp Pro Ile Thr Phe Gly Gln Gly Thr
    130                 135                 140

Arg Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175
```

-continued

```
Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
        210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu
                245                 250                 255

<210> SEQ ID NO 403
<211> LENGTH: 177
<212> TYPE: PRT
<213> ORGANISM: Macaca fasciularis

<400> SEQUENCE: 403

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65              70                  75                  80

His Leu Tyr Leu Lys Ala Arg Val Cys Glu Asn Cys Met Glu Met Asp
                85                  90                  95

Val Met Ala Val Ala Thr Ile Val Ile Val Asp Ile Cys Ile Thr Leu
            100                 105                 110

Gly Leu Leu Leu Leu Val Tyr Tyr Trp Ser Lys Asn Arg Lys Ala Lys
        115                 120                 125

Ala Lys Pro Val Thr Arg Gly Ala Gly Ala Gly Gly Arg Gln Arg Gly
        130                 135                 140

Gln Asn Lys Glu Arg Pro Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 404
<211> LENGTH: 177
<212> TYPE: PRT
<213> ORGANISM: Macaca mulatta

<400> SEQUENCE: 404

Gln Asp Gly Asn Glu Glu Met Gly Ser Ile Thr Gln Thr Pro Tyr His
1               5                   10                  15

Val Ser Ile Ser Gly Thr Thr Val Ile Leu Thr Cys Ser Gln His Leu
            20                  25                  30

Gly Ser Glu Val Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
```

-continued

```
65                  70                  75                  80
His Leu Tyr Leu Lys Ala Arg Val Cys Glu Asn Cys Met Glu Met Asp
                    85                  90                  95
Val Met Ala Val Ala Thr Ile Val Ile Val Asp Ile Cys Ile Thr Leu
                    100                 105                 110
Gly Leu Leu Leu Leu Val Tyr Tyr Trp Ser Lys Asn Arg Lys Ala Lys
                    115                 120                 125
Ala Lys Pro Val Thr Arg Gly Ala Gly Ala Gly Gly Arg Gln Arg Gly
        130                 135                 140
Gln Asn Lys Glu Arg Pro Pro Pro Val Pro Asn Pro Asp Tyr Glu Pro
145                 150                 155                 160
Ile Arg Lys Gly Gln Gln Asp Leu Tyr Ser Gly Leu Asn Gln Arg Arg
                    165                 170                 175
Ile
```

```
<210> SEQ ID NO 405
<211> LENGTH: 125
<212> TYPE: PRT
<213> ORGANISM: Mus Musculus

<400> SEQUENCE: 405

Glu Val Lys Leu Leu Glu Ser Gly Gly Gly Leu Val Gln Pro Lys Gly
1                   5                   10                  15
Ser Leu Lys Leu Ser Cys Ala Ala Ser Gly Phe Thr Phe Asn Thr Tyr
                    20                  25                  30
Ala Met Asn Trp Val Arg Gln Ala Pro Gly Lys Gly Leu Glu Trp Val
            35                  40                  45
Ala Arg Ile Arg Ser Lys Tyr Asn Asn Tyr Ala Thr Tyr Tyr Ala Asp
        50                  55                  60
Ser Val Lys Asp Arg Phe Thr Ile Ser Arg Asp Asp Ser Gln Ser Ile
65                  70                  75                  80
Leu Tyr Leu Gln Met Asn Asn Leu Lys Thr Glu Asp Thr Ala Met Tyr
                    85                  90                  95
Tyr Cys Val Arg His Gly Asn Phe Gly Asn Ser Tyr Val Ser Trp Phe
                    100                 105                 110
Ala Tyr Trp Gly Gln Gly Thr Leu Val Thr Val Ser Ala
            115                 120                 125
```

```
<210> SEQ ID NO 406
<211> LENGTH: 109
<212> TYPE: PRT
<213> ORGANISM: Mus Musculus

<400> SEQUENCE: 406

Gln Ala Val Val Thr Gln Glu Ser Ala Leu Thr Thr Ser Pro Gly Glu
1                   5                   10                  15
Thr Val Thr Leu Thr Cys Arg Ser Ser Thr Gly Ala Val Thr Thr Ser
                    20                  25                  30
Asn Tyr Ala Asn Trp Val Gln Glu Lys Pro Asp His Leu Phe Thr Gly
            35                  40                  45
Leu Ile Gly Gly Thr Asn Lys Arg Ala Pro Gly Val Pro Ala Arg Phe
        50                  55                  60
Ser Gly Ser Leu Ile Gly Asp Lys Ala Ala Leu Thr Ile Thr Gly Ala
65                  70                  75                  80
Gln Thr Glu Asp Glu Ala Ile Tyr Phe Cys Ala Leu Trp Tyr Ser Asn
                    85                  90                  95
```

-continued

```
Leu Trp Val Phe Gly Gly Gly Thr Lys Leu Thr Val Leu
            100                 105

<210> SEQ ID NO 407
<211> LENGTH: 330
<212> TYPE: PRT
<213> ORGANISM: Homo Sapiens

<400> SEQUENCE: 407

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 408
<211> LENGTH: 106
<212> TYPE: PRT
```

<213> ORGANISM: Homo Sapiens

<400> SEQUENCE: 408

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 409
<211> LENGTH: 330
<212> TYPE: PRT
<213> ORGANISM: Artificial Sequence
<220> FEATURE:
<223> OTHER INFORMATION: Synthetic

<400> SEQUENCE: 409

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 410
<211> LENGTH: 27
<212> TYPE: DNA
<213> ORGANISM: Artificial Sequence
<220> FEATURE:
<223> OTHER INFORMATION: Synthetic

<400> SEQUENCE: 410
gcttcgcgat gtacgggcca gatatac                                        27

<210> SEQ ID NO 411
<211> LENGTH: 41
<212> TYPE: DNA
<213> ORGANISM: Artificial Sequence
<220> FEATURE:
<223> OTHER INFORMATION: Synthetic

<400> SEQUENCE: 411 ggatacccccc tagagcccca gctgcgcaga tctgctatgg c                        41

<210> SEQ ID NO 412
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 412

Gly Phe Thr Phe Asn Xaa Tyr Ala
1               5

<210> SEQ ID NO 413
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 413

Ile Arg Ser Lys Tyr Asn Xaa Tyr Ala Thr
1               5               10

<210> SEQ ID NO 414
```

```
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 414

Val Arg Xaa Gly Asn Phe Gly Asn Ser Tyr Val Ser Trp Phe Ala Tyr
1               5                   10                  15

<210> SEQ ID NO 415
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 415

Val Arg His Gly Asn Phe Gly Asn Ser Tyr Val Xaa Trp Phe Ala Tyr
1               5                   10                  15

<210> SEQ ID NO 416
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: Xaa can be any naturally occurring amino acid

<400> SEQUENCE: 416

Val Arg His Gly Asn Phe Gly Asn Ser Tyr Val Ser Trp Phe Ala Xaa
1               5                   10                  15

<210> SEQ ID NO 417
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 417

Val Arg His Gly Asn Phe Xaa Asn Ser Tyr Val Ser Trp Phe Ala Tyr
1               5                   10                  15
```